US009592248B2

(12) United States Patent
Ritter et al.

(10) Patent No.: US 9,592,248 B2
(45) Date of Patent: *Mar. 14, 2017

(54) PREBIOTIC FORMULATIONS AND METHODS OF USE

(71) Applicant: Ritter Pharmaceuticals, Inc., Los Angeles, CA (US)

(72) Inventors: Andrew J. Ritter, Los Angeles, CA (US); Dennis Savaiano, West Lafayette, IN (US); David Barnes, Dexter, MI (US); Todd Klaenhammer, Raleigh, NC (US)

(73) Assignee: Ritter Pharmaceuticals, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/860,233

(22) Filed: Sep. 21, 2015

(65) Prior Publication Data

US 2016/0008384 A1 Jan. 14, 2016

Related U.S. Application Data

(63) Continuation of application No. 14/293,784, filed on Jun. 2, 2014, now abandoned, which is a continuation of application No. 13/096,711, filed on Apr. 28, 2011, now Pat. No. 8,785,160, and a continuation-in-part of application No. 12/707,037, filed on Feb. 17, 2010, now Pat. No. 8,492,124.

(60) Provisional application No. 61/328,991, filed on Apr. 28, 2010, provisional application No. 61/372,836, filed on Aug. 11, 2010, provisional application No. 61/155,150, filed on Feb. 24, 2009, provisional application No. 61/272,622, filed on Oct. 13, 2009.

(51) Int. Cl.
| | |
|---|---|
| *C12P 19/04* | (2006.01) |
| *A61K 31/702* | (2006.01) |
| *A61K 31/715* | (2006.01) |
| *A61K 35/742* | (2015.01) |
| *A61K 35/744* | (2015.01) |
| *A61K 9/48* | (2006.01) |

(52) U.S. Cl.
CPC ......... *A61K 31/702* (2013.01); *A23L 33/10* (2016.08); *A23L 33/135* (2016.08); *A23L 33/21* (2016.08); *A61K 9/4825* (2013.01); *A61K 9/4891* (2013.01); *A61K 31/715* (2013.01); *A61K 35/742* (2013.01); *A61K 35/744* (2013.01); *A23V 2002/00* (2013.01)

(58) Field of Classification Search
CPC ....... A61K 9/48; A61K 9/4825; A61K 9/4891
See application file for complete search history.

(56) References Cited

U.S. PATENT DOCUMENTS

| | | | |
|---|---|---|---|
| 3,048,526 A | 8/1962 | Boswell | |
| 3,108,046 A | 10/1963 | Harbit et al. | |
| 3,536,809 A | 10/1970 | Appleweig | |
| 3,598,123 A | 8/1971 | Zaffaroni | |
| 3,627,583 A | 12/1971 | Troy et al. | |
| 3,718,739 A | 2/1973 | Cayle | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,478,822 A | 10/1984 | Haslam et al. | |
| 4,532,126 A | 7/1985 | Ebert et al. | |
| 4,625,494 A | 12/1986 | Iwatschenko et al. | |
| 4,629,694 A | 12/1986 | Harpel | |
| 4,656,066 A | 4/1987 | Wittwer | |
| 4,671,953 A | 6/1987 | Stanley et al. | |
| 4,786,505 A | 11/1988 | Lovgren et al. | |
| 4,800,083 A | 1/1989 | Hom et al. | |
| 4,806,368 A | 2/1989 | Reddy | |
| 4,888,171 A | 12/1989 | Okonogi et al. | |
| 4,904,479 A | 2/1990 | Illum | |
| 4,919,939 A | 4/1990 | Baker | |
| 4,935,243 A | 6/1990 | Borkan et al. | |
| 4,944,952 A | 7/1990 | Kobayashi et al. | |
| 4,950,484 A | 8/1990 | Olthoff et al. | |
| 4,957,763 A | 9/1990 | Saita et al. | |
| 4,959,234 A | 9/1990 | Ahmed et al. | |
| 4,987,150 A | 1/1991 | Kurono et al. | |
| 5,013,726 A | 5/1991 | Ivy et al. | |

(Continued)

FOREIGN PATENT DOCUMENTS

| | | |
|---|---|---|
| AU | 624590 B2 | 6/1989 |
| AU | 2006257751 B2 | 12/2006 |

(Continued)

OTHER PUBLICATIONS

Cole, E. "Liquid filled and sealed hard gelatin capsules", Capsugel Library, 2000.*

(Continued)

*Primary Examiner* — Gina Justice

(74) *Attorney, Agent, or Firm* — Knobbe Martens Olson & Bear LLP

(57) ABSTRACT

The invention provides methods and pharmaceutical compositions for treating symptoms associated with lactose intolerance and for overall improvement in gastrointestinal health. Described herein are methods and pharmaceutical compositions for improving overall gastrointestinal health or for decreasing symptoms of lactose intolerance by administering to subject in need thereof a pharmaceutical composition comprising a prebiotic, optionally in combination with effective amount of a probiotic microbe or microbes.

16 Claims, 33 Drawing Sheets

(56) References Cited

U.S. PATENT DOCUMENTS

| | | |
|---|---|---|
| 5,032,509 A | 7/1991 | Matsumoto et al. |
| 5,059,595 A | 10/1991 | Le Grazie |
| 5,073,543 A | 12/1991 | Marshall et al. |
| 5,118,521 A | 6/1992 | Sonoike et al. |
| 5,120,548 A | 6/1992 | McClelland et al. |
| 5,139,575 A | 8/1992 | Matsuda et al. |
| 5,149,640 A | 9/1992 | Onishi et al. |
| 5,219,842 A | 6/1993 | Okada et al. |
| 5,225,202 A | 7/1993 | Hodges et al. |
| 5,294,546 A | 3/1994 | Dombou et al. |
| 5,354,556 A | 10/1994 | Sparks et al. |
| 5,378,833 A | 1/1995 | Katta et al. |
| 5,439,893 A | 8/1995 | Richards et al. |
| 5,466,472 A | 11/1995 | Kuma et al. |
| 5,550,106 A | 8/1996 | Petschow et al. |
| 5,591,767 A | 1/1997 | Mohr et al. |
| 5,610,184 A | 3/1997 | Shahinian, Jr. |
| 5,623,071 A | 4/1997 | Kitahata et al. |
| 5,639,476 A | 6/1997 | Oshlack et al. |
| 5,641,759 A | 6/1997 | Patterson et al. |
| 5,644,012 A | 7/1997 | Iritani et al. |
| 5,674,533 A | 10/1997 | Santus et al. |
| 5,709,857 A | 1/1998 | Morelli et al. |
| 5,716,615 A | 2/1998 | Cavaliere Vesely et al. |
| 5,733,556 A | 3/1998 | Schrier et al. |
| 5,733,575 A | 3/1998 | Mehra et al. |
| 5,744,134 A | 4/1998 | Paul |
| 5,827,526 A | 10/1998 | Dohnalek et al. |
| 5,837,284 A | 11/1998 | Mehta et al. |
| 5,840,860 A | 11/1998 | Annison et al. |
| 5,861,289 A | 1/1999 | Nakayama et al. |
| 5,871,776 A | 2/1999 | Mehta |
| 5,895,648 A | 4/1999 | Cavaliere Vesely et al. |
| 5,902,632 A | 5/1999 | Mehta |
| 5,906,982 A | 5/1999 | Prieto et al. |
| 5,952,021 A | 9/1999 | Santus |
| 5,952,205 A | 9/1999 | Catani et al. |
| 5,962,275 A | 10/1999 | Horsch et al. |
| 6,093,425 A | 7/2000 | Kamarei |
| 6,139,875 A | 10/2000 | Adams et al. |
| 6,197,758 B1 | 3/2001 | Ohtsuki et al. |
| 6,221,350 B1 | 4/2001 | Brown et al. |
| 6,241,983 B1 | 6/2001 | Paul et al. |
| 6,258,380 B1 | 7/2001 | Overholt |
| 6,368,641 B1 | 4/2002 | Khatchatrian et al. |
| 6,399,124 B1 | 6/2002 | Lesens et al. |
| 6,420,473 B1 | 7/2002 | Chittamuru et al. |
| 6,423,833 B1 | 7/2002 | Catani et al. |
| 6,451,584 B2 | 9/2002 | Tomita et al. |
| 6,455,052 B1 | 9/2002 | Marcussen et al. |
| 6,461,607 B1 | 10/2002 | Farmer |
| 6,468,525 B1 | 10/2002 | Watson et al. |
| 6,471,999 B2 | 10/2002 | Couzy et al. |
| 6,482,435 B1 | 11/2002 | Stratton et al. |
| 6,544,568 B2 | 4/2003 | La Droitte et al. |
| 6,569,457 B2 | 5/2003 | Ullah et al. |
| 6,572,871 B1 | 6/2003 | Church et al. |
| 6,576,251 B1 | 6/2003 | Stahl et al. |
| 6,599,882 B1 | 7/2003 | Rogoff et al. |
| 6,706,287 B2 | 3/2004 | Ranganathan et al. |
| 6,750,331 B1 | 6/2004 | Takaichi et al. |
| 6,783,780 B1 | 8/2004 | De Jong et al. |
| 6,797,266 B2 | 9/2004 | Naidu |
| 6,835,376 B1 | 12/2004 | Neeser et al. |
| 6,841,181 B2 | 1/2005 | Jager et al. |
| 6,863,918 B2 | 3/2005 | Bindels et al. |
| 6,884,445 B2 | 4/2005 | Navarro et al. |
| 6,929,793 B2 | 8/2005 | Spivey-Krobath et al. |
| 6,936,598 B2 | 8/2005 | Khoo et al. |
| 6,960,341 B2 | 11/2005 | Viscomi et al. |
| 6,989,166 B2 | 1/2006 | Te Hennepe et al. |
| 7,029,702 B2 | 4/2006 | Ritter |
| 7,101,553 B2 | 9/2006 | Haschke et al. |
| 7,101,565 B2 | 9/2006 | Monte |
| 7,166,451 B1 | 1/2007 | Yang et al. |
| 7,172,777 B2 | 2/2007 | Schmitt et al. |
| 7,195,906 B2 | 3/2007 | Collins et al. |
| 7,214,370 B2 | 5/2007 | Naidu |
| 7,422,764 B2 | 9/2008 | Navarro et al. |
| 7,435,431 B2 | 10/2008 | Johnson |
| 7,491,518 B2 | 2/2009 | Okada et al. |
| 7,794,746 B2 | 9/2010 | Gibson et al. |
| 7,879,363 B2 | 2/2011 | Ritter |
| 8,202,842 B2 | 6/2012 | Sinclair et al. |
| 8,486,668 B2 | 7/2013 | Ritter et al. |
| 8,492,124 B2 | 7/2013 | Ritter et al. |
| 8,591,981 B2 | 11/2013 | Sprenger et al. |
| 8,784,886 B2 | 7/2014 | Fawzy et al. |
| 8,785,160 B2 | 7/2014 | Ritter et al. |
| 2002/0034496 A1 | 3/2002 | Ritter |
| 2002/0187134 A1* | 12/2002 | Ranganathan ............ A23L 1/30 424/93.45 |
| 2003/0040492 A1 | 2/2003 | Haschke et al. |
| 2003/0147995 A1 | 8/2003 | Koss et al. |
| 2004/0005305 A1 | 1/2004 | Spivey-Krobath et al. |
| 2004/0057943 A1 | 3/2004 | Xaus Pey et al. |
| 2004/0131659 A1 | 7/2004 | Gibson et al. |
| 2004/0161422 A1 | 8/2004 | Ranganathan |
| 2004/0213828 A1 | 10/2004 | Smith |
| 2004/0219157 A1 | 11/2004 | Rochat et al. |
| 2005/0074442 A1 | 4/2005 | Ranganathan |
| 2005/0079244 A1 | 4/2005 | Giffard et al. |
| 2005/0119222 A1 | 6/2005 | Norton et al. |
| 2005/0147710 A1 | 7/2005 | Teckoe et al. |
| 2005/0164340 A1 | 7/2005 | Schlothauer et al. |
| 2005/0164368 A1 | 7/2005 | Ji et al. |
| 2005/0180962 A1 | 8/2005 | Raz et al. |
| 2005/0288250 A1 | 12/2005 | Rautonen et al. |
| 2006/0008574 A1 | 1/2006 | Begli et al. |
| 2006/0034993 A1 | 2/2006 | Saelzer |
| 2006/0040001 A1 | 2/2006 | Johnson |
| 2006/0093592 A1 | 5/2006 | Cheruvanky et al. |
| 2006/0104965 A1 | 5/2006 | Ritter |
| 2006/0141097 A1 | 6/2006 | Guo |
| 2006/0165670 A1 | 7/2006 | Beer et al. |
| 2006/0182727 A1 | 8/2006 | Yamahira et al. |
| 2006/0234980 A1 | 10/2006 | Hashimoto et al. |
| 2006/0246179 A1 | 11/2006 | Ammann et al. |
| 2006/0287276 A1 | 12/2006 | Rhoades et al. |
| 2007/0098762 A1 | 5/2007 | Stahl et al. |
| 2007/0104700 A1 | 5/2007 | Rodenas et al. |
| 2007/0134391 A1 | 6/2007 | Prakash et al. |
| 2007/0196439 A1 | 8/2007 | Catani et al. |
| 2007/0196463 A1* | 8/2007 | Podili .................. A61K 9/4825 424/456 |
| 2007/0196890 A1 | 8/2007 | Vulevic et al. |
| 2007/0207132 A1 | 9/2007 | Speelmans et al. |
| 2007/0248649 A1 | 10/2007 | Sawatzki et al. |
| 2007/0274955 A1 | 11/2007 | Gibson et al. |
| 2007/0274983 A1 | 11/2007 | Kluijtmans et al. |
| 2008/0031814 A1 | 2/2008 | Hageman et al. |
| 2008/0044493 A1 | 2/2008 | Sato et al. |
| 2008/0064657 A1 | 3/2008 | Day et al. |
| 2008/0108548 A1 | 5/2008 | Luyer et al. |
| 2008/0112941 A1 | 5/2008 | Ritter |
| 2008/0112942 A1 | 5/2008 | Farmer et al. |
| 2008/0124323 A1 | 5/2008 | Boehm et al. |
| 2008/0126195 A1 | 5/2008 | Ritter |
| 2008/0171720 A1 | 7/2008 | Garssen et al. |
| 2008/0193406 A1 | 8/2008 | Rull Prous et al. |
| 2008/0193485 A1 | 8/2008 | Gorbach et al. |
| 2008/0193627 A1 | 8/2008 | Van Eert et al. |
| 2008/0199444 A1 | 8/2008 | Cui |
| 2008/0207559 A1 | 8/2008 | Sawatzki et al. |
| 2008/0213341 A1 | 9/2008 | Haji Begli et al. |
| 2008/0233092 A1 | 9/2008 | Ritter |
| 2008/0260893 A1 | 10/2008 | Giffard et al. |
| 2008/0261916 A1 | 10/2008 | Jaszberenyi et al. |
| 2008/0280852 A1 | 11/2008 | Speelmans et al. |
| 2009/0004164 A1 | 1/2009 | Speelmans et al. |
| 2009/0011078 A1 | 1/2009 | Johnson |
| 2009/0022852 A1 | 1/2009 | Simmons et al. |
| 2009/0035813 A1 | 2/2009 | Sprenger et al. |
| 2009/0041736 A1 | 2/2009 | Sprenger et al. |

(56) References Cited

U.S. PATENT DOCUMENTS

| | | |
|---|---|---|
| 2010/0016214 A1 | 1/2010 | Sawatzki et al. |
| 2010/0069320 A1 | 3/2010 | Speelmans |
| 2010/0069322 A1 | 3/2010 | Sinclair et al. |
| 2010/0215738 A1 | 8/2010 | Ritter et al. |
| 2011/0065152 A1 | 3/2011 | Avalakki et al. |
| 2011/0086093 A1 | 4/2011 | Ritter |
| 2011/0189148 A1 | 8/2011 | Ritter et al. |
| 2011/0223248 A1 | 9/2011 | Ritter et al. |
| 2011/0236480 A1 | 9/2011 | Ritter et al. |
| 2011/0287072 A1 | 11/2011 | Ritter et al. |
| 2013/0034601 A1 | 2/2013 | Ritter |
| 2013/0165407 A1 | 6/2013 | Ritter et al. |
| 2013/0177612 A1 | 7/2013 | Ritter et al. |
| 2013/0244969 A1 | 9/2013 | Ritter et al. |
| 2013/0316972 A1 | 11/2013 | Ritter et al. |
| 2014/0234407 A1 | 8/2014 | Ritter |

FOREIGN PATENT DOCUMENTS

| | | |
|---|---|---|
| CA | 2056167 A1 | 5/1993 |
| CA | 2532062 A1 | 7/2006 |
| CN | 1777671 A | 5/2006 |
| CN | 101366734 A | 2/2009 |
| CN | 101396048 A | 4/2009 |
| CN | 101926831 A | 12/2010 |
| DE | 20202562 U1 | 5/2002 |
| DE | 202005009120 U1 | 11/2005 |
| EP | 0272095 A1 | 6/1988 |
| EP | 0435657 | 7/1991 |
| EP | 0474230 A1 | 3/1992 |
| EP | 0458358 B1 | 5/1994 |
| EP | 0199535 B2 | 11/1995 |
| EP | 0549478 B1 | 9/1997 |
| EP | 1175905 A1 | 1/2002 |
| EP | 1195095 A2 | 4/2002 |
| EP | 1105002 B1 | 7/2002 |
| EP | 0957692 B1 | 8/2003 |
| EP | 0946111 B1 | 2/2004 |
| EP | 1195095 A3 | 2/2004 |
| EP | 1242436 B1 | 11/2004 |
| EP | 1514551 A1 | 3/2005 |
| EP | 1352967 B1 | 8/2005 |
| EP | 1614357 A1 | 1/2006 |
| EP | 0778885 B1 | 11/2006 |
| EP | 1255449 B1 | 3/2007 |
| EP | 1644482 B1 | 4/2007 |
| EP | 1776877 A1 | 4/2007 |
| EP | 1803358 A1 | 7/2007 |
| EP | 1832179 A1 | 9/2007 |
| EP | 1887017 A1 | 2/2008 |
| EP | 1897449 A1 | 3/2008 |
| EP | 1811864 B1 | 5/2008 |
| EP | 1927292 A1 | 6/2008 |
| EP | 1890553 B1 | 8/2008 |
| EP | 1685763 B1 | 11/2008 |
| EP | 1988096 A1 | 11/2008 |
| EP | 1513541 B1 | 1/2009 |
| EP | 2014181 A2 | 1/2009 |
| EP | 2027863 A1 | 2/2009 |
| EP | 1965669 A1 | 9/2009 |
| JP | 60-078540 | 5/1985 |
| JP | 61063618 A | 4/1986 |
| JP | 2006-509797 | 3/2006 |
| JP | 2007-527199 | 9/2007 |
| JP | 2007-530542 | 11/2007 |
| KR | 10-2003-0064030 | 7/2003 |
| WO | WO 91/17672 A1 | 11/1991 |
| WO | WO 97/02829 A2 | 1/1997 |
| WO | WO 97/02829 A3 | 3/1997 |
| WO | WO 00/61155 A1 | 10/2000 |
| WO | WO 01/64225 A1 | 9/2001 |
| WO | WO 02/18614 A1 | 3/2002 |
| WO | WO 02/060276 A1 | 8/2002 |
| WO | WO 02/062363 A1 | 8/2002 |
| WO | WO 02/060276 A1 | 10/2002 |
| WO | WO 02/080946 A1 | 10/2002 |
| WO | WO 02/102168 A1 | 12/2002 |
| WO | WO 03/041512 A1 | 5/2003 |
| WO | WO 02/060276 A8 | 10/2003 |
| WO | WO 03/090546 A1 | 11/2003 |
| WO | WO 2004/013343 A2 | 2/2004 |
| WO | WO 2004/013343 A3 | 6/2004 |
| WO | WO 2004/052121 A1 | 6/2004 |
| WO | WO 2004/067013 A1 | 8/2004 |
| WO | WO 2004/093571 A1 | 11/2004 |
| WO | WO 2004/098622 A2 | 11/2004 |
| WO | WO 2004/098622 A3 | 3/2005 |
| WO | WO 2009/024429 A2 | 2/2006 |
| WO | WO 2006/113027 A2 | 10/2006 |
| WO | WO 2007/009529 A2 | 1/2007 |
| WO | WO 2007/023226 A2 | 3/2007 |
| WO | WO 2007/046698 | 4/2007 |
| WO | WO 2007/054459 A2 | 5/2007 |
| WO | WO 2007/009529 A3 | 6/2007 |
| WO | WO 2007/023226 A3 | 6/2007 |
| WO | WO 2007/054459 A3 | 7/2007 |
| WO | WO 2007/095425 A1 | 8/2007 |
| WO | WO 2007/104268 A1 | 9/2007 |
| WO | WO 2007/105945 A2 | 9/2007 |
| WO | WO 2007/105945 A3 | 11/2007 |
| WO | WO 2007/124596 A1 | 11/2007 |
| WO | WO 2007/125558 A1 | 11/2007 |
| WO | WO 2006/113027 A3 | 12/2007 |
| WO | WO 2008/041843 A1 | 4/2008 |
| WO | WO 2008/054193 A1 | 5/2008 |
| WO | WO 2008/091756 A1 | 7/2008 |
| WO | WO 2008/103023 A1 | 8/2008 |
| WO | WO 2008/111832 A1 | 9/2008 |
| WO | WO 2008/127134 A1 | 10/2008 |
| WO | WO 2008/128345 A1 | 10/2008 |
| WO | WO 2008/135959 A1 | 11/2008 |
| WO | WO 2008/153377 A1 | 12/2008 |
| WO | WO 2008/153391 A2 | 12/2008 |
| WO | WO 2008/156354 A1 | 12/2008 |
| WO | WO 2009/008717 A1 | 1/2009 |
| WO | WO 2008/153391 A3 | 2/2009 |
| WO | WO 2009/113030 A2 | 9/2009 |
| WO | WO 2009/024429 A3 | 12/2009 |
| WO | WO 2009/113030 A3 | 12/2009 |
| WO | WO 2010/008491 A2 | 1/2010 |
| WO | WO 2010/008491 A3 | 3/2010 |
| WO | WO 2010/098822 A1 | 9/2010 |
| WO | WO 2010/136742 A1 | 12/2010 |
| WO | WO 2011/016008 | 2/2011 |

OTHER PUBLICATIONS

Advanced Dairy Chemistry, vol. 3, Apr. 1, 2009, p. 156 5.5.2 β.

Albayrak et al. Immobilization of beta-galactosidase on fibrous polyethyleneimine for production of galacto-oligosaccharides from lactose. Biotechnology progress. 2002; 18(2):p240-51.

Alles, et al. Fate of fructo-oligosaccharides in the human intestine. Br J Nutr. 1996.76(2):211-221.

Alliet, et al. Effect of prebiotic galacto-oligosaccharide, long-chain fructo-oligosaccharide infant formula on serum cholesterol and triacylglycerollevels. Nutrition. 2007; 23: 719-723.

Alliet, et al. J. An infant formula containing a specific prebiotic mixture of GOS/lcFOS leads to higher faecal secretory IgA in infants. JPGN Journal of Pediatric Gastroenterology and Nutrition. 2007; 44:120.

Amaretti, et al. Kinetics and metabolism of Bifidobacterium adolescentis MB 239 growing on glucose, galactose, lactose, and galactooligosaccharides. Appl Environ Microbiol. Jun. 2007; 73(I1):3637-44.

Andersen, et al. Transcriptional and functional analysis of galactooligosaccharide uptake by lacS in Lactobacillus acidophilus. Proc Natl Acad Sci USA. Oct. 25, 2011;108(43):17785-90. Epub Oct. 17, 2011.

Anthony, et al. 90-Day oral (gavage) study in rats with galactooligosaccharides syrup. Food Chem. Toxicol. 2006; 44(6):819-826.

(56) References Cited

OTHER PUBLICATIONS

Appel, et al. 1997. Effects of dietary galactooligosaccharide on azaserine-induced acinar pancreatic carcinogenesis in male Wistar rats. Nutr Cancer 29(1): 35-41.

Arunachalam, et al. Role of Bifidobacteria in nutrition, medicine and technology. Nutrition Research. 1999; 19(10):1559-1597.

Asakuma, et al. Sialyl oligosaccharides of human colostrum: changes in concentration during the first three days of lactation. Biosci Biotechnol Biochem. Jun. 2007;71(6): 1447-51.

Bakker-Zierikzee, et al. Effects of infant formula containing a mixture of galacto- and fructo-oligosaccharides or viable Bifidobacterium animalis on the intestinal microflora during the first 4 months of life. Br J Nutr. 2005; 94:783-790.

Ballongue, et al. Bifidobacteria and probiotic action in lactic acid bacteria. S. Selminen, A von Wright (eds). New York, Marcel Dekker, 1993, 357-428.

Barger-Lux, et al. The role of calcium intake in preventing bone fragility, hypertension and certain cancers. Journal of Nutrition, 124, 1406S-1411S, 1994.

Barrangou, et al. Functional and comparative genomic analyses of an operon involved in fructooligosaccharide utilization by Lactobacillus acidophilus. Proc. Natl. Acad. Sci. USA. Jul. 22, 2003; 100(15):8957-62.

Bartram, et al. Does yogurt enriched with Bifidobacterium longum affect colonic microbiology and fecal metabolites in health subjects? Am J Clin Nutr. Feb. 1994; 59(2):428-32.

Ben, et al. Low levels of galacto-oligosaccharride in infant formula stimulates growth of intestinal Bifidobacteria and Lactobacilli. 2008; 14(2):6564-6568.

Ben, et al. Supplementation of milk formula with galacto-oligosaccharides improves intestinal micro-flora and fermentation in term infants. Chin Med J (Engl). 2004;117:927-931.

Bhatnagar, et al. Lactose intolerance. BMJ, 334, 1331-1332, Jun. 30, 2007.

Boehm, et al. Oligosaccharides from milk. J Nutr. 2007; 137: 847s-9s.

Boehm, et al. Supplementation of a bovine milk formula with an oligosaccharide mixture increases counts of faecal bifidobacteria in preterm infants. Arch. Dis. Child Fetal Neonatal Ed. 2002; 86: F178-81.

Bond, et al. Colonic conservation of mal absorbed carbohydrates. Gastroenterology, 78,444-447,1980.

Bongers et al. The clinical effect of a new infant formula in term infants with constipation: a double-blind, randomized cross-over trial. Nutrition Journal. 2007; 6:8.

Bongers, et al. The clinical effect of a new infant formula in term infants with constipation: A double-blind, randomized trial. JPGN Journal of Pediatric Gastroenterology and Nutrition. 2005; 41: S78.

Bouhnik, et al. Lactulose ingestion increases faecal bifidobacterial counts: a randomised double-blind study in healthy humans. Eur. J. Clin. Nutr. Mar. 2004.; 58(3):462-6.

Bouhnik, et al. The capacity of nondigestible carbohydrates to stimulate fecal bifidobacteria in healthy humans: a double-blind, randomized, placebo-controlled, parallel-group, dose-response relation study. Am J Clin. Nutr. Dec. 2004; 80(6):1658-64.

Brannon, et al. NIH Consensus Development Conference Statement: Lactose Intolerance and Health. NIH Consens State Sci Statements. Feb. 24, 2010;27(2).

Briet, et al. Bacterial adaptation in patients with short bowel and colon in continuity. Gastroenterology. Nov. 1995; 109(5): 1446-53.

Briet, et al. Improved clinical tolerance to chronic lactose ingestion in subjects with lactose intolerance: a placebo effect? Gut, 41, 632-635, 1997.

Broussalian, et al. Influence of lactose concentration of milk and yogurt on growth rate of rats. J Dairy Science, 66 (3), 438-443, 1983.

Bruins, M.E. Oligosaccharide Production with Thermophilic Enzymes. Thesis. WageningenUniversiteit, 2003. ISBN 9058088405.

Buchowski, et al. Dietary calcium intake in lactose maldigesting intolerant and tolerant African-American women. Journal of the American College of Nutrition, 21 (1), 47-54, 2002.

Cashman, K. Prebiotics and Calcium Bioavailability. In: Chapter 6, Tannock G, ed. Probiotics and Prebiotics: Where Are We Going? University of Otago, Dunedin: New Zealand. 2002; 149-174.

Chao-Chun, C. et al. "Production of High-content Galacto-oligosaccharide by Enzyme Catalysis and Fermentation with *Kluyveromyces marcianus*", Biotechnology Letters (Jun. 10, 2006) vol. 28 No. 11, pp. 793-797.

Cheeseman Director, Office of Food Additive Safety, Food and Drug Administration. Letter to Constance Francis Ph.D., GTC Nutrition Golden, CO 80401, Sep. 4, 2009 Re: Agency Response Letter GRAS Notice No. GRN 000286.

Chen et al. Synthesis of galacto-oligosaccharides by immobilized Bacillus stearothermophilus. Acta microbiologica Sinica. 2001; 41(3):357-62. (in Chinese with English abstract).

Cheng et al. Production of high-content galacto-oligosaccharide by enzyme catalysis and fermentation with Kluyveromyces marxianus. Biotechnology Letters. 2006; 28 (11): 793-7.

Chockchaisawasdee et al. Synthesis of galacto-oligosaccharide from lactose using beta-galactosidase from Kluyveromyces lactis: Studies on batch and continuous UF membrane-fitted bioreactors. Biotechnology and bioengineering. 2005; 89(4): 434-43.

Chonan, et al. Undigestibility of galactooligosaccharides. Nihon Shokuhin Kagaku Kogakkaishi. 2004; 51(1):28-33.

Chouraqui et al. Assessment of the safety, tolerance, and protective effect against diarrhea of infant formulas containing mixtures ofprobiotics or probiotics and prebiotics in a randomized controlled trial. Am. J. Clin. Nutr. 2008; 87(5): 1365-73.

Collins, et al. Proximate, Nutritional and Microbiological Analyses of Milk-Sweet Potato Mixtures Fermented with Yogurt Bacteria. Journal of Food Science. 1991; 56:682-684.

Crittenden, R. G. Prebiotics. Probiotics: A Critical Review. Tannock, G. (ed.) Horizon Scientific Press, Wymondham.1999; 141-156, 157.

Curda, et al. Dried buttermilk containing galactooligosaccharides—process layout and its verification. Journal of Food Engineering. Dec. 2006; 77(3):468-471.

Cure Your Lactose Intolerance!, copy of advertisement for the Daily Bruin Classified, Monday, Jan. 12, 1998, p. 39.

De Vrese, et al. Probiotics, prebiotics, and synbiotics. Adv Biochem Eng Biotechnol. 2008;111: 1-66.

De Vrese, et al. Probiotics—compensation for lactase insufficiency. American Journal of Clinical Nutrition, 2001; 73 (supplement): 421S-429S.

Deguchi, et al. Effects of beta-I-4.galactooligosaccharides administration on defecation of healthy volunteers with constipation tendency. Japanese Journal of Nutrition. 1997; 55:13-22.

Delmont, J. (Ed.). Milk intolerances and rejection. Karger, Basel, 1983.

Depeint et al. Prebiotic evaluation of a novel galactooligosaccharide mixture produced by the enzymatic activity of Bifidobacterium bifidum NCIMB 41171, in healthy humans: a randomized, double-blind, crossover, placebo-controlled intervention study. Am J Clin Nutr. 2008; 87(3):785-91.

DFO-Nutrition Services: Spotlight for Sep., 1995. Lactose Intolerance: Common Concerns. Available at http://www.milk.org/spotsept.htm. Accessed May 17, 1999.

Di Stefano, et al. Lactose malabsorption and intolerance and peak bone mass. Gastroenterology. Jun. 2002; 122(7): 1793-9.

Donovan. Human milk oligosaccharides—the plot thickens. Br J Nutr. May 2009;101(9):1267-9. Epub Dec. 15, 2008.

Drakoularakou, et al. A double-blind, placebo-controlled, randomized human study assessing the capacity of a novel galacto-oligosaccharide mixture in reducing travellers' diarrhea. Eur J Clin Nutr. 2010;64: 146-152.

Drakoularakou, et al. A double-blind, placebo-controlled, randomized human study assessing the capacity of a novel galacto-oligosaccharide mixture in reducing travellers' diarrhea. Eur. J. Clin. Nutr. 2010;64:146-152.

Drossman. The functional gastrointestinal disorders and the Rome III process. Gastroenterology. Apr. 2006; 130(5): 1377-90.

(56) References Cited

OTHER PUBLICATIONS

Ekstrom, et al. Effects of a diet containing 40% dried whey on the performance and lactase activities in the small intestine and cecum of Hampshire and Chester white pigs. Journal of Animal Science, 42, 106-113, 1976.

Ekstrom, et al. Effect of diets containing dried whey on the lactase activity of the small intestinal mucosa and the contents of the small intestine and cecum of the pig. Journal of Nutrition, 105,851-860, 1975.

Engstrom, et al. Intestinal disaccharidase activities of three breeds of swine. Journal of Animal Science, 48, 1349-1356, 1979.

European Search Report dated Oct. 7, 2011 for EP Application No. 9798259.9.

European Search Report dated and opinion Aug. 30, 2013 for EP Application No. 11775567.8.

Fanaro, et al. Galacto-oligosaccharides are bifidogenic and safe at weaning: A double-blind blind randomized multicenter study. J. Pediatr. Gastroenterol. Nutr. 2009; 48: 82-88.

Fisler. Cardiac effects of starvation and semistarvation diets: safety and mechanisms of action. Am J Clin Nutr. Jul. 1992;56(1 Suppl):230S-234S.

Flourie, et al. Can diarrhea induced by lactulose be reduced by prolonged ingestion of lactulose? Am J Clin Nutr. Sep. 1993;58(3):369-75.

Fujita, K. 2000; 3(2): i-66-72. (in Japanese).

Gershon-Cohen, et al. The relationship of dietary calcium to osteoporosis. Metabolism, Clinical and experimental. 1964; 13(3):221-226. DOI: 10.1016/0026-0495(64)90101-5.

Gibson, et al. Dietary modulation of the human colonic microbiota: introducing the concept of prebiotics. J. Nutr. Jun. 1995; 125(6): 1401-12.

Gibson, et al. Dietary modulation of the human colonic microbiota: Updating the concept of prebiotics. Nutrition Research Reviews. 2004; 17:259-275.

Gibson, et al. Dietary modulation of the human gut microflora using the prebiotics oligofructose and inulin. Journal of Nutrition. 1999; 129(7S): 1438S-1441S.

Gibson, et al. Emichment of bifidobacteria from human gut contents by oligofructose using continuous culture. FEMS Microbiol Lett. May 1, 1994;118(1-2):121-127.

Gibson, et al. Regulatory effects of bifidobacteria on the growth of other colonic bacteria. J. Appl. Bacteriol. 1994; 77: 412-420.

Gibson, et al. Selective stimulation of bifidobacteria in the human colon by oligofructose and inulin. Gastroenterology. Apr. 1995; 108(4): 975-82.

Gilat, et al. Lactase in man: a nonadaptable enzyme. Gastroenterology. Jun. 1972; 62(6): 1125-7.

Gomes, et al. *Bifidobacterium* spp. and *Lactobacillus acidophilus*: biological, biochemical, technological and therapeutical properties relevant for use as probiotics. Trends in Food Science and Technology. 1999; 10:139-157.

Goulas, et al. Development of a process for the production and purification of alpha- and beta-galactooligosaccharides from Bifobacterium bifidum NCIMB 41171. International Dairy Journal. 2007; 17 (6):648-656.

Great Smokies Diagnostic Laboratory. Was it something you ate or drank? http://www.gsdl.com/NP/services/patbroch/actpb.htm1, 1995-6.

GTC Nutrition Purimune High Purity GOS webpage. Available at http://www.gtcnutrition.com/EN/products/purimune/index. php. Accessed Feb. 8, 2010.

GTC Nutrition Slides—Introducing Pruimune. Sep. 22, 2009.

Hamilton, Great Smokies Diagnostic Laboratory Application Guide. Lactose Intolerance Breath Test. Asheville, 1996.

Hamilton-Miller, J.M.T. Probiotics and prebiotics in the elderly. Postgrad Med J. 2004;80(946):447-51.

He, et al. Colonic fermentation may playa role in lactose intolerance in humans. Journal of Nutrition, 136, 58-63, 2006.

He, et al. Effects of yogurt and bifidobacteria supplementation on the colonic microbiota in lactose-intolerant subjects. J. Applied Microbiol. 2008; 104(2): 595-604.

He et al. The role of colonic metabolism in lactose intolerance. Eur J Clin Invest. 2008; 38(8): 541-547.

He, T. Dissertation—Lactose intolerance: the role of colonic metabolism. Drukkerij C. Regenboog, Groningen, The Netherlands. 2006.

Hertzler, et al. Colonic adaptation to daily lactose feeding in lactose maldigesters reduces lactose intolerance. American Journal of Clinical Nutrition. 1996; 64: 232-236.

Hertzler, et al. Fecal hydrogen production and consumption measurements: response to daily lactose ingestion by lactose maldigesters. Digestive Diseases and Sciences, 42 (2), 348-353, 1997.

Hoover, D.G. Bifidobacterium. In the Encyclopedia of Food Microbiology. Carl Batt and P.D. Patel (Eds). Academic Press, San Diego. 2000; 210-217.

Hsu et al. Enzymatic production of galactooligosaccharides by beta-galactosidase from Bifidobacterium longum BCRC 15708. Journal of agricultural and food chemistry. 2007; 55(6): 2225-30.

http:/ ldigestive.niddk.nih.gov/ddiseases/pubs/lactoseintolerance. Accessed Apr. 26, 2010.

International search report and written opinion dated Feb. 26, 2013 for PCT/US2012/067488.

International search report and written opinion dated Jun. 20, 2011 for PCT Application No. US2011/034346.

International search report and written opinion dated Mar. 29, 2010 for PCT Application No. US10/00447.

International search report dated Feb. 2, 2010 for PCT Application No. US2009/03834.

International search report dated Mar. 31, 2006 for PCT Application No. US2005/26095.

International search report dated Jun. 14, 2007 for PCT Application No. US2007/061464.

Ito, et al. Effects of Administration of Galactooligosaccharides on the Human Faecal Microflora, Stool Weight and Abdominal Sensation. Microbial Ecology in Health Disease. 1990;3 :285-92.

Ito, et al. Effects of transgalactosylated disaccharides on the human intestinal microflora and their metabolism. J. Nutr. Sci. Vitaminol. (Tokyo). 1993; 39(3): 279-88.

Jackson, et al. Lactose maldigestion, calcium intake and osteoporosis in African-Asian- and Hispanic-Americans. Journal of the American College of Nutrition, 20 (2), 1985-207S, 2001.

Jia Jian-Ping et al, Advance in the research of galactooligosaccharides, China Dairy Industry, 2003, 31(1), 23-26.

Jiang, et al. Improvement of lactose digestion in humans by ingestion of unfermented milk containing Bifidobacterium longum. J. Dairy Sci. 1996; 79: 750-757.

Johnson, et al. Adaptation of lactose maldigesters to continued milk intakes. American Journal of Clinical Nutrition. 1993; 58: 879-881.

Keepkidshealth.com. Infant Formula. A pediatrician's guide to your children's health and safety. Available at http://www.keepkidshealthy.comlcgi-biniMasterPFP.cgi. Accessed on Nov. 10, 2010.

Khan, et al. Torsades de pointes: a case with multiple variables. Am. J. Emerg Med. Jan. 1999; 17(1):80-5.

Kikuchi, et al. 1996. Effect of two levels oftransgalatosylated oligosaccharide intake in rats associated with human faecal microflora on bacterial glycolytic activity, end-products of fermentation and bacterial steroid transformation. J. Appl. Bacteriol. 80:439-446.

Kim, et al. In vitro measurements of the lactase activity and the fermentation products of lactose in the cecal and colonic contents of rats fed a control or 30% lactose diet. Journal of Nutrition, 109,856-63, 1979.

Kim, et al. Lactobacillus acidophilus as a dietary adjunct for milk to aid lactose digestion in humans. J Dairy Sci. 1983; 66(5):959-66.

Kirii, et al. Calcium, vitamin D and dairy intake in relation to type 2 diabetes risk in a Japanese cohort. Diabetologia. Dec. 2009;52(12):2542-50.

Klaenhammer, T.R. 2010. Research Report: Comparative Growth of *Lactobacillus acidophilus* and Different Species and Strains of

(56) References Cited

OTHER PUBLICATIONS

*Bifidobacterium* and *Escherichia coli* on the Highly Purified Galactooligosaccharide Preparation, RP-G28. North Carolina State University.
Knol, et al., Colon microtlora in infants fed formula with gal acto- and fructo-oligosaccharides: More like breast-fed infants. J Pediatr Gastroenterol Nutr. 2005;40:36-42.
Knol, et al. Increase of faecal bifidobacteria due to dietary oligosaccharides induces a reduction of clinically relevant pathogen germs in the faeces offormula-fed preterm infants. Acta. Paediatr. Suppl. 2005;94: 31-33.
Kobayashi, et al. 2003. Ninety-day repeated oral dose toxicity study of GOS in rats. Yakuruto Kenkyujo Kenkyu Hokokushu (23):25-42. (English abstract and tables).
Kobayashi, et al. Safety of a novel galacto-oligosaccharide: Genotoxicity and repeated oral dose studies. Hum Exp Toxicol. Oct. 2009; 28(10): 619-30.
Kretchmer, N. Lactose and lactase—a historical perspective. Gastroenterology. Dec. 1971; 61(6): 805-13.
Kukkonen, et al. Long-term safety and impact on infection rates of postnatal probiotic and prebiotic (synbiotic) treatment: randomized, double-blind, placebo-controlled trial. Pediatrics. Jul. 2008; 122(I):8-12.
Kukkonen, et al. Probiotics and prebiotic galacto-oligosaccharides in the prevention of allergic diseases: A randomized, double-blind, placebo-controlled trial. J. Allergy Clin. Immunol. 2007; 119: 192-198.
Kullen, et al. Use of ON A sequence of variable regions of the 16SrRNA gene for rapid and accurate identification of bacteria in the *Lactobacillus acidophilus* complex. J. Appl. Microbiol. 2000; 89: 511-518.
Kunz, et al. Nutritional and biochemical properties of human milk, Part I: general aspects, proteins, and carbohydrates. Clin. Perinatol. 1999; 26(2):307-333.
Kunz, et al. Oligosaccharides in human milk: structural, functional, and metabolic aspects. Annu. Rev. Nutr. 2000; 20: 699-722.
Landon, et al. A double-blind test of the ability of lactagen formula to reduce symptoms of lactose intolerance. Lactagen Clinical Study. Published Jun. 28, 2005 at www.lactagen.com.
Landon, et al. A randomized controlled trial to evaluate effectiveness of a pre- and probiotic formula to treat patients with self-reported severe intolerance to dairy products. Poster presentation at FASEB meeting, Apr. 2006 (see Appendix 2).
Landon, et al. A Randomized trial of a pre and probiotic formula to reduce symptoms of dairy products in patients and dairy intolerance. Federation of American Societies for Experiment Biology Journal. 2006; 20, N05., Abstract A105.
Li, et al. Production of non-monosaccharide and high-purity galactooligosaccharides by immobilized enzyme catalysis and fermentation with immobilized yeast cells. Process Biochemistry. 2008; 43(8):896-899.
Lisker, R. Book review of Lactose digestion—Clinical and Nuritional Implications. Edited by D.M. Paige Paige OM and Bayless TM. The Johns Hopkins University Press, Baltimore, 1981.
Lu et al. Recent progress on galacto-oligosaccharides synthesis by microbial beta-galactosidase—a review. Acta microbiologica Sinica. 2008;48(7):980-5. (in Chinese with English abstract).
Lye, et al. The improvement of hypertension by probiotics: effects on cholesterol, diabetes, renin, and phytoestrogens. Int J Mol Sci. Aug. 27, 2009; 1 0(9):3755-75.
Maischberger et al. Production of lactose-free galacto-oligosaccharide mixtures: comparison of two cellobiose dehydrogenases for the selective oxidation of lactose to lactobionic acid. Carbohydrate research. 2008; 343(12): 2140-7.
Manzanares, et al. The role of prebiotics and synbiotics in critically ill patients. Curr. Opin. Clin. Nutr. Metab. Care. Nov. 2008; 11(6): 782-9.
Manzi, et al. New functional milk-based products in the Italian market. Food Chemistry. 2007; 104(2):808-813.
Martini, et al. Lactose digestion from yogurt: influence of a meal and additional lactose. Am. J. Clin. Nutr. 1991; 53(5):1253-1258.
Martini, et al. Strains and species of lactic acid bacteria in fermented milks (yogurts): effect on in vivo lactose digestion. Am. J. Clin. Nutr. Dec. 1991; 54(6):1041-6.
Matlik et al. Perceived milk intolerance is related to bone mineral content in 10- to 13-year old female adolescents. Pediatrics 2007;120(3);e669-77.
Matsumoto, et al. 1993. Galactooligosaccharides. Chapter 5 in Oligosaccharides: Production, Properties and Application. Nakakuki, T. (Ed.). Gordon and Breach Science Publishers. Tokyo. Japanese Technology Reviews, vol. 3, pp. 90-106, 222-225 (Refs).
Matsumoto, et al. 2004. Effects oftransgalactosylated oligosaccharides mixture (N-GOS) on human intestinal microflora. Chonai Saikingaku Zasshi 18(1):25-35. (English abstract and tables).
Maukonen, et at. Diversity and temporal stability of fecal bacterial populations in elderly subjects consuming galacto-oligosaccharide containing probiotic yoghurt. Int. Dairy 1. 2008; 18:386-395.
McBain, et al. Modulation of genotoxic enzyme activities by non-digestible oligos-accharide metabolism in in-vitro human gut bacterial ecosystems. J. Med. Microbiol. 2001; 50: 833-842.
McBean, Dairy Council Digest. National Dairy Council: Rosemont, IL, Mar./Apr. 1994, vol. 65, #2.
McCarron, et al. Estimated healthcare savings associated with adequate dairy food intake. American Journal of Hypertension. 17 (1) ,88-97,2004.
Metagenics' Product Catalog—Science-based nutraceuticals for improved patient health. Published Oct. 15, 2006 at www.metagenics.com.
Morita, et al. The QT syndromes: long and short. Lancet. Aug. 30, 2008; 372(9640):750-63.
Moro, et al. A mixture of prebiotic oligosaccharides reduces the incidence of atopic dermatitis during the first six months of age. Arch. Dis. Child. 2006; 91: 814-819.
Moro, et al. Dietary prebiotic oligosaccharides are detectable in the faeces of formula-fed infants. Acta. Paediatr. Suppl. 2005; 94:27-30.
Moro, et al. Dosage-related bifidogenic effects of galacto- and fructooligosaccharides in formula-fed term infants. J. Pediatr. Gastroenterol. Nutr. Mar. 2002; 34(3):291-5.
Moro, et al. Effects of a new mixture of prebiotics on faecal flora and stools in term infants. Acta. Paediatr. Suppl. Sep. 2003; 91(441): 77-9.
Nakamura, et al. Molecular ecological analysis of fecal bacterial populations from term infants fed formula supplemented with selected blends of prebiotics. Appl. Environ. Microbiol. Feb. 2009; 75(4):1121-8.
Nakkhara T et al. Lactose hydrolysis and formation of galactooligosaccharides by a novel immobilized beta-galactosidase from the thermophilic fungus *Talaromyces thermophilus*. Applied biochemistry and biotechnology. 2006; 129-132:215-25.
Napoli, et al. Bifidogenic effects of feeding infant formula containing galacto-oligosaccharides in healthy formula-fed infants. School of Molecular and Microbial Biosciences, University of Sydney, NSW 2006.
National Digestive Disease. Lactose Intolerance. Available at http://www.niddk.nih.gov/health/digest/pubs/lactose/lactose.htm. Accessed May 17, 1999.
National Digestive Diseases Information Clearinghouse. Lactose Intolerance. http://niddk.nih.gov/LactoseIntolerance/LactoseIntolerance.html, Apr. 1994.
NIH (National Institutes of Health)—Consensus Development Conference:.Optimal Calcium Intake. Washington DC. US Department of Health and Human Services, Public Health Service. Jun. 6-8, 1994.
NIH Website—Lactose Intolerance. Available at http:/ Idigestive.niddk.nih.govIddiseases/pubsllactoseintolerance. Accessed Apr. 26, 2010.
Obermayer-Pietsch, et al. Genetic predisposition for adult lactose intolerance and relation to diet, bone density, and bone fractures. J Bone Miner Res. Jan. 2004; 19(1):42-7.
Office action dated Jun. 27, 2014 for U.S. Appl. No. 13/770,750.
Office action dated Jan. 10, 2013 for U.S. Appl. No. 13/096,711.
Office action dated Jan. 25, 2012 for U.S. Appl. No. 12/055,936.

(56) References Cited

OTHER PUBLICATIONS

Office action dated Jan. 26, 2010 for U.S. Appl. No. 11/670,195.
Office action dated Jan. 26, 2010 for U.S. Appl. No. 11/670,198.
Office action dated Feb. 3, 2010 for U.S. Appl. No. 12/055,936.
Office action dated Feb. 4, 2013 for U.S. Appl. No. 13/629,926.
Office action dated Feb. 11, 2011 for U.S. Appl. No. 12/055,936.
Office action dated Feb. 29, 2012 for U.S. Appl. No. 12/707,037.
Office action dated Mar. 5, 2001 for U.S. Appl. No. 09/346,479.
Office action dated Mar. 9, 2012 for U.S. Appl. No. 13/198,416.
Office action dated Mar. 19, 2010 for U.S. Appl. No. 12/013,161.
Office action dated Mar. 26, 2014 for U.S. Appl. No. 13/083,340.
Office action dated Jun. 28, 2012 for U.S. Appl. No. 12/973,501.
Office action dated Jul. 17, 2007 for U.S. Appl. No. 11/330,369.
Office action dated Aug. 5, 2009 for U.S. Appl. No. 12/055,936.
Office action dated Aug. 9, 2011 for U.S. Appl. No. 11/632,289.
Office action dated Aug. 11, 2010 for U.S. Appl. No. 12/013,161.
Office action dated Sep. 28, 2000 for U.S. Appl. No. 09/346,479.
Office action dated Oct. 4, 2013 for U.S. Appl. No. 12/996,975.
Ohtsuka, et al. 1990. Availability of 4'galactosyllactose (O-β-D-galactopyranosyl-(1à4)-O-β-D-galactopyranosyl-(1à4)D-glucopyranose) in rat. J. Nutr. Sci. Vitaminol. 36(3):265-276.
Ohtsuka, et al. 1991. Utilization and metabolism of [U-(14)C]4' galactosyllactose (0-13-D-galactopyranosyl-(1+4 )-O-P-D-galactopyranosyl-(1+4)-D-glucopyranose) in rats. J. Nutr. Sci. Vitaminol. 37(2):173-184.
Ohtsuka, et al. Effects of administration of galactooligosaccharides on faecal character in dogs and cats. Bulletin of the Faculty of Agriculture, Tottori University. 1995; 48: 145-149. (English abstract only).
Oku, et al. Effect of administration of 4G-beta-D-galactosylsucrose (lactosucrose) on abdominal symptoms in lactose-intolerant subjects. Journal of Japanese Society of Nutrition and Food Science. 2002; 55:353-356 (in Japanese with English abstract).
Onwulata, et al. Relative efficiency of yogurt, sweet acidophilus milk, hydrolyzed—lactose milk, and a commercial lactase tablet in alleviating lactose maldigestion. Am J Clin Nutr. 1989; 49(6):1233-1237.
Palframan, et al. Effect of pH and dose on the growth of gut bacteria on prebiotic carbohydrates in vitro. Anaerobe. Oct. 2002; 8(5): 287-92.
Perman, et al. Role of pH in production of hydrogen from carbohydrates by colonic bacterial flora. Journal of Clinical Investigation. 67, 643-650, 1981.
Piirainen et al. In school-aged children a combination of galacto-oligosaccharides and lactobacillus GG increases bifidobacteria more than lactobacillus GG on its own. Ann. Nutr. Metab. 2008; 52(3): 204-8.
Pittas, et al. Vitamin D and calcium intake in relation to type 2 diabetes in women. Diabetes Care. Mar. 2006;29(3):650-6.
Pribila, et al. Improved lactose digestion and intolerance among African-American adolescent girls fed a dairy-rich diet. Journal of the American Dietetic Association, 2000; 100(5): 524-528.
Puccio, et al. Clinical evaluation of a new starter formula for infants containing live Bifidobacterium longum BL999 and prebiotics. Nutrition. Jan. 2007;23 (I): 1-8.
Puccio, et al. Clinical evaluation of a new starter formula for infants containing live Bifidobacterium longum BL999 and prebiotics. Nutrition. Jan. 2007;23(I):1-8.
"Rakuno Kagaku, Shokuhin no Kenkyu (Japanese Journal of Dairy and Food Science)", 1985, vol. 34, No. 6, p. A169-A182.
Rania, et al. Effect of maternal prebiotic supplementation on selected fetal immune parameters. Immunobiology. 2005; 210:420.
Remington: The Science and Practice of Pharmacy, supra; Modified-Release Drug Deliver Technology, Rathbone et al., Eds., Drugs and the Pharmaceutical Science, Marcel Dekker, Inc.: New York, N.Y., 2002; vol. 126, Remington's Pharmaceutical Sciences, 17th edition (1985).

Rinne, et al. Similar bifidogenic effects of pre biotic-supplemented partially hydrolyzed infant formula and breastfeeding on infant gut microbiota. FEMS Immunol Med Microbiol. Jan. 1, 2005 ;43(1):59-65.
Rivero-Urgell, et al. Oligosaccharide: application in infant food. Early Hum Dev. 2001; 65 Suppl:S43-52.
Roberfroid, et al. Dietary Fructans. Annu. Rev. Nutr. 1998; 18: 117-43.
Roberfroid, M. Prebiotics and probiotics: are they functional foods? Am J Clin Nutr. Jun. 2000;71(6 Suppl):1682S-75.
Ross et al. The 2011 report on dietary reference intakes for calcium and vitamin D from the Institute of Medicine: what clinicians need to know. J Clin. Endocrinol. Metab. Jan. 2011;96(1):53-8. Epub Nov. 29, 2010.
Rowland, et al. 1993. The effects of transgalactosylated oligosaccharides on gut flora metabolism in rats associated with a human faecal microflora. J. Appl. Bacteriol. 74:667-674.
Saavedra, et al. Feeding of *Bifidobacterium bifidum* and *Streptococcus thermophilus* to infants in hospital for prevention of diarrhoea and shedding of rotavirus. Lancet. Oct. 15, 1994;344(8929):1046-9.
Sairanen, et al. Yoghurt containing galacto-oligosaccharides, prunes and linseed reduces the severity of mild constipation in elderly subjects. Eur. J Clin. Nutr. Dec. 2007.;61 (12): 1423-8.
Satokari, et al. Polymerase chain reaction and denaturing gradient gel electrophoresis monitoring of fecal Bifidobacterium populations in a prebiotic and probiotic feeding trial. Syst. Appl. Microbiol. 2001; 24(2): 227-231.
Savaiano, et al. Lactose malabsorption from yogurt, pasteurized yogurt, sweet acidophilus milk, and cultured milk in lactase-deficient individuals: Am J. Clin. Nutr. Dec. 1984; 40(6): 1219-23.
Savaiano. Lactose intolerance: a self-fulfilling prophecy leading to osteoporosis? Nutr. Rev. Jun. 2003; 61(6 Pt 1):221-3.
Savino, et al. "Minor" feeding problems during the first months of life: Effect of a partially hydrolysed milk formula containing fructo- and galacto-oligosaccharides, Acta Paediatr Suppl. 2003;91 :86-90.
Sazawal, et al. Efficacy of milk fortified with a probiotic *Bifidobacterium lactis* (DR-I0) and prebiotic galacto-oligosaccharides in prevention of morbidity and on nutritional status. Asia Pac. J. Cli.n. Nutr. 2004;13 (Suppl): S28.
Sazawal, et al. Zinc supplementation for four months dose not affect plasma cooper concentration in infants. Acta. Paediatr. May 2004; 93(5): 599-602.
Schaafsma, et al. Lactose and lactose derivatives as bioactive ingredients in human nutrition. International Dairy Journal. 2008; 18:458-465.
Schmelzle, et al. Randomized double-blind study of the nutritional efficacy and bifidogenicity of a new infant formula containing partially hydrolyzed protein, a high beta-palmitic acid level, and nondigestible oligosaccharides. J Pediatr Gastroenterol Nutr. 2003;36(3):343-51.
Scholtens, et al. Bifidogenic effects of solid weaning foods with added prebiotic oligosaccharides: A randomised controlled clinical trial. JPGN Journal of Pediatric Gastroenterology and Nutrition, 2006; 42: 553-559.
Scholtens, et al. Fecal secretory immunoglobulin A is increased in healthy infants who receive a formula with short-chain galacto-oligosaccharides and long-chain fructo-oligosaccharides. J. Nutr. 2008; 138: 1141-1147.
Schrezenmeir, et al. Probiotics, prebiotics, and synbiotics—approaching a definition. Am. J. Clin. Nutr. Feb. 2001; 73(2 Suppl.): 361S-364S.
Scrimshaw, et al. The acceptability of milk and milk products in populations with a high prevalence of lactose intolerance. Am. J. Clin. Nutr. Oct. 1988; 48 (4 Suppl): 1079-159.
Sela, et al. The genome sequence of *Bifidobacterium longum* subsp. *infantis* reveals adaptations for milk utilization within the infant microbiome. Proc. Natl. Acad. Sci. 105(48) 18964-18969.
Shadid, et al. Effects of galactooligosaccharide and long-chain fructooligosaccharide supplementation during pregnancy on maternal and neonatal microbiota and immunity—a randomized, double-blind, placebo-controlled study. Am J Clin Nutr. Nov. 2007;86(5): 1426-37.

(56) References Cited

OTHER PUBLICATIONS

Siddons, et al. The influence of the intestinal microflora on disaccharidase activities in the chick. British Journal of Nutrition, 27, 101-112, 1972.

Silk, et al.. 2008. Clinical trial: the effects of a trans-galactooligosaccharide prebiotic on faecal microbiota and symptoms in irritable bowel syndrome. Aliment Pharmacol. Ther. [advance electronic publication—Dec. 2, 2008].

Smiricky-Tjardes, et al. 2003. Dietary galactooligosaccharides affect ileal and total-tract nutrient digestibility, ileal and fecal bacterial concentrations, and ileal fermentative characteristics of growing pigs. J. Anim. Sci. 81: 2535-2545.

Splechtna et al. Comparison between discontinuous and continuous lactose conversion processes for the production of pre biotic galacto-oligosaccharides using beta-galactosidase from Lactobacillus reuteri. Journal of agricultural and food chemistry. 2007;55(16):6772-7.

Splechtna et al. Process development for the production of pre biotic galacto-oligo saccharides from lactose using beta-galactosidase from *Lactobacillus* sp. Biotechnology journal. 2007;2(4):480-5.

Splechtna, et al. Production of pre biotic galacto-oligosaccharides from lactose using beta-galactosidases from Lactobacillus reuteri. J. Agric. Food. Chern. Jul. 12, 2006; 54(14): 4999-5006.

Splechtna, et al. Production of a lactose-free galacto-oligosaccharide mixture by using selective enzymatic oxidation of lactose into lactobionic acid. Enzyme and Microbial Technology [Enzyme Microb. Technol.]. 2001; 29(6-7):434-440.

Suarez, et al. A comparison of symptoms after the consumption of milk or lactose-hydrolyzed milk by people with self-reported severe lactose intolerance. N Engl J Med. Jul. 6, 1995;333(1):1-4.

Suarez, et al. Tolerance to the daily ingestion of two cups of milk by individuals claiming lactose intolerance. Am J Clin Nutr. May 1997;65(5):1502-6.

Szilagyi, et al. Differential impact of lactose/lactase phenotype on colonic microflora. Can J Gastroenterol. Jun. 2010;24(6):373-9.

Szilagyi, et al. Improved parameters of lactose maldigestion using lactulose. Dig Dis Sci. Jul. 2001;46(7):1509-19.

Tanaka, et al. Effects of administration of TOS and Bifidobacterium breve 4006 on the human fecal flora. Bifidobact Microflora. 1983; 2(1): 17-24.

Tarantino, LM, Director, Office of Food Additive Safety, Food and Drug Administration. Letter to Gavin Thompson, Ph.D., Environ International Corp. Arlington, VA. Jul. 28, 2008 Re: Agency Response Letter GRAS Notice No. GRN 000236.

Teuri, et al. Galacto-oligosaccharides relieve constipation in elderly people. Ann. Nutr. Metab. 1998; 42: 319-327.

Teuri, et al. Increased fecal frequency and gastrointestinal symptoms following ingestion of galacto-oligosaccharide-containing yogurt. J Nutr Sci Vitaminol (Tokyo). Jun. 1998; 44(3): 465-71.

Thomas, et al. Carbohydrate metabolism is essential for the colonization of *Streptococcus thermophilus* in the digestive tract of gnotobiotic rats. PLoS One. 2011;6(12):e28789. Epub Dec. 22, 2011.

Tuohy, et al. Modulation of the Human Gut Microflora Towards Improved Health Using Prebiotics—Assessment of Efficacy. Current Pharmaceutical Design. 2005; 11 :75-90.

Tzortzis, et al. 2005. A novel galactooligosaccharide mixture increases the bifidobacterial population numbers in a continuous in vitro fermentation system and in the proximal colonic contents of pigs in vivo. J. Nutr. 135(7): 1726-1731.

Tzortzis, G. Functional properties of the second generation prebiotic galacto-oligosaccharide (B-GOS). Agro Food Industry Hi-Tech, Tekno Scienze, IT. 2009; 20(3), Suppl:43-46.

Van Den Heuvel, et al. Nondigestible oligosaccharides do not interfere with calcium and nonheme-iron absorption in young, healthy men. Am. J. Clin. Nutr. 1998;67:445-451.

Van Den Heuvel, et al. Transgalactooligosaccharides Stimulate Calcium Absorption in Postmenopausal Woman. Journal of Nutrition. 2000; 130(12):2938-2942.

Van Dokkum, et al. Effect of nondigestible oligosaccharides on large-bowel functions, blood lipid concentrations and glucose absorption in young healthy male subjects. Eur. J. Clin. Nutr. 1999; 53:1-7.

Van Hoffen, et al. A specific mixture of short-chain galacto-oligosaccharides and long-chain fructo-oligosaccharides induces a beneficial immunoglobulin profile in infants at high risk for allergy. Allergy. 2009; 64: 484-487.

Van Meer, et al. Prebiotic oligosaccharides and the enterohepatic circulation of bile salts in rats. Am. J. Physiol. Gastrointest. Liver Physiol. Feb. 2008; 294(2): G540-7.

Vulevic, et al. Modulation of the fecal microflora profile and immune function by a novel trans-galactooligosaccharide mixture (B-GOS) in healthy elderly volunteers. Am. J. Clin. Nutr. 2008; 88(5): 1438-46.

Wan et al. The investigation of dietary calcium intake and bone mass development of preschool children in the west of China. Bone. 2008; 43:S91. DO1:10.1016/J.BONE.200807.123.

Wang, et al. Effects of the in vitro fermentation of oligofructose and inulin by bacteria growing in the human large intestine. J. Appl. Bacteriol. Oct. 1993; 75(4):373-80.

Ward, et al. In vitro fermentation fbreast milk oligosaccharides by Bifidobacterium infantis and Lactobacillus gasseri. Appl Environ Microbiol. Jun. 2006;72(6):4497-9.

Wen, et al. Lactose feeding in lactose-intolerant monkeys. American Journal of Clinical Nutrition. 26, 1224-1228, 1973.

Wijnands, et al. 2001. Effect of dietary galacto-oligosaccharides on azoxymethane-induced aberrant crypt foci and colorectal cancer in Fischer 344 rats. Carcinogenesis 22(1):127-132.

Wijnands, et al. 1999. A comparison of the effects of dietary cellulose and fermentable galacto-oligosaccharide, in a rat model of colorectal carcinogenesis: Fermentable fiber confers greater protection than non-fermentable fiber in both high and low fat backgrounds. Carcinogenesis 20(4): 651-656.

Wisker, et al. 1985. Dietary fibre in cereals. In: Pomeranz, Y. (Ed.). Advances in Cereal Science and Technology. American Association of Cereal Chemists; St. Paul, Minn., vol. VII, pp. 169-238.

World Health Organization (WHO). 1993. Annex II. Environmental Health Criteria 104. Principles for the Toxicologocal Assessment of Pesticide Residues in Food. p. 113.

Yamashita, et al. Production of a-Linked Galactooligosaccharide (a-GOS) by a Galactosidase from Aspergillus niger APC-9319 and Its Physical and Physiological Properties. J. Appl. Glycosci. 2004; 51: 115-121.

Yasutake, et al. 2003. Safety of GOS: bacterial reverse mutation, micronucleus, and chromosomal aberration tests. Yakuruto Kenkyujo Kenkyu Hokokushu 23:13-24. (English abstract and tables).

Zheng, et al. Production of galacto-oligosaccharides by immobilized recombinant beta-galactosidase galactosidase from Aspergillus candidus. Biotechnology journal. 2006;1(12):1464-70.

Zhong, et al. The role of colonic microbiotica in lactose intolerance. Digestive Diseases and Sciences, 49 (1), 78-83, 2004.

Ziegler, et al. Term infants fed formula supplemented with selected blends of prebiotics grow normally and have soft stools similar to those reported for breast-fed infants. J Pediatr Gastroenterol Nutr. 2007;44:359-364.

\* cited by examiner

Lactulose

Raffinose

Stachyose

Inulin

FIGURE 5

| Day | 70% GOS (g) | Total weight (g) | Weight GOS (g) |
|---|---|---|---|
| 1 | 0.50 | 0.50 | 0.35 |
| 2 | 0.50 | 0.50 | 0.35 |
| 3 | 0.50 | 0.50 | 0.35 |
| 4 | 1.00 | 1.00 | 0.7 |
| 5 | 1.50 | 1.50 | 1.05 |
| 6 | 2.00 | 2.00 | 1.4 |
| 7 | 2.50 | 2.50 | 1.75 |
| 8 | 3.00 | 3.00 | 2.1 |
| 9 | 3.50 | 3.50 | 2.45 |
| 10 | 4.00 | 4.00 | 2.8 |
| 11 | 4.50 | 4.50 | 3.15 |
| 12 | 5.00 | 5.00 | 3.5 |
| 13 | 5.50 | 5.50 | 3.85 |
| 14 | 6.00 | 6.00 | 4.2 |
| 15 | 6.50 | 6.50 | 4.55 |
| 16 | 7.00 | 7.00 | 4.9 |
| 17 | 7.50 | 7.50 | 5.25 |
| 18 | 8.00 | 8.00 | 5.6 |
| 19 | 8.00 | 8.00 | 5.6 |
| 20 | 8.00 | 8.00 | 5.6 |
| 21 | 8.00 | 8.00 | 5.6 |
| 22 | 8.00 | 8.00 | 5.6 |
| 23 | 8.00 | 8.00 | 5.6 |
| 24 | 8.00 | 8.00 | 5.6 |
| 25 | 8.00 | 8.00 | 5.6 |
| 26 | 8.00 | 8.00 | 5.6 |
| 27 | 8.00 | 8.00 | 5.6 |
| 28 | 8.00 | 8.00 | 5.6 |
| 29 | 8.00 | 8.00 | 5.6 |
| 30 | 8.00 | 8.00 | 5.6 |
| 31 | 8.00 | 8.00 | 5.6 |
| 32 | 8.00 | 8.00 | 5.6 |
| 33 | 8.00 | 8.00 | 5.6 |
| 34 | 8.00 | 8.00 | 5.6 |

FIGURE 6

| Day | 70% GOS (g) | Total weight (g) | Weight GOS (g) |
|---|---|---|---|
| 1 | 0.29 | 0.62 | 0.21 |
| 2 | 0.29 | 0.62 | 0.21 |
| 3 | 0.29 | 0.62 | 0.21 |
| 4 | 0.59 | 1.25 | 0.41 |
| 5 | 0.88 | 1.87 | 0.62 |
| 6 | 1.17 | 2.50 | 0.82 |
| 7 | 1.46 | 3.12 | 1.03 |
| 8 | 1.76 | 3.75 | 1.23 |
| 9 | 2.05 | 4.37 | 1.44 |
| 10 | 2.34 | 4.99 | 1.64 |
| 11 | 2.64 | 5.62 | 1.85 |
| 12 | 2.93 | 6.24 | 2.05 |
| 13 | 3.22 | 6.87 | 2.26 |
| 14 | 3.52 | 7.49 | 2.46 |
| 15 | 3.81 | 8.11 | 2.67 |
| 16 | 4.10 | 8.74 | 2.87 |
| 17 | 4.39 | 9.36 | 3.08 |
| 18 | 4.69 | 9.99 | 3.28 |
| 19 | 4.69 | 9.99 | 3.28 |
| 20 | 4.69 | 9.99 | 3.28 |
| 21 | 4.69 | 9.99 | 3.28 |
| 22 | 4.69 | 9.99 | 3.28 |
| 23 | 4.69 | 9.99 | 3.28 |
| 24 | 4.69 | 9.99 | 3.28 |
| 25 | 4.69 | 9.99 | 3.28 |
| 26 | 4.69 | 9.99 | 3.28 |
| 27 | 4.69 | 9.99 | 3.28 |
| 28 | 4.69 | 9.99 | 3.28 |
| 29 | 4.69 | 9.99 | 3.28 |
| 30 | 4.69 | 9.99 | 3.28 |
| 31 | 4.69 | 9.99 | 3.28 |
| 32 | 4.69 | 9.99 | 3.28 |
| 33 | 4.69 | 9.99 | 3.28 |
| 34 | 4.69 | 9.99 | 3.28 |

FIGURE 7

| Day | 90% GOS (g) | Total weight (g) | Weight GOS (g) |
|---|---|---|---|
| 1 | 0.42 | 0.42 | 0.38 |
| 2 | 0.42 | 0.42 | 0.38 |
| 3 | 0.42 | 0.42 | 0.38 |
| 4 | 0.84 | 0.84 | 0.76 |
| 5 | 1.26 | 1.26 | 1.14 |
| 6 | 1.68 | 1.68 | 1.52 |
| 7 | 2.11 | 2.11 | 1.89 |
| 8 | 2.53 | 2.53 | 2.27 |
| 9 | 2.95 | 2.95 | 2.65 |
| 10 | 3.37 | 3.37 | 3.03 |
| 11 | 3.79 | 3.79 | 3.41 |
| 12 | 4.21 | 4.21 | 3.79 |
| 13 | 4.63 | 4.63 | 4.17 |
| 14 | 5.05 | 5.05 | 4.55 |
| 15 | 5.47 | 5.47 | 4.93 |
| 16 | 5.89 | 5.89 | 5.31 |
| 17 | 6.32 | 6.32 | 5.68 |
| 18 | 6.74 | 6.74 | 6.06 |
| 19 | 6.74 | 6.74 | 6.06 |
| 20 | 6.74 | 6.74 | 6.06 |
| 21 | 6.74 | 6.74 | 6.06 |
| 22 | 6.74 | 6.74 | 6.06 |
| 23 | 6.74 | 6.74 | 6.06 |
| 24 | 6.74 | 6.74 | 6.06 |
| 25 | 6.74 | 6.74 | 6.06 |
| 26 | 6.74 | 6.74 | 6.06 |
| 27 | 6.74 | 6.74 | 6.06 |
| 28 | 6.74 | 6.74 | 6.06 |
| 29 | 6.74 | 6.74 | 6.06 |
| 30 | 6.74 | 6.74 | 6.06 |
| 31 | 6.74 | 6.74 | 6.06 |
| 32 | 6.74 | 6.74 | 6.06 |
| 33 | 6.74 | 6.74 | 6.06 |
| 34 | 6.74 | 6.74 | 6.06 |

FIGURE 8

| Day | 93% GOS (g) | Total weight (g) | Weight GOS (g) |
|-----|-------------|------------------|----------------|
| 1   | 0.42        | 0.42             | 0.38           |
| 2   | 0.42        | 0.42             | 0.38           |
| 3   | 0.42        | 0.42             | 0.38           |
| 4   | 0.84        | 0.84             | 0.76           |
| 5   | 1.26        | 1.26             | 1.14           |
| 6   | 1.68        | 1.68             | 1.52           |
| 7   | 2.11        | 2.11             | 1.89           |
| 8   | 2.53        | 2.53             | 2.27           |
| 9   | 2.95        | 2.95             | 2.65           |
| 10  | 3.37        | 3.37             | 3.03           |
| 11  | 3.79        | 3.79             | 3.41           |
| 12  | 4.21        | 4.21             | 3.79           |
| 13  | 4.63        | 4.63             | 4.17           |
| 14  | 5.05        | 5.05             | 4.55           |
| 15  | 5.47        | 5.47             | 4.93           |
| 16  | 5.89        | 5.89             | 5.31           |
| 17  | 6.32        | 6.32             | 5.68           |
| 18  | 6.74        | 6.74             | 6.06           |
| 19  | 6.74        | 6.74             | 6.06           |
| 20  | 6.74        | 6.74             | 6.06           |
| 21  | 6.74        | 6.74             | 6.06           |
| 22  | 6.74        | 6.74             | 6.06           |
| 23  | 6.74        | 6.74             | 6.06           |
| 24  | 6.74        | 6.74             | 6.06           |
| 25  | 6.74        | 6.74             | 6.06           |
| 26  | 6.74        | 6.74             | 6.06           |
| 27  | 6.74        | 6.74             | 6.06           |
| 28  | 6.74        | 6.74             | 6.06           |
| 29  | 6.74        | 6.74             | 6.06           |
| 30  | 6.74        | 6.74             | 6.06           |
| 31  | 6.74        | 6.74             | 6.06           |
| 32  | 6.74        | 6.74             | 6.06           |
| 33  | 6.74        | 6.74             | 6.06           |
| 34  | 6.74        | 6.74             | 6.06           |

FIGURE 9

| Day | 95% GOS (g) | Total weight (g) | Weight GOS (g) |
|-----|-------------|------------------|----------------|
| 1   | 0.42        | 0.42             | 0.38           |
| 2   | 0.42        | 0.42             | 0.38           |
| 3   | 0.42        | 0.42             | 0.38           |
| 4   | 0.84        | 0.84             | 0.76           |
| 5   | 1.26        | 1.26             | 1.14           |
| 6   | 1.68        | 1.68             | 1.52           |
| 7   | 2.11        | 2.11             | 1.89           |
| 8   | 2.53        | 2.53             | 2.27           |
| 9   | 2.95        | 2.95             | 2.65           |
| 10  | 3.37        | 3.37             | 3.03           |
| 11  | 3.79        | 3.79             | 3.41           |
| 12  | 4.21        | 4.21             | 3.79           |
| 13  | 4.63        | 4.63             | 4.17           |
| 14  | 5.05        | 5.05             | 4.55           |
| 15  | 5.47        | 5.47             | 4.93           |
| 16  | 5.89        | 5.89             | 5.31           |
| 17  | 6.32        | 6.32             | 5.68           |
| 18  | 6.74        | 6.74             | 6.06           |
| 19  | 6.74        | 6.74             | 6.06           |
| 20  | 6.74        | 6.74             | 6.06           |
| 21  | 6.74        | 6.74             | 6.06           |
| 22  | 6.74        | 6.74             | 6.06           |
| 23  | 6.74        | 6.74             | 6.06           |
| 24  | 6.74        | 6.74             | 6.06           |
| 25  | 6.74        | 6.74             | 6.06           |
| 26  | 6.74        | 6.74             | 6.06           |
| 27  | 6.74        | 6.74             | 6.06           |
| 28  | 6.74        | 6.74             | 6.06           |
| 29  | 6.74        | 6.74             | 6.06           |
| 30  | 6.74        | 6.74             | 6.06           |
| 31  | 6.74        | 6.74             | 6.06           |
| 32  | 6.74        | 6.74             | 6.06           |
| 33  | 6.74        | 6.74             | 6.06           |
| 34  | 6.74        | 6.74             | 6.06           |

GOS da idroisi lattosio

N° di aralist: _____/09          Note: carboidrati

Struireato: LC 1
Colonna: Transgenomic ICE SEP ION 300
Flusso: 0.4ml/min
Tcoloina: 40°C
Detector: RE SERIE 200

| Peak # | Time [min] | Component Nane | Conc. % | Area [μN-s] | Response factor | Amount norm. % | Area Norm. [%] |
|---|---|---|---|---|---|---|---|
| 1 | 9.375 | GOS1 | 1.601037 | 314941 | 9.0834e+06 | 5.3 | 2.2 |
| 2 | 9.708 | GOS2 | 6.693966 | 1316773 | 9.0834e+06 | 22.3 | 9.4 |
| 3 | 10.245 | GOS3 | 19.613919 | 3858262 | 9.0834e+06 | 65.3 | 27.4 |
| 4 | 11.095 | GOS4 | 0.000229 | 7886229 | 1.5932e+12 | 0.0 | 56.1 |
| 5 | 12.150 |  | 4.136e-94 | 89574 | 1.000e+100 | 1e-93 | 0.6 |
| 6 | 12.599 | Lattosio | 1.431672 | 281625 | 9.0834e+06 | 4.8 | 2.0 |
| 7 | 13.200 | GOS6 | 0.000229 | 191882 | 3.8764e+10 | 0.0 | 1.4 |
| 8 | 16.161 | Galattosio | 0.695751 | 129716 | 8.6091e+06 | 2.3 | 0.9 |
|  |  |  | 30.036802 | 14069002 |  | 100.0 | 100.0 |

*LACTOBACILLUS acidophilus* NCFM on GOS1 (95%) or Glucose

FIGURE 26

Interviewer Instructions

Prior to the interview:

- Confirm eligibility of patient.

- Confirm completion of written informed consent.

The interview should be conducted in the following manner:

- Probes have been added for several questions. These are to be used if the discussion is not satisfactory, only after the patient has been given sufficient time to respond. In all instances, the patient must be given the opportunity to respond to a question in his/her own manner before any probes are used.

FIGURE 27

Study Introduction

(5 minutes)

Objective:

To provide an overview of the study background, structure of the discussion, information on general "housekeeping" issues, and reassurance of confidentiality

Introduction

- *Thank you for taking the time to help us.*
- *My name is [first name] and I work with Mapi Values, a consulting firm that works closely with pharmaceutical companies to assess the symptoms and impacts of health conditions on people's lives.*

Discuss the goals of the interview

- *For this study, we are gathering information from adults with self-reported or diagnosed symptoms associated with lactose intolerance. Specifically, we will ask you questions about your experience with lactose intolerance.*
- *We are conducting ~25 interviews like this one with people who have been diagnosed with lactose intolerance or people who experience symptoms associated with lactose intolerance.*

Reassure the patient of confidentiality

- *Your name and contact information will remain with Mapi Values and the clinical study site and will only be provided to people directly involved with this project.*

Discuss audio recording of the discussion and the presence of observers

- *Our conversation today will be audio recorded so that I can pay careful attention to what you say, and to make certain I accurately capture the information you provide.*
- *Please try to speak clearly and loudly enough so that you can be heard and understood on the recording. Please be open in your discussion today and don't be afraid to voice any of your opinions. There are no right or wrong answers.*
- *You may stop the interview at any point if you want*
- *You don't have to answer a specific question if you don't want to.*
- *Our discussion today will last approximately 45 minutes.*

Turn on the audio recorder and begin with the following:

Note to Interviewer: State subject's ID and your first name

- *Do you consent to have this interview audio recorded?*
- *Do you have any questions at this point?*

FIGURE 28

Symptoms of Lactose Intolerance (30 minutes)

Objective:

To gather information about the symptoms of lactose intolerance the subject is currently experiencing 1. Would you please tell me how you're feeling right now?
2. Are you experiencing any symptoms that you associate with lactose intolerance?
    a. What symptoms are you experiencing?

LISTEN FOR FOUR CORE SYMPTOMS:
- Abdominal pain or cramps
- Bloating
- Flatulence (Gas)
- Diarrhea (Loose stools)

3. ASK FOR EACH SYMPTOM MENTIONED:
    a. Could you describe to me what that feels like?
    b. Since when have you been experiencing this symptom today?
    c. Is this something you've experienced before with lactose intolerance?
        i. Are today's symptoms different in any way from what you've experienced before with lactose intolerance? How so?
    d. How often do you experience this symptom in your everyday life?
        i. Daily?
        ii. Weekly?
        iii. Monthly?
4. Which of these symptoms do you find most bothersome? Please explain.
5. Can you tell me what symptom you first started experiencing today? When did you experience it? Can you describe the symptom? How long did it last? Did you experience any other symptom after this? Can you describe when that happened and what you felt? Did any of these symptoms change over time? How? How long did these other symptoms last? *(Listen for severity)*

*Note to Interviewer: Listen for sequence of symptoms that the patient experienced after the lactose challenge. Check how long after lactose challenge did the patients first start experiencing symptoms.*

6. Do you ever experience symptoms that you associate with lactose intolerance other than those you're experiencing now?

*Note to Interviewer: If the symptoms of abdominal pain or cramping are mentioned, ask the patient to describe the symptom in as much detail as possible.*

FIGURE 29

Additional Lactose Intolerance Information (10 minutes)

Objective:

To gather additional information about the symptoms of lactose intolerance and the impact on the subject's life.

7. How worried are you about having lactose intolerance symptoms?
    a. Not worried
    b. Slightly worried
    c. Moderately worried
    d. Very worried 8. Do you do anything to prevent symptoms? If so, what?

9. On a day-to-day basis, do you do anything to manage your lactose intolerance? Please explain.

10. How much does lactose intolerance impact your daily life?
    a. No impact
    b. Mild impact
    c. Moderate impact
    d. Severe impact 11. What is it like being lactose intolerant?

12. Does lactose intolerance affect your life? If so, how? How often does it affect your life (daily, weekly, etc.)?

13. Does lactose intolerance affect your social life? If so, how? How often does it affect your life (daily, weekly, etc.)?

14. Do you worry about any health risks associated with your inability to consume products containing lactose? What do you worry about?

Please administer the Lactose Load Symptom Questionnaire to the patient at the end of the subject's 6-hour lactose load.

FIGURE 30

LACTOSE LOAD SYMPTOM QUESTIONNAIRE

*Instructions:* Circle the number next to each symptom to indicate the degree to which you experienced each of these symptoms <u>at their worst</u> during the last 6 hours. If you did not experience the symptom, select 0 (0 = none). The more discomfort you felt, the larger the number.

|  | None | Slight | Mild | Moderate | Moderately Severe | Severe |
|---|---|---|---|---|---|---|
| Abdominal pain [cramps] | 0 | 1 | 2 | 3 | 4 | 5 |
| Bloating | 0 | 1 | 2 | 3 | 4 | 5 |
| Flatulence [gas] | 0 | 1 | 2 | 3 | 4 | 5 |
| Diarrhea [loose stools]) | 0 | 1 | 2 | 3 | 4 | 5 |

|  | None | Slight | Mild | Moderate | Moderately Severe | Severe |
|---|---|---|---|---|---|---|
| Nausea [upset stomach] | 0 | 1 | 2 | 3 | 4 | 5 |

🌸 *Thank you for your time, we appreciate your participation in this study.*

FIGURE 31

DAILY SYMPTOM DIARY

To be completed by subjects daily as instructed during Placebo Run-in and Treatment.
*Instructions:* Circle the number next to each symptom to indicate the degree to which you experienced each of these symptoms for the specified day. If you do not experience the symptom, select 0 (0 = none). The more discomfort you feel, the larger the number.

|                          | None | Slight | Mild | Moderate | Moderately Severe | Severe |
|---|---|---|---|---|---|---|
| Abdominal pain [cramps]  | 0    | 1      | 2    | 3        | 4                 | 5      |
| Bloating                 | 0    | 1      | 2    | 3        | 4                 | 5      |
| Flatulence [gas]         | 0    | 1      | 2    | 3        | 4                 | 5      |
| Diarrhea [loose stools]  | 0    | 1      | 2    | 3        | 4                 | 5      |

|                          | None | Slight | Mild | Moderate | Moderately Severe | Severe |
|---|---|---|---|---|---|---|
| Nausea [upset stomach]   | 0    | 1      | 2    | 3        | 4                 | 5      |

FIGURE 32

DAILY SYMPTOM AND MILK PRODUCT DIARY

To be completed by subjects daily as instructed during Follow-up.

*Instructions:* Circle the number next to each symptom to indicate the degree to which you experienced each of these symptoms for the specified day. If you do not experience the symptom, select 0 (0 = none). The more discomfort you feel, the larger the number. There is a page for each day in the follow-up phase of the study.

|  | None | Slight | Mild | Moderate | Moderately Severe | Severe |
|---|---|---|---|---|---|---|
| Abdominal pain [cramps] | 0 | 1 | 2 | 3 | 4 | 5 |
| Bloating | 0 | 1 | 2 | 3 | 4 | 5 |
| Flatulence [gas] | 0 | 1 | 2 | 3 | 4 | 5 |
| Diarrhea [loose stools] | 0 | 1 | 2 | 3 | 4 | 5 |

|  | None | Slight | Mild | Moderate | Moderately Severe | Severe |
|---|---|---|---|---|---|---|
| Nausea [upset stomach] | 0 | 1 | 2 | 3 | 4 | 5 |

*Instructions:* Every day during the follow-up period, write down the milk and milk-containing products (such as yogurt, ice cream, cottage cheese and cheese) and how much you ate, as shown below. 1/2 cup milk, yogurt, cottage cheese or ice cream = 1 point

| Diary Date |||
|---|---|---|
| Morning | Afternoon | Evening |
| *8:00 a.m. 1 cup of milk with cereal* | *1:00 p.m. 1/2 cup of cottage cheese* | *8:00 p.m. One medium dish of ice cream* |
| *Total = 2* | *Total = 1* | *Total = 2* |
| Total for Day = 5 |||

PREBIOTIC FORMULATIONS AND METHODS OF USE

CROSS-REFERENCE

This application claims the benefit of each of the following applications; it is a continuation application of U.S. Ser. No. 14/293,784, filed Jun. 2, 2014 (now abandoned), which is a continuation application of U.S. Ser. No. 13/096,711, filed Apr. 28, 2011 (now U.S. Pat. No. 8,785,160); which claims the benefit of U.S. Provisional Application Nos. 61/328,991, filed Apr. 28, 2010, and 61/372,836, filed Aug. 11, 2010; and which is a continuation-in-part application of Ser. No. 12/707,037, filed Feb. 17, 2010 (now U.S. Pat. No. 8,492,124); which claims the benefit of U.S. Provisional Application Nos. 61/155,150, filed Feb. 24, 2009, and 61/272,622, filed Oct. 13, 2009. Each of the above-referenced applications is incorporated herein by reference in its entirety.

BACKGROUND OF THE INVENTION

According to NIH estimates in 2008, 30-50 million Americans are lactose intolerant" (the Food and Drug Administration's Consumer Health Information on the agency's website). In the 1960s and 1970s, it was reported that 70% of the adults in the world had lactose intolerance. In 1995, it was reported that 75% of the adults in the world and 25% of the adults in the U.S. were categorized as being lactose intolerant. In 1994, it was reported that 75% of African Americans and Native Americans and 90% of Asian Americans had lactose intolerance. It has also been reported that 30% of adults who are mostly North American descendants of Europeans have adapted to high lactase activity into adulthood. Research concludes that this adaptation is genetically controlled, permanent, and related to a long tradition of milk and milk product consumption in these regions of the world.

Lactose intolerance is the inability to digest significant amounts of lactose, a major natural sugar found in milk and milk products of all mammals. Lactose intolerance is caused by a shortage of the enzyme lactase, which is produced by the cells that line the small intestine and is essential to lactose digestion. Lactase breaks down lactose, a disaccharide, into two simpler forms of sugar called glucose and galactose, which are then transported across the cell membrane and absorbed into the bloodstream. If lactase is not present, or not present in sufficient levels, excess undigested lactose passes through the small intestines into the large intestine where it is fermented by bacteria in the colon ("colonic microbiota," "gut microbiota," "intestinal microbiota," or "commensal gut microbiota"). The fermentation of lactose in the large intestine produces hydrogen and methane which can lead to bloating, gas, and diarrhea. These symptoms are caused by a very low activity of lactase in the intestines and are found in subjects who are lactose intolerant. Not all subjects deficient in lactase have the symptoms commonly associated with lactose intolerance, but those who do are said to have lactose intolerance.

This decrease in lactase activity results in a demonstrated maldigestion of the sugar lactose, either with or without symptoms, after ingesting dairy products such as milk, ice cream, cheese and pizza. Lactose maldigestion, with or without the symptoms commonly associated with lactose intolerance, is often defined more specifically as an "increase in blood glucose concentration of <1.12 mmol/L or breath hydrogen of >20 ppm after ingestion of 1 g/kg body weight or 50 g lactose" (de Vrese et al., 2001).

If a subject suspects that he or she has lactose intolerance, it is potentially harmful for him or her to restrict his or her diet because restriction can result in a nutrition shortage or a failure to detect a more serious disease. Milk and other dairy products are major sources for nutrition in the basic American diet. The primary nutrients in milk are protein, calcium, riboflavin, vitamin A, and vitamin D. Calcium is an important part of the recommended daily allowance of vitamins and minerals and any deficiency therein can lead to increased risk of osteoporosis and hypertension (McCarron and Heaney 2004) and possibly cancer (Barger-Lux and Heaney 1994; Consensus Conference: Optimal Calcium Intakes, NIH 1994).

Young children who have lactose intolerance are very rare. The amount of the enzyme lactase a body produces generally reaches a maximum immediately after birth and then decreases in the majority of people during the ages of about 3-15.

Generally, humans develop lactose intolerance from a primary or secondary cause. The primary cause is an onset of loss of lactase that is believed to be a permanent condition. This onset can occur at a variable period after the weaning period. The primary cause is also genetically determined. The secondary cause is generally a temporary condition that occurs as a result of another disease or event that damages the lining of the small intestine where lactase is active. This temporary condition can be caused by acute diarrhea, disease, parasitic infection, Cohn's disease, celiac disease, gastrointestinal surgery, or the intake of certain medications.

In addition to the primary and secondary causes, certain human ethnic and racial populations have more of a predisposition for lactose intolerance. In these populations, social and cultural habits and attitudes influence lactose intolerance. Lactose activity can also decrease with age in certain ethnic and racial populations, including those populations which have origins in Europe, the African plains, and the Siberian Steppes. Humans who are most likely to have or develop lactose intolerance include those of Asian, Middle Eastern, North American, African, and Latin American decent.

Currently, there is no universally accepted therapy for the treatment of lactose intolerance. As such, most lactose intolerant individuals avoid the ingestion of milk and dairy products, while others substitute non-lactose containing products in their diet. The avoidance of lactose makes the occurrence of symptoms more likely when dairy foods are consumed.

Nutritional supplements currently sold often offer no proven benefit or in some instances, must be ingested prior to eating dairy, where the outcome is dependent on the dose of the supplement and relative to the amount of lactose consumed. In some instances, use of a nutritional supplement to manage the symptoms associated with lactose intolerance may require large dosages, such as five or more pills per day.

There is need in the medical community for a tolerable and convenient treatment that allows for all levels of milk and dairy product consumption in people suffering from mild to severe lactose intolerance. A treatment that provides a simplified dosing regimen as well as the potential for extended relief from symptoms following a limited therapy regimen (e.g., ≤30 days) would result in greater compliance and address an unmet medical need.

"Prebiotics" are non-digestible food ingredients that stimulate the growth or activity of bacteria in the digestive system that are beneficial to the health of the body (Gibson and Roberfroid 1995). Typically, prebiotics are carbohydrates such as oligosaccharides, but the definition does not preclude non-carbohydrates.

Prebiotics have been further defined as fulfilling three criteria (Gibson et al. 2004):

1) Resistance to gastric acidity, hydrolysis by mammalian enzymes and gastrointestinal absorption;

2) Fermentation by intestinal microflora; and

3) Selective stimulation of the growth and/or selective activity of intestinal bacteria associated with health and well-being.

Substantial data exist to support the strategy that colonic bacteria adapt readily to undigested carbohydrates, resulting in dramatically improved lactose tolerance. A purified GOS preparation, can promote the selective growth of beneficial colonic bacteria, including multiple species and strains of bifidobacteria and lactobacilli. Bifidobacteria carry out non hydrogen-producing lactose fermentation reactions in addition to inhibiting hydrogen producing bacteria, such as *Escherichia coli* (*E. coli*). It is this excessive hydrogen production that defines lactose malabsorption and ultimately is responsible for the symptoms associated with lactose intolerance (Ballongue 1993; Gibson 1994, 1995). A recent study indicates that higher purity GOS formulations have a greater potential to selectively promote the growth of beneficial lactobacilli and bifidobacteria (Klaenhammer 2010).

SUMMARY OF THE INVENTION

Disclosed herein are methods of treating lactose intolerance in a subject experiencing one or more symptoms of lactose intolerance comprising administering a pharmaceutical composition to the subject, wherein the pharmaceutical composition comprises GOS. In one embodiment, at least about 80% of the total weight of the composition is GOS. In one embodiment, at least about 95% of the total weight of the composition is GOS. In one embodiment, the composition comprises about 0.1 g to 20 g GOS. In one embodiment, the composition comprises about 1.5 g to 15 g GOS. In one embodiment, the composition is a syrup or liquid. In one embodiment, the syrup or liquid is provided in a capsule or softgel. In one embodiment, the syrup or liquid is provided in a bottle. In one embodiment, the syrup or liquid is diluted with water prior to consumption. In one embodiment, the composition is provided in a dosing unit. In one embodiment, the dosing unit is a capsule, tablet, softgel, ephervescant tablet, or lozenge. In one embodiment, the dosing unit further comprises an enteric coating. In one embodiment, the composition further comprises a probiotic. In one embodiment, the probiotic comprises *Lactobacillus* or bifidobacteria. In one embodiment, the composition does not contain a probiotic. In one embodiment, the composition is administered each day for a predetermined number of days. In one embodiment, the predetermined number of days is 10 to 40 days. In one embodiment, the predetermined number of days is 35 days. In one embodiment, the predetermined number of days is 30 days. In one embodiment, the predetermined number of days is 14 days. In one embodiment, the method comprises administering a lower dosage of GOS on the first day of administration than the last day of administration. In one embodiment, the subject is administered 1.5 grams of GOS on the first day and 15 grams of GOS on the final day. In one embodiment, the method comprises administering the same dosage of GOS on the first day of administration as the last day of administration. In one embodiment, the method comprises administering the composition once a day. In one embodiment, the method comprises administering the composition twice a day. In one embodiment, the composition is provided without a meal. In one embodiment, the composition is provided with a meal. In one embodiment, the subject is a human subject. In one embodiment, the subject is a pediatric subject. In one embodiment, the subject is an adult. In one embodiment, the subject is an elderly person. In one embodiment, the subject is a post-menopausal woman. In one embodiment, the one or more symptoms comprise flatulence, heartburn, upset stomach, nausea, bloating, diarrhea, abdominal pain, cramping, or vomiting. In one embodiment, the subject has a nutritional deficiency. In one embodiment, the nutritional deficiency is a calcium deficiency.

Disclosed here are methods of preventing lactose intolerance in a subject experiencing one or more symptoms of lactose intolerance comprising administering a pharmaceutical composition to the subject, wherein the pharmaceutical composition comprises GOS. In one embodiment, at least about 80% of the total weight of the composition is GOS. In one embodiment, at least about 95% of the total weight of the composition is GOS. In one embodiment, the composition comprises about 0.1 g to 20 g GOS. In one embodiment, the composition comprises about 1.5 g to 15 g GOS. In one embodiment, the composition is a syrup or liquid. In one embodiment, the syrup or liquid is provided in a capsule or softgel. In one embodiment, the syrup or liquid is provided in a bottle. In one embodiment, the syrup or liquid is diluted with water prior to consumption. In one embodiment, the composition is provided in a dosing unit. In one embodiment, the dosing unit is a capsule, tablet, softgel, ephervescant tablet, or lozenge. In one embodiment, the dosing unit further comprises an enteric coating. In one embodiment, the composition further comprises a probiotic. In one embodiment, the probiotic comprises *Lactobacillus* or bifidobacteria. In one embodiment, the composition does not contain a probiotic. In one embodiment, the composition is administered each day for a predetermined number of days. In one embodiment, the predetermined number of days is 10 to 40 days. In one embodiment, the predetermined number of days is 35 days. In one embodiment, the predetermined number of days is 30 days. In one embodiment, the predetermined number of days is 14 days. In one embodiment, the method comprises administering a lower dosage of GOS on the first day of administration than the last day of administration. In one embodiment, the subject is administered 1.5 grams of GOS on the first day and 15 grams of GOS on the final day. In one embodiment, the method comprises administering the same dosage of GOS on the first day of administration as the last day of administration. In one embodiment, the method comprises administering the composition once a day. In one embodiment, the method comprises administering the composition twice a day. In one embodiment, the composition is provided without a meal. In one embodiment, the composition is provided with a meal. In one embodiment, the subject is a human subject. In one embodiment, the subject is a pediatric subject. In one embodiment, the subject is an adult. In one embodiment, the subject is an elderly person. In one embodiment, the subject is a post-menopausal woman. In one embodiment, the one or more symptoms comprise flatulence, heartburn, upset stomach, nausea, bloating, diarrhea, abdominal pain, cramping, or vomiting. In one embodiment, the subject has a nutritional deficiency. In one embodiment, the nutritional deficiency is a calcium deficiency.

Disclosed herein are methods of treating lactose intolerance in a subject experiencing one or more symptoms of lactose intolerance comprising: administering a hydrogen breath test (HBT) to the subject; diagnosing the subject as having or not having lactose intolerance based upon a HBT result; and, administering a pharmaceutical composition to the subject diagnosed as having lactose intolerance based upon the HBT result, wherein the pharmaceutical composition comprises GOS. In one embodiment, the HBT result is an increase in breath hydrogen of greater than about 12 ppm. In one embodiment, the HBT result is an increase in breath hydrogen of greater than about 15 ppm. In one embodiment, the HBT result is an increase in breath hydrogen of greater than about 20 ppm. Also disclosed here are methods of treating lactose intolerance in a subject experiencing one or more symptoms of lactose intolerance comprising: administering a lactose intolerance diagnostic questionnaire; diagnosing the subject as having or not having lactose intolerance based upon a lactose intolerance diagnostic questionnaire result; and, administering a pharmaceutical composition to the subject diagnosed with lactose intolerance based upon the lactose intolerance diagnostic questionnaire result, wherein the pharmaceutical composition comprises GOS. In one embodiment, the lactose intolerance diagnostic questionnaire result is a single symptom rating of moderately severe to severe. In one embodiment, the lactose intolerance diagnostic questionnaire result is two or more symptom ratings of moderate or higher. In one embodiment, the lactose intolerance diagnostic questionnaire result is a single symptom rating of moderate or higher at two different timepoints. In one embodiment, the lactose intolerance diagnostic questionnaire is administered after a lactose or milk challenge. Also disclosed herein are methods of treating lactose intolerance in a subject experiencing one or more symptoms of lactose intolerance comprising: administering a hydrogen breath test (HBT) to the subject; administering a lactose intolerance diagnostic questionnaire to the subject; diagnosing the subject as having or not having lactose intolerance based upon a HBT result and a lactose intolerance diagnostic questionnaire result; and administering a pharmaceutical composition to the subject diagnosed with lactose intolerance based upon the HBT result and the lactose intolerance diagnostic questionnaire result, wherein the pharmaceutical composition comprises GOS. In one embodiment, the HBT result is an increase in breath hydrogen of greater than 12 ppm. In one embodiment, the HBT result is an increase in breath hydrogen of greater than 15 ppm. In one embodiment, the HBT result is an increase in breath hydrogen of greater than 20 ppm. In one embodiment, the lactose intolerance diagnostic questionnaire result is a single symptom rating of moderately severe to severe. In one embodiment, the lactose intolerance diagnostic questionnaire result is two or more symptom ratings of moderate or higher. In one embodiment, the lactose intolerance diagnostic questionnaire result is a single symptom rating of moderate or higher at two different timepoints. In some embodiments, at least about 80% of the total weight of the composition is GOS. In some embodiments, at least about 95% of the total weight of the composition is GOS. In some embodiments, the composition comprises about 0.1 g to 20 g GOS. In some embodiments, the composition comprises about 1.5 g to 15 g GOS. In some embodiments, the composition is a syrup or liquid. In some embodiments, the syrup or liquid is provided in a capsule or softgel. In some embodiments, the syrup or liquid is provided in a bottle. In some embodiments, the syrup or liquid is diluted with water prior to consumption. In some embodiments, the composition is provided in a dosing unit. In some embodiments, the dosing unit is a capsule, tablet, softgel, ephervescant tablet, or lozenge. In some embodiments, the dosing unit further comprises an enteric coating. In some embodiments, the composition further comprises a probiotic. In some embodiments, the probiotic comprises *Lactobacillus* or bifidobacteria. In some embodiments, the composition does not contain a probiotic. In some embodiments, the composition is administered each day for a predetermined number of days. In some embodiments, the predetermined number of days is 10 to 40 days. In some embodiments, the predetermined number of days is 35 days. In some embodiments, the predetermined number of days is 30 days. In some embodiments, the predetermined number of days is 14 days. In some embodiments, the method comprises administering a lower dosage of GOS on the first day of administration than the last day of administration. In some embodiments, the subject is administered 1.5 grams of GOS on the first day and 15 grams of GOS on the final day. In some embodiments, the method comprises administering the same dosage of GOS on the first day of administration as the last day of administration. In some embodiments, the method comprises administering the composition once a day. In some embodiments, the method comprises administering the composition twice a day. In some embodiments, the composition is provided without a meal. In some embodiments, the composition is provided with a meal. In some embodiments, the subject is a human subject. In some embodiments, the subject is a pediatric subject. In some embodiments, the subject is an adult. In some embodiments, the subject is an elderly person. In some embodiments, the subject is a post-menopausal woman. In some embodiments, the one or more symptoms comprise flatulence, heartburn, upset stomach, nausea, bloating, diarrhea, abdominal pain, cramping, or vomiting. In some embodiments, the subject has a nutritional deficiency. In some embodiments, the nutritional deficiency is a calcium deficiency.

Disclosed herein are methods of treating a subject with a calcium deficiency, wherein the subject is experiencing one or more symptoms of lactose intolerance, comprising administering a pharmaceutical composition to the subject, wherein the pharmaceutical composition comprises GOS. Also disclosed herein are methods of treating a subject with a calcium deficiency wherein the subject is experiencing one or more symptoms of lactose intolerance comprising: administering a hydrogen breath test (HBT) to the subject; diagnosing the subject as having or not having lactose intolerance based upon a HBT result; and, administering a pharmaceutical composition to the subject diagnosed as having lactose intolerance based upon the HBT result, wherein the pharmaceutical composition comprises GOS. In one embodiments, the method of treatment further comprising administering a lactose intolerance diagnostic questionnaire to the subject and diagnosing the subject as having or not having lactose intolerance based upon the HBT result and a lactose intolerance diagnostic questionnaire result. Also disclosed herein are methods of treating a subject with a calcium deficiency wherein the subject is experiencing one or more symptoms of lactose intolerance comprising: administering a lactose intolerance diagnostic questionnaire; diagnosing the subject as having or not having lactose intolerance based upon a lactose intolerance diagnostic questionnaire result; and, administering a pharmaceutical composition to the subject diagnosed with lactose intolerance based upon the lactose intolerance diagnostic questionnaire results, wherein the pharmaceutical composition comprises GOS. In one embodiment, the HBT result is an increase in breath hydrogen of greater than 12 ppm. In one embodiment, the HBT result is an increase in breath hydrogen of greater than 15 ppm. In one embodiment, the HBT result is an increase in breath hydrogen of greater than 20 ppm. In one embodiment, the lactose intolerance diagnostic questionnaire result is a single symptom rating of moderately severe to severe. In one embodiment, the lactose intolerance diagnostic questionnaire result is two or more symptom ratings of moderate or higher. In one embodiment, the lactose intolerance diagnostic questionnaire result is a single symptom rating of moderate or higher at two different timepoints. In one embodiment, the lactose intolerance diagnostic questionnaire is administered after a lactose or milk challenge. In some embodiments, the subject has bone loss, osteoporosis, hypertension, weak bone density and/or cardiac arrhythmias. In some embodiments, at least about 80% of the total weight of the composition is GOS. In some embodiments, at least about 95% of the total weight of the composition is GOS. In some embodiments, the composition comprises about 0.1 g to 20 g GOS. In some embodiments, the composition comprises about 1.5 g to 15 g GOS. In some embodiments, the composition is a syrup or liquid. In some embodiments, the syrup or liquid is provided in a capsule or softgel. In some embodiments, the syrup or liquid is provided in a bottle. In some embodiments, the syrup or liquid is diluted with water prior to consumption. In some embodiments, the composition is provided in a dosing unit. In some embodiments, the dosing unit is a capsule, tablet, softgel, ephervescant tablet, or lozenge. In some embodiments, the dosing unit further comprises an enteric coating. In some embodiments, the composition further comprises a probiotic. In some embodiments, the probiotic comprises *Lactobacillus* or bifidobacteria. In some embodiments, the composition does not contain a probiotic. In some embodiments, the composition is administered each day for a predetermined number of days. In some embodiments, the predetermined number of days is 10 to 40 days. In some embodiments, the predetermined number of days is 35 days. In some embodiments, the predetermined number of days is 30 days. In some embodiments, the predetermined number of days is 14 days. In some embodiments, the method comprises administering a lower dosage of GOS on the first day of administration than the last day of administration. In some embodiments, the subject is administered 1.5 grams of GOS on the first day and 15 grams of GOS on the final day. In some embodiments, the method comprises administering the same dosage of GOS on the first day of administration as the last day of administration. In some embodiments, the method comprises administering the composition once a day. In some embodiments, the method comprises administering the composition twice a day. In some embodiments, the composition is provided without a meal. In some embodiments, the composition is provided with a meal. In some embodiments, the subject is a human subject. In some embodiments, the subject is a pediatric subject. In some embodiments, the subject is an adult. In some embodiments, the subject is an elderly person. In some embodiments, the subject is a post-menopausal woman. In some embodiments, the one or more symptoms comprise flatulence, heartburn, upset stomach, nausea, bloating, diarrhea, abdominal pain, cramping, or vomiting.

Disclosed herein are pharmaceutically acceptable oral dosage forms of GOS comprising one or more dosing units, each of the dosing units comprising 0.1 to 2 g of a GOS composition wherein the GOS composition is a liquid encapsulated in a gelatin capsule. Also disclosed herein are pharmaceutically acceptable oral dosage forms of GOS comprising one or more dosing units, each of the dosing units comprising 0.1 to 2 g of a GOS composition wherein the GOS composition is a viscous syrup or liquid encapsulated in a gelatin capsule. In some embodiments, the gelatin capsule is size 000, 00, 0, 1, 2, 3, 4, or 5. In some embodiments, the GOS composition comprises at least about 80% GOS by weight. In some embodiments, the GOS composition comprises at least about 95% GOS by weight. In some embodiments, the gelatin capsule further comprises an enteric coating. In some embodiments the, GOS composition further comprises a probiotic. In some embodiments, the probiotic comprises *Lactobacillus* or bifidobacteria. In some embodiments, the GOS composition does not contain a probiotic.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 5 illustrates a treatment regimen with a 70% GOS composition.

FIG. 6 illustrates another treatment regimen with a 70% GOS composition.

FIG. 7 illustrates a treatment regimen with a 90% GOS composition.

FIG. 8 illustrates another treatment regimen with a 93% GOS composition.

FIG. 9 illustrates a treatment regimen with a 95% GOS composition.

FIG. 26 illustrates a set of interviewer instructions for a pre-screening interview.

FIG. 27 illustrate a study introduction script for a pre-screening interview.

FIG. 28 illustrates a lactose intolerance symptom script/guidelines for a pre-screening interview.

FIG. 29 illustrates a lactose intolerance life-style script/guidelines for a pre-screening interview.

FIG. 30 illustrates a Lactose Load Symptom Questionnaire for a pre-screening interview.

FIG. 31 illustrates a Daily Symptom Diary for use during Placebo Run-in and Treatment studies.

FIG. 32 illustrates a Daily Symptom and Milk Product Diary for use during the Follow-up studies.

DETAILED DESCRIPTION OF THE INVENTION

I. Overview

Described herein are methods, compositions, kits, and business methods useful for the reduction of symptoms of lactose intolerance in a subject in need thereof, and for improving overall gastrointestinal (GI) health. Symptoms of lactose intolerance include gas, heartburn, stomach upset, bloating, flatulence, diarrhea, abdominal pain, cramping, nausea, or vomiting. Minor digestive problems related to the GI also include occasional bloating, diarrhea, constipation, gas, heartburn, or stomach upset. The methods and compositions described herein are useful for reducing or eliminating one or more of these symptoms, for example through colonic adaptation. Fructose and sorbitol malabsorption are also common when lactose malabsorption is present. The methods and compositions described herein can also be useful for reducing or eliminating malabsorption of saccharides or carbohydrates such as lactose, fructose, or sorbitol.

In one aspect of the methods described, the reduction or elimination of symptoms persists after treatment of a condition has concluded. Thus, the described methods need not be used on a continuous basis but rather can be utilized for a discrete time period and then discontinued. In another aspect of the methods, reduction or elimination of symptoms can be temporary, and after an amount of time has passed, treatment can be administered when symptoms reappear to maintain the effects of the methods described herein. In yet another aspect of the methods, the methods described can be administered on a regular basis for reducing symptoms of lactose intolerance and for improving overall gastrointestinal (GI) health.

Figure 1:
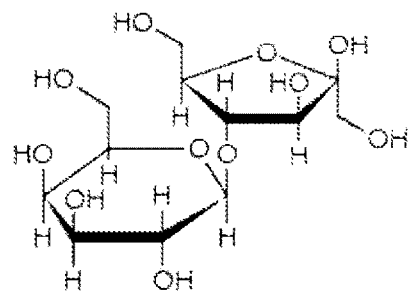
FIG. 1 illustrates the chemical structure of lactulose.
Figure 2:
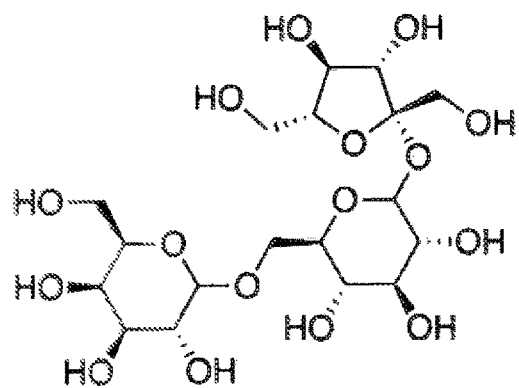
FIG. 2 illustrates the chemical structure of raffinose.
Figure 3:
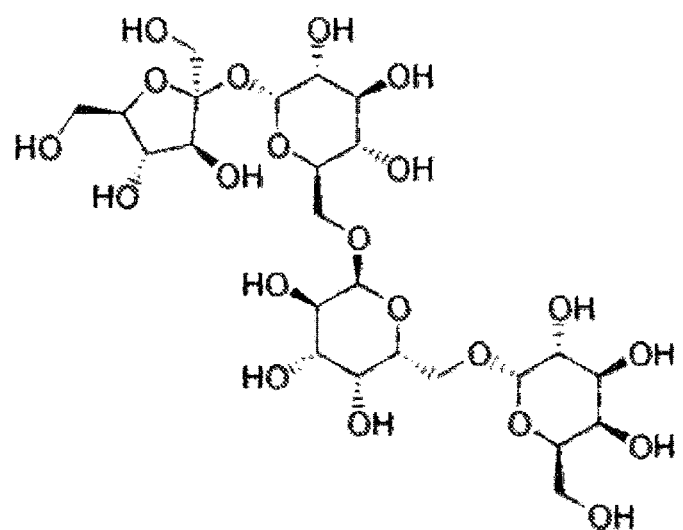
FIG. 3 illustrates the chemical structure of stachyose.
Figure 10:
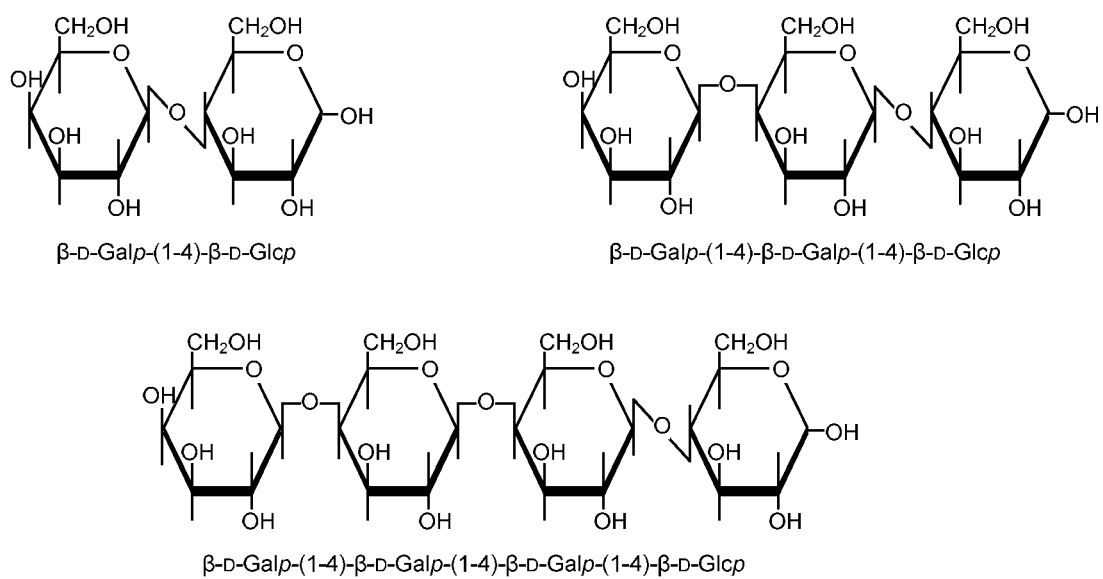
FIG. 10 illustrates a non-limiting example of different GOS with a DP of 2, 3, and 4.

In another aspect compositions and methods comprising a prebiotic composition are provided that are useful for treatment of lactose intolerance, reduction of symptoms of lactose intolerance, and for improving overall gastrointestinal (GI) health. In one embodiment, a prebiotic composition is a pharmaceutical composition. In one embodiment a prebiotic composition comprises one or more saccharides (herein, interchangeably also referred to as carbohydrates or sugars) which are non-digestible by a human digestive system. In another embodiment a prebiotic composition consists essentially of a saccharide which is non-digestible by a human digestive system. In one embodiment, the one or more saccharides are oligosaccharides wherein the degree of polymerization (DP) is from 2 to 20. In one embodiment the degree of polymerization can be 2 (e.g., see FIG. 10), 3 (e.g., see FIG. 10), 4 (e.g., see FIG. 10), 5, 6, 7, 8, 9, 10, 11, 12, 13, 14, 15, 16, 17, 18, 19, or 20. In another embodiment, the one or more saccharides are a polysaccharide wherein the degree of polymerization is greater than 10. In another embodiment, the saccharide comprises a mixture of non-digestible oligosaccharides or polysaccharides. In another embodiment a prebiotic composition comprises one or more digestible saccharides and one or more non-digestible oligosaccharides or polysaccharides. In one embodiment the saccharide is an oligosaccharide, such as a disaccharide, a trisaccharide, a tetrasaccharide, a pentasaccharide, a hexasaccharide, a heptasaccharide, an octasaccharide, a nanasaccharide, or a decasaccharide. Saccharides that are not digestible by humans include, but are not limited to, transgalactooligosaccharides, galacto-oligosaccharides, lactulose (FIG. 1), raffinose (FIG. 2), stachyose (FIG. 3), lactosucrose, fructo-oligosaccharides, isomalto-oligosaccharides, xylo-oligosaccharides, paratinose oligosaccharides, difructose anhydride III, sorbitol, maltitol, lactitol, reduced paratinose, cellulose, β-glucose, β-galactose, β-fructose, verbascose, galactinol, and β-glucan, guar gum, pectin, high sodium alginate, and lambda carrageenan.

Figure 4:
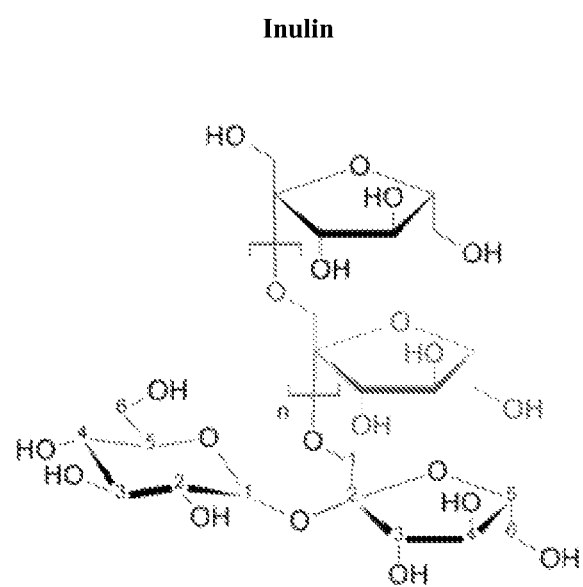
FIG. 4 illustrates the chemical structure of inulin.

In one embodiment a prebiotic composition comprises a saccharide that is inulin (FIG. 4), fructo-oligosaccharide (FOS), lactulose, galacto-oligosaccharide (GOS), raffinose, or stachyose. In another embodiment the saccharide is an oligosaccharide that is non-digestible by a human digestive system, contains at least one beta-glycosidic (e.g., beta galactosidic or beta glucosidic) bond, and would induce lactose digestion when fed to a subject in need thereof. In one embodiment the subject in need thereof is a human. In another embodiment the saccharide is an oligosaccharide that is non-digestible by a human digestive system and contains at least one beta-glycosidic (e.g., beta galactosidic or beta glucosidic) bond that can be digested by a bacterium. In one embodiment the bacterium is a probiotic. In one embodiment the saccharide is an oligosaccharide that is non-digestible by a human digestive system and contains at least one alpha-glycosidic bond. In one embodiment the bacterium is a lactobacilli or a bifidobacteria. In one embodiment the saccharide is GOS.

In another embodiment the saccharide is an oligosaccharide that is non-digestible by a human digestive system, contains at least one alpha-glycosidic (e.g., alpha galactosidic or alpha glucosidic) bond, and would induce lactose digestion when fed to a subject in need thereof. In one embodiment the subject in need thereof is a human. In another embodiment the saccharide is an oligosaccharide that is non-digestible by a human digestive system and contains at least one alpha-glycosidic (e.g., alpha galactosidic or alpha glucosidic) bond that can be metabolized by a bacterium. In one embodiment the bacterium is a probiotic. In one embodiment the bacterium is a lactobacilli or a bifidobacteria. In one embodiment the saccharide is GOS.

In one embodiment, a prebiotic composition comprises at least one non-digestible saccharide and optionally contains one or more digestible saccharides or oligosaccharides. Digestible saccharides are those which are digestible by a human digestive system. In one embodiment, the one or more digestible saccharide is lactose, galactose, or glucose. In another embodiment, a prebiotic composition does not contain lactose. In one embodiment, a prebiotic composition does not contain any probiotic bacteria. In another embodiment, a prebiotic composition contains at least one strain of probiotic bacteria.

In one embodiment, a prebiotic composition contains an oligosaccharide that increases β-galactosidase activity in the large intestine. In one embodiment, a prebiotic composition contains an oligosaccharide that increases the amount of probiotic activity in the large intestine.

II. Prebiotics

Prebiotics are non-digestible substances that when consumed provide a beneficial physiological effect on the host by selectively stimulating the favorable growth or activity of a limited number of indigenous bacteria (Gibson G R, Roberfroid M B. Dietary modulation of the human colonic microbiota: introducing the concept of prebiotics. J Nutr. 1995 June; 125(6): 1401-12). A prebiotic is generally a saccharide that is non-digestible or essentially non-digestible by a human and acts to encourage the growth of probiotic bacteria in the gut, increase adhesion of probiotic bacteria in the gut, displace pathogens, or provide a fermentable dose of carbohydrate to probiotic bacteria (symbiotic) or selected commensal bacteria and increase the levels of those microbial populations (notably lactobacilli and bifidobacteria) in the gastrointestinal tract. A prebiotic can be a saccharide that is non-digestible by the human host and can act as a non-digestible fiber in the diet. This non-digestibility is because humans lack the enzymes to break down some or all of the prebiotic oligosaccharide as it travels through the digestive tract. When a prebiotic reaches the small intestine and colon, bacteria encoding an enzyme or enzymes capable of digesting the prebiotic can break down the prebiotic into simple sugars that the bacteria can use. For example, bifidobacteria and lactobacilli have been reported to digest prebiotic saccharides.

Suitable prebiotics can include one or more of a carbohydrate, carbohydrate monomer, carbohydrate oligomer, or carbohydrate polymer. In one embodiment, the prebiotics are non-non-digestible saccharides, which include non-non-digestible monosaccharides, non-digestible oligosaccharides, or non-non-digestible polysaccharides. In one embodiment, the sugar units of an oligosaccharide or polysaccharide can be linked in a single straight chain or can be a chain with one or more side branches. The length of the oligosaccharide or polysaccharide can vary from source to source. In one embodiment, small amounts of glucose can also be contained in the chain. In another embodiment, the prebiotic composition can be partially hydrolyzed or contain individual sugar moieties that are components of the primary oligosaccharide.

In one embodiment, a prebiotic composition described herein consists essentially of one or more non-digestible saccharides. In another embodiment, a prebiotic composition consists essentially of one or more non-digestible oligosaccharides. In one embodiment, the non-digestible oligosaccharides are GOS. In other embodiments, a composition described herein consists essentially of non-digestible GOS and does not contain a probiotic microbe, or microbes.

In one embodiment a prebiotic composition of the invention allows the colonic microbiota, comprising microorganisms known to increase the ability of a subject to tolerate fermentable carbohydrates, to be regularly maintained or replenished through consumption of the prebiotic composition. In one embodiment, adaptation of the intestinal and colonic microbiota increases the intestine and colon's capacity to use lactose without producing gas. Adaptive changes in microbiota of the gastrointestinal tract can be useful for the reduction of bloating, diarrhea, gastric distention, pain, or flatulence from the consumption of dairy products and other lactose containing compositions. In one embodiment, tolerance of a human subject to dairy products, in general, can be improved through regular consumption of a prebiotic composition.

Prebiotics can promote colonic bacteria that slow fermentation. For example, FOS, neosugar, or inulin promotes the growth of acid-forming bacteria in the colon such as bacteria belonging to the genera *Lactobacillus* or *Bifidobacterium*. For instance, *Lactobacillus acidophilus* and *Bifidobacterium bifidus* can play a role in reducing the number of pathogenic bacteria in the colon. Additional properties, such as the effect of prebiotics on colonic pH and stool bulking provide for their classification as dietary fibers. In experimental models, prebiotics can improve the bioavailability of essential minerals. As a fiber, prebiotics are thought to slow digestion. Other polymers, such as various galactans and carbohydrate based gums, such as psyllium, guar, carrageen, gellan, and konjac, are also known to improve gastrointestinal (GI) health. The carbohydrate lactulose can also improve GI health.

In one embodiment a prebiotic composition comprises one or more of GOS, lactulose, raffinose, stachyose, lactosucrose, FOS (i.e. oligofructose or oligofructan), inulin, isomalto-oligosaccharide, xylo-oligosaccharide, paratinose oligosaccharide, transgalactosylated oligosaccharides (i.e. transgalacto-oligosaccharides), transgalactosylate disaccharides, soybean oligosaccharides (i.e. soyoligosaccharides), gentiooligosaccharides, glucooligosaccharides, pecticoligosaccharides, palatinose polycondensates, difructose anhydride III, sorbitol, maltitol, lactitol, polyols, polydextrose, reduced paratinose, cellulose, β-glucose, β-galactose, β-fructose, verbascose, galactinol, and β-glucan, guar gum, pectin, high, sodium alginate, and lambda carrageenan, or mixtures thereof.

In one embodiment, a prebiotic composition comprises a mixture of one or more non-digestible oligosaccharides, non-digestible polysaccharides, free monosaccharides, non-digestible saccharides, starch, or non-starch polysaccharides. In one embodiment, a prebiotic component of a prebiotic composition is a GOS composition. In one embodiment, a prebiotic composition is a pharmaceutical composition. In one embodiment, a pharmaceutical composition is a GOS composition.

In one embodiment a prebiotic composition reduces or eliminates one or more symptoms associated with lactose intolerance or with lactose digestive problems, including but not limited to cramps, flatulence, stomach pain, vomiting, bloating, diarrhea, nausea, gastric distention and intestinal pain, in a subject in need thereof. In one embodiment the subject is a patient. In another embodiment the subject is a human. In another embodiment the subject is a non-human animal.

The term "about" means the referenced numeric indication plus or minus 10% of that referenced numeric indication.

The term "percent by weight," as used in reference to the percent by weight of a component in a composition, means the percentage of the component's weight in comparison to the total dry weight of the composition.

A. Oligosaccharide Structure

Oligosaccharides are generally considered to have a reducing end and a non-reducing end, whether or not the saccharide at the reducing end is in fact a reducing sugar. In accordance with accepted nomenclature, most oligosaccharides are depicted herein with the non-reducing end on the left and the reducing end on the right. Most oligosaccharides described herein are described with the name or abbreviation for the non-reducing saccharide (e.g., Gal or D-Gal), preceded or followed by the configuration of the glycosidic bond (α or β), the ring bond, the ring position of the reducing saccharide involved in the bond, and then the name or abbreviation of the reducing saccharide (e.g., Glc or D-Glc). The linkage (e.g., glycosidic linkage, galactosidic linkage, glucosidic linkage) between two sugar units can be expressed, for example, as 1,4, 1-->4, or (1-4) Each saccharide is in the cyclic form (i.e. pyranose or furanose form). For example, lactose is a disaccharide composed of cyclic forms of galactose and glucose joined by a beta (1-4) linkage where the acetal oxygen bridge is in the beta orientation. Lactose exists as alpha- and beta-lactose (see structures below). β-lactose can be expressed as β-D-galactopyranosyl-(1-4)β-D-glucopyranose, β-D-Gal-(1-4)-β-D-Glc or as Gal β(1-4)-Glc. α-lactose can be expressed as β-D-galactopyranosyl-(1-4) α-D-glucopyranose, β-D-Gal-(1-4)-α-D-Glc or as Gal β(1-4)-Glc.

Both FOS and GOS are non-digestible saccharides. β glycosidic linkages of saccharides, such as those found in, but not limited to, FOS and GOS, make these prebiotics mainly non-digestible and unabsorbable in the stomach and small intestine (see below). Also, α-linked GOS (α-GOS) is not hydrolyzed by human salivary amylase, but can be used by *Bifidobacterium bifidum* and *Clostridium butyricum* (Yamashita A. et al. (2004) J. Appl. Glycosci. 51:115-122). FOS and GOS can pass through the small intestine and into the large intestine (colon) mostly intact, except where probiotic and commensal microbes are able to metabolize the oligosaccharides.

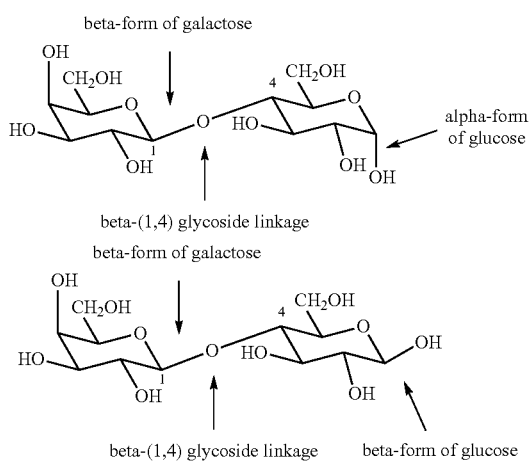

B. GOS

1. Introduction

GOS (also known as galacto-oligosaccharides, galactooligosaccharides, trans-oligosaccharide (TOS), trans-galactooligosaccharide (TGOS), and trans-galactooligosaccharide) are oligomers or polymers of galactose molecules ending mainly with a glucose or sometimes ending with a galactose molecule and have varying degree of polymerization (generally the DP is between 2-20) and type of linkages. In one embodiment, GOS comprises galactose and glucose molecules. In another embodiment, GOS comprises only galactose molecules. In a further embodiment, GOS are galactose-containing oligosaccharides of the form of [β-D-Gal-(1-6)]$_n$-β-D-Gal-(1-4)-D-Glc wherein n is 2-20. In another embodiment, GOS are galactose-containing oligosaccharides of the form Glc α1-4[β Gal 1-6]$_n$ where n=2-20. In another embodiment, GOS are in the form of α-D-Glc (1-4)-[β-D-Gal-(1-6)-]$_n$ where n=2-20. Gal is a galactopyranose unit and Glc (or Glu) is a glucopyranose unit.

In one embodiment, a prebiotic composition comprises a GOS-related compound. A GOS-related compound can have the following properties: a) a "lactose" moiety; e.g., GOS with a gal-glu moiety and any polymerization value or type of linkage; or b) be stimulatory to "lactose fermenting" microbes in the human GI tract; for example, raffinose (gal-fru-glu) is a "related" GOS compound that is stimulatory to both lactobacilli and bifidobacteria.

In one embodiment, a prebiotic composition comprises GOS with a low degree of polymerization. In one embodiment a prebiotic composition comprising GOS with a low degree of polymerization increases growth of probiotic and select commensal bacteria to a greater extent than an equivalent amount of a prebiotic composition comprising GOS with a high degree of polymerization. In one embodiment, a prebiotic composition comprising a high percentage of GOS with a low degree of polymerization increases growth of probiotic and beneficial commensal bacteria to a greater extent than an equivalent amount of a prebiotic composition comprising a low percentage of GOS with a low degree of polymerization. In one embodiment a prebiotic composition comprises GOS with a degree of polymerization less than 20, such as less than 10, less than 9, less than 8, less than 7, less than 6, less than 5, less than 4, or less than 3. In another embodiment a prebiotic composition comprising GOS with a low degree of polymerization increases growth of probiotic and/or beneficial commensal microbes in the GI tract of a subject.

2. GOS Synthesis

GOS is found in human and bovine maternal milk. GOS can be produced from lactose syrup using the transgalactosylase activity of the enzyme β-galactosidase (Crittenden, (1999) Probiotics: A Critical Review. Tannock, G. (ed) Horizon Scientific Press, Wymondham, pp. 141-156). β-D-galactosidase is known to catalyze not only the hydrolysis of the β-D-galactoside linkage of lactose to give D-glucose and D-galactose but also to carry out transgalactosylation reactions where the D-galactosyl group of a β-D-galactoside is transferred onto a hydroxylated acceptor. For example, when a β-D-galactoside such as lactose or another carbohydrate is present, it is possible to obtain new glycoside linkages between the D-galactose unit and the acceptor. The starting galactoside such as lactose can also be present in a GOS mixture following the transgalactosylation reactions. As used herein, GOS comprises one or more saccharides that have been produced from a glycoside and the transgalactosylation reaction of a β-galactosidase. Thus, GOS includes saccharides such as transgalactosylated oligosaccharides (i.e. transgalacto-oligosaccharides) or transgalactosylate disaccharides. The DP of the formed oligosaccharide can vary, typically from 2-20, depending on the enzyme source. In one embodiment, a GOS composition is a blend of one more saccharides with a DP range of 2-6 (i.e. di- through hexasaccharides). In another embodiment, a GOS composition is a blend of one or more saccharides with a DP range of 2-8 (i.e. di- through octasaccharides). In another embodiment, a GOS composition is a blend of one or more saccharides with a DP range of greater than 8. In yet another embodiment, a GOS composition is a blend of one or more saccharides with a DP range of 9-15. In another embodiment, a GOS composition is a blend of one or more saccharides with a DP of 1, a DP range of 2-6, a DP range of 6-8, and DP range of greater than 8.

3. GOS Linkages

Linkages between the individual sugar units found in GOS include β-(1-6), β-(1-4), β-(1-3) and β-(1-2) linkages. β-(1-3) linkages are less common than β-(1-6) or β-(1-4) linkages. In one embodiment, GOS comprises a number of β-(1-6) linked or β-(1-4) galactopyranosyl units linked to a terminal glucopyranosyl residue through an α-(1-4) glycosidic bond. In another embodiment, GOS comprises a number of β-(1-6) linked or β-(1-4) galactopyranosyl units linked to a terminal glucopyranosyl residue through a β-(1-4) glycosidic bond. In another embodiment, GOS formed by transgalactosylation comprise β-D-galactopyranosyl-(1-3) linkages. In one embodiment, GOS are branched saccharides. Branched oligosaccharides can be formed as an artifact of the transgalactosylation reaction. In another embodiment, GOS are linear saccharides. Non-limiting GOS examples include the following shown below:

contains 36% tri-, tetra-, penta- and hexa-GOS, 16% disaccharides galactosyl-glucose and galactosyl-galactose, 38% monosaccharides, and 10% lactose.

In one embodiment a strain of *Bifidobacterium bifidum* (for example, accession number NCIMB 41171) produces a galactosidase activity that converts lactose to a GOS mixture comprising the disaccharide Gal α (1-6) Gal, at least one trisaccharide selected from Gal β (1-6)-Gal β (1-4)-Glc and Gal β (1-3)-Gal β (1-4)-Glc, the tetrasaccharide Gal β (1-6)-Gal β (1-6)-Gal β (1-4)-Glc and the pentasaccharide Gal β (1-6)-Gal β (1-6)-Gal β (1-6)-Gal β (1-4)-Glc. In one embodiment, a GOS composition is a mixture of 10 to 45% w/v of the disaccharide, 10 to 45% w/v of the trisaccharide, 10 to 45% w/v of the tetrasaccharide and 10 to 45% w/v of the pentasaccharide.

In another embodiment, a GOS composition is a mixture of oligosaccharides comprising 20-28% by weight of β (1-3) linkages, 20-25% by weight of β (1-4) linkages, and 45-55% by weight of β (1-6) linkages. In one embodiment, a GOS composition is a mixture of oligosaccharides comprising 26% by weight of β (1-3) linkages, 23% by weight of β (1-4) linkages, and 51% by weight of β (1-6) linkages.

Alpha-GOS (also called alpha-bond GOS or alpha-linked GOS) are oligosaccharides having an alpha-galactopyranosyl group. Alpha-GOS comprises at least one alpha glycosidic linkage between the saccharide units. Alpha-GOS are generally represented by α-(Gal)$_n$ (n usually represents an integer of 2 to 10) or α-(Gal)$_n$ Glc (n usually represents an

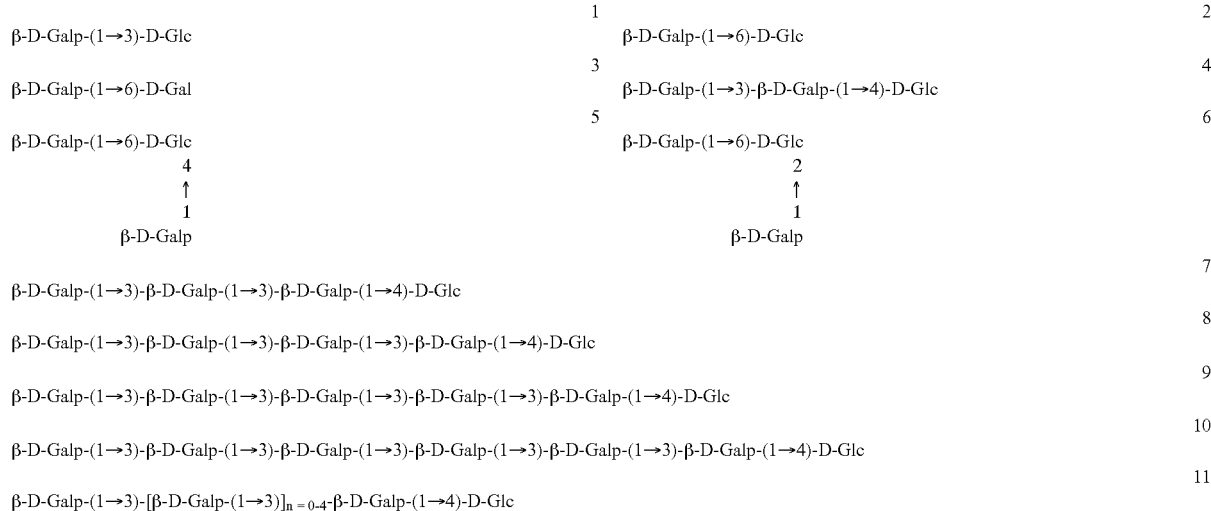

integer of 1 to 9). Examples include a mixture of α-galactosylglucose, α-galactobiose, α-galactotriose, α-galactotetraose, and higher oligosaccharides. Additional non-limiting examples include melibiose, manninootriose, raffinose, stachyose, and the like, which can be produced from beat, soybean oligosaccharide, and the like.

Commercially available and enzyme synthesized alpha-GOS products are also useful for the compositions described herein. Synthesis of alpha-GOS with an enzyme is conducted utilizing the dehydration condensation reaction of α-galactosidase with the use of galactose, galactose-containing substance, or glucose as a substrate. The galactose-containing substance includes hydrolysates of galactose-containing substances, for example, a mixture of galactose and glucose obtained by allowing beta-galactosidase to act The source of the β-galactosidase can determine the GOS end products from transgalactosylation reactions. For example, β-galactosidase from *Streptococcus thermophilus* can produce a collection of transgalactosylated disaccharides including Galβ (1-6) Glc, Galβ (1-3) Glc, Galβ (1-2) Glc, and Galβ (1-6) Gal (Matsumoto et al., (1992), Chapter 5: Galactooligosaccharides, in Japanese Technology Reviews, ed. by Karbe, I., Gordon and Breach, NY, pp. 90-160). Transgalactosylated oligosaccharides (TOS) can be produced using β-galactosidase from *Aspergillus oryzae* (Tanaka et al, (1983) *Bifidobacteria Microflora*, 2, 17-24), and consists of tri-, tetra-, penta- and hexa-GOS. In another embodiment GOS are prepared using β-galactosidase from *A. oryzae* and *Streptococcus thermophilus* (Ito et al., (1990), *Microbial Ecology in Health and Disease*, 3, 285-292) and on lactose, and the like. Glucose can be mixed separately with galactose and be used as a substrate with α-galactosidase (see e.g., WO 02/18614). Methods of preparing alpha-GOS have been described (see e.g., EP1514551 and EP2027863).

In one embodiment, a GOS composition comprises a mixture of saccharides that are alpha-GOS and saccharides that are produced by transgalactosylation using β-galactosidase. In another embodiment, GOS comprises alpha-GOS. In another embodiment, alpha-GOS comprises α-(Gal)$_2$ from 10% to 100% by weight. In one embodiment, GOS comprises only saccharides that are produced by transgalactosylation using β-galactosidase.

In one embodiment, a GOS composition can comprise GOS with alpha linkages and beta linkages.

4. GOS Saccharide Unit Composition

In one embodiment, a GOS composition is a mixture of oligosaccharides comprising 1-20% by weight of di-saccharides, 1-20% by weight tri-saccharides, 1-20% by weight tetra-saccharide, and 1-20% by weight penta-saccharides. In another embodiment, a GOS composition is a mixture of oligosaccharides consisting essentially of 1-20% by weight of di-saccharides, 1-20% by weight tri-saccharides, 1-20% by weight tetra-saccharide, and 1-20% by weight penta-saccharides. In one embodiment, a GOS composition is a mixture of oligosaccharides comprising 1-20% by weight of saccharides with DP of 1-3, 1-20% by weight of saccharides with DP of 4-6, 1-20% by weight of saccharides with DP of 7-9, and 1-20% by weight of saccharides with DP of 10-12, 1-20% by weight of saccharides with DP of 13-15.

In another embodiment, a GOS composition is a 1:1:1:1:1 ratio of saccharides with a DP of 2:3:4:5:6. In one embodiment, a GOS composition is a 1:2:3:2:1:1 ratio of saccharides with a DP of 1:2:3:4:5:6. In another embodiment, a GOS composition is a (12 to 13):(4 to 5):1 ratio of saccharides with a DP of 3:4:5. In one embodiment, a GOS composition is a 12.3:4.8:1 ratio of saccharides with a DP of 3:4:5. In one embodiment, a GOS composition is a (8-10):(10-15):(4-6):(1-3) ratio of saccharides with a DP of 2:3:4:5.

In another embodiment, a GOS composition is a mixture of oligosaccharides comprising 50-55% by weight of di-saccharides, 20-30% by weight tri-saccharides, 10-20% by weight tetra-saccharide, and 1-10% by weight penta-saccharides. In one embodiment, a GOS composition is a mixture of oligosaccharides comprising 52% by weight of di-saccharides, 26% by weight tri-saccharides, 14% by weight tetra-saccharide, and 5% by weight penta-saccharides.

In another embodiment, a GOS composition is a mixture of oligosaccharides comprising 45-55% by weight tri-saccharides, 15-25% by weight tetra-saccharides, 1-10% by weight penta-saccharides. In another embodiment, a GOS composition is a mixture of oligosaccharides comprising 49.3% by weight tri-saccharides, 19% by weight tetra-saccharides, 4% by weight penta-saccharides.

In another embodiment, a GOS composition is a mixture of oligosaccharides comprising 2-5% by weight of a mixture of tri- to hexa-saccharides, 25-35% by weight Galβ (1-6) Glc, 5-15% by weight Galβ (1-3) Glc, 5-15% by weight Galβ (1-2) Glc, 25-30% by weight Galβ (1-6) Gal, and 1-5% by weight Galβ (1-3) Gal, and optionally further contains one or more digestible saccharides or oligosaccharides. In another embodiment, a GOS composition is a mixture of oligosaccharides comprising 3.9% by weight of a mixture of tri- to hexa-saccharides, 32.6% by weight Galβ (1-6) Glc, 7.6% by weight Galβ (1-3) Glc, 9.4% by weight Galβ (1-2) Glc, 27.2% by weight Galβ (1-6) Gal, and 2.5% Galβ (1-3) Gal, and optionally further contains one or more digestible saccharides or oligosaccharides. Digestible saccharides or oligosaccharides are carbohydrates that can be digested by the human digestive system, and include but are not limited to lactose, galactose, or glucose. In one embodiment digestible saccharides found in a GOS composition comprise lactose, galactose, or glucose. In another embodiment, a GOS composition is a mixture of non-digestible oligosaccharides and lactose, glucose or galactose. In another embodiment, a GOS composition is composed of 62% by weight oligosaccharides and 38% digestible saccharides.

5. GOS and Saccharimetric Measurement

In another embodiment, a GOS composition comprises a mixture of oligosaccharides, wherein the composition has a saccharimetric measurement at least about 50, 55, 60, 65, 70, 75, 80, 85, 90, 95, or 100 degrees Brix. In another embodiment, a GOS composition comprises a mixture of oligosaccharides, wherein the composition has a saccharimetric measurement of between about 50-100, 50-80, 60-80, or 70-80 degrees Brix. In another embodiment, a GOS composition has a saccharimetric measurement of between about 72 and 78 degrees Brix. For example, a GOS composition can comprise greater than about 93% GOS and have a saccharimetric degree of 75 degrees Brix. In another embodiment, a GOS composition can comprise greater than about 93% GOS, less than about 5% digestible saccharides (such as lactose, glucose, and galactose), and have a saccharimetric degree of 75± degrees Brix. In yet another embodiment, a GOS composition can comprise greater than about 93% GOS, less than about 5% digestible saccharides, less than about 10 ppm heavy metals, less than 0.1% sulphated ash, and have a saccharimetric measurement of 75 degrees Brix.

In another embodiment a GOS composition can comprise greater than about 95% GOS and have a saccharimetric degree of 75 degrees Brix. In another embodiment, a GOS composition can comprise greater than about 95% GOS, less than about 5% digestible saccharides (such as lactose, glucose, and galactose), and have a saccharimetric degree of 75± degrees Brix. In yet another embodiment, a GOS composition can comprise greater than about 95% GOS, less than about 5% digestible saccharides, less than about 10 ppm heavy metals, less than 0.1% sulphated ash, and have a saccharimetric measurement of 75 degrees Brix.

In another embodiment a GOS composition can comprise greater than about 96% GOS and have a saccharimetric degree of 75 degrees Brix. In another embodiment, a GOS composition can comprise greater than about 96% GOS, less than about 5% digestible saccharides (such as lactose, glucose, and galactose), and have a saccharimetric degree of 75± degrees Brix. In yet another embodiment, a GOS composition can comprise greater than about 96% GOS, less than about 5% digestible saccharides, less than about 10 ppm heavy metals, less than 0.1% sulphated ash, and have a saccharimetric measurement of 75 degrees Brix.

6. Percentages and Amounts of GOS in Prebiotic Compositions

In another embodiment, a prebiotic composition comprises a GOS composition wherein the GOS composition comprises 1-100% by weight GOS. The percentage by weight of GOS refers to the weight of GOS relative to the total dry weight of the GOS composition. In this application, compositions containing GOS may be referred to as GOS [Number], where [Number] refers to the percent by weight of GOS relative to the total dry weight of the GOS composition within the actual composition contains between 90 to 100% of the claimed amount. For example, GOS 60 refers to a composition that contains between 54% and 66% GOS by weight relative to the total dry weight of the composition. In another embodiment, a prebiotic composition comprises a GOS composition wherein the GOS composition comprises about 1% by weight GOS. In another embodiment, a prebiotic composition comprises a GOS composition wherein the GOS composition comprises about 5% by weight GOS. In another embodiment, a prebiotic composition comprises a GOS composition wherein the GOS composition comprises about 10% by weight GOS. In another embodiment, a prebiotic composition comprises a GOS composition wherein the GOS composition comprises about 20% by weight GOS. In another embodiment, a prebiotic composition comprises a GOS composition wherein the GOS composition comprises about 30% by weight GOS. In another embodiment, a prebiotic composition comprises a GOS composition wherein the GOS composition comprises about 40% by weight GOS. In another embodiment, a prebiotic composition comprises a GOS composition wherein the GOS composition comprises about 50% by weight GOS. In another embodiment, a prebiotic composition comprises a GOS composition wherein the GOS composition comprises about 60% by weight GOS. In another embodiment, a prebiotic composition comprises a GOS composition wherein the GOS composition comprises about 70% by weight GOS. In another embodiment, a prebiotic composition comprises a GOS composition wherein the GOS composition comprises 72.3% by weight GOS. In another embodiment, a prebiotic composition comprises a GOS composition wherein the GOS composition comprises about 80% by weight GOS. In another embodiment, a prebiotic composition comprises a GOS composition wherein the GOS composition comprises about 85% by weight GOS. In another embodiment, a prebiotic composition comprises a GOS composition wherein the GOS composition comprises about 90% by weight GOS. In another embodiment, a prebiotic composition comprises a GOS composition wherein the GOS composition comprises about 91% by weight GOS. In another embodiment, a prebiotic composition comprises a GOS composition wherein the GOS composition comprises about 92% by weight GOS. In another embodiment, a prebiotic composition comprises a GOS composition wherein the GOS composition comprises about 93% by weight GOS. In another embodiment, a prebiotic composition comprises a GOS composition wherein the GOS composition comprises about 94% by weight GOS. In another embodiment, a prebiotic composition comprises a GOS composition wherein the GOS composition comprises about 95% by weight GOS. In another embodiment, a prebiotic composition comprises a GOS composition wherein the GOS composition comprises about 96% by weight GOS. In another embodiment, a prebiotic composition comprises a GOS composition wherein the GOS composition comprises about 96.8% by weight GOS. In another embodiment, a prebiotic composition comprises a GOS composition wherein the GOS composition comprises about 97% by weight GOS. In another embodiment, a prebiotic composition comprises a GOS composition wherein the GOS composition comprises about 98% by weight GOS. In another embodiment, a prebiotic composition comprises a GOS composition wherein the GOS composition comprises about 99% by weight GOS. In another embodiment, a prebiotic composition comprises a GOS composition wherein the GOS composition comprises about 100% by weight GOS. In another embodiment, a prebiotic composition comprises a GOS composition wherein the GOS composition comprises between 0.1% and 100% GOS. In another embodiment, a prebiotic composition comprises a GOS composition wherein the GOS composition comprises about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79% 80%, 81%, 82%, 83%, 84%, 85%, 86%, 87%, 88%, 89%, 90%, 91%, 92%, 93%, 94%, 95%, 96%, 97%, 98%, 99%, 99.5%, or 100% by weight GOS. The percentage by weight of GOS refers to the weight of GOS relative to the total dry weight of the prebiotic or GOS composition.

In another embodiments, a prebiotic composition or pharmaceutical composition comprises a GOS composition, wherein the GOS composition comprises about 90%, 90.1%, 90.2%, 90.3%, 90.4%, 90.5%, 90.6%, 90.7%, 90.8%, 90.9%, 91%, 91.1%, 91.2%, 91.3%, 91.4%, 91.5%, 91.6%, 91.7%, 91.8%, 91.9%, 92%, 92.1%, 92.2%, 92.3%, 92.4%, 92.5%, 92.6%, 92.7%, 92.8%, 92.9%, 93%, 93.1%, 93.2%, 93.3%, 93.4%, 93.5%, 93.6%, 93.7%, 93.8%, 93.9%, 94%, 94.1%, 94.2%, 94.3%, 94.4%, 94.5%, 94.6%, 94.7%, 94.8%, 94.9%, 95%, 95.1%, 95.2%, 95.3%, 95.4%, 95.5%, 95.6%, 95.7%, 95.8%, 95.9%, 96%, 96.1%, 96.2%, 96.3%, 96.4%, 96.5%, 96.6%, 96.7%, 96.8%, 96.9%, 97%, 97.1%. 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, 100% by weight GOS. The percentage by weight of GOS refers to the weight of GOS relative to the total dry weight of the prebiotic or GOS composition.

In another embodiment, a prebiotic composition comprises a GOS composition wherein the GOS composition comprises about 1-90%, about 10-90%, about 20-90%, about 30-90%, about 40-90%, about 40-80%, about 40-70%, about 40-60%, about 40-50%, about 50-90%, about 50-80%, about 50-70%, about 50-60%, about 60-90%, about 60-80%, about 60-70%, about 70-90%, about 70-80%, about 70-90%, about 70-80%, about 80-90%, about 90-96%, about 93-96%, about 93-95%, about 94-98%, about 93-99%, or about 90-100% by weight GOS. The percentage by weight of GOS refers to the weight of GOS relative to the total dry weight of the prebiotic or GOS composition.

In another embodiment a prebiotic composition comprises 0.01-20 g of a GOS composition, such as about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or about 20 g of GOS composition. In another embodiment a prebiotic composition comprises about 0.1-2 g of a GOS composition.

A prebiotic product can comprise GOS for improving gut health by promoting the growth of bifidobacteria in the gut. In one embodiment, high purity GOS compositions (about or greater than 85% GOS by weight, e.g. GOS 95) selectively increases intestinal populations of beneficial bacteria or enteric colonization of lactose metabolizing bacteria, such as bifidobacteria and lactobacilli, without increasing the growth of harmful bacteria or without a similar and proportionate increase in many undesirable microbes, such as *Escherichia coli* (*E. coli*). This can be in contrast to compositions with lower percentage by weight GOS. For example, contaminating simple carbohydrates (e.g., glucose, galactose, lactose) may have been sufficient to stimulate the growth of *E. coli* strains to levels equal to free glucose. Thus, higher purity GOS formulations can have a greater potential to selectively promote the growth of beneficial lactobacilli and bifidobacteria. Increased colonization of lactose metabolizing colonic bacteria, such as beneficial, lactose-fermenting lactobacilli and bifidobacteria, has been associated with increased β-galactosidase activity and GOS utilization, thereby increasing the fermentation of lactose into galactose, glucose and short chain fatty acids. In one embodiment, a high purity GOS composition reduces lactose-derived gas production and mitigates the symptoms of lactose intolerance. In one embodiment, metabolism of a GOS composition by lactobacilli and bifidobacteria yields organic acids and other agents that inhibit enteric pathogens. In another embodiment, a GOS composition provides a selective advantage for organisms in the gut that can use them. In another embodiment, a GOS composition acts as anti-adhesives for bacteria in the gut. In another embodiment a mixture of oligosaccharides is useful for the preparation of a medicament for preventing the adhesion of pathogens or toxins produced by pathogens to the gut wall. In another embodiment, the beneficial effect of high purity GOS compositions on the bacterial flora is with acute administration (≤30 days). In one embodiment, the dose of GOS (~95%) is titrated from a starting dose as low as 1.5 g/day to a final dose of 12 g/day (6 g BID) at the end of either a 15-day or 30-day treatment period. In one embodiment, the dose of GOS (~95%) is equivalent to 200 mg/kg/day for a 60 kg adult.

In one embodiment a composition is provided that comprises a suitable amount of a prebiotic composition that is effective for promoting the growth of probiotics such that fermentation in the gut is slowed or gastrointestinal health is improved. In one embodiment prebiotics can be administered in an amount per serving from about 1 mg to about 20 g, or about 1 mg to about 15 g, or about 1 mg to about 10 g, or about 1 mg to about 5 g, or about 2 mg to about 1000 mg, or about 2 mg to about 500 mg, or about 2 mg to about 200 mg, or about 2 mg to about 100 mg, or about 2 mg to about 50 mg, or about 2 mg to about 20 mg, or about 5 mg to about 10 mg, or about 5, 6, 7, 7.5, 8, 9, or 10 mg or about 0.25 g to about 1.7 g. In another embodiment a prebiotic can be administered in an amount per serving of about 1 g, about 2 g, about 3 g, about 4 g, about 5 g, about 6 g, about 7 g, about 8 g, about 9 g, about 10 g, about 11 g, about 12 g, about 13 g, about 14 g, about 15 g, about 16 g, about 17 g, about 18 g, about 19 g, or about 20 g. In another embodiment, the prebiotic used can be from about 0.1 g to about 15 g, or about 0.1 g to about 1 g, or about 0.1 g to about 0.5 g or about 0.1 g to about 2 g, or about 0.5 g to about 1 g, or about 0.2 g to about 1 g, or about 1 g to about 5 g, or about 1 g to about 15 g per serving.

In one embodiment, the smallest effective amount of prebiotic is used. The prebiotic can be about 0.5% to about 100% by weight of a prebiotic composition. In one embodiment a prebiotic composition (e.g., GOS) can be administered in a dose from about 1 mg to about 25 g, or about 1 mg to about 5 g, or about 1 mg to about 1000 mg, or about 1 mg to about 500 mg, or about 1 mg to about 200 mg, or about 1 mg to about 100 mg, or about 1 mg to about 50 mg, or about 2 mg to about 20 mg, or about 5 mg to about 10 mg, or about 5, 6, 7, 7.5, 8, 9, or 10 mg. In another embodiment, a prebiotic composition is used in a dose of about 7.5 mg. In one embodiment the dose of a prebiotic composition administered to a subject can be increased from about 1 g to about 10 g over time. In one embodiment an initial dose of a prebiotic composition can be 1-3 grams. This dose can be increased over time (e.g., days or a week) so that the final dose is about 10 g of GOS. In one embodiment, a high percentage GOS composition (e.g., GOS 95) is derived from a lower percentage GOS composition (e.g., GOS 60). In one embodiment, a high percentage GOS composition is a purified form of the food ingredient β-linked galacto-oligosaccharide.

In one embodiment, the GOS has a molecular weight of $342.29+(162.15)_{n-1}$, and an empirical formula of $C_{n6}H_{22+(n-1)10}O_{6+n5}$. In one embodiment, the GOS has one or more of the following physical characteristics: clear or pale yellow syrup, sweet taste, freely soluble in water, slightly soluble in alcohols, insoluble in ether and chlorinated solvents, and a density >1.30 gram/mL.

In one embodiment, a GOS composition is an odorless, colorless to pale yellow, viscous liquid or syrup. In one embodiment, a GOS syrup is filled directly into high density polyethylene (HDPE) bottles containing one dose per bottle, without additional ingredients. In one embodiment, a GOS composition has the specification as shown in Table 1.

TABLE 1

Example of a GOS composition specification

| Parameter | Method | Acceptance Criteria |
|---|---|---|
| Appearance | Visual | Clear, slightly yellow viscous syrup |
| Identification | HPLC | Retention time matches that of reference material |
| Assay | HPLC | 90-110% label claim |
| Related substances | HPLC | Report related substances and individual impurities ≥LOQ (≥0.05% of sum of GOS peaks) Report total related substances and impurities |
| Dose Variation | USP <905> | Complies |
| Deliverable Volume | USP <698> | Complies |
| Microbial Limits | USP <61> | Complies |

In one embodiment, a GOS syrup is stable when filled into HDPE bottles fitted with the cap. In one embodiment, capped bottles containing low and high dose GOS compositions have a stability at 25° C./60% RH and 40° C./75% RH for at least six months.

In one embodiment, a lower percentage GOS composition is purified to a pharmaceutical grade by the elimination of residual glucose, lactose and galactose by the organisms used in making bread (*Saccharomyces cerevisiae*) and yogurt (*Streptococcus thermophilis*) to yield a high percentage GOS composition. Further processing can include ultrafiltration, nanofiltration, decolorization, deionization, and concentration to yield high percentage GOS compositions. High percentage GOS compositions can contain the same galacto oligosaccharides as low percentage GOS compositions. In one embodiment, the lower purity GOS composition is non-digestible fibers derived from lactose. In one embodiment, high percentage GOS compositions are manufactured according to the process outlined in FIG. 19. In one embodiment, the purity of a high percentage GOS composition (e.g., GOS 95) is assessed by high performance liquid chromatography (HPLC) analysis.

7. GOS and Other Components of GOS Compositions

Table 2 contains a product specification for a high purity GOS composition (GOS 95), illustrating the criteria used to evaluate purity of a GOS composition such as GOS 95.

TABLE 2

Specification for a high purity GOS composition (GOS 95)

| Test | Results |
| --- | --- |
| Appearance | Colorless or slightly yellow syrup |
| Saccharometric degrees | 75 ± 3° Brix |
| Purity HPLC | |
| $\Sigma_{GOS}$ | >93% RS |
| $\Sigma_{lactose+glucose+galactose}$ | <5% RS |
| Density | >1.300 g/mL |
| Color (420 nm) | <0.5 AU |
| Appearance of 10% solution | Clear and colorless |
| pH (10% solution) | 3.0 ÷ 7.0 |
| Conductivity (10% solution) | <100 μS/cm |
| Viscosity | Run and report |
| Specific Optical rotation (10% solution) | +48.0° ÷ +55.0° |
| Heavy metals ($Pb^{2+}$) | ≤10 ppm |
| Sulphated ash | ≤10% |
| Organic volatile impurity | |
| Ethanol | <5000 ppm |
| Methanol | <3000 ppm |
| Microbiology | |
| Bacterial count | <100 ufc/g |
| Mould and yeasts | <10 ufc/g |
| E. Coli | Absent/g |
| Salmonella sp | Absent/10 g |

Table 3 contains data from a certificate of analysis of a 96.8% GOS composition, illustrating other components that can be in a prebiotic composition comprising a GOS composition.

TABLE 3

Certificate of analysis

| Test | Results |
| --- | --- |
| Refractometric dried substance | 76.5° BxRDS |
| Purity GOS | 96.8% |
| Related substances | |
| Lactose | 2.0% |
| Glucose | <0.1% |
| Galactose | 1.1% |
| Density | 1,383 g/ml |
| Color (420 nm) | 0.041 A.U. |
| Appearance of solution | Clear |
| pH (10% solution) | 5.8 |
| Conductance (10% solution) | 22.7 μS/cm |
| Viscosity | 7295 cP |
| Organic Volatile Impurities | |
| Methanol | 17.0 ppm |
| Ethanol | <10 ppm |
| Heavy metals ($Pb^{2+}$) | <10 ppm |
| Sulphated ashes | 0.07% |
| Specific optical rotation | +44.6° |
| T.A.M.C. (total aerobic microbial count) | 40 cfu/ml |
| T.Y.M.C. (total combined Yeasts and Molds count) | 5 cfu/ml |
| Salmonella s. | Absent cfu/10 ml |
| Escherichia coli | Absent cfu/ml |

In one embodiment, a prebiotic composition comprises a GOS composition wherein the GOS composition comprises about 70% by weight GOS, about 3% by weight moisture, about 30% by weight other saccharides, about 0.1% by weight ash, about 1 ppm heavy metal (e.g., Pb), and about 1 ppm arsenic ($As_2O_3$). In another embodiment, a prebiotic composition comprises a GOS composition wherein the GOS composition comprises about 70-75% by weight GOS, about 1-3% by weight moisture, about 20% by weight lactose, less than 1% by weight glucose, less than 1% by weight galactose, about 0.1% by weight ash, about 1 ppm heavy metal (e.g., Pb), and about 1 ppm arsenic ($As_2O_3$).

In another embodiment a GOS composition comprises GOS and one or more of water or digestible saccharides. In one embodiment a GOS composition comprises less than about 10 ppm of a heavy metal (such as arsenic or lead), including but not limited to less than about 10, 9, 8, 7, 6, 5, 4, 3, 2, or 1 ppm of a heavy metal. In another embodiment a GOS composition comprises less than about 0.10% sulphated ash, including but not limited to less than about 0.9, 0.8, 0.7, 0.6, 0.5, 0.4, 0.3, 0.2, or 0.1% sulphated ash. In another embodiment, a GOS composition can comprise greater than about 90% GOS, less than about 5% digestible saccharides, less than about 10 ppm of heavy metals, and less than about 0.10% sulphated ash. In another embodiment, a GOS composition comprises less than about 5000 ppm ethanol and less than about 3000 ppm methanol. In another embodiment, a GOS composition comprises a bacterial count of less than about 100 cfu/g, and a mold count of less than about 10 cfu/g.

In one embodiment, a GOS composition comprises about 1-90%, about 10-90%, about 20-90%, about 30-90%, about 40-90%, about 40-80%, about 40-70%, about 40-60%, about 40-50%, about 50-90%, about 50-80%, about 50-70%, about 50-60%, about 60-90%, about 60-80%, about 60-70%, about 70-90%, about 70-80%, about 70-90%, about 70-80%, about 80-90%, about 92-100%, about 93-99%, about 94-98%, about 92-96%, about 93-96%, or about 93-95% by weight GOS and less than about 10 ppm heavy metals and less than about 0.10% sulphated ash. Standard analytical methods can be used to determine the amount of the various components in the prebiotic or GOS composition, such as but not limited to HPLC, colorimetry (e.g., sodium sulfide colorimetry), or spectrophotometry (e.g., atomic absorption spectrophotometry).

In another embodiment, the absorbance of a GOS composition at about $A_{420}$ can be from about 0.3 AU to about 0.6 AU. In another embodiment, the pH of a GOS composition can be from about 3 to about 7. In one embodiment, the conductance of a GOS composition can be less than about 100 μS/cm.

Figure 11:
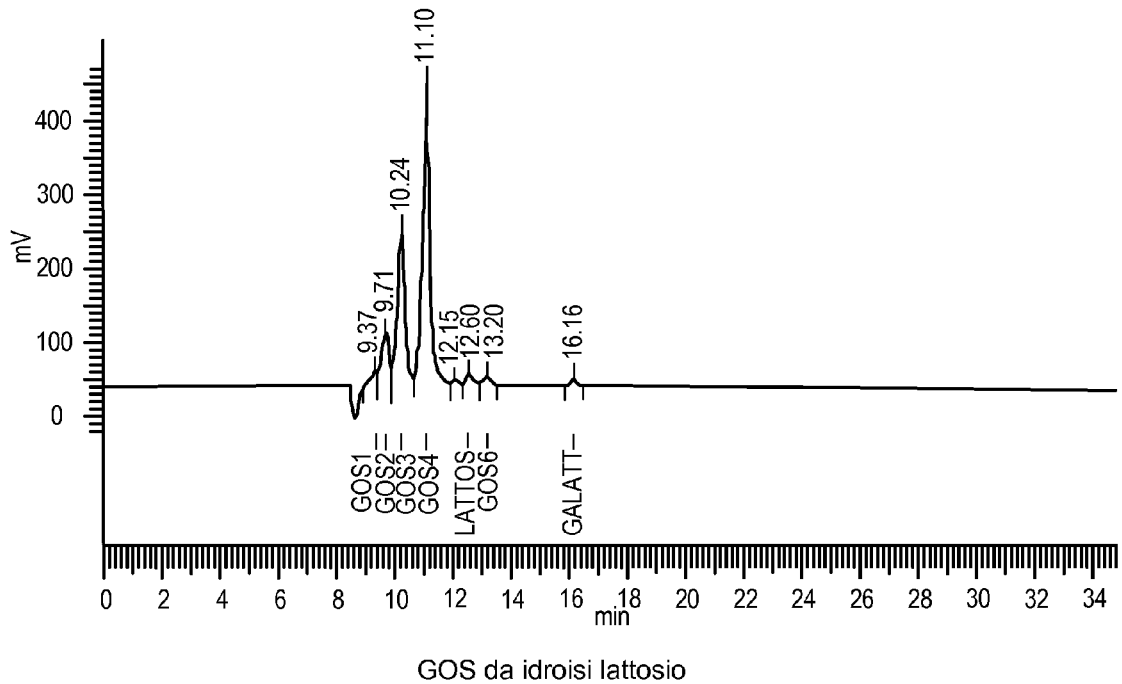
FIG. 11 illustrates an HPLC chromatograph of a sample containing high purity GOS.

FIG. 11 illustrates an HPLC chromatograph of a sample of one embodiment of a high purity GOS composition.

8. GOS and Digestible Saccharides

In one embodiment, a GOS composition can comprise about 1-5% digestible saccharides, such as lactose, glucose or galactose. In another embodiment, a GOS composition can comprise about 0.001 to about 1% glucose or about 0.01 to about 0.1% glucose. In another embodiment, a GOS composition can comprise about 0.1% galactose to about 2% galactose. In another embodiment, the density of a GOS composition can be about 1200 to about 1500 g/mL.

In one embodiment, a GOS composition comprises about 1-90%, about 1-80%, about 1-70%, about 1-60%, about 1-50%, about 1-40%, about 40-90%, about 40-80%, about 40-70%, about 40-60%, about 40-50%, about 50-90%, about 50-80%, about 50-70%, about 50-60%, about 60-90%, about 60-80%, about 60-70%, about 70-90%, about 70-80%, about 70-90%, about 70-80%, about 80-90%, about 90-96%, about 93-96%, about 93-95%, about 94-98%, about 93-99%, or about 92-100% by weight GOS and no digestible saccharides. In another embodiment, a prebiotic composition comprises a GOS composition wherein the GOS composition comprises about 1-90%, about 1-80%, about 1-70%, about 1-60%, about 1-50%, about 1-40%, about 40-90%, about 40-80%, about 40-70%, about 40-60%, about 40-50%, about 50-90%, about 50-80%, about 50-70%, about 50-60%, about 60-90%, about 60-80%, about 60-70%, about 70-90%, about 70-80%, about 70-90%, about 70-80%, about 80-90%, about 92-100%, about 93-99%, about 94-98%, about 92-96%, about 93-96%, or about 93-95% by weight GOS and less than about 6% (such as about 5, 4, 3, 2, or 1%) digestible saccharides.

In one embodiment a GOS composition comprises about 70% GOS and about 20% digestible saccharides. In another embodiment a GOS composition comprises about 70-75% GOS and about 5-30% digestible saccharides.

In another embodiment a GOS composition comprises about 1%, 5%, 10%, 15%, 20%, 25%, 30%, 35%, 40%, 45%, 50%, 55%, 60%, 65%, 70%, 75%, 80%, 85%, 90%, 91%, 92%, or 95% by weight GOS and about 1-10% by weight digestible saccharides. In one embodiment these digestible saccharides are byproducts of the GOS synthesis process.

In one embodiment a GOS composition comprises about 92% GOS. In another embodiment a GOS composition comprises about 92% GOS and digestible saccharides. In another embodiment a GOS composition comprises about 92% GOS and about 8% digestible saccharides. In another embodiment a GOS composition comprises about 92% GOS and no digestible saccharides. In another embodiment a GOS composition comprises about 92% GOS and no lactose, glucose, or galactose. In another embodiment a GOS composition comprises about 92% GOS and about 1-8% digestible saccharides. In another embodiment a GOS composition comprises about 92% by weight GOS and about 8% by weight digestible saccharides. In another embodiment a GOS composition comprises about 92% by weight GOS and about 5% by weight digestible saccharides.

In one embodiment a GOS composition comprises about 93% GOS. In another embodiment a GOS composition comprises about 93% GOS and digestible saccharides. In another embodiment a GOS composition comprises about 93% GOS and about 7% digestible saccharides. In another embodiment a GOS composition comprises about 93% GOS and no lactose. In another embodiment a GOS composition comprises about 93% GOS and no lactose, glucose, or galactose. In another embodiment a GOS composition comprises about 93% GOS and about 1-7% digestible saccharides. In another embodiment a GOS composition comprises about 93% by weight GOS and about 1-7% by weight digestible saccharides. In another embodiment a GOS composition comprises about 93% by weight GOS and about 7% by weight digestible saccharides. In another embodiment a GOS composition comprises about 93% by weight GOS and about 5% by weight digestible saccharides.

In one embodiment a GOS composition comprises about 94% GOS. In another embodiment a GOS composition comprises about 94% GOS and digestible saccharides. In another embodiment a GOS composition comprises about 94% GOS and about 6% digestible saccharides. In another embodiment a GOS composition comprises about 94% GOS and no lactose. In another embodiment a GOS composition comprises about 94% GOS and no lactose, glucose, or galactose. In another embodiment a GOS composition comprises about 94% GOS and about 1-6% digestible saccharides. In another embodiment a GOS composition comprises about 94% by weight GOS and about 5% by weight digestible saccharides.

In one embodiment a GOS composition comprises about 95% GOS. In another embodiment a GOS composition comprises about 95% GOS and digestible saccharides. In another embodiment a GOS composition comprises about 95% by weight GOS and about 5% by weight digestible saccharides. In another embodiment a GOS composition comprises about 95% GOS and no lactose. In another embodiment a GOS composition comprises about 95% GOS and no lactose, glucose, or galactose. In another embodiment a GOS composition comprises about 95% GOS and about 1-5% digestible saccharides. In another embodiment a GOS composition comprises about 95% by weight GOS and about 1-5% by weight digestible saccharides, such as digestible saccharides.

In one embodiment a GOS composition comprises about 96% GOS. In another embodiment a GOS composition comprises about 96% GOS and digestible saccharides. In another embodiment a GOS composition comprises about 96% by weight GOS and about 4% by weight digestible saccharides. In another embodiment a GOS composition comprises about 96% GOS and no lactose. In another embodiment a GOS composition comprises about 96% GOS and no lactose, glucose, or galactose. In another embodiment a GOS composition comprises about 96% GOS and about 1-4% digestible saccharides. In another embodiment a GOS composition comprises about 96% by weight GOS and about 1-4% by weight digestible saccharides.

In one embodiment a GOS composition comprises about 97% GOS. In another embodiment a GOS composition comprises about 97% GOS and digestible saccharides. In another embodiment a GOS composition comprises about 97% GOS and about 3% digestible saccharides. In another embodiment a GOS composition comprises about 97% GOS and no lactose. In another embodiment a GOS composition comprises about 97% GOS and no lactose, glucose, or galactose. In another embodiment a GOS composition comprises about 97% GOS and about 1-3% digestible saccharides. In another embodiment a GOS composition comprises about 97% by weight GOS and about 1-3% by weight digestible saccharides. In another embodiment a GOS composition comprises about 97% by weight GOS and about 3% by weight digestible saccharides.

In one embodiment a GOS composition comprises about 98% GOS. In another embodiment a GOS composition comprises about 98% GOS and digestible saccharides. In another embodiment a GOS composition comprises about 98% by weight GOS and about 2% by weight digestible saccharides. In another embodiment a GOS composition comprises about 98% GOS and no lactose. In another embodiment a GOS composition comprises about 98% GOS and no lactose, glucose, or galactose. In another embodiment a GOS composition comprises about 98% GOS and about 0.1-2% digestible saccharides.

In one embodiment a GOS composition comprises about 99% GOS. In another embodiment a GOS composition comprises about 99% GOS and digestible saccharides. In another embodiment a GOS composition comprises about 99% GOS and lactose, glucose, galactose or a combination thereof. In another embodiment a GOS composition comprises about 99% by weight GOS and about 1% by weight digestible saccharides. In another embodiment a GOS composition comprises about 99% GOS and no lactose. In another embodiment a GOS composition comprises about 99% GOS and no lactose, glucose, or galactose. In another embodiment a GOS composition comprises about 99% GOS and about 0.1-1% digestible saccharides.

In one embodiment a GOS composition comprises about 100% GOS.

In some embodiments, a GOS composition comprises about 1%, about 2%, about 3%, about 4%, about 5%, about 6%, about 7%, about 8%, about 9%, about 10%, about 15%, or about 20% by weight of digestible saccharides. In another embodiment a GOS composition comprises about 99.9%, 99.5%, 99%, 98.5%, 98%, 97.5%, 97%, 96.5%, 96%, 95.5%, 95%, 94.5%, 94%, 93.5%, 93%, 92.5%, 92%, 91.5%, 91%, 90.5%, 90%, 80%, 75%, 70%, 65%, 60%, 55%, 50%, 45%, 40%, 35%, 30%, 25%, 20%, 15%, 10%, 5%, or 1% by weight GOS and one or more digestible saccharides.

In one embodiment a prebiotic composition comprises GOS. In one embodiment, a prebiotic composition comprising GOS is a pharmaceutical composition. In one embodiment a prebiotic composition consists essentially of GOS. In one embodiment a prebiotic composition consists essentially of GOS and is prepared or administered without any lactose. In another embodiment a prebiotic composition consists essentially of GOS and comprises one or more digestible saccharides such as lactose, galactose, or glucose. These digestible saccharides can be present in trace amounts (e.g., less than 5% by weight of the composition) and can be byproducts of the synthesis of the GOS.

In one embodiment a prebiotic composition comprising GOS comprises about 70% GOS and about 30% digestible saccharides by weight. For example, 8 g of a prebiotic composition comprising GOS can comprise 5.6 g of GOS, 1.6 g lactose, and 0.8 g of other digestible saccharides.

In one embodiment, a prebiotic composition comprising GOS, and optionally digestible carbohydrates, are used in a method to stimulate lactose fermenting commensal microbes of the human gastrointestinal tract in an adaptation process designed to alleviate lactose intolerance symptoms. In one embodiment, gradual feeding of a prebiotic composition comprising GOS, at increasing doses over a defined time frame, can adapt the lactose fermenting commensal microbes to efficiently metabolize lactose in lactose-intolerant individuals. In one embodiment this adaptation is permanent.

9. GOS and Non-Digestible Saccharides

In one embodiment a prebiotic composition comprises an effective amount of GOS and optionally another non-digestible saccharide. In one embodiment a prebiotic composition increases Beta-galactosidase activity of species of the *Lactobacillus* and/or *Bifidobacterium* species. In another embodiment a prebiotic composition comprises an effective amount of GOS or another non-digestible saccharide to increase the lactase activity of intestinal bacteria (e.g., *Lactobacillus* and/or *Bifidobacterium*) which breaks down the lactose that is not digested by a lactose intolerant human.

In one embodiment a method of treatment is provided for the use of GOS and optionally another non-digestible saccharide to increase Beta-galactosidase activity of lactobacilli or bifidobacteria. In another embodiment a method of treatment is provided for the use of GOS and optionally another non-digestible saccharide to increase the lactase activity of intestinal bacteria (e.g., lactobacilli or bifidobacteria). In another embodiment a method of treatment is provided for the use of GOS and optionally another non-digestible saccharide to prevent, treat, or reduce a symptom of lactose intolerance in a human. In another embodiment a symptom of lactose intolerance in a human is treated, prevented, or reduced by administration of a composition comprising GOS and optionally another non-digestible saccharide.

In one embodiment a prebiotic composition comprises between 80-99.9% GOS and no lactose. In another embodiment, a prebiotic composition comprises between 80-99.9% GOS and 20%-0.1% digestible saccharides. In another embodiment, a prebiotic composition comprises between 80-99.9% GOS, between 0.1-20% digestible saccharides, and between 0.1-20% non-digestible saccharides other than GOS.

In one embodiment a prebiotic composition comprising GOS comprises about 90% GOS and no lactose. For example 8 g of a prebiotic composition comprising GOS can comprise about 7.2 g of GOS. In another embodiment, a prebiotic composition comprises about 90% GOS and about 5% digestible saccharides. For example, 8 g of a prebiotic composition comprising GOS can comprise 7.2 g of GOS and about 0.4 g of digestible saccharides. In another embodiment, a prebiotic composition comprises about 90% GOS, about 5% digestible saccharide, and about 2% non-digestible saccharides other than GOS. For example, 8 g of a prebiotic composition comprising GOS can comprise about 7.2 g of GOS, about 0.4 g digestible saccharide, and about 0.16 g of other non-digestible saccharides.

In one embodiment a prebiotic composition comprising GOS comprises about 91% GOS and no lactose. For example 8 g of a prebiotic composition comprising GOS can comprise about 7.28 g of GOS. In another embodiment, a prebiotic composition comprises about 91% GOS and about 5% digestible saccharides. For example, 8 g of a prebiotic composition comprising GOS can comprise 7.28 g of GOS and about 0.4 g of digestible saccharides. In another embodiment, a prebiotic composition comprises about 91% GOS, about 5% digestible saccharides, and about 2% non-digestible saccharides other than GOS. For example, 8 g of a prebiotic composition comprising GOS can comprise about 7.28 g of GOS, about 0.4 g of digestible saccharides, and about 0.16 g of other non-digestible saccharides.

In one embodiment a prebiotic composition comprising GOS comprises about 92% GOS and no lactose. For example 8 g of a prebiotic composition comprising GOS can comprise about 7.36 g of GOS. In another embodiment, a prebiotic composition comprises about 92% GOS and about 5% digestible saccharides. For example, 8 g of a prebiotic composition comprising GOS can comprise 7.36 g of GOS and about 0.4 g of digestible saccharides. In another embodiment, a prebiotic composition comprises about 92% GOS, about 5% digestible saccharides, and about 2% non-digestible saccharides other than GOS. For example, 8 g of a prebiotic composition comprising GOS can comprise about 7.36 g of GOS, about 0.4 g of digestible saccharides, and about 0.16 g of other non-digestible.

In one embodiment a prebiotic composition comprises about 93% GOS and no lactose. For example 8 g of a prebiotic composition comprising GOS can comprise about 7.44 g of GOS. In another embodiment, a prebiotic composition comprises about 93% GOS and about 5% digestible saccharides. For example, 8 g of a prebiotic composition comprising GOS can comprise 7.44 g of GOS and about 0.4 g of digestible saccharides. In another embodiment, a prebiotic composition comprises about 93% GOS, about 5% digestible saccharides, and about 2% non-digestible saccharides other than GOS. For example, 8 g of a prebiotic composition comprising GOS can comprise about 7.44 g of GOS, about 0.4 g of digestible saccharides, and about 0.16 g of other non-digestible.

In one embodiment a prebiotic composition comprises about 94% GOS and no lactose. For example 8 g of a prebiotic composition comprising GOS can comprise about 7.52 g of GOS. In another embodiment, a prebiotic composition comprises about 94% GOS and about 5% digestible saccharides. For example, 8 g of a prebiotic composition comprising GOS can comprise 7.52 g of GOS and about 0.4 g of digestible saccharides. In another embodiment, a prebiotic composition comprises about 94% GOS, about 5% digestible saccharides, and about 1% non-digestible saccharides other than GOS. For example, 8 g of a prebiotic composition comprising GOS can comprise about 7.52 g of GOS, about 0.4 g of digestible saccharides, and about 0.08 g of other non-digestible saccharides.

In one embodiment a prebiotic composition comprises about 95% GOS and no lactose. For example 8 g of a prebiotic composition comprising GOS can comprise about 7.6 g of GOS. In another embodiment, a prebiotic composition comprises about 95% GOS and about 5% digestible saccharides. For example, 8 g of a prebiotic composition comprising GOS can comprise 7.6 g of GOS and about 0.4 g of digestible saccharides.

In one embodiment a prebiotic composition comprises about 96% GOS and no lactose. For example 8 g of a prebiotic composition comprising GOS can comprise about 7.68 g of GOS. In other embodiments, a prebiotic composition comprising about 96% GOS comprises about 4% digestible saccharides. For example, 8 g of a prebiotic composition comprising GOS can comprise 7.68 g of GOS and about 0.32 g of digestible saccharides.

In one embodiment a prebiotic composition comprises about 97% GOS and no lactose. For example 8 g of a prebiotic composition comprising GOS can comprise about 7.76 g of GOS. In other embodiments, a prebiotic composition comprising about 97% GOS comprises about 3% digestible saccharides. For example, 8 g of a prebiotic composition comprising GOS can comprise 7.76 g of GOS and about 0.24 g of digestible saccharides.

In one embodiment a prebiotic composition comprises about 98% GOS and no lactose. For example 8 g of a prebiotic composition comprising GOS can comprise about 7.84 g of GOS. In other embodiments, a prebiotic composition comprising about 96% GOS comprises about 2% digestible saccharides. For example, 8 g of a prebiotic composition comprising GOS can comprise 7.84 g of GOS and about 0.16 g of digestible saccharides.

In one embodiment a prebiotic composition comprises about 99% GOS and no lactose. For example 8 g of a prebiotic composition comprising GOS can comprise about 7.92 g of GOS. In other embodiments, a prebiotic composition comprising about 99% GOS comprises about 1% digestible saccharides. For example, 8 g of a prebiotic composition comprising GOS can comprise 7.92 g of GOS and about 0.08 g of digestible saccharides.

In one embodiment a prebiotic composition comprises about 100% GOS and no lactose. For example 8 g of a prebiotic composition comprising GOS can comprise about 8.0 g of GOS. In other embodiments, a prebiotic composition comprising about 99.9% GOS comprises less than about 1% digestible saccharides. For example, 8 g of a prebiotic composition comprising GOS can comprise 8.0 g of GOS and about 0.1 g of digestible saccharides.

10. GOS Effects

In one embodiment a GOS composition reduces or eliminates one or more symptoms associated with lactose intolerance or with lactose digestive problems, including but not limited to cramps, flatulence, stomach pain, vomiting, bloating, diarrhea, nausea, gastric distention and intestinal pain, in a subject in need thereof. In one embodiment the subject is a patient. In another embodiment the subject is a human. In another embodiment the subject is a non-human animal.

C. FOS

FOS are chain oligomers or polymers of the sugar fructose that are found in a variety of foods. The sugar units can be linked in a single straight chain or can be a chain with side branches. In many cases small amounts of glucose are also contained in the chain. The length of the fructose chains can vary from source to source. FOS are primarily polyfructans with a degree of polymerization (DP) generally ranging from 2 to 20 (oligofructose) or greater than 20 (inulin). Generally, the D-fructose moieties in FOS are joined by β-(2-1) linkages and the oligomers or polymers are terminated with a D-glucose molecule linked to fructose by an α-(1-2) bond.

In one embodiment a prebiotic composition comprises a FOS composition, wherein the FOS composition comprises about 1% or more of the composition by weight, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% FOS. In other embodiments, the FOS composition comprises about 0.5% or more of FOS in the FOS composition by weight, such as about 0.5%, 1%, 5%, 10%, 15%, 20%, 25%, 30%, or 35% FOS. In another embodiment the prebiotic or FOS composition comprises 0.01-20 g of FOS, such as about 0.01, 0.03, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, or 20 g of FOS. In another embodiment the prebiotic or FOS composition comprises FOS and water and one or more digestible saccharides. In one embodiment a prebiotic composition comprises less than about 10 ppm of a heavy metal (such as arsenic or lead), including but not limited to less than about 10, 9, 8, 7, 6, 5, 4, 3, 2, or 1 ppm of a heavy metal.

In another embodiment, a prebiotic composition comprises a mixture of FOS and GOS. In one embodiment, about 90% by weight of the prebiotic component is GOS and about 10% by weight of the prebiotic component is FOS. In one embodiment, about 50% by weight of the prebiotic component is GOS and about 50% by weight of the prebiotic component is FOS. In one embodiment, 1-90% by weight of the prebiotic component is GOS and 10-60% by weight of the prebiotic component is FOS. In another embodiment, the prebiotic component of a prebiotic composition is 90-100% by weight GOS.

D. Inulin

Inulin is an example of a longer chained compound that is considered to be a FOS. The shorter (lower molecular weight) compounds tend to have a sweet taste. The size and complexity of the FOS molecules gives it desirable characteristics. Although the simple sugars fructose and glucose are quickly absorbed into the body by the intestines, FOS for the most part is non-digestible and therefore acts as a fiber in the diet. This is because humans do not have the enzymes to break down the FOS as it travels down the digestive tract. When the FOS reaches the large intestine and the colon, the bacteria that are found there start to break down the FOS. These bacteria have the enzymes needed to break down FOS. Some *Bifidobacterium* and *Lactobacillus* species have been reported to use FOS. It is believed that foods that promote the growth of bifidobacteria are beneficial for gastrointestinal health.

In one embodiment a prebiotic composition comprises inulin, wherein the inulin comprises 1% or more of the composition by weight, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, or 100% inulin. In another embodiment a prebiotic composition comprises 1-20 g of inulin, such as about 1, 2, 3, 4, 5, 6, 7, 8, 9, 10, 11, 12, 13, 14, 15, 16, 17, 18, 19, or 20 g of inulin. In another embodiment a prebiotic composition comprises inulin, water, or one or more digestible saccharides. In one embodiment a prebiotic composition comprises less than about 10 ppm of a heavy metal (such as arsenic or lead), including but not limited to less than about 10, 9, 8, 7, 6, 5, 4, 3, 2, or 1 ppm of a heavy metal.

E. Lactulose

Lactulose is a disaccharide that is formed from one molecule of fructose and galactose. It can be produced by isomerization of lactose. In one embodiment a prebiotic composition comprises lactulose (4-O-β-D-Galactopyranosyl-β-D-fructofuranose), wherein lactulose comprises about 1% or more of the composition by weight, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, or 100% lactulose. In another embodiment a prebiotic composition comprises 1-20 g of lactulose, such as about 1, 2, 3, 4, 5, 6, 7, 8, 9, 10, 11, 12, 13, 14, 15, 16, 17, 18, 19, or 20 g of lactulose. In another embodiment a prebiotic composition comprises lactulose, water, or one or more digestible saccharides. In one embodiment the composition comprises less than about 10 ppm of a heavy metal (such as arsenic or lead), including but not limited to less than about 10, 9, 8, 7, 6, 5, 4, 3, 2, or 1 ppm of a heavy metal.

F. Raffinose

Raffinose (melitose, melitriose, gossypose, α-D-galactosylsucrose) is a trisaccharide composed of galactose, fructose, and glucose. The enzyme α-galactosidase, which is not found in the human digestive tract, can hydrolyze raffinose. Thus, in humans, raffinose passes through the stomach and upper intestine and is digested by bacteria that do contain α-galactosidase in the lower intestine. In one embodiment a prebiotic composition comprises raffinose, wherein the raffinose comprises 1% or more of the composition by weight, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, or 100% raffinose. In another embodiment a prebiotic composition comprises 1-20 g of raffinose, such as about 1, 2, 3, 4, 5, 6, 7, 8, 9, 10, 11, 12, 13, 14, 15, 16, 17, 18, 19, or 20 g of raffinose. In another embodiment a prebiotic composition comprises raffinose or one or more digestible saccharides. In one embodiment a prebiotic composition comprises less than about 10 ppm of a heavy metal (such as arsenic or lead), including but not limited to less than about 10, 9, 8, 7, 6, 5, 4, 3, 2, or 1 ppm of a heavy metal.

G. Stachyose

Stachyose is a tetrasaccharide that consists of two α-D-galactose units, one α-D-glucose unit, and one β-D-fructose unit. It is linked as gal(α1→6) gal(α1→6)glc(α1↔2β)fru. Stachyose is not completely digestible by humans. In one embodiment a prebiotic composition comprises stachyose, wherein the stachyose comprises 1% or more of the composition by weight, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 89, 90, 91, 92, 93, 94, 95, 96, 97, 98, 99, or 100% stachyose. In another embodiment a prebiotic composition comprises 1-20 g of stachyose, such as about 1, 2, 3, 4, 5, 6, 7, 8, 9, 10, 11, 12, 13, 14, 15, 16, 17, 18, 19, or 20 g of stachyose. In another embodiment a prebiotic composition comprises stachyose, water, or one or more digestible saccharides. In one embodiment a prebiotic composition comprises less than about 10 ppm of a heavy metal (such as arsenic), including but not limited to less than about 10, 9, 8, 7, 6, 5, 4, 3, 2, or 1 ppm of a heavy metal.

H. GOS and Inulin

In one embodiment, a prebiotic composition comprises GOS and inulin. In another embodiment, the ratio of GOS:inulin is about 99:1, about 95:1, about 90:1, about 85:1, about 80:1, about 75:1, about 70:1, about 65:1, about 60:1, about 55:1, about 50:1, about 45:1, about 40:1, about 35:1, about 30:1, about 25:1, about 20:1, about 15:1, about 10:1, about 9:1, about 8:1, about 22:3, about 7:1, about 6:1, about 5:1, about 4:1, about 3:1, about 2:1, or about 1:1. In one embodiment a prebiotic composition comprising GOS and inulin comprises between 0.4 g to 20 g GOS and inulin. A prebiotic composition comprising GOS and inulin can contain about 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 g GOS and inulin.

III. Probiotics

A. Introduction

Probiotics (or probiotic bacteria) typically refer to beneficial live microorganisms, e.g., bacteria, found in the gastrointestinal tract and, when administered in adequate amounts, confer a health benefit on the host (or subject in need thereof). Reports indicate that probiotic microbes favorably alter the intestinal microbiota balance, inhibit the growth of harmful bacteria, promote good digestion, modulate immune functions, and increase resistance to both viral and bacterial infections. Probiotics are also reported to produce angiotensin-converting enzyme (ACE) inhibitory peptides, a key clinical target for blood pressure control. Bacterial cultures that are generally recognized as safe (GRAS) or known commensal or probiotic microbes could be used to assist in the reduction or elimination of lactose intolerance-like symptoms or improving overall GI health, for example through colonic adaptation, are applicable in the methods and compositions described herein.

B. Bacteria

Examples of probiotics include, but are not limited to, those that acidify the colon such as those from the genera *Lactobacillus* or *Bifidobacterium*, which are thought to maintain a healthy balance of intestinal microbiota by producing organic acids (lactic & acetic acids), hydrogen peroxide, and bacteriocins which are documents to inhibit enteric pathogens. Bacteriocins are small antimicrobial peptides which can kill both closely-related bacteria, or exhibit a broader spectrum of activity (e.g., nisin) which includes most Gram-positive pathogens (e.g., *Listeria, Staphylococcus*, and *Clostridium* species).

Non-exclusive examples of probiotic bacteria that can be used in the methods and compositions described herein include *L. acidophilus*, a probiotic microbe which is an important member of the microbiota of the GI tract and has been used extensively and successfully as a probiotic cultures in dietary supplements, foods, and dairy products. These beneficial bacteria have been reported to modulate immune function, inhibit carcinogenesis, facilitate metabolism of cholesterol, and assist in digestion. Numerous reports over many *Lactobacillus* species are reported to promote a healthy microbiota, reduce putrefaction, and reduce endotoxemia. Other *Lactobacillus* bacteria which can be employed include, but are not limited to, *L. crispatus, L. casei, L. rhamnosus, L. reuteri, L. fermentum, L. plantarum, L. sporogenes*, and *L. bulgaricus*. Other probiotic bacteria suitable for the compositions include *Bifidobacterium lactis, B. animalis, B. bifidum, B. longum, B. adolescentis*, and *B. infantis*. Yeasts, such as *Saccharomyces boulardii*, are also suitable as probiotics and may act to restore the intestinal microbiota. Mixtures of one or more species or strains of bacteria can be used. For example, yogurt is a product which already contains bacteria species, such as *Lactobacillus bulgaricus* and *Streptococcus thermophilus*, which are used for fermentation. Yogurt can be supplemented with prebiotics and additional bacterial species that are considered probiotic cultures.

Other strains of probiotic bacteria that can be used in the methods and compositions described herein include, for example, *Bacillus coagulans* GBI-30, 6086; *Bifidobacterium animalis* subsp. *lactis* BB-12; *Bifidobacterium breve* Yakult; *Bifidobacterium infantis* 35624; *Bifidobacterium animalis* subsp. *lactis* HN019 (DR10); *Bifidobacterium longum* BB536; *Escherichia coli* M-17; *Escherichia coli* Nissle 1917; *Lactobacillus acidophilus* DDS-1; *Lactobacillus acidophilus* LA-5; *Lactobacillus acidophilus* NCFM; *Lactobacillus casei* DN114-001 (*Lactobacillus casei* Immunitas(s)/Defensis); *Lactobacillus casei* CRL431; *Lactobacillus casei* F19; *Lactobacillus paracasei* St11 (or NCC2461); *Lactobacillus johnsonii* La1 (*Lactobacillus* LC1, *Lactobacillus johnsonii* NCC533); *Lactococcus lactis* L1A; *Lactobacillus plantarum* 299V; *Lactobacillus reuteri* ATCC 55730 (*Lactobacillus reuteri* SD2112); *Lactobacillus rhamnosus* ATCC 53013; *Lactobacillus rhamnosus* LB21; *Saccharomyces cerevisiae* (*boulardii*) lyo; mixture of *Lactobacillus rhamnosus* GR-1 and *Lactobacillus reuteri* RC-14; mixture of *Lactobacillus acidophilus* NCFM and *Bifidobacterium lactis* BB-12 or BL-04; mixture of *Lactobacillus acidophilus* CL1285 and *Lactobacillus casei*; and a mixture of *Lactobacillus helveticus* R0052 and *Lactobacillus rhamnosus* R0011.

In one embodiment, a composition comprises a prebiotic and probiotic. In one embodiment a prebiotic composition comprises or consists essentially of GOS. In one embodiment, a prebiotic composition is administered with increasing doses of probiotics during the period of treatment. In another embodiment, a prebiotic composition is administered with constant doses (dose amounts that do not change) of probiotics during the period of treatment. In another embodiment, a prebiotic composition is administered with both increasing doses of probiotics for a portion of the treatment and a constant dose of probiotics during another portion of the treatment period.

C. Dose Timing and Size of Probiotics

In one embodiment, probiotic bacteria, such as *L. acidophilus*, are given prior to beginning treatment with a prebiotic. In one embodiment, probiotic bacteria, such as *L. acidophilus*, are given in conjunction with treatment with a prebiotic (e.g., comprising or consisting essentially of GOS), for part or all of the treatment with the prebiotic. Thus, in one embodiment, some or all doses of a prebiotic (e.g., comprising or consisting essentially of GOS) are accompanied by a dose of bacteria, e.g., live cultured bacteria, e.g., *L. acidophilus*. In one embodiment, bacteria, e.g., *L. acidophilus* are given initially with a prebiotic (e.g., comprising or consisting essentially of GOS), but then use of the bacteria is discontinued. For example, the initial one, two, three, four, five, six, seven, eight, nine, ten, or more than ten days of treatment with a prebiotic (e.g., comprising or consisting essentially of GOS) further comprises doses of bacteria, with the use of bacteria discontinued after that time. In one embodiment, bacteria, (e.g., bacteria in yogurt), or bacteria by themselves, can be given for the first two days of treatment; then the administration of bacteria is discontinued. In another embodiment, probiotic bacteria, either alone or in combination with other substances or treatments are used after the treatment with a prebiotic (comprising or consisting essentially of GOS) is terminated. The bacteria can be taken for any suitable period after the termination of treatment with prebiotic and can be taken daily or at regular or irregular intervals. Doses can be as described below.

Any suitable amount of probiotic per serving can be used that allows an effective microbiota in the GI. Typically, probiotics are given as live cultured bacteria. The dose can be about 0.001 mg to about 1 mg, or about 0.5 mg to about 5 mg, or about 1 mg to about 1000 mg, or about 2 mg to about 200 mg, or about 2 mg to about 100 mg, or about 2 mg to about 50 mg, or about 4 mg to about 25 mg, or about 5 mg to about 20 mg, or about 10 mg to about 15 mg, or about 50 mg to about 200 mg, or about 200 mg to about 1000 mg, or about 10, 11, 12, 12.5, 13, 14, or 15 mg per serving. In one embodiment, *L. acidophilus* is used in a dose of about 12.5 mg per serving. The probiotic bacteria can also be about 0.5% w/w to about 20% w/w of the final composition. The dose of probiotics can be given in combination with one or more prebiotics. Another common way of specifying the amount of probiotics is as a colony forming unit (cfu). A cfu is an individual cell which is able to clone itself into an entire colony of identical cells. In one embodiment, one or more strains of probiotic bacteria are ingested in an amount of about $1\times10^6$ to about $1\times10^9$ cfu's, or about $1\times10^6$ cfu's to about $1\times10^9$ cfu's, or about $10\times10^6$ cfu's to about $0.5\times10^9$ cfu's, or about $113\times10^5$ cfu's to about $113\times10^6$ cfu's, or about $240\times10^5$ cfu's to about $240\times10^6$ cfu's, or about $0.3\times10^9$ cfu's per serving. In another embodiment, one or more strains of probiotic bacteria are administered as part of a dairy product. In one embodiment, a typical serving size for a dairy product such as fluid milk is about 240 g. In other embodiments, a serving size is about 245 g, or about 240 g to about 245 g, or about 227 to about 300 g. In one embodiment the dairy product is yogurt. Yogurt can have a serving size of about 4 oz, or about 6 oz, or about 8 oz, or about 4 oz to 10 oz, or about half cup, or about 1 cup, or about 113 g, or about 170 g, or about 227 g, or about 245 g or about 277 g, or about 100 g to about 350 g.

In one embodiment probiotic bacteria are given as live cultured bacteria, e.g., in combination with a prebiotic (e.g., comprising or consisting essentially of GOS) and, optionally, other substances. The dose can be about 1 mg to about 1000 mg, or about 2 mg to about 200 mg, or about 2 mg to about 100 mg, or about 2 mg to about 50 mg, or about 4 mg to about 25 mg, or about 5 mg to about 20 mg, or about 10 mg to about 15 mg, or about 10, 11, 12, 12.5, 13, 14, or 15 mg of probiotic bacteria. In one embodiment, *L. acidophilus* is used in a dose of about 12.5 mg. In one embodiment, as the administration of a prebiotic (e.g., comprising or consisting essentially of GOS) dose to a subject increases, the dose of bacteria increases as well. For example, an initial dose of a prebiotic (e.g., comprising or consisting essentially of GOS) can be about 0.6 g to 1.0 g, e.g., 0.8 g, given in combination with about 10-15 mg, e.g., about 12.5 mg, of *L. acidophilus*. The dose of a prebiotic (e.g., comprising or consisting essentially of GOS) can be increased incrementally by about 0.6 g to 1.0 g, e.g., 0.8 g, and the accompanying dose of *L. acidophilus* can be increased by about 10-15 mg, e.g., about 12.5 mg, of *L. acidophilus*.

IV. GOS Formulations

A. Formulations Introduction

In one aspect a prebiotic composition for the treatment of the symptoms of lactose intolerance is provided. In one embodiment a prebiotic composition comprises inulin, FOS, lactulose, GOS, raffinose, stachyose, or a combination thereof. In one embodiment a prebiotic composition comprises or consists essentially of GOS. In another embodiment a prebiotic composition comprises GOS and one or more digestible saccharides. Digestible saccharides are saccharides that are digestible by humans and include, but are not limited to lactose, glucose, and galactose. In one embodiment a prebiotic composition comprises GOS and less than 20% of one or more digestible saccharides. In one embodiment a prebiotic composition comprises GOS and less than 10% of one or more digestible saccharides. In one embodiment a prebiotic composition comprises GOS and less than 5% of one or more digestible saccharides. In another embodiment a prebiotic composition contains less than 5% lactose. In another embodiment a prebiotic composition contains less than 4% lactose. In another embodiment a prebiotic composition contains less than 3% lactose. In another embodiment a prebiotic composition contains less than 2% lactose. In another embodiment a prebiotic composition contains less than 1% lactose. In another embodiment a prebiotic composition contains less than 0.5% lactose. In another embodiment a prebiotic composition contains less than 0.4% lactose. In another embodiment a prebiotic composition contains less than 0.3% lactose. In another embodiment a prebiotic composition contains less than 0.2% lactose. In another embodiment a prebiotic composition contains less than 0.1% lactose. In another embodiment a prebiotic composition contains less than 0.05% lactose. In another embodiment a prebiotic composition contains less than 0.01% lactose. In another embodiment a prebiotic composition contains less than 0.005% lactose. In one embodiment a prebiotic composition comprises GOS and essentially no lactose. In one embodiment a prebiotic composition does not contain any lactose. In another embodiment a prebiotic composition contains GOS and at least one probiotic bacteria strain. In another embodiment a prebiotic composition comprises GOS and optionally one or more of lactose, at least one probiotic bacteria strain, or a buffer. Additional ingredients include ingredients to improve handling, preservatives, antioxidants, flavorings and the like.

In one embodiment, a prebiotic composition comprises GOS or a probiotic. In other embodiment, a prebiotic composition is in the form of a powder, tablet, capsule, or liquid. In one embodiment, a prebiotic composition can be administered with a dairy product and is in the form of milk or other common dairy product such as a yogurt, shake, smoothie, cheese, and the like.

In embodiments where a prebiotic composition comprises less than 100% by weight of GOS the remaining ingredients can be any suitable ingredients intended for the consumption of the subject in need thereof, e.g., human, including, but not limited to, other prebiotics (e.g., FOS), a buffer, one or more digestible saccharides, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings, and the like.

B. Buffer Components

One or more buffers, optionally with a calcium counterion, can also be administered in methods and compositions described herein. Any buffer suitable for consumption by the subject being treated, e.g., human, are useful for the compositions herein. The buffer neutralizes stomach acidity which can, e.g., allow live bacteria to reach the gut. Buffers include citrates, phosphates, and the like. One embodiment utilizes a buffer with a calcium counterion, such as Calcium Phosphate Tribasic. The calcium can serve to restore the calcium that many lactose intolerant subjects are missing in their diet. A recent study demonstrated the ability of calcium phosphate to protect *Lactobacillus acidophilus* from bile. Calcium phosphate can help neutralize stomach acidity.

In one embodiment, a buffer such as calcium phosphate is given prior to beginning treatment with a prebiotic composition (such as a composition comprising or consisting essentially of GOS), optionally in conjunction with administration of bacteria. In one embodiment, a buffer such as calcium phosphate is given in conjunction with treatment with a prebiotic composition (e.g., a composition comprising or consisting essentially of GOS), for part or all of the treatment with lactose. Thus, in one embodiment, some or all doses of a prebiotic composition are accompanied by a dose of a buffer such as calcium phosphate. In one embodiment, a buffer such as calcium phosphate is given initially with a prebiotic composition (such as a composition comprising or consisting essentially of GOS), but then its use is discontinued. For example, the initial one, two, three, four, five, six, seven, eight, nine, ten, or more than ten days of treatment with a prebiotic composition can include doses of a buffer such as calcium phosphate, with the use of the buffer discontinued after that time. In one embodiment, a buffer such as calcium phosphate can be given for the first two days of treatment, and then the administration of buffer is discontinued. In one embodiment, a buffer such as calcium phosphate, either alone or in combination with other substances or treatments is used after the treatment with a prebiotic composition is terminated. A buffer such as calcium phosphate can be taken for any suitable period after the termination of treatment with lactose, and can be taken daily or at regular or irregular intervals. Doses can be as described below.

Numerous buffers suitable for human consumption are known in the art, and any suitable buffer can be used in the methods and compositions described herein. Calcium triphosphate is an exemplary buffer, and its counterion supplies a nutrient that is often lacking in lactose-intolerant subjects, i.e. calcium. In one embodiment a buffer can be used in a dose from about 2 mg to about 2000 mg, or about 4 mg to about 400 mg, or about 4 mg to about 200 mg, or about 4 mg to about 100 mg, or about 8 mg to about 50 mg, or about 10 mg to about 40 mg, or about 20 mg to about 30 mg, or about 20, 21, 22, 23, 24, 25, 26, 27, 28, 29, or 30 mg. In another embodiment a prebiotic composition further comprises an amount of a buffer from 1-50 mg, such as about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg. In one embodiment, buffer is used in a dose of about 25 mg. In one embodiment, calcium phosphate is used in a dose of about 25 mg. The dose can be given in combination with a prebiotic composition (e.g., a composition comprising or consisting essentially of GOS). In one embodiment, as a prebiotic composition dose increases, the dose of buffer increases as well. For example, an initial dose of a prebiotic composition can be about 0.6 g to 1.0 g, e.g., 0.8 g, given in combination with about 20-30 mg, e.g., about 25 mg, of buffer, e.g., calcium phosphate. The dose of a prebiotic composition can be increased incrementally by about 0.6 g to 1.0 g, e.g., 0.8 g, and the accompanying dose of buffer, e.g., calcium phosphate, can be increased by about 20-30 mg, e.g., about 25 mg, of buffer, e.g., calcium phosphate.

C. Compositions Comprising GOS and at Least One Probiotic Bacteria Strain

In one embodiment, a prebiotic composition comprises GOS and at least one probiotic bacteria strain. The GOS can comprise more than 1% of the weight of the composition while the at least one probiotic bacteria strain will typically comprise less than about 10%, 5%, 4%, 3%, or 2% by weight of the compositions (herein all percentages are weight percent unless otherwise indicated). For example, the GOS can be present at about 1-99.75% by weight and the at least one probiotic bacteria strain at about 0.25-2% by weight, or the GOS can be present at about 89-96% by weight and the bacteria at about 1.2-3.7% by weight. In one embodiment, GOS are present at about 92% by weight and at least one probiotic bacteria strain, (e.g., *L. acidophilus* or *Bifidobacterium lactis*), is present at about 1.5% by weight. In one embodiment, GOS are present at about 92% by weight and at least one probiotic bacteria strain, (e.g., *L. acidophilus* or *Bifidobacterium lactis*), is present at about 1.5% by weight. In another embodiment, GOS are present at about 93% by weight and at least one probiotic bacteria strain, (e.g., *L. acidophilus* or *Bifidobacterium lactis*), is present at about 1.5% by weight. In another embodiment, GOS are present at about 94% by weight and at least one probiotic bacteria strain, (e.g., *L. acidophilus* or *Bifidobacterium lactis*), is present at about 1.5% by weight. In another embodiment, GOS are present at about 95% by weight and at least one probiotic bacteria strain, (e.g., *L. acidophilus* or *Bifidobacterium lactis*), is present at about 1.5% by weight. In another embodiment, GOS are present at about 96% by weight and at least one probiotic bacteria strain, (e.g., *L. acidophilus* or *Bifidobacterium lactis*), is present at about 1.5% by weight. In another embodiment, GOS are present at about 97% by weight and at least one probiotic bacteria strain, (e.g., *L. acidophilus* or *Bifidobacterium lactis*), is present at about 1.5% by weight. In another embodiment, GOS are present at about 98% by weight and at least one probiotic bacteria strain, (e.g., *L. acidophilus* or *Bifidobacterium lactis*), is present at about 1.5% by weight. In another embodiment, GOS are present at about 98.5% by weight and at least one probiotic bacteria strain, (e.g., *L. acidophilus* or *Bifidobacterium lactis*), is present at about 1.5% by weight. If the at least one probiotic bacteria strain and GOS do not make up 100% by weight of the prebiotic composition, the remaining ingredients can be any suitable ingredients intended for consumption by the subject in need thereof, e.g., human, including, but not limited to, other prebiotics (e.g., FOS), one or more buffers, digestible saccharides ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

D. Compositions Comprising GOS and a Buffer

In another embodiment, a prebiotic composition comprises GOS and a buffer (e.g., calcium phosphate tribasic). For example, GOS can be present at about 1-100% by weight and the buffer at about 0.50-4% by weight, or GOS can be present at about 1-96% by weight and the buffer at about 1 to about 3.75% by weight. In one embodiment, GOS are present at about 1% by weight and buffer is present at about 3% by weight. In one embodiment, GOS are present at about 5% by weight and buffer is present at about 3% by weight. In one embodiment, GOS are present at about 10% by weight and buffer is present at about 3% by weight. In one embodiment, GOS are present at about 15% by weight and buffer is present at about 15% by weight. In one embodiment, GOS are present at about 20% by weight and buffer is present at about 3% by weight. In one embodiment, GOS are present at about 25% by weight and buffer is present at about 3% by weight. In one embodiment, GOS are present at about 30% by weight and buffer is present at about 3% by weight. In one embodiment, GOS are present at about 35% by weight and buffer is present at about 3% by weight. In one embodiment, GOS are present at about 40% by weight and buffer is present at about 3% by weight. In one embodiment, GOS are present at about 50% by weight and buffer is present at about 3% by weight. In one embodiment, GOS are present at about 60% by weight and buffer is present at about 3% by weight. In one embodiment, GOS are present at about 70% by weight and buffer is present at about 3% by weight. In another embodiment, GOS are present at about 90% by weight and buffer is present at about 3% by weight. In one embodiment, GOS are present at about 92% by weight and buffer is present at about 3% by weight. In another embodiment, GOS are present at about 93% by weight and buffer is present at about 3% by weight. In another embodiment, GOS are present at about 94% by weight and buffer is present at about 3% by weight. In another embodiment, GOS are present at about 95% by weight and buffer is present at about 3% by weight. In another embodiment, GOS are present at about 96% by weight and buffer is present at about 3% by weight. In another embodiment, GOS are present at about 97% by weight and buffer is present at about 2% by weight. In another embodiment, GOS are present at about 98% by weight and buffer is present at about 1% by weight. In another embodiment, GOS are present at about 99% by weight and buffer is present at about 1% by weight. In another embodiment, GOS are present at about 100% by weight and buffer is present at less than about 1% by weight. If the buffer and GOS do not make up 100% by weight of the composition, the remaining ingredients can be any suitable ingredients intended for consumption by the subject (e.g., a human) including, but not limited to, probiotics (e.g., beneficial bacteria) or other prebiotics (e.g., FOS), but also including ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

E. Compositions Comprising a Digestible Saccharide, a Probiotic Bacteria, and GOS In one embodiment, a prebiotic composition comprises a digestible saccharide, a probiotic bacteria (e.g., *L. acidophilus* or *Bifidobacterium*), and GOS. In one embodiment, lactose can be present at about 1-20% by weight, bacteria at about 0.25-2.10% by weight, and GOS at about 1-98.75% by weight. In another embodiment lactose can be present at about 5-20% by weight, bacteria at about 0.91-1.95% by weight, and GOS at about 1 to about 96% by weight. In another embodiment, lactose is present at about 20% by weight, bacteria at about 1.5% by weight, and GOS are present at about 1% by weight. In another embodiment, lactose is present at about 20% by weight, bacteria at about 1.5% by weight, and GOS are present at about 50% by weight. In another embodiment, lactose is present at about 20% by weight, bacteria at about 1.5% by weight, and GOS are present at about 60% by weight. In another embodiment, lactose is present at about 20% by weight, bacteria at about 1.5% by weight, and GOS are present at about 70% by weight. In another embodiment, lactose is present at about 5% by weight, bacteria at about 1.5% by weight, and GOS are present at about 90% by weight. In another embodiment, lactose is present at about 5% by weight, bacteria at about 1.5% by weight, and GOS are present at about 92% by weight. In another embodiment, lactose is present at about 5% by weight, bacteria at about 1.5% by weight, and GOS are present at about 93% by weight. In another embodiment, lactose is present at about 5% by weight, bacteria at about 1% by weight, and GOS are present at about 94% by weight. In another embodiment, lactose is present at about 4.5% by weight, bacteria at about 1.5% by weight, and GOS are present at about 94% by weight. In another embodiment, lactose is present at about 4.5% by weight, bacteria at about 0.5% by weight, and GOS are present at about 95% by weight. In another embodiment, lactose is present at about 3.5% by weight, bacteria at about 0.5% by weight, and GOS are present at about 96% by weight. In another embodiment, lactose is present at about 2.5% by weight, bacteria at about 0.5% by weight, and GOS are present at about 97% by weight. In another embodiment, lactose is present at about 1.5% by weight, bacteria at about 0.5% by weight, and GOS are present at about 98% by weight. In another embodiment, lactose is present at about 0.5% by weight, bacteria at about 0.5% by weight, and GOS are present at about 99% by weight. If the bacteria, GOS and lactose do not make up 100% of the composition, the remaining ingredients can be any suitable ingredients intended for consumption by the subject, e.g., a human, including, but not limited to a buffer, digestible saccharides (e.g., lactose, glucose, or galactose), ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

F. Compositions Comprising GOS, a Probiotic Bacteria, and Buffer

In one embodiment, a prebiotic composition comprises GOS, a probiotic bacteria strain, and buffer. In one embodiment, GOS can be present at about 1-100% by weight, a probiotic bacteria strain at about 0.25-2% by weight, and the buffer at about 0.50-4% by weight. In another embodiment, GOS can be present at about 1-95% by weight, a probiotic bacteria strain at about 0.91-1.95% by weight, and the buffer at about 1.2-3.75% by weight. In another embodiment, GOS are present at about 1% by weight, a probiotic bacteria strain at about 1.5% by weight, and buffer is present at about 3% by weight. In another embodiment, GOS are present at about 5% by weight, a probiotic bacteria strain at about 1.5% by weight, and buffer is present at about 3% by weight. In another embodiment, GOS are present at about 10% by weight, a probiotic bacteria strain at about 1.5% by weight, and buffer is present at about 3% by weight. In another embodiment, GOS are present at about 15% by weight, a probiotic bacteria strain at about 1.5% by weight, and buffer is present at about 3% by weight. In another embodiment, GOS are present at about 20% by weight, a probiotic bacteria strain at about 1.5% by weight, and buffer is present at about 3% by weight. In another embodiment, GOS are present at about 25% by weight, a probiotic bacteria strain at about 1.5% by weight, and buffer is present at about 3% by weight. In another embodiment, GOS are present at about 30% by weight, a probiotic bacteria strain at about 1.5% by weight, and buffer is present at about 3% by weight. In another embodiment, GOS are present at about 35% by weight, a probiotic bacteria strain at about 1.5% by weight, and buffer is present at about 3% by weight. In another embodiment, GOS are present at about 40% by weight, a probiotic bacteria strain at about 1.5% by weight, and buffer is present at about 3% by weight. In another embodiment, GOS are present at about 50% by weight, a probiotic bacteria strain at about 1.5% by weight, and buffer is present at about 3% by weight. In another embodiment, GOS are present at about 60% by weight, a probiotic bacteria strain at about 1.5% by weight, and buffer is present at about 3% by weight. In another embodiment, GOS are present at about 70% by weight, a probiotic bacteria strain at about 1.5% by weight, and buffer is present at about 3% by weight. In another embodiment, GOS are present at about 90% by weight, a probiotic bacteria strain at about 1.5% by weight, and buffer is present at about 3% by weight. In another embodiment, GOS are present at about 92% by weight, a probiotic bacteria strain at about 1.5% by weight, and buffer is present at about 3% by weight. In another embodiment, GOS are present at about 93% by weight, a probiotic bacteria strain at about 1.5% by weight, and buffer is present at about 3% by weight. In another embodiment, GOS are present at about 94% by weight, a probiotic bacteria strain at about 1.5% by weight, and buffer is present at about 3% by weight. In another embodiment, GOS are present at about 95% by weight, a probiotic bacteria strain at about 1.5% by weight, and buffer is present at about 3% by weight. In another embodiment, GOS are present at about 96% by weight, a probiotic bacteria strain at about 1.5% by weight, and buffer is present at about 2% by weight. In another embodiment, GOS are present at about 97% by weight, a probiotic bacteria strain at about 1.5% by weight, and buffer is present at about 1.5% by weight. In another embodiment, GOS are present at about 99% by weight, a probiotic bacteria strain at about 0.5% by weight, and buffer is present at about 0.5% by weight. In another embodiment, GOS are present at about 100% by weight, a probiotic bacteria strain at less than about 0.5% by weight, and buffer is present at less than about 0.5% by weight. If the probiotic bacteria strain, buffer, and GOS do not make up 100% of the composition, the remaining ingredients can be any suitable ingredients intended for the consumption of a subject (e.g., human) including, but not limited to, other prebiotics (e.g., FOS), digestible saccharides (e.g., lactose, glucose or galactose), ingredients intended to inhibit clumping and increase pourability, such as silicone dioxide and microcrystalline cellulose, or similar ingredients as are well-known in the art.

Remaining ingredients can also include ingredients to improve handling, preservatives, antioxidants, flavorings and the like.

G. Compositions Comprising a Digestible Saccharide, GOS, and a Buffer

In one embodiment, a prebiotic composition comprises a digestible saccharide, GOS, and a buffer. For example, lactose can be present at about 1-20% by weight, GOS at about 1-100% by weight, and the buffer at about 0.50-4% by weight, or the lactose can be present at about 5-20% by weight, GOS at about 1-96% by weight, and the buffer at about 1.2-3.75% by weight. In one embodiment, lactose is present at about 20% by weight, GOS at about 1% by weight, and buffer is present at about 3% by weight. In one embodiment, lactose is present at about 5% by weight, GOS at about 1% by weight, and buffer is present at about 3% by weight. In one embodiment, lactose is present at about 20% by weight, GOS at about 10% by weight, and buffer is present at about 3% by weight. In one embodiment, lactose is present at about 20% by weight, GOS at about 15% by weight, and buffer is present at about 3% by weight. In one embodiment, lactose is present at about 20% by weight, GOS at about 20% by weight, and buffer is present at about 3% by weight. In one embodiment, lactose is present at about 20% by weight, GOS at about 25% by weight, and buffer is present at about 3% by weight. In one embodiment, lactose is present at about 20% by weight, GOS at about 30% by weight, and buffer is present at about 3% by weight. In one embodiment, lactose is present at about 20% by weight, GOS at about 35% by weight, and buffer is present at about 3% by weight. In one embodiment, lactose is present at about 20% by weight, GOS at about 40% by weight, and buffer is present at about 3% by weight. In one embodiment, lactose is present at about 20% by weight, GOS at about 50% by weight, and buffer is present at about 3% by weight. In one embodiment, lactose is present at about 20% by weight, GOS at about 60% by weight, and buffer is present at about 3% by weight. In one embodiment, lactose is present at about 20% by weight, GOS at about 70% by weight, and buffer is present at about 3% by weight. In another embodiment, lactose is present at about 5% by weight, GOS at about 90% by weight, and buffer is present at about 3% by weight. In another embodiment, lactose is present at about 5% by weight, GOS at about 92% by weight, and buffer is present at about 3% by weight. In another embodiment, lactose is present at about 4% by weight, GOS at about 93% by weight, and buffer is present at about 3% by weight. In another embodiment, lactose is present at about 3% by weight, GOS at about 94% by weight, and buffer is present at about 3% by weight. In another embodiment, lactose is present at about 2% by weight, GOS at about 95% by weight, and buffer is present at about 3% by weight. In another embodiment, lactose is present at about 1% by weight, GOS at about 96% by weight, and buffer is present at about 3% by weight. If GOS, buffer and lactose do not make up 100% of the composition by weight, the remaining ingredients can be any suitable ingredients intended for consumption by a subject (e.g., human) including, but not limited to, bacteria, ingredients intended to inhibit clumping and increase pourability, such as silicone dioxide and microcrystalline cellulose, or similar ingredients as are well-known in the art. Remaining ingredients can also include ingredients to improve handling, preservatives, antioxidants, flavorings and the like.

H. Compositions Comprising a Digestible Saccharide, Bacteria, GOS, and a Buffer

In one embodiment, a prebiotic composition comprises a digestible saccharide, bacteria, GOS, and buffer. For example, lactose can be present at about 1-20% by weight, bacteria at about 0.25-2.10% by weight, GOS at about 1-100% by weight, and the buffer at about 0.50-4% by weight, or the lactose can be present at about 5-20% by weight, bacteria at about 0.91-1.95% by weight, GOS at about 70-95% by weight, and the buffer at about 1.2-3.75% by weight. In one embodiment, lactose is present at about 20% by weight, bacteria at about 1.47% by weight, GOS at about 1% by weight, and buffer is present at about 3% by weight. In one embodiment, lactose is present at about 20% by weight, bacteria at about 1.47% by weight, GOS at about 10% by weight, and buffer is present at about 3% by weight. In one embodiment, lactose is present at about 20% by weight, bacteria at about 1.47% by weight, GOS at about 15% by weight, and buffer is present at about 3% by weight. In one embodiment, lactose is present at about 20% by weight, bacteria at about 1.47% by weight, GOS at about 20% by weight, and buffer is present at about 3% by weight. In one embodiment, lactose is present at about 20% by weight, bacteria at about 1.47% by weight, GOS at about 25% by weight, and buffer is present at about 3% by weight. In one embodiment, lactose is present at about 20% by weight, bacteria at about 1.47% by weight, GOS at about 30% by weight, and buffer is present at about 3% by weight. In one embodiment, lactose is present at about 20% by weight, bacteria at about 1.47% by weight, GOS at about 35% by weight, and buffer is present at about 3% by weight. In one embodiment, lactose is present at about 20% by weight, bacteria at about 1.47% by weight, GOS at about 40% by weight, and buffer is present at about 3% by weight. In one embodiment, lactose is present at about 20% by weight, bacteria at about 1.47% by weight, GOS at about 50% by weight, and buffer is present at about 3% by weight. In one embodiment, lactose is present at about 20% by weight, bacteria at about 1.47% by weight, GOS at about 60% by weight, and buffer is present at about 3% by weight. In one embodiment, lactose is present at about 20% by weight, bacteria at about 1.47% by weight, GOS at about 70% by weight, and buffer is present at about 3% by weight. In one embodiment, lactose is present at about 5% by weight, bacteria at about 1.47% by weight, GOS at about 90% by weight, and buffer is present at about 3% by weight. In one embodiment, lactose is present at about 3% by weight, bacteria at about 1.47% by weight, GOS at about 92% by weight, and buffer is present at about 3% by weight. In one embodiment, lactose is present at about 2% by weight, bacteria at about 1.47% by weight, GOS at about 93% by weight, and buffer is present at about 3% by weight. In one embodiment, lactose is present at about 1% by weight, bacteria at about 1.47% by weight, GOS at about 94% by weight, and buffer is present at about 3% by weight. In one embodiment, lactose is present at about 0.5% by weight, bacteria at about 1.47% by weight, GOS at about 95% by weight, and buffer is present at about 3% by weight. If the bacteria, GOS, buffer and lactose do not make up 100% of the composition by weight, the remaining ingredients can be any suitable ingredients intended for consumption by a subject, e.g., human, including, but not limited to, ingredients intended to inhibit clumping and increase pourability, such as silicone dioxide and microcrystalline cellulose, or similar ingredients as are well-known in the art.

Remaining ingredients can also include ingredients to improve handling, preservatives, antioxidants, flavorings and the like.

I. Additional Ingredients

Additional ingredients include ingredients to improve handling, preservatives, antioxidants, flavorings and the like. For example, in one embodiment, a prebiotic composition in powdered form can include flavorings such that when mixed in a liquid (e.g., water), the powder can flavor the liquid with various flavors such as grape, strawberry, lime, lemon, chocolate, and the like. In one embodiment, the compositions include microcrystalline cellulose or silicone dioxide. Preservatives can include, for example, benzoic acid, alcohols, for example, ethyl alcohol, and hydroxybenzoates. Antioxidants can include, for example, butylated hydroxyanisole (BHA), butylated hydroxytoluene (BHT), tocopherols (e.g., Vitamin E), and ascorbic acid (Vitamin C).

V. Dosage Forms

A. General

Compositions described herein include any suitable form, including liquid or powder. Powdered compositions can be as pure powder, or can be in the form of capsules, tablets, or the like. Powder can be packaged in bulk (e.g., in a container containing sufficient prebiotic or other substances for a subject to follow for an entire course of treatment with increasing doses of prebiotic, or a portion of a course of treatment), or as individual packets (e.g., packets containing a single dose of prebiotic plus other components, or packets containing the dose of prebiotic and other components needed for a particular day of a prebiotic treatment regimen). If packaged in bulk, the powder can be in any suitable container, such as a packet, sachet, canister, ampoule, ramekin, or bottle. The container can also include one or more scoops or similar serving devices of a size or sizes appropriate to measure and serve one or more doses of prebiotic and, optionally, other ingredients included in the powder. Liquid compositions contain prebiotic and, optionally, other ingredients, in a suitable liquid, e.g., water or buffer. Liquid compositions can be provided in bulk (e.g., in a container containing sufficient prebiotic or other substances for one subject in need thereof to follow an entire course of treatment with increasing doses of prebiotic, or a portion of a course of treatment), or as individual containers, such as cans, bottles, soft packs, and the like (e.g., containers containing a single dose of prebiotic plus other components in suitable liquid, or containers containing the dose of prebiotic and other components needed for a particular day of a prebiotic treatment regimen). The container can also include one or more measuring cups or similar serving devices of a size or sizes appropriate to measure and serve one or more doses of prebiotic and, optionally, other ingredients included in the liquid.

B. Oral Dosage Forms and Components

In one aspect provided herein are methods and compositions formulated for oral delivery to a subject in need thereof. In one embodiment a composition is formulated to deliver a composition comprising a prebiotic to a subject in need thereof. In another embodiment, a pharmaceutical composition is formulated to deliver a composition comprising a prebiotic to a subject in need thereof. In another embodiment a composition is formulated to deliver a composition comprising prebiotic and a probiotic to a subject in need thereof.

1. Forms

In one embodiment, a composition is administered in solid, semi-solid, micro-emulsion, gel, or liquid form. Examples of such dosage forms include tablet forms disclosed in U.S. Pat. Nos. 3,048,526, 3,108,046, 4,786,505, 4,919,939, and 4,950,484; gel forms disclosed in U.S. Pat. Nos. 4,904,479, 6,482,435, 6,572,871, and 5,013,726; capsule forms disclosed in U.S. Pat. Nos. 4,800,083, 4,532,126, 4,935,243, and 6,258,380; or liquid forms disclosed in U.S. Pat. Nos. 4,625,494, 4,478,822, and 5,610,184; each of which is incorporated herein by reference in its entirety.

Forms of the compositions that can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, antioxidant, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut (e.g., colon, lower intestine) other than the stomach. All formulations for oral administration can be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds (prebiotics or probiotics) can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, or titanium dioxide, lacquer solutions, and suitable organic solvents or solvent mixtures. Dyestuffs or pigments can be added to the tablets or Dragee coatings for identification or to characterize different combinations of active compound doses.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethylene glycol or an oil medium, for example peanut oil, liquid paraffin, or olive oil.

Oral liquid preparations can be in the form of, for example, aqueous or oily suspensions, solutions, emulsions syrups or elixirs, or can be presented as a dry product for reconstitution with water or other suitable vehicle before use. Such liquid preparations can contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, acacia; nonaqueous vehicles (which can include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

In one embodiment, a provided prebiotic composition includes a softgel formulation. A softgel can contain a gelatin based shell that surrounds a liquid fill. The shell can be made of gelatin, plasticiser (e.g., glycerin and/or sorbitol), modifier, water, color, antioxidant, or flavor. The shell can be made with starch or carrageenan. The outer layer can be enteric coated. In one embodiment, a softgel formulation can include a water or oil soluble fill solution, or suspension of a composition, for example, a prebiotic composition, covered by a layer of gelatin.

An enteric coating can control the location of where a prebiotic composition is absorbed in the digestive system. For example, an enteric coating can be designed such that a prebiotic composition does not dissolve in the stomach but rather travels to the small intestine, where it dissolves. An enteric coating can be stable at low pH (such as in the stomach) and can dissolve at higher pH (for example, in the small intestine). Material that can be used in enteric coatings includes, for example, alginic acid, cellulose acetate phthalate, plastics, waxes, shellac, and fatty acids (e.g., stearic acid, palmitic acid). Enteric coatings are described, for example, in U.S. Pat. Nos. 5,225,202, 5,733,575, 6,139,875, 6,420,473, 6,455,052, and 6,569,457, all of which are herein incorporated by reference in their entirety. The enteric coating can be an aqueous enteric coating. Examples of polymers that can be used in enteric coatings include, for example, shellac (trade name EmCoat 120 N, Marcoat 125); cellulose acetate phthalate (trade name aquacoat CPD®, Sepifilm™ LP, Klucel®, Aquacoat® ECD, and Metolose®); polyvinylacetate phthalate (trade name Sureteric®); and methacrylic acid (trade name Eudragit®).

In one embodiment, an enteric coated prebiotic composition is administered to a subject. In another embodiment, an enteric coated probiotic composition is administered to a subject. In another embodiment, an enteric coated probiotic and prebiotic composition is administered to a subject. In one embodiment, probiotic bacteria can be administered to a subject using an enteric coating. The stomach has an acidic environment that can kill probiotics. An enteric coating can protect probiotics as they pass through the stomach and small intestine.

Enteric coatings can be used to (1) prevent the gastric juice from reacting with or destroying the active substance, (2) prevent dilution of the active substance before it reaches the intestine, (3) ensure that the active substance is not released until after the preparation has passed the stomach, and (4) prevent live bacteria contained in the preparation from being killed because of the low pH-value in the stomach.

Enteric coatings can also be used for avoiding irritation of or damage to the mucous membrane of the stomach caused by substances contained in the oral preparation, and for counteracting or preventing formation or release of substances having an unpleasant odor or taste in the stomach. Finally, such coatings can be used for preventing nausea or vomiting on intake of oral preparations.

In one embodiment a prebiotic composition is provided as a tablet, capsule, or caplet with an enteric coating. In one embodiment the enteric coating is designed to hold the tablet, capsule, or caplet together when in the stomach. The enteric coating is designed to hold together in acid conditions of the stomach and break down in non-acid conditions and therefore release the drug in the intestines.

Softgel delivery systems can also incorporate phospholipids or polymers or natural gums to entrap a composition, for example, a prebiotic composition, in the gelatin layer with an outer coating to give desired delayed/control release effects, such as an enteric coating.

Formulations of softgel fills can be at pH 2.5-7.5.

A softgel formulation can be sealed tightly in an automatic manner. A softgel formulation can easily be swallowed, allow for product identification using colors and several shapes, allow uniformity, precision and accuracy between dosages, be safe against adulteration, provide good availability and rapid absorption, and offer protection against contamination, light and oxidation. Furthermore, softgel formulations can avoid unpleasant flavors due to content encapsulation.

A composition comprising a softgel formulation can be in any of number of different sizes, including, for example, round, oblong, oval, tube, droplet, or suppositories.

In one embodiment a composition is provided in a dosage form which comprises an effective amount of prebiotic and one or more release controlling excipients as described herein. Suitable modified release dosage vehicles include, but are not limited to, hydrophilic or hydrophobic matrix devices, water-soluble separating layer coatings, enteric coatings, osmotic devices, multi-particulate devices, and combinations thereof. In one embodiment the dosage form is a tablet, caplet, capsule or lollipop. In another embodiment, the dosage form is a liquid, oral suspension, oral solution, or oral syrup. In yet another embodiment, the dosage form is a gel capsule, soft gelatin capsule, or hard gelatin capsule.

In one embodiment, the dosage form is a gelatin capsule having a size indicated in Table 4.

TABLE 4

| Gel cap sizes allowable for human consumption Empty Gelatin Capsule Physical Specifications | | | |
|---|---|---|---|
| Size | Outer Diameter (mm) | Height or Locked Length (mm) | Actual Volume (ml) |
| 000 | 9.97 | 26.14 | 1.37 |
| 00 | 8.53 | 23.30 | 0.95 |
| 0 | 7.65 | 21.7 | 0.68 |
| 1 | 6.91 | 19.4 | 0.50 |
| 2 | 6.35 | 18.0 | 0.37 |
| 3 | 5.82 | 15.9 | 0.3 |
| 4 | 5.31 | 14.3 | 0.21 |
| 5 | 4.91 | 11.1 | 0.13 |

Note:
sizes and volumes are approximate.

In another embodiment a composition comprising a prebiotic is provided in effervescent dosage forms. The compositions can also comprise non-release controlling excipients.

In another embodiment, a composition comprising a prebiotic is provided in a dosage form that has at least one component that can facilitate release of the prebiotic. In a further embodiment the dosage form can be capable of giving a discontinuous release of the compound in the form of at least two consecutive pulses separated in time from 0.1 up to 24 hours. The compositions can comprise one or more release controlling and non-release controlling excipients, such as those excipients suitable for a disruptable semipermeable membrane and as swellable substances.

In another embodiment a composition comprising a prebiotic is provided in an enteric coated dosage form. The composition can also comprise non-release controlling excipients.

In another embodiment a composition comprising a prebiotic is provided in a dosage form for oral administration to a subject in need thereof, which comprises one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

In one embodiment a composition comprising a prebiotic is provided in the form of enteric-coated granules, for oral administration. The compositions can further comprise cellulose, disodium hydrogen phosphate, hydroxypropyl cellulose, hypromellose, lactose, mannitol, and sodium lauryl sulfate.

In another embodiment a composition comprising a prebiotic is provided in the form of enteric-coated pellets, for oral administration. The compositions can further comprise glyceryl monostearate 40-50, hydroxypropyl cellulose, hypromellose, magnesium stearate, methacrylic acid copolymer type C, polysorbate 80, sugar spheres, talc, and triethyl citrate.

In one embodiment a composition comprising a prebiotic is provided in the form of enteric-coated granules, for oral administration. The compositions can further comprise carnauba wax, crospovidone, diacetylated monoglycerides, ethylcellulose, hydroxypropyl cellulose, hypromellose phthalate, magnesium stearate, mannitol, sodium hydroxide, sodium stearyl fumarate, talc, titanium dioxide, and yellow ferric oxide.

In another embodiment a composition comprising a prebiotic can further comprise calcium stearate, crospovidone, hydroxypropyl methylcellulose, iron oxide, mannitol, methacrylic acid copolymer, polysorbate 80, povidone, propylene glycol, sodium carbonate, sodium lauryl sulfate, titanium dioxide, and triethyl citrate.

The compositions provided herein can be in unit-dosage forms or multiple-dosage forms. Unit-dosage forms, as used herein, refer to physically discrete units suitable for administration to human or non-human animal subject in need thereof and packaged individually. Each unit-dose can contain a predetermined quantity of an active ingredient(s) sufficient to produce the desired therapeutic effect, in association with other pharmaceutical carriers or excipients. Examples of unit-dosage forms include, but are not limited to, ampoules, syringes, and individually packaged tablets and capsules. Unit-dosage forms can be administered in fractions or multiples thereof. A multiple-dosage form is a plurality of identical unit-dosage forms packaged in a single container, which can be administered in segregated unit-dosage form. Examples of multiple-dosage forms include, but are not limited to, vials, bottles of tablets or capsules, or bottles of pints or gallons. In another embodiment the multiple dosage forms comprise different pharmaceutically active agents. For example a multiple dosage form can be provided which comprises a first dosage element comprising a composition comprising a prebiotic and a second dosage element comprising lactose or a probiotic, which can be in a modified release form.

In this example a pair of dosage elements can make a single unit dosage. In one embodiment a kit is provided comprising multiple unit dosages, wherein each unit comprises a first dosage element comprising a composition comprising a prebiotic and a second dosage element comprising probiotic, lactose or both, which can be in a modified release form. In another embodiment the kit further comprises a set of instructions.

In one embodiment compositions can be formulated in various dosage forms for oral administration. The compositions can also be formulated as a modified release dosage form, including immediate-, delayed-, extended-, prolonged-, sustained-, pulsatile-, controlled-, extended, accelerated-, fast-, targeted-, programmed-release, and gastric retention dosage forms. These dosage forms can be prepared according to known methods and techniques (see, Remington: The Science and Practice of Pharmacy, supra; Modified-Release Drug Deliver Technology, Rathbone et al., Eds., Drugs and the Pharmaceutical Science, Marcel Dekker, Inc.: New York, N. Y., 2002; Vol. 126, which is herein incorporated by reference in its entirety).

In one embodiment, the compositions are in one or more dosage forms. For example, a composition can be administered in a solid or liquid form. Examples of solid dosage forms include but are not limited to discrete units in capsules or tablets, as a powder or granule, or present in a tablet conventionally formed by compression molding. Such compressed tablets can be prepared by compressing in a suitable machine the three or more agents and a pharmaceutically acceptable carrier. The molded tablets can be optionally coated or scored, having indicia inscribed thereon and can be so formulated as to cause immediate, substantially immediate, slow, controlled or extended release of a composition comprising a prebiotic. Furthermore, dosage forms of the invention can comprise acceptable carriers or salts known in the art, such as those described in the Handbook of Pharmaceutical Excipients, American Pharmaceutical Association (1986), incorporated by reference herein in its entirety.

In one embodiment, an effective amount of a composition comprising a prebiotic is mixed with a pharmaceutical excipient to form a solid preformulation composition comprising a homogeneous mixture of compounds described herein. When referring to these compositions as "homogeneous," it is meant that the agents are dispersed evenly throughout the composition so that the composition can be subdivided into unit dosage forms such as tablets, caplets, or capsules. This solid preformulation composition can then be subdivided into unit dosage forms of the type described above comprising from, for example, about 1 g to about 20 mg of a prebiotic composition. A prebiotic composition can be formulated, in the case of caplets, capsules or tablets, to be swallowed whole, for example with water.

The compositions described herein can be in liquid form. The liquid formulations can comprise, for example, an agent in water-in-solution and/or suspension form; and a vehicle comprising polyethoxylated castor oil, alcohol, and/or a polyoxyethylated sorbitan mono-oleate with or without flavoring. Each dosage form comprises an effective amount of an active agent and can optionally comprise pharmaceutically inert agents, such as conventional excipients, vehicles, fillers, binders, disintegrants, pH adjusting substances, buffer, solvents, solubilizing agents, sweeteners, coloring agents, and any other inactive agents that can be included in pharmaceutical dosage forms for oral administration. Examples of such vehicles and additives can be found in Remington's Pharmaceutical Sciences, 17th edition (1985).

2. Manufacturing

The dosage forms described herein can be manufactured using processes that are well known to those of skill in the art. For example, for the manufacture of tablets, an effective amount of a prebiotic can be dispersed uniformly in one or more excipients, for example, using high shear granulation, low shear granulation, fluid bed granulation, or by blending for direct compression. Excipients include diluents, binders, disintegrants, dispersants, lubricants, glidants, stabilizers, surfactants and colorants. Diluents, also termed "fillers," can be used to increase the bulk of a tablet so that a practical size is provided for compression. Non-limiting examples of diluents include lactose, cellulose, microcrystalline cellulose, mannitol, dry starch, hydrolyzed starches, powdered sugar, talc, sodium chloride, silicon dioxide, titanium oxide, dicalcium phosphate dihydrate, calcium sulfate, calcium carbonate, alumina and kaolin. Binders can impart cohesive qualities to a tablet formulation and can be used to help a tablet remain intact after compression. Non-limiting examples of suitable binders include starch (including corn starch and pregelatinized starch), gelatin, sugars (e.g., glucose, dextrose, sucrose, lactose and sorbitol), celluloses, polyethylene glycol, waxes, natural and synthetic gums, e.g., acacia, tragacanth, sodium alginate, and synthetic polymers such as polymethacrylates and polyvinylpyrrolidone. Lubricants can also facilitate tablet manufacture; non-limiting examples thereof include magnesium stearate, calcium stearate, stearic acid, glyceryl behenate, and polyethylene glycol. Disintegrants can facilitate tablet disintegration after administration, and non-limiting examples thereof include starches, alginic acid, crosslinked polymers such as, e.g., crosslinked polyvinylpyrrolidone, croscarmellose sodium, potassium or sodium starch glycolate, clays, celluloses, starches, gums and the like. Non-limiting examples of suitable glidants include silicon dioxide, talc, and the like. Stabilizers can inhibit or retard drug decomposition reactions, including oxidative reactions. Surfactants can also include and can be anionic, cationic, amphoteric or nonionic. If desired, the tablets can also comprise nontoxic auxiliary substances such as pH buffering agents, preservatives, e.g., antioxidants, wetting or emulsifying agents, solubilizing agents, coating agents, flavoring agents, and the like.

In one embodiment, a softgel formulation is made with a gelatin mass for the outer shell, and a composition including one or more substances, for example prebiotics and/or probiotics, for the capsule fill can be prepared. To make the gelatin mass, gelatin powder can be mixed with water and glycerin, heated, and stirred under vacuum. Additives, for example, flavors or colors, can be added to molten gelatin using a turbine mixer and transferred to mobile vessels. The gelatin mass can be kept in a steam jacketed storage vessel at a constant temperature.

The encapsulation process can begin when the molten gel is pumped to a machine and two thin ribbons of gel are formed on either side of machine. These ribbons can then pass over a series of rollers and over a set of die that determine the size and shapes of capsules. A fill composition, for example a prebiotic and/or probiotic fill composition, can be fed to a positive displacement pump, which can dose the fill and inject it between two gelatin ribbons prior to sealing them together through the application of heat and pressure. To remove excess water, the capsules can pass through a conveyer into tumble dryers where a portion of the water can be removed. The capsules can then be placed on, for example, trays, which can be stacked and transferred into drying rooms. In the drying rooms, dry air can be forced over capsules to remove any excess moisture.

3. Release Formulations

Immediate-release formulations of an effective amount of a prebiotic composition can comprise one or more combinations of excipients that allow for a rapid release of a pharmaceutically active agent (such as from 1 minute to 1 hour after administration). In one embodiment an excipient can be microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, Avicel PH200, and combinations of such excipients.

"Controlled-release" formulations (also referred to as sustained release (SR), extended-release (ER, XR, or XL), time-release or timed-release, controlled-release (CR), or continuous-release) refer to the release of a prebiotic composition from a dosage form at a particular desired point in time after the dosage form is administered to a subject. Controlled-release formulations can include one or more excipients, including but not limited to microcrystalline cellulose, sodium carboxymethyl cellulose, sodium starch glycolate, corn starch, colloidal silica, Sodium Laurel Sulphate, Magnesium Stearate, Prosolve SMCC (HD90), croscarmellose Sodium, Crospovidone NF, or Avicel PH200. Generally, controlled-release includes sustained but otherwise complete release. A sudden and total release in the large intestine at a desired and appointed time or a release in the intestines such as through the use of an enteric coating are both considered controlled-release. Controlled-release can occur at a predetermined time or in a predetermined place within the digestive tract. It is not meant to include a passive, uncontrolled process as in swallowing a normal tablet. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,556; 5,871,776; 5,902,632; and 5,837,284 each of which is incorporated herein by reference in its entirety.

In one embodiment a controlled release dosage form begins its release and continues that release over an extended period of time. Release can occur beginning almost immediately or can be sustained. Release can be constant, can increase or decrease over time, can be pulsed, can be continuous or intermittent, and the like. Generally, however, the release of at least one pharmaceutically active agent from a controlled-release dosage form will exceed the amount of time of release of the drug taken as a normal, passive release tablet. Thus, for example, while all of at least one pharmaceutically active agent of an uncoated aspirin tablet should be released within, for example, four hours, a controlled-release dosage form could release a smaller amount of aspirin over a period of six hours, 12 hours, or even longer. Controlled-release in accordance with the compositions and methods described herein generally means that the release occurs for a period of six hours or more, such as 12 hours or more.

In another embodiment a controlled release dosage refers to the release of an agent, from a composition or dosage form in which the agent is released according to a desired profile over an extended period of time. In one embodiment, controlled-release results in dissolution of an agent within 20-720 minutes after entering the stomach. In another embodiment, controlled-release occurs when there is dissolution of an agent within 20-720 minutes after being swallowed. In another embodiment, controlled-release occurs when there is dissolution of an agent within 20-720 minutes after entering the intestine. In another embodiment, controlled-release results in substantially complete dissolution after at least 1 hour following administration. In another embodiment, controlled-release results in substantially complete dissolution after at least 1 hour following oral administration. For example, controlled-release compositions allow delivery of an agent to a subject in need thereof over an extended period of time according to a predetermined profile. Such release rates can provide therapeutically effective levels of agent for an extended period of time and thereby provide a longer period of pharmacologic or diagnostic response as compared with conventional rapid release dosage forms. Such longer periods of response provide for many inherent benefits that are not achieved with immediate-release dosages. When used in connection with the dissolution profiles discussed herein, the term "controlled-release" refers to wherein all or less than all of the total amount of a dosage form, made according to methods and compositions described herein, delivers an active agent over a period of time greater than 1 hour.

In one aspect, controlled-release refers to delayed release of an agent, from a composition or dosage form in which the agent is released according to a desired profile in which the release occurs after a period of time.

When present in a controlled-release oral dosage form, the compositions described herein can be administered at a substantially lower daily dosage level than immediate-release forms.

In one embodiment, the controlled-release layer is capable of releasing about 30 to about 40% of the one or more active agents (e.g., prebiotic or probiotic) contained therein in the stomach of a subject in need thereof in about 5 to about 10 minutes following oral administration. In another embodiment, the controlled-release layer is capable of releasing about 90% of the one or more active agents (e.g., prebiotic or probiotic) is released in about 40 minutes after oral administration.

In some embodiment, the controlled-release layer comprises one or more excipients, including but not limited to silicified microcrystalline cellulose (e.g., HD90), croscarmellose sodium (AC-Di-Sol), hydroxyl methyl propyl cellulose, magnesium stearate, or stearic acid. In one embodiment, a controlled release formulation weighs between about 100 mg to 3 g.

Pharmaceutical carriers or vehicles suitable for administration of the compounds provided herein include all such carriers known to those skilled in the art to be suitable for the particular mode of administration. In addition, the compositions can one or more components that do not impair the desired action, or with components that supplement the desired action, or have another action.

In another embodiment, an effective amount of the prebiotic is formulated in an immediate release form. In this embodiment the immediate-release form can be included in an amount that is effective to shorten the time to its maximum concentration in the blood. By way of example, certain immediate-release pharmaceutical preparations are taught in United States Patent Publication US 2005/0147710A1 entitled, "Powder Compaction and Enrobing," which is incorporated herein in its entirety by reference.

The dosage forms described herein can also take the form of pharmaceutical particles manufactured by a variety of methods, including but not limited to high-pressure homogenization, wet or dry ball milling, or small particle precipitation (nano spray). Other methods to make a suitable powder formulation are the preparation of a solution of active ingredients and excipients, followed by precipitation, filtration, and pulverization, or followed by removal of the solvent by freeze-drying, followed by pulverization of the powder to the desired particle size.

In a further aspect the dosage form can be an effervescent dosage form. Effervescent means that the dosage form, when mixed with liquid, including water and saliva, evolves a gas. Some effervescent agents (or effervescent couple) evolve gas by means of a chemical reaction which takes place upon exposure of the effervescent disintegration agent to water or to saliva in the mouth. This reaction can be the result of the reaction of a soluble acid source and an alkali monocarbonate or carbonate source. The reaction of these two general compounds produces carbon dioxide gas upon contact with water or saliva. An effervescent couple (or the individual acid and base separately) can be coated with a solvent protective or enteric coating to prevent premature reaction. Such a couple can also be mixed with previously lyophilized particles (such as a prebiotic). The acid sources can be any which are safe for human consumption and can generally include food acids, acid and hydrite antacids such as, for example: citric, tartaric, amalic, fumeric, adipic, and succinics. Carbonate sources include dry solid carbonate and bicarbonate salt such as, preferably, sodium bicarbonate, sodium carbonate, potassium bicarbonate and potassium carbonate, magnesium carbonate and the like. Reactants which evolve oxygen or other gasses and which are safe for human consumption are also included. In one embodiment citric acid and sodium bicarbonate are used.

In another aspect the dosage form can be in a candy form (e.g., matrix), such as a lollipop or lozenge. In one embodiment an effective amount of a prebiotic is dispersed within a candy matrix. In one embodiment the candy matrix comprises one or more sugars (such as dextrose or sucrose). In another embodiment the candy matrix is a sugar-free matrix. The choice of a particular candy matrix is subject to wide variation. Conventional sweeteners such as sucrose can be utilized, or sugar alcohols suitable for use with diabetic patients, such as sorbitol or mannitol can be employed. Other sweeteners, such as the aspartanes, can also be easily incorporated into a composition in accordance with compositions described herein. The candy base can be very soft and fast dissolving, or can be hard and slower dissolving. Various forms will have advantages in different situations.

A candy mass composition comprising an effective amount of the prebiotic can be orally administered to a subject in need thereof so that an effective amount of the prebiotic will be released into the subject's mouth as the candy mass dissolves and is swallowed. A subject in need thereof includes a human adult or child.

In one embodiment a candy mass is prepared that comprises one or more layers which can comprise different amounts or rates of dissolution of the prebiotic. In one embodiment a multilayer candy mass (such as a lollipop) comprises an outer layer with a concentration of the prebiotic differing from that of one or more inner layers. Such a drug delivery system has a variety of applications.

The choices of matrix and the concentration of the drug in the matrix can be important factors with respect to the rate of drug uptake. A matrix that dissolves quickly can deliver drug into the subject's mouth for absorption more quickly than a matrix that is slow to dissolve. Similarly, a candy matrix that contains the prebiotic in a high concentration can release more of the prebiotic in a given period of time than a candy having a low concentration. In one embodiment a candy matrix such as one disclosed in U.S. Pat. No. 4,671,953 or US Application Publication No. 2004/0213828 (which are herein incorporated by reference in their entirety) is used to deliver the prebiotic.

The dosage forms described herein can also take the form of pharmaceutical particles manufactured by a variety of methods, including but not limited to high-pressure homogenization, wet or dry ball milling, or small particle precipitation (e.g., nGimat's NanoSpray). Other methods useful to make a suitable powder formulation are the preparation of a solution of active ingredients and excipients, followed by precipitation, filtration, and pulverization, or followed by removal of the solvent by freeze-drying, followed by pulverization of the powder to the desired particle size. In one embodiment the pharmaceutical particles have a final size of 3-1000 µM, such as at most 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950, 1000 µM. In another embodiment the pharmaceutical particles have a final size of 10-500 µM. In another embodiment the pharmaceutical particles have a final size of 50-600 µM. In another embodiment the pharmaceutical particles have a final size of 100-800 µM.

In one embodiment an oral dosage form (such as a powder, tablet, or capsule) is provided comprising a prebiotic composition comprising about 0.7 g of GOS, about 0.2 g of lactose, about 0.01 g of glucose, about 0.01 g of galactose, about 0.1-0.2 g of a binder, about 0.1-0.2 g of a dispersant, about 0.1-0.2 g of a solubilizer, wherein the GOS are composed of about 1-25% disaccharides, about 1-25% trisaccharides, about 1-25% tetrasaccharides, and about 1-25% pentasaccharides. The oral dosage form can be in the form of a powder, capsule, or tablet. Suitable amounts of binders, dispersants, and solubilizers are known in the art for preparation of oral tablets or capsules.

In another embodiment an oral dosage form (such as a powder, tablet or capsule) is provided comprising a prebiotic composition comprising about 1-99.9% by weight of GOS, about 0.5-20% by weight of lactose, about 0.1-2% by weight of glucose, about 0.1-2% by weight of galactose, about 0.05-2% by weight of a binder, about 0.05-2% by weight of a dispersant, about 0.05-2% by weight of a solubilizer, wherein the GOS are composed of about 1-25% by weight disaccharides, about 1-25% by weight trisaccharides, about 1-25% by weight tetrasaccharides, and about 1-25% by weight pentasaccharides.

In another embodiment an oral dosage form (such as a powder, tablet, or capsule) is provided comprising a prebiotic composition comprising about 1, 10, 20, 30, 40, 50, 60, 70, 80, 90, 95, 99.5, 100% by weight of GOS, about 0, 5, 10, 15, or 20% by weight of lactose, about 0.1, 0.5, 1, or 2% by weight of glucose, about 0.1, 0.5, 1, or 2% by weight of galactose, about 0.05, 0.1, 0.5, 1, or 2% by weight of a binder, about 0.05, 0.1, 0.5, 1, or 2% by weight of a dispersant, about 0.05, 0.1, 0.5, 1, or 2% by weight of a solubilizer, wherein the GOS are composed of about 1, 5, 10, 15, 20, or 25% by weight disaccharides, about 1, 5, 10, 15, 20, or 25% by weight trisaccharides, about 1, 5, 10, 15, 20, or 25% by weight tetrasaccharides, and about 1, 5, 10, 15, 20, or 25% by weight pentasaccharides.

In another embodiment, an oral dosage form is provided comprising a prebiotic composition, wherein the oral dosage form is a syrup. The syrup can comprise about 1%, 5%, 10%, 15%, 20%, 25%, 30%, 35%, 40%, 45%, 50%, 55%, 60%, 65%, 70%, 75%, 80%, or 85% solid. The syrup can comprise about 15%, 20%, 25%, 30%, 35%, 40%, 45%, or 50% liquid, for example, water. The solid can comprise a prebiotic composition. The solid can be, for example, about 1-96%, 10-96%, 20-96%, 30-96%, 40-96%, 50-96%, 60-96%, 70-96%, 80-96%, or 90-96% prebiotic composition. The solid can be, for example, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, or 96% prebiotic composition. In one embodiment a prebiotic composition comprises GOS. In another embodiment a prebiotic composition comprises GOS and another prebiotic. In another embodiment a prebiotic composition comprises GOS and inulin or GOS and FOS.

In one embodiment, the softgel capsule is about 0.25 mL, 0.5 mL, 1.0 mL, 1.25 mL, 1.5 mL, 1.75 mL, or 2.0 mL. In another embodiment, a softgel capsule comprises about 0.1 g to 2.0 g of prebiotic composition. In another embodiment, a softgel capsule comprises about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 g of a prebiotic composition. In one embodiment the prebiotic composition comprises GOS. In another embodiment the prebiotic composition consists essentially of GOS. In another embodiment, a softgel capsule comprises GOS and inulin or FOS.

In another embodiment, the prebiotic composition will be delivered in a gelatin capsule containing an amount of GOS within the ranges listed in Table 5. In another embodiment, the number of pills taken per day will be within the ranges listed in Table 5.

TABLE 5

Exemplary GOS dosing units
Exemplary GOS Composition Dosages in Gel Caps

| Size | GOS/Pill (g) | # pills per day |
|---|---|---|
| 000 | 1-2 | 1-15 |
| 00 | 0.6-1.5 | 1-25 |
| 0 | 0.4-1.1 | 1-38 |
| 1 | 0.3-0.8 | 1-50 |
| 2 | 0.25-0.6 | 1-60 |
| 3 | 0.2-0.5 | 1-75 |
| 4 | 0.14-0.3 | 1-107 |

In another embodiment, a prebiotic composition is provided that does not contain a preservative. In another embodiment, a prebiotic composition is provided that does not contain an antioxidant. In another embodiment, a prebiotic composition is provided that does not contain a preservative or an antioxidant. In one embodiment a prebiotic composition comprising GOS does not contain a preservative or an antioxidant.

In another embodiment, a prebiotic composition is formulated as a viscous fluid. In another embodiment, a prebiotic composition is formulated such that its water content is low enough that it does not support microbial growth. In another embodiment, a prebiotic composition is formulated as a viscous fluid without a preservative in a gel capsule. In another embodiment, a prebiotic composition comprising GOS is a viscous fluid. In another embodiment, a prebiotic composition comprises a high percentage of GOS that does not support microbial growth. In another embodiment, the prebiotic composition comprises GOS and inulin or FOS.

In another embodiment, an oral dosage form is provided comprising a prebiotic composition, wherein the oral dosage form is a softgel. In one embodiment the softgel comprises a syrup. In one embodiment the syrup comprises a prebiotic composition. In one embodiment the prebiotic composition comprises GOS. In another embodiment the prebiotic composition comprises more than 80% GOS. In another embodiment the prebiotic composition comprises between 80-99.9% GOS. In another embodiment the prebiotic composition comprises more than 80% GOS. In another embodiment the prebiotic composition comprises about 80, 81, 82, 83, 84, 85, 86, 87, 88, 89, 90, 91, 92, 93, 94, 95, 96, 97, 98, 99, or 99.9% GOS.

In one embodiment a GOS composition is formulated for delivery in a soft gel capsule. In one embodiment a GOS composition formulated for delivery in a soft gel capsule is a high percentage GOS composition, such as a 90-100% GOS composition (e.g., 90, 91, 92, 93, 94, 95, 96, 97, 98, 99 or 100% GOS composition by weight). In another embodiment a GOS composition formulated for delivery in a soft gel capsule comprises about 95% GOS. In another embodiment a GOS composition formulated for delivery in a soft gel capsule comprises about 96% GOS. In another embodiment, the GOS composition is formulated such that its water content is low enough that it does not support microbial growth. In another embodiment, the GOS composition is formulated as a viscous fluid without a preservative in a gel capsule. In another embodiment, the GOS composition is formulated as a viscous fluid without an antioxidant in a gel capsule. In another embodiment the soft gel capsule comprises about 0.1-2 g of a GOS composition.

In another embodiment a prebiotic composition can be formulated as described, in U.S. Pat. No. 6,750,331, which is herein incorporated by reference in its entirety. A prebiotic composition can be formulated to comprise an oligosaccharide, a foaming component, a water-insoluble dietary fiber, or a neutralizing component. In one embodiment a prebiotic composition can be in the form of a chewable tablet.

In one embodiment a foaming component can be at least one member selected from the group consisting of sodium hydrogencarbonate, sodium carbonate, and calcium carbonate. In one embodiment a neutralizing component can be at least one member selected from the group consisting of citric acid, L-tartaric acid, fumaric acid, L-ascorbic acid, DL-malic acid, acetic acid, lactic acid, and anhydrous citric acid. In one embodiment a water-insoluble dietary fiber can be at least one member selected from the group consisting of crystalline cellulose, wheat bran, oat bran, cone fiber, soy fiber, and beet fiber. The formulation can contain a sucrose fatty acid ester, powder sugar, fruit juice powder, and/or flavoring material.

Formulations of the provided invention can include additive components selected from various known additives. Such additives include, for example, saccharides (excluding oligosaccharides), sugar alcohols, sweeteners and like excipients, binders, disintegrators, lubricants, thickeners, surfactants, electrolytes, flavorings, coloring agents, pH modifiers, fluidity improvers, and the like. Specific examples of the additives include wheat starch, potato starch, corn starch, dextrin and like starches; sucrose, glucose, fructose, maltose, xylose, lactose and like saccharides (excluding oligosaccharides); sorbitol, mannitol, maltitol, xylitol and like sugar alcohols; calcium phosphate, calcium sulfate and like excipients; starch, saccharides, gelatine, gum arabic, dextrin, methyl cellulose, polyvinylpyrrolidone, polyvinyl alcohol, hydroxypropylcellulose, xanthan gum, pectin, gum tragacanth, casein, alginic acid and like binders and thickeners; leucine, isoleucine, L-valine, sugar esters, hardened oils, stearic acid, magnesium stearate, talc, macrogols and like lubricants; CMC, CMC-Na, CMC-Ca and like disintegrators; polysorbate, lecithin and like surfactants; aspartame, alitame and like dipeptides; silicon dioxide and like fluidity improvers; and stevia, saccharin, and like sweeteners. The amounts of these additives can be properly selected based on their relation to other components and properties of the preparation, production method, etc.

In one embodiment, a GOS composition is a chewable oral dosage formulation. In one embodiment the chewable formulation can comprises between about 1-99.9% GOS. In one embodiment, a GOS composition comprises about 80% GOS, about 5% L-ascorbic acid, about 2% anhydrous citric acid, about 3% sodium hydrogencarbonate, about 3% calcium carbonate, about 2% sucrose fatty acid, about 3% fruit juice powder, and about 2% potassium carbonate.

In another embodiment, a GOS composition comprises about 85% GOS, about 5% L-ascorbic acid, about 3% sodium hydrogencarbonate, about 2% sodium carbonate, about 2% sucrose fatty acid ester, about 2% fruit juice powder, and about 1% potassium carbonate.

In another embodiment, a GOS composition comprises about 90% GOS, about 2% L-ascorbic acid, about 1% anhydrous citric acid, about 2% sodium hydrogencarbonate, about 2% sodium carbonate, about 2% sucrose fatty acid ester, and about 1% potassium carbonate.

In another embodiment, a GOS composition comprises about 95% GOS, about 2% L-ascorbic acid, about 1% sodium hydrogencarbonate, and about 2% fruit juice powder. In another embodiment, a GOS composition comprises about 95% GOS and about 5% of L-ascorbic acid, anhydrous citric acid, sodium hydrogencarbonate, calcium carbonate, sucrose fatty acid, fruit juice powder, or potassium carbonate.

In another embodiment, a GOS composition comprises about 95% GOS and about 5% of L-ascorbic acid, anhydrous citric acid, sodium hydrogencarbonate, calcium carbonate, sucrose fatty acid, fruit juice powder, and potassium carbonate.

VI. Treatment

A. Lactose Intolerance

The invention provides methods and prebiotic compositions useful for the reduction of symptoms of lactose intolerance and for improving overall gastrointestinal (GI) health. Symptoms of lactose intolerance include gas, bloating, diarrhea, abdominal pain, cramping, and vomiting. Minor digestive problems related to the GI also include occasional bloating, diarrhea, constipation, gas, heartburn, or stomach upset. The methods and compositions described herein can be useful for reducing or eliminating one or more of these symptoms, for example through colonic adaptation. These compositions are expected to modify the colonic microbiota, which may result in an increased tolerance to lactose and other fermentable carbohydrates. Furthermore, these compositions can allow the colonic microbiota, comprising microorganisms known to increase the ability of an individual to tolerate fermentable carbohydrates, to be regularly replenished through consumption of the compositions. Adaptation of the intestinal and colonic microbiota, improve the composition of the intestinal microbiota, and the capacity for consumption of foods comprising lactose can be increased. For example, an individual's tolerance to dairy in general can be improved through regular consumption of a prebiotic composition. This change in colonic microbiota is useful for the reduction of bloating, diarrhea, gastric distention and pain, and/or flatulence from the consumption of dairy products or other foods comprising lactose. In one embodiment, a method of treating lactose intolerance is disclosed. In another embodiment, a method of treating at least one symptom of lactose intolerance is disclosed.

There are at least three types of lactose intolerance. Primary lactose intolerance results from a decrease in lactase production as a subject ages. Secondary lactose intolerance can result when a subject's small intestine decreases lactase production after an illness, surgery, or injury to the small intestine. Secondary lactose intolerance can occur as a result of Crohn's disease, celiac disease, or gastroenteritis. This type of lactose intolerance can be temporary or permanent. A third type of lactose intolerance is congenital lactose intolerance, in which a subject is born with lactose intolerance. Risk factors that can make a person more prone to lactose intolerance include, for example, age (lactose intolerance usually has an onset of after age 5), ethnicity (lactose intolerance is more common in black, Asian, Hispanic, and American Indian populations), and premature birth (infants born 28 to 32 weeks of gestation).

B. Testing Lactose Intolerance

Lactose intolerance can be tested either indirectly or directly. Indirect testing methods include, but are not limited to: a hydrogen breath test, a stool acidity test, a blood glucose test, or milk challenge test. In the hydrogen breath test, the breath is measured to determine the amount of hydrogen produced after consuming a measured amount of lactose, typically 15 g. The lactose is administered by drinking a lactose mixture, and the subject exhales into a vacuum-sealed collection tube at three one hour time intervals. A high level of hydrogen in the breath indicates an improper digestion of lactose. In a stool test, the stool is tested to determine the amount of acid. In a blood glucose test, the blood is tested to determine the amount of glucose (sugar) content after administering a predetermined amount of lactose-containing product to the subject. Lactose maldigestion is often defined more specifically as an "increase in blood glucose concentration of <1.12 mmol/L or breath hydrogen of >20 ppm after ingestion of 1 g/kg body weight or 50 g lactose" (de Vrese et al., 2001). The direct method measures lactase activity in a mucosal biopsy specimen.

The stool acidity test is typically used to test lactose intolerance in infants and young children. The hydrogen breath test is typically not recommended for young children since dehydration can occur due to diarrhea after ingestion of the lactose-containing drink.

Effectiveness of treatment can be measured in a number of ways. Conventional measurements, such as those described, can be used before and after treatment. Alternatively, or in addition, the amount of lactose-containing product that can be administered before the onset of one or more symptoms can be measured or evaluated before and after treatment. Thus, for example, treatment can be considered fully or partially effective if, after treatment, less hydrogen is produced on average in a subject after challenge with a food comprising lactose (such as a dairy product).

In one embodiment, the Hydrogen Breath Test (HBT) is utilized to determine facilitation of lactose metabolism by GOS containing compositions (e.g. GOS 95), thereby resulting in less hydrogen production following lactose challenge as compared to baseline levels. In one embodiment the GOS composition is a high percentage composition, such as about 90% or greater (e.g., about 90, 91, 92, 93, 94, 95, 96, 97, 98, 99, or 100% by weight). In one embodiment, the HBT test involves administering 25 mg of lactose and determining the amount of hydrogen in the breath at periodic intervals, usually for four to eight hours (Bhatnagar and Aggarwal 2007). In another embodiment, fecal bacteria levels are assessed for bacterial DNA samples to assess bacterial adaptation. In another embodiment, treatment with GOS compositions (e.g. GOS 95) is expected to provide relief from one or more lactose intolerance symptoms beyond the treatment phase. In one embodiment the GOS composition is a high percentage composition, such as about 90% or greater (e.g., about 90, 91, 92, 93, 94, 95, 96, 97, 98, 99, or 100% by weight).

More commonly, a subject cannot precisely test the amount of hydrogen or use a blood glucose test to measure effectiveness. Instead, a subject can subjectively determine the quantity of lactose-containing products they can consume, and the types and degree of symptoms experienced after such consumption. "Partial" elimination of symptoms of lactose intolerance includes a subjective or measurable increase in the amount of lactose that can be consumed before the onset of symptoms. "Substantial" elimination of symptoms of lactose intolerance, as used herein, encompasses an effect where at least about twice the amount of lactose or a lactose containing food can be consumed after treatment before the onset of symptoms as could have been consumed before treatment. "Complete" or "substantially complete" elimination of symptoms of lactose intolerance, as used herein, indicates that normal amounts of lactose can be consumed after treatment (i.e., the amount of lactose in a typical diet for the area or culture in which the subject normally lives) without symptoms, or with only the rare occurrence of symptoms.

In one embodiment a subject in need thereof can consume one half cup (4 oz.; about 120 mL) of milk with no, or minimal, symptoms of lactose intolerance. However, consumption of 1 or more cups (about 240 mL) of milk causes symptoms of lactose intolerance, such as gas or diarrhea, to occur. After treatment with a composition and/or dosing regimen disclosed herein, a subject can find that 1 and one-half cups (about 360 mL) of milk can be consumed in a single administration without causing any symptoms of lactose intolerance. The subject would experience the substantial elimination of the symptoms of lactose intolerance. In another embodiment a subject can find that after treatment with a composition and/or dosing regimen disclosed a normal diet for their geographical or cultural region can be consumed with no, or rare, symptoms of lactose intolerance.

In another embodiment effectiveness can be measured by a percentage decrease in one or more symptoms of lactose intolerance. In this measurement, the severity of a predetermined symptom, or set of symptoms is measured before and after treatment, e.g., using pre and post Likert scale. Exemplary symptoms include gas, bloating, diarrhea, cramping, abdominal pain, and vomiting. Any one or more than one, of the symptoms can be measured. For example, a subject can be asked to rate one or more symptoms on a scale of increasing severity from 1 to 5. In one embodiment, a set of symptoms is rated, and the ratings are added; for example, gas, bloating, diarrhea, abdominal pain, abdominal distension, vomiting, nausea, or cramping can be rated. In another embodiment a percentage change in one or more symptoms of lactose intolerance can be calculated based on a subject's ratings before and after treatment with a composition or method disclosed herein. In one embodiment the composition is a prebiotic composition. In one embodiment the prebiotic composition comprises GOS. In one embodiment symptoms of lactose intolerance can be considered to be reduced by the a subject's reported decrease in one or more specific symptoms after challenge with a food comprising lactose (e.g., if there is a 50% decrease in symptoms, then symptoms of lactose intolerance are reduced by 50%).

In another embodiment a milk challenge test is used to determine if a subject is lactose intolerant. In the milk challenge test, a subject fasts overnight, and then the person drinks a glass of milk in the morning. After drinking the milk, nothing else is eaten or drunk for three to five hours. If a subject experiences one or more symptoms of lactose intolerance within several hours after consuming the milk then the subject is lactose intolerant.

In one embodiment, a lactose intolerance diagnostic device is used to determine if a subject is lactose intolerant. In one embodiment, a diagnostic device is a lactose intolerance diagnostic questionnaire wherein a subject rates the severity of exemplary symptoms of lactose intolerance. In one embodiment, the symptoms are rated on a scale of 0 to 5, wherein 0 indicates no symptoms, 1 indicates slight symptoms, 2 indicates mild symptoms, 3 indicates moderate symptoms, 4 indicates moderately severe symptoms, and 5 indicates severe symptoms. In one embodiment, the symptoms include abdominal pain/cramps, bloating, flatulence, diarrhea and/or nausea/upset stomach. In one embodiment, a questionnaire can be filled out after a lactose challenge. In another embodiment, a questionnaire can be filled out after a milk challenge. In another embodiment, a questionnaire can be filled out without a challenge. In one embodiment, a single score of 4 or 5 indicates a subject has lactose intolerance. In another embodiment, two or more scores of 3 or greater indicates a subject has lactose intolerance. In another embodiment, a score of 3 or greater for a single symptom at two different timepoints indicates a subject has lactose intolerance. In another embodiment, a change in the average scores over time is used to evaluate the effectiveness of a treatment regimen.

In another embodiment a subject is directly tested for lactose intolerance by biopsying the intestinal lining and measuring lactase levels in the lining.

C. Types of Lactose Intolerance and Treatments

People can have different degrees of lactose intolerance. Lactose intolerance can also be psychologically induced. There are also many different variations of lactose intolerance depending on the subject. For example, some subjects cannot consume cheese, melted cheese, plain milk, or warm dairy containing products like milk in coffee without experiencing one or more symptoms of lactose intolerance. In another embodiment a subject cannot consume any dairy products without experiencing one or more symptoms of lactose intolerance. In some embodiment a lactose intolerant subject is limited to consuming special "lactose free" foods that have been manufactured to be free of lactose. Some examples of these "lactose free" foods are: MOCHA MIX® ice cream, TOFUTTI® ice cream and ice cream sandwiches, LACTAID® brand milk, FORMAGG™ cheese, TOFUTTI® "Better than Cream Cheese", and margarine.

In one embodiment a subject consumes a lactase tablet to help digest the lactose in milk or a milk product. Each lactase tablet typically hydrolyzes up to 99% of the ingested lactose within 24 hours and is designed to be ingested with the lactose containing food. Other possible techniques for dealing with lactose maldigestion are to use microgranules containing bioactive compounds or microorganisms (see, e.g., U.S. Pat. No. 5,952,021, which is herein incorporated by reference in its entirety). The use of an active lactase composition for treatment of lactase deficiency is described in U.S. Pat. No. 3,718,739, which is herein incorporated by reference in its entirety. Digestive Advantage™ Lactose Intolerance Therapy, which includes probiotics and digestive enzymes, can also be used for dietary management of lactose maldigestion.

D. Administration of Prebiotic Compositions

In one embodiment a prebiotic composition is used in a method by administering increasing doses of the composition to a subject who is suffering from lactose intolerance, experiencing symptoms of lactose intolerance, or is in need of improving overall gastrointestinal (GI) health. In one embodiment the subject experiences a reduction or elimination of one or more symptoms of lactose intolerance or an improvement in overall gastrointestinal health after administration of the prebiotic composition. In one embodiment the prebiotic composition comprises GOS. In one embodiment a GOS composition can optionally comprise digestible saccharides. In one embodiment, a GOS composition is administered in about equal doses over a period of time to a subject with lactose intolerance or symptoms of lactose intolerance, or to a subject in need of improved gastrointestinal health. In one embodiment a GOS composition is administered in increasing doses, for a period of time, to a subject with lactose intolerance or symptoms of lactose intolerance, or to a subject in need of improved gastrointestinal health. In one embodiment a GOS composition is provided in any form suitable for oral consumption, such as by a liquid, tablet, capsule, or powdered form. In one embodiment a subject is treated with just a GOS composition, without supplementation with a probiotic.

In another embodiment, other substances can be administered in combination with a GOS composition. In one embodiment lactose is simultaneously administered with a GOS composition. In one embodiment lactose is administered before a GOS composition (e.g., before a regimen of increasing doses of a GOS composition begins, or before a dose of a GOS composition during such a regimen). In another embodiment a digestible saccharide is administered after a dose of GOS composition (e.g., after a regimen of increasing doses of GOS compositions begins, or after a dose of GOS compositions during such a regimen). In another embodiment, a digestible saccharide can be administered simultaneously with, before, or after the administration of the GOS composition or any combination thereof.

In another embodiment a GOS composition is supplemented with one or more other non-digestible saccharides, such as inulin, FOS, lactulose, raffinose, stachyose, or a combination thereof. In another embodiment the GOS composition is supplemented with one or more strains of probiotic bacteria. In another embodiment the GOS composition is supplemented with one or more digestible saccharides, salts, or buffers, e.g., phosphates.

In another embodiment a GOS composition is administered in combination with lactase, or with a product containing pre-digested lactose. In another embodiment a GOS composition is administered in an increasing dose, in combination with lactase or with a product containing pre-digested lactose. In another embodiment a GOS composition is administered in an about equal doses over time, in combination with lactase or with a product containing pre-digested lactose.

In one embodiment, colonic bacteria adapt readily to undigested carbohydrates, such as high purity GOS compositions (e.g. GOS 95), resulting in dramatically improved lactose tolerance. In one embodiment the GOS composition is a high percentage composition, such as about 90% or greater (e.g., about 90, 91, 92, 93, 94, 95, 96, 97, 98, 99, or 100% by weight). In one embodiment GOS promotes the selective growth of beneficial lactose-metabolizing colonic bacteria (multiple species and strains of bifidobacteria and lactobacilli). Bifidobacteria carry out non-hydrogen-producing lactose fermentation reactions in addition to inhibiting hydrogen-producing bacteria, such as *E. coli*. It is this excessive hydrogen production that defines lactose malabsorption and ultimately is responsible for the symptoms associated with lactose intolerance (Gibson 1994, 1995).

In another embodiment, one or more symptoms of lactose intolerance in a subject exhibiting symptoms of lactose intolerance are decreased or eliminated by administering to the subject a GOS composition for a period of time. In one embodiment the administration comprises increasing the amounts of a GOS composition administered to a subject over time. In another embodiment the administration comprises administering about equal amounts of a GOS composition to a subject over time. In one embodiment, a symptom of lactose intolerance remains partially, substantially, or completely eliminated or decreased in severity in a subject for at least about 1 day, 1 week, 1 month, 2 months, 3 months, 4 months, 5 months, 6 months, 9 months, one year, 18 months, two years, three years, four years, or five years after the termination of treatment. In another embodiment a symptom of lactose intolerance remains partially, substantially, or completely eliminated or decreased in severity in a subject for more than 5 years. In another embodiment a symptom of lactose intolerance is permanently eliminated or decreased in severity in a subject after the termination of treatment. In another embodiment, the methods herein decrease symptoms of lactose intolerance in a subject exhibiting symptoms of lactose intolerance by administering to the subject increasing amounts of a GOS composition for a period of time, wherein symptoms of lactose intolerance are substantially eliminated for at least about one month after treatment is terminated.

In another embodiment, a symptom of lactose intolerance in a subject exhibiting symptoms of lactose intolerance is decreased or eliminated by administering to the subject increasing amounts of a prebiotic composition for a period of time, wherein the symptoms of lactose intolerance, measured as described herein, are decreased by an average of about 10%, 20%, 30%, 40%, 50%, 60%, 70%, 80%, 90%, 95%, or about 100% when compared to symptoms prior to the administration of a prebiotic composition. An "average" decrease is a decrease as measured in a group of subjects exhibiting symptoms of lactose intolerance, such as more than about 2, 3, 4, 5, 10, 20, or 30 subjects. In one embodiment, the decrease in or elimination of a symptom of lactose intolerance persists for at least about 1 day, 1 week, 1 month, 2 months, 3 months, 4 months, 5 months, 6 months, 9 months, one year, 18 months, two years, three years, four years, or five years. In another embodiment a symptom of lactose intolerance remains partially, substantially, or completely eliminated or decreased in severity in a subject for more than 5 years after the termination of treatment. In one embodiment, the decrease or elimination of a symptom is permanent. In another embodiment, the invention provides a method of decreasing symptoms of lactose intolerance in a subject exhibiting symptoms of lactose intolerance by administering to the subject increasing amounts of a prebiotic composition for a period of time, wherein one or more symptoms of lactose intolerance, measured as described herein, are decreased by an average of at least about 20% and remain decreased by at least about 20% for at least about one month after treatment is terminated.

In another embodiment, the methods herein decrease symptoms of lactose intolerance in a subject exhibiting symptoms of lactose intolerance by administering to the subject increasing amounts of a prebiotic composition for a period of time, wherein one or more symptoms of lactose intolerance, measured as described herein, are decreased by an average of about least about 50% and remain decreased by at least about 50% for at least about one month after treatment is terminated.

In another embodiment, the methods herein decrease symptoms of lactose intolerance in a subject exhibiting symptoms of lactose intolerance by administering to the subject increasing amounts of a prebiotic composition for a period of time, wherein one or more symptoms of lactose intolerance, measured as described herein, are decreased by an average of about least about 75% and remain decreased by at least about 75% for at least about one month after treatment is terminated.

In one embodiment the total duration of treatment of lactose intolerance can be from about one week to about 12 weeks, or about four weeks to about ten weeks, or about four weeks to about eight weeks, or about six weeks. During this period of time, the subject is started on a program of taking increasing amounts of a prebiotic composition described herein (such as a composition comprising or consisting essentially of GOS), optionally along with ingestion of lactose containing food products. In one embodiment a prebiotic composition can also be administered in combination with another substance (such as a probiotic), as described herein. In one embodiment, the total duration of treatment is about 5 days to about 35 days. In one embodiment, the total duration of treatment is about 7 days to about 90 days, or about 7 days to about 60 days, or about 14 days to about 50 days, or about 14 days to about 40 days, or about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days. In another embodiment, the total duration of treatment is about 30 days. In another embodiment, the total duration of treatment is about 34 days. In another embodiment, the total duration of treatment is about 36 days. In another embodiment, the total duration of treatment is about 38 days. In another embodiment, the total duration of treatment is about 42 days. In another embodiment, the total duration of treatment is about 60 days. In another embodiment, the total duration of treatment is about 90 days.

In another embodiment, the total duration of treatment is based on a subject's response to the treatment. For example, an individual can experience a reduction in lactose intolerance symptoms after 14 days of treatment with a prebiotic composition. In another example an individual can experience a reduction in lactose intolerance symptoms after 30 days of treatment with a prebiotic composition. Thus, the duration of treatment is determined by an individual subject's response to a prebiotic composition and the onset of relief from one or more lactose intolerance symptoms.

In one embodiment the treatment is continuous. In one embodiment, the duration of the treatment is based on a subject's symptoms of lactose intolerance. Thus, a subject can experience symptoms at a given dose of a prebiotic composition (e.g., a composition comprising or consisting essentially of GOS), and can require that the subject stay at that dose, or a lower dose, until symptoms subside. Thus, in one embodiment, the duration of the treatment is not determined at the outset, but continues until the maximum dose of a prebiotic composition (such as a composition comprising or consisting essentially of GOS), is achieved per day, or until the desired level of lactose tolerance is achieved. In one embodiment the maximum amount of prebiotic composition (e.g., a composition comprising or consisting essentially of GOS), administered per day is between 0.4 g and 20 g, such as about 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or 20 g per day. In another embodiment, a dose can be about 0.4 g to 6 g.

In one embodiment, a subject can be given one dose for a period of time during a treatment regimen and a second dose during a second period of time during the treatment regimen. For example, a subject can be administered one dose of prebiotic composition for a one or two week period and a second dose for a subsequent one or two week period. In one embodiment the prebiotic composition comprises GOS.

In one embodiment an increasing dosage of a prebiotic composition (e.g., a composition comprising or consisting essentially of GOS), can be achieved by increasing the number of doses per day of the composition administered, increasing the amount of a prebiotic composition administered per dose, or both. In one embodiment, both strategies are used. Thus, in one embodiment, a prebiotic composition (e.g., a composition comprising or consisting essentially of GOS), is initially administered once per day, at increasing doses, for a pre-determined number of days. This can be followed by a period of time when a prebiotic composition is administered twice per day as a first and second dose. The first dose of a prebiotic composition can be administered at a constant dose while the second dose can be administered in increasing doses, for a pre-determined number of days. In one embodiment the prebiotic composition comprises GOS. In one embodiment, the dose can be administered to a subject at a frequency of once per day, twice per day, or three times per day. The number of days of administration can last for a period of about 1 to 90 days, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days.

In another embodiment, a prebiotic composition can be administered twice per day. The first dose of the prebiotic composition (e.g., a composition comprising or consisting essentially of GOS), can remain constant while the second dose increases over time. In another embodiment, the prebiotic composition (e.g., a composition comprising or consisting essentially of GOS), can be administered an average of about once per day, twice per day, three, four, five, six, or more than six timer per day, or any combination thereof. The prebiotic composition can be administered for a period of about 1 to 90 days, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days.

In another embodiment the prebiotic composition is administered at the same dosage level at each administration. Thus, in one embodiment, a prebiotic composition (e.g., a composition comprising or consisting essentially of GOS), is initially administered once to six times per day at the same dosage level. The prebiotic composition can be administered for a period of about 1 to 90 days, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days.

In one embodiment, a subject who has completed a treatment regimen consumes dairy products at least once every 4-5 days in order to maintain the reduction in symptoms of lactose intolerance.

In another embodiment, a subject self-administers a prebiotic composition (e.g., a composition comprising or consisting essentially of GOS). In one embodiment, the prebiotic composition (e.g., a composition comprising or consisting essentially of GOS), composition is supplied or recommended by a health professional, e.g., a dietician, nutritionist, nurse, physician, or other qualified health professional. In another embodiment, the prebiotic composition (e.g., a composition comprising or consisting essentially of GOS), is administered by a health professional or results of the program are monitored by a health professional. In one embodiment, a prebiotic composition (e.g., a composition comprising or consisting essentially of GOS), is labeled as a medical food.

In one embodiment a subject in need thereof can repeat courses of treatment with a prebiotic composition. The course of treatment can be repeated when symptoms of lactose intolerance reappear or increase to an undesirable level. Alternatively, the course of treatment can be repeated at regular or predetermined intervals. Thus, treatment can be repeated after about one month, two months, three months, four months, six months, eight months, ten months, one year, 18 months, two years, three years, four years, five years, or more than five years, or any combination thereof (e.g., treatment can be repeated after one year, then every two to five years thereafter). The treatment can be repeated in the same form (e.g., duration, dosage, timing of dosage, additional substances, etc.) as used in the first treatment or it can be modified. For example, treatment duration can be shortened or lengthened, dosage can be increased more quickly or slowly or a higher or lower starting dose of a prebiotic composition, a different prebiotic composition (such as a composition comprising inulin, FOS, lactulose, raffinose, stachyose or combinations thereof) can be used (e.g., containing more or less of other substances, or fewer or more substances in addition to GOS or digestible saccharides), and the like.

In one embodiment an initial dose of a prebiotic composition is administered to a subject in need thereof as part of a dosing regimen with incremental increases in the dosage of the prebiotic composition over time. The incremental increases in a prebiotic composition dosage can be any suitable dose size. In one embodiment, the starting dose of a prebiotic composition is about 0.05 g to 4.0 g, or about 0.1 g to about 3 g, or about 0.2 g to about 3.0 g, or about 0.2 g to about 2 g, or about 0.4 g to about 1.6 g, or about 0.4 g to about 1.4 g, or about 0.6 g to about 1.2 g, or about 0.6 g to about 1.0 g, or about 0.7 g to about 0.9 g, or about 0.8 g. In another embodiment, the starting dose of a prebiotic composition is about 0.2 g to about 4.7 g, about 0.5 g to about 8.0 g, or about 0.4 g to about 6.8 g. In one embodiment, the incremental increase in prebiotic or GOS composition dosage can vary, or each increase can be the same, or any combination thereof. In another embodiment, an amount of a prebiotic composition administered to a subject in need thereof can be increased incrementally by about 0.05 g to 4.0 g, or about 0.1 g to about 3 g, or about 0.2 g to about 3.0 g, or about 0.2 g to about 2 g, or about 0.4 g to about 1.6 g, or about 0.4 g to about 1.4 g, or about 0.6 g to about 1.2 g, or about 0.6 g to about 1.0 g, or about 0.7 g to about 0.9 g, or about 0.8 g. In another embodiment, an amount of a prebiotic composition administered to a subject in need thereof can be increased incrementally by about 0.5 g, about 0.29 g, about 0.30 g, or about 0.42 g, about 0.43 g. In another embodiment, an amount of a prebiotic composition administered to a subject in need thereof can be increased incrementally by 0.1, 0.2, 0.3, 0.4, 0.5, 0.6, 0.7, 0.8, 0.9, or 1 g per dose. The maximum dose reached in treatment can be any suitable dose size, depending on the subject being treated and the outcome desired. In one embodiment the maximum dose of a prebiotic composition administered in a single dose can be about 1 g to about 2 g, about 3 g to about 4 g, about 5 g to about 6 g, about 6 g to about 60 g, or about 12 g to about 48 g, or about 14 g to about 36 g, or about 16 g to about 36 g, or about 18 g to about 34 g, or about 20 g to about 32 g, or about 22 g to about 30 g, or about 23 g to about 29 g, or about 24 g to about 28 g, or about 25 to about 27 g, or about 25.5 g to about 26.5 g, or about 25.5 g, 25.6 g, or 25.7 g per dose. In one embodiment the maximum dose of prebiotic composition administered is about 12 g per dose.

In one embodiment of the invention, an initial dose of prebiotic composition is about 0.4 g, and the dose is increased by 0.4 g over time, for example, daily, until a maximum dose of 20 g to 25 g of a prebiotic composition is reached. In another embodiment, the initial dose of a prebiotic composition is about 0.5 g, and the dose is increased by 0.5 g over time, for example, daily, until a maximum of 8.0 g to 15 g of prebiotic composition per day is reached.

In another embodiment, the doses of a high purity GOS composition (e.g. GOS 95) are gradually increased over 35 days beginning with 1.5 gm/day and increasing to 15 gm/day (7.5 gm twice daily). In one embodiment the GOS composition is a high percentage composition, such as about 90% or greater (e.g., about 90, 91, 92, 93, 94, 95, 96, 97, 98, 99, or 100% by weight).

A prebiotic composition can be administered in any suitable form, such as a powder, capsules, tablets, a powder that can be dissolved in a liquid prior to consumption, or in liquid form, (e.g., GOS pre-dissolved in a liquid). Any grade or form of prebiotics that is suitable for consumption by the subject being treated, e.g., by a human, can be used. A prebiotic composition comprising GOS can be distributed in a syrup form. A GOS syrup can be diluted with water prior to ingestion. A GOS syrup can be administered with a meal. In one embodiment a GOS composition is administered to a subject in one or more capsules. In one embodiment the GOS composition comprises a high percentage of GOS (e.g., about 90% by weight of GOS or more). In one embodiment the one or more capsules are 000, 00 or 0 size capsules. In one embodiment, the subject is administered the one or more capsules at least twice a day. In one embodiment, the subject is administered the one or more capsules for two or more days. In one embodiment the subject is administered more capsules on the last day than on the first day. In another embodiment the subject is administered the same number of capsules on the last day as on the first day.

Additional substances can be given in conjunction with a prebiotic composition or GOS composition. These substances can enhance the action of the increasing doses of prebiotic by, e.g., encouraging the growth of bacteria in the gut that alleviate symptoms of lactose intolerance, increasing adhesion of probiotic or beneficial commensal bacteria, or allowing doses of probiotic bacteria to more readily pass through the stomach without being destroyed. These substances can be given prior to treatment with prebiotic, during treatment with prebiotic, after treatment with prebiotic, or any combination thereof. If administered during prebiotic treatment, they can be administered with the dose of prebiotic being given, or before or after the dose of prebiotic, or any combination thereof.

In one embodiment substances of use in the invention in conjunction with a prebiotic composition include a probiotic microbe(s), lactase or other lactose digestive enzymes, or buffers (such as phosphates). One or more of these substances can be used in combination with prebiotic composition at any suitable time before, during, after treatment, or some combination thereof. In one embodiment, during some or all of the treatment, a prebiotic composition is administered in conjunction with live bacteria. In another embodiment, during some or all of the treatment, a prebiotic composition is administered in conjunction with lactase or other lactose digestive enzymes. In another embodiment, during some or all of the treatment, a prebiotic composition is administered in conjunction with a buffer (e.g., phosphates). In another embodiment, during some or all of the treatment, a prebiotic composition (e.g., GOS) comprises trace amounts of digestible saccharides, such as lactose, glucose or galactose. In one embodiment the trace amounts of digestible saccharides make up 5% by weight (such as 4%, 3%, 2%, 1%, 0.5%, or 0.1%) or less of the prebiotic composition. In another embodiment the trace amounts of digestible saccharides make up about 20% by weight (such as about 20%, 19%, 18%, 17%, 16%, 15%, 14%, 13%, 12%, 11%, 10%, 9%, 8%, 7%, 6%, 5%, 4%, 3%, 2%, 1%, 0.5%, or 0.1%) or less of the prebiotic composition.

In one embodiment, a high purity GOS composition (e.g., GOS 95) is used. In one embodiment, the dose of GOS 95 is from 1.5 g to 12 g/day (6 g BID). In one embodiment the GOS composition is a high percentage composition, such as about 90% or greater (e.g., about 90, 91, 92, 93, 94, 95, 96, 97, 98, 99, or 100% GOS by weight). In one embodiment, the dose of a high purity GOS composition is administered for 15 days or 30 days. In another embodiment, a high percentage GOS composition is administered at escalating dosages for 15 or 30 days. In one embodiment, a therapeutic dose of a high purity GOS composition is based on human exposure-response relationship and pharmacokinetics. In one embodiment, the starting dose for a high percentage GOS composition has a low potential for undesirable GI adverse effects. In another embodiment, a dosing regimen for a high purity GOS composition results in a steady-state exposure of the gut to GOS facilitating optimal gut microflora re-population.

In one embodiment, after a 15 day administration of GOS, the doses of GOS are gradually increased over 30 days or at a more rapid rate over 15 days beginning with 1.5 g-3 g/day and increasing to 12 g/day (6 g BID); doses are in liquid form and are mixed with water and taken as directed by the dosing scheme.

In one embodiment, GOS is administered for about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 days. In one embodiment, GOS is administered for about 15 days. In another embodiment, GOS is administered for 30 days. In another embodiment, GOS is administered for 35 days. In one embodiment, GOS is administered for about 1-60 days about 1-30 days, about 5-25 days, about 10-20 days, or about 12 to 18 days. In one embodiment, the prebiotic comprises GOS. The percent of GOS in the prebiotic composition can be about 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% GOS. The percent of GOS in the prebiotic composition can be about 90-100%, about 95-100%, about 96-100%, about 97-100%, about 98-100%, or about 99 to 100%. In one embodiment, the prebiotic composition comprises at least about 95% GOS. In another embodiment, the prebiotic composition comprises at least about 96% GOS. In another embodiment, the prebiotic composition comprises at least about 96.8% GOS. In one embodiment, the prebiotic composition is GOS 95. The number of days the doses of prebiotic composition comprising GOS can be gradually increased can be about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 days. In another embodiment, the number of days the doses of prebiotic composition can be gradually increased can be about 2-30 days, about 2-38 days, about 10-20 days, about 20-100 days, about 20-50 days, about 20-40 days, or about 20-30 days. In another embodiment, the number of days the doses of prebiotic composition can be increased at can be about 2, 3, 4, 5, 6, 7, 8, 9, 10, 11, 12, 13, 14, 15, 16, 17, 18, or 19 days, or about 1-20 days, about 1-15 days, or about 10-20 days. In one embodiment, the beginning dose of prebiotic composition can about 1.5 g/day to 3 g/day, about 0.1 g/day to 20 g/day, about 0.1 g/day to 15 g/day, or about 0.1 g/day to 10 g/day. In another embodiment, the beginning dose of prebiotic composition can be about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 g/day. In another embodiment, the dose of prebiotic composition can be increased to about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, or 24 g/day. In another embodiment, the dose of prebiotic can be increased to about 2-24, 5-20, 7-18, or 10-15 g/day. In one embodiment, the prebiotic composition can be administered once a day, twice a day, three times a day, four times a day, five times a day, or six times a day. In one embodiment, the prebiotic composition comprising GOS is GOS 95. Examples of GOS 95 dosages are shown in Table 6.

TABLE 6

Examples of Dosages of GOS 95

| Starting Dose | | Highest Dose | |
|---|---|---|---|
| GOS 95 Dose | Equivalent Dose to GOS 60 | GOS 95 Dose | Equivalent Dose to GOS 60 |
| 1.5 g/day | 2.4 g/day | 12 g/day for up to 7 days | 19 g/day |
| 25 mg/kg/day | 40 mg/kg/day | | |
| 3.0 g/day | 4.8 g/day | 200 mg/kg/day | 317 mg/kg/day |
| 50 mg/kg/day | 80 mg/kg/day | | |

The subject to whom the prebiotic composition can be administered can include, for example, a human, for example, a preterm newborn, a full term newborn, an infant up to one year of age, young children (e.g., 1 yr to 12 yrs), teenagers, (e.g., 13-19 yrs), adults (e.g., 20-64 yrs), pregnant women, and elderly adults (65 yrs and older). The age of the subject can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, or 110 years. In one embodiment, the prebiotic composition is comprises a high percentage of GOS, such as about 90% or greater (e.g., about 90, 91, 92, 93, 94, 95, 96, 97, 98, 99, or 100% GOS by weight). In one embodiment, the prebiotic composition is GOS 95.

The subject to whom the prebiotic composition can be administered can be a pediatric subject aged birth up to the 16th birthday. The pediatric subject can be from any of the recognized pediatric age categories. The subject can be a neonate, aged 0-1 months; an infant, aged 1 month to 2 years; a child, aged 2 to 12 years; or an adolescent, aged 12 to 16 years. In one embodiment, the pediatric subject is administered a liquid formulation of the prebiotic composition, for example a GOS composition. In another embodiment the pediatric subject is administered a GOS composition in a capsule or tablet. In one embodiment, the prebiotic composition is comprises a high percentage of GOS, such as about 90% or greater (e.g., about 90, 91, 92, 93, 94, 95, 96, 97, 98, 99, or 100% GOS by weight).

In another embodiment, the dose of the GOS composition (e.g. GOS 95) is gradually increased over 15 days or at a slower rate over 30 days beginning with 1.5-3 g/day and increasing to 12 g/day (6 g BID) to reach the corresponding level of lactose per day in approximately 24 ounces of milk. This level of 24 ounces of milk was chosen to develop tolerance to a total of three servings of dairy per day, the recommended level in the US Dietary Guidelines to meet calcium and other nutrient needs. In another embodiment, subjects who are lactose intolerant and treated with GOS 95 develop tolerance. In one embodiment, developing tolerance is from gradually increasing the dose of GOS 95. Gradual and continuous exposure of the gut through step-wise titration of lactose-containing products has resulted in optimized efficacy and tolerance of these products in the adaptation of colonic re-population and amelioration of lactose intolerance symptoms (Landon et al. 2006). In one embodiment, the prebiotic composition is comprises a high percentage of GOS, such as about 90% or greater (e.g., about 90, 91, 92, 93, 94, 95, 96, 97, 98, 99, or 100% GOS).

In another embodiment, a high percentage GOS composition (e.g. GOS 95) is administered over a 35 day period to improve lactose metabolism via the adaptation of intestinal bacterial metabolism in subjects who are lactose intolerant. The dose of the high percentage GOS composition can be gradually increased over 35 days, beginning with 1.5 g/day and increasing to 15 g/day (7.5 g/dose, twice per day). The dose of the high percentage GOS composition can be 1.5 g/day for days 1-5, 3 g/day for days 6-10, 6 g/day for days 11-15, 7.5 g/day (a 1.5 g dose and a 6.0 g dose) for days 16-20, 9 g/day (a 3.0 g dose and a 6.0 g dose) for days 21-25, 12 g/day (two 6.0 g doses) for days 26-30, and 15 g/day (two 7.5 g doses) for days 31-35. In another embodiment, an improvement in lactose tolerance would be expected to last for at least 30 days after cessation of treatment. In one embodiment, the high percentage GOS composition comprises about 90% or more GOS (e.g., about 90, 91, 92, 93, 94, 95, 96, 97, 98, 99, or 100% GOS).

In one embodiment, a subject undergoes a booster program after completion of the primary treatment program, which comprises administering a prebiotic composition comprising GOS to a subject. The length of a booster program can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 days, or more. In one embodiment the dose of the prebiotic composition comprising GOS (e.g. GOS 95, etc.) administered during the booster program can be about 0.5 g, 1 g, 1.5 g, 2 g, 2.5 g, 3 g, 3.5 g, 4 g, 4.5 g, 5 g, 5.5 g, 6 g, 6.5 g, 7 g, 7.5 g, 8 g, 8.5 g, 9 g, 9.5 g, 10 g, 10.5 g, 11 g, 11.5 g, 12 g, 12.5 g, 13 g, 13.5 g, 14 g, 14.5 g, 15 g, or more. In one embodiment, the same dose of the prebiotic composition comprising GOS (e.g. GOS 95) is administered each day of a booster program. In another embodiment, a larger dose of the prebiotic composition comprising GOS (e.g. GOS 95) is administered on the final day of a booster program than is administered on the first day. In one embodiment, the length of a booster program can be 10 days. In another embodiment, about 3 g of the prebiotic composition comprising GOS (e.g. GOS 95) is administered on days 1-5 of a booster program and about 6 g of the prebiotic composition comprising GOS (e.g. GOS 95) is administered on days 6-10 of a booster program. In some embodiments, the prebiotic composition comprising GOS (e.g. GOS 95) is administered in a dosing unit, for example a gelatin capsule. The number of gelatin capsules administered each day of a booster program can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more. A prebiotic composition can be administered 1, 2, 3, 4, 5 or more times a day during a booster program. In some embodiments, a prebiotic composition (e.g. a GOS composition) is administered once per day during a booster program. In some embodiments, the prebiotic composition comprising GOS (e.g. GOS 95) is administered twice per day during a booster program. In some embodiments, the prebiotic composition comprising GOS (e.g. GOS 95) is administered once per day for days 1-5 of a booster program and twice per day for days 6-10 of a booster program.

Modulating Psychological Aversion to Dairy Products

In one embodiment a subject has a psychological aversion to the consumption of dairy products. In one embodiment the subject's psychological aversion is caused by the experience of one or more symptoms of lactose intolerance when the subject consumes a dairy product. In one embodiment, a subject has a psychological aversion to a dairy product because the subject is aware the dairy product contains lactose. In another embodiment, a subject has a psychological aversion to a dairy product because the subject is aware the dairy product contains lactose, and the subject previously personally experienced one or more symptoms of lactose intolerance when the subject consumed the dairy product. In another embodiment, a subject has a psychological aversion to a dairy product because the subject is aware the dairy product contains lactose, and the subject is aware that a genetically related person previously experienced one or more symptoms of lactose intolerance when the genetically related person consumed the dairy product. In one embodiment, a method of treating psychological aversion of a subject to intake of dairy products is provided comprising administering a prebiotic composition to said subject. In one embodiment, the prebiotic composition comprises, consists essentially of, or consists of GOS. In another embodiment the prebiotic composition comprises a high percentage of GOS. In another embodiment, the prebiotic composition comprises, consists essentially of, or consists of GOS and one or more probiotics. In one embodiment, a subject does not have a psychological aversion to ingesting or consuming a prebiotic composition. In one embodiment, a subject does not have a psychological aversion to ingesting or consuming GOS.

In one embodiment, a subject with a psychological aversion to dairy products is administered a therapeutic composition comprising, consisting essentially of, or consisting of a prebiotic composition to modulate the psychological aversion to dairy products. In another embodiment, a subject with a psychological aversion to dairy products is administered a therapeutic composition comprising, consisting essentially of, or consisting of GOS to modulate the psychological aversion to dairy products. In another embodiment, a subject with a psychological aversion to dairy products is administered a therapeutic composition comprising, consisting essentially of, or consisting of GOS and a probiotic to modulate the psychological aversion to dairy products. In one embodiment, the modulation is a decrease in psychological aversion of the subject to dairy products. In another embodiment, the modulation of the psychological aversion can result in an increase in consumption of dairy products by the subject. In another embodiment, modulation of the psychological aversion can result in increased blood calcium levels or bone density in the subject. In one embodiment, the subject is a preterm newborn, a full term newborn, an infant up to one year of age, a young child (e.g., 1 yr to 12 yrs), a teenager, (e.g., 13-19 yrs), an adult (e.g., 20-64 yrs), an elderly adult (65 yrs and older), a pregnant women, a man or a woman. In one embodiment, the subject is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 1060, 107, 108, 109, 110, 111, 112, 113, 114, 115, 116, 117, 118, 119, or 120 years old. In one embodiment, the subject is an elderly adult. In another embodiment, the subject has osteoporosis. In another embodiment, the subject has low bone density. In another embodiment, the subject is an elderly adult who has osteoporosis. In another embodiment, the subject is a woman over the age of about 30, 40, 50, 60, 70, 80, 90, 100, 110, or 120 years old. In another embodiment, the woman is a post-menopausal woman. In another embodiment a subject with a psychological aversion to dairy products is administered a therapeutic composition comprising GOS, which modulates the subject's aversion to psychological aversion to dairy products. In another embodiment a subject with a psychological aversion to dairy products is administered a therapeutic composition comprising GOS, which reduces the subject's aversion to psychological aversion to dairy products. In another embodiment a subject with a psychological aversion to dairy products is administered a therapeutic composition comprising GOS, which inhibits the subject's aversion to psychological aversion to dairy products. In another embodiment an a subject with a psychological aversion to dairy products is administered a therapeutic composition comprising GOS, which modulates the subject's aversion to psychological aversion to dairy products by decreasing one or more symptom's of lactose intolerance. In another embodiment an a subject with a psychological aversion to dairy products is administered a therapeutic composition comprising GOS, which modulates the subject's aversion to psychological aversion to dairy products by decreasing one or more symptom's of lactose intolerance and leading to increased consumption of dairy products by the subject. In one embodiment increased consumption of dairy products by the subject results in increased calcium consumption by the subject. In another embodiment increased consumption of dairy products by the subject results increases the bone density of the subject.

Nutritional Deficiency

A subject that has one or more symptoms of lactose intolerance and/or a psychological aversion to dairy products restricts his or her diet, which can result in a nutrition shortage and/or disease. Milk and other lactose containing dairy products are a source of nutrients in the American diet, including protein, calcium, riboflavin, vitamin A, and vitamin D. Studies have linked a sufficient daily intake of calcium and vitamin D with reduced incidence of type 2 diabetes. Intake recommendations for calcium are provided in the Dietary Reference Intakes (DRIs) which were developed by the Food and Nutrition Board at the Institute of Medicine for the National Academies. If a subject restricts intake of dairy products, e.g., because of lactose intolerance or psychological aversion to dairy products, the individual can become hypocalcemic. Hypocalcaemia is the presence of low serum calcium levels in the blood. Long term hypocalcaemia can result in bone loss, osteoporosis, hypertension, and/or weak bone density. Other symptoms of hypocalcaemia include petechia; oral, perioral, and acral parasthesias; carpopedal and generalized tetany; largent tetany; hyperactive tendon reflexes; laryngospasm; and cardiac arrhythmias. Petechiae are small red or purple spots on the body caused by a minor hemorrhage (i.e. broken capillary blood vessels. Paresthesias are a tingling sensation, often in the mouth, lips and extremities of the hands and feet. Tetany is the involuntary contraction of muscles, which can be caused by the inability of muscle fibers to depolarize due to low calcium levels in the blood. Laryngospasms are particularly dangerous form of tetany where the contraction of laryngeal cords can result in a partial blockage of the breathing canal. Cardiac arrhythmia, which is caused by abnormal electrical activity in the heart, encompasses any abnormal heart beat pattern. The heart beat may be too fast, too slow, or irregularly timed. Long QT syndrome is an arrhythmia that can be acquired due to hypocalcaemia.

In one embodiment, a subject that restricts his or her intake of dairy products because of lactose intolerance or psychological aversion to dairy products is administered a therapeutic composition comprising, consisting essentially of, or consisting of a prebiotic composition to modulate the restriction of dairy products. In another embodiment, a subject that restricts his or her intake of dairy products because of lactose intolerance or psychological aversion to dairy products is administered a therapeutic composition comprising, consisting essentially of, or consisting of a GOS to modulate the restriction of dairy products. In another embodiment, a subject that restricts his or her intake of dairy products because of lactose intolerance or psychological aversion to dairy products is administered a therapeutic composition comprising, consisting essentially of, or consisting of a GOS and one or more probiotics to modulate restriction of dairy products. In one embodiment, the modulation comprises an increase in consumption of dairy products. In one embodiment, the subject is a preterm newborn, a full term newborn, an infant up to one year of age, a young child (e.g., 1 yr to 12 yrs), a teenager, (e.g., 13-19 yrs), an adult (e.g., 20-64 yrs), an elderly adult (65 yrs and older) a pregnant women, a man or a woman. In one embodiment, the subject is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 1060, 107, 108, 109, 110, 111, 112, 113, 114, 115, 116, 117, 118, 119, or 120 years old. In one embodiment, the subject is an elderly adult. In another embodiment, the subject has osteoporosis. In another embodiment, the subject has low bone density. In another embodiment, the subject is an elderly adult who has osteoporosis. In another embodiment, the subject is a woman over the age of about 30, 40, 50, 60, 70, 80, 90, 100, 110, or 120 years old. In another embodiment, the woman is a postmenopausal woman. In another embodiment, the subject is a woman with osteoporosis over the age of about 30, 40, 50, 60, 70, 80, 90, 100, 110, or 120 years old. In another embodiment, the woman is postmenopausal.

Osteoporosis is a condition in which the bone mineral density (BMD) is reduced in a subject. Bone density can be determined using, e.g., dual energy X-ray absorptiometry (DXA or DEXA), ultrasound, quantitative computerized tomography (CT) scanning, or single-photon absorptiometry. Bones in a subject with osteoporosis can become brittle; mild stresses, such as coughing, or falls, can result in a bone fracture. A man or a woman can have osteoporosis. Signs and symptoms of osteoporosis can include, e.g., back pain, loss of height over time, fracture of the vertebra, hip, wrist, or other bone, or a stooped posture. In one embodiment a person with low bone density or osteoporosis comprises a postmenopausal woman with at least one risk factor for osteoporosis, a woman older than 65 years old, a man over 70 years old, a man between the age of 50 to 70 who has at least one osteoporosis risk factor, a woman who experienced early menopause, a postmenopausal woman who has recently stopped taking hormone therapy, a person older than 50 with a history of a broken bone, or a person who takes medications, such as prednisone, aromatase inhibitors, or anti-seizure drugs, that are associated with osteoporosis (see, e.g., www.mayoclinic.com/health/osteoporosis/DS00128). Risk factors for osteoporosis can include, e.g., low calcium intake, tobacco use, eating disorders (e.g., anorexia nervosa or bulimia), sedentary lifestyle (e.g., lack of walking, running, jumping, dancing, and weightlifting), excessive alcohol consumption, long-term use of corticosteroid medications (e.g., prednisone, cortisone, prednisolone and dexamethasone), long-term use of aromatase inhibitors, selective serotonin reuptake inhibitors (SSRIs), methotrexate, some anti-seizure medications, proton-pump inhibitors, or aluminum containing antacids. Some medications have been associated with an increased risk of osteoporosis, including, e.g., barbiturates, L-thyroxine over-replacement, depot preogesterone, gonadotropin-releasing hormone agonist, anticoagulants (e.g., warfarin), thiazolidinediones (e.g., rosiglitazone, inhibitors of PPARγ), and chronic lithium therapy.

Diseases and disorders can be associated with osteoporosis. A hypogonadal state, e.g., Kallmann syndrome, Klinefelter syndrome, Turner syndrome, anorexia nervosa, andropause, hyperprolactinemia, hypothalamic amenorrhea, bilateral oophorectomy (surgical removal of the ovaries), premature ovarian failure, or testosterone deficiency (e.g., andropause or after surgical removal of the testes) can cause secondary osteoporosis. Endocrine disorders that can induce bone loss include, e.g., acromegaly, adrenal insufficiency, Cushing's syndrome, diabetes mellitus type 1 and 2, hyperparathyroidism, hypothyroidism, and thyrotoxicosis. Reversible bone loss can also occur during lactation and pregnancy.

Malnutrition, parenteral nutrition and malabsorption can lead to osteoporosis. Nutritional and gastrointestinal disorders that can predispose a subject to osteoporosis include, e.g., coeliac disease, Crohn's disease, lactose intolerance, severe liver disease (e.g., primary biliary cirrhosis), and surgery (e.g., after gastrectomy, intestinal bypass surgery, or bowel resection). A subject with an adequate calcium intake can develop osteoporosis due to the inability to absorb calcium and/or vitamin D.

Subjects with rheumatologic disorders, e.g., rheumatoid arthritis, ankylosing spondylitis, systemic lupus erythematosus, and polyarticular juvenile idiopathic arthritis are at increased risk of osteoporosis, e.g., as part of their disease or because of other risk factors (e.g., corticosteroid therapy). Systemic diseases such as amyloidosis and sarcoidosis can also lead to osteoporosis. Renal insufficiency can lead to osteodystrophy. Hematologic disorders linked to osteoporosis can include, e.g., hemophilia, lymphoma, leukemia, mastocytosis, multiple myeloma, other monoclonal gammopathies, sickle-cell disease and thalassemia.

Inherited disorders linked to osteoporosis include, e.g., Ehlers-Danlos syndrome, epidermolysis bullosa, Gaucher's disease, glycogen storage diseases, hemochromatosis, hypophosphatasia, homocystinuria, osteogenesis imperfecta, Marfan syndrome, Menkes' syndrome, and porphyria, A subject with scoliosis can have a higher risk of osteoporosis. Bone loss can be a feature of complex regional pain syndrome. Accelerated bone loss can be found in subjects with Parkinson's disease and chronic obstructive pulmonary disease.

In one embodiment, a person that has one or more symptoms of lactose intolerance and/or a psychological aversion to dairy products and who has low bone density, osteoporosis, a sign or symptom of osteoporosis, or a risk factor for osteoporosis, is administered a therapeutic composition comprising, consisting essentially of, or consisting of a prebiotic composition to modulate restriction of dairy products. In another embodiment, a person that has one or more symptoms of lactose intolerance and/or a psychological aversion to dairy products and who has low bone density, osteoporosis, a sign or symptom of osteoporosis, or a risk factor for osteoporosis, is administered a therapeutic composition comprising, consisting essentially of, or consisting of a GOS to modulate restriction of dairy products. In one embodiment, a person that has one or more symptoms of lactose intolerance and/or a psychological aversion to dairy products and who has low bone density, osteoporosis, a sign or symptom of osteoporosis, or a risk factor for osteoporosis, is administered a therapeutic composition comprising, consisting essentially of, or consisting of a GOS and a probiotic to modulate the restriction of dairy products. In one embodiment, the modulation of restriction of dairy products comprises an increase in dairy product consumption.

Medications that can help slow bone loss and/or maintain bone mass include, for example, antiresorptive agents (e.g., bisphosphonates (e.g., alendronate (Fosamax), ibandronate (Boniva), risedronate (Actonel) and zoledronic acid (Reclast), estrogen analogs, selective estrogen receptor modulators (SERMS) (e.g., raloxifene (Evista)), and calcitonin). Medications that can help slow bone loss and/or maintain bone mass include, for example, bone anabolic agents, e.g., teriparatide (Forteo), calcium salts, and sodium fluoride. Medications that can help slow bone loss and/or maintain bone mass include, for example, RANKL inhibitors (e.g., denosumab), strontium ranelate, calcium, and vitamin D.

Hormone therapy, exercise, and physical therapy can be used to help slow bone loss and maintain bone mass.

In one embodiment, a person with lactose intolerance and who has low bone density, osteoporosis, a sign or symptom of osteoporosis, or a risk factor for osteoporosis, can be administered a therapeutic composition comprising, consisting essentially of, or consisting of a prebiotic composition to modulate restriction of dairy products, and one more or medications to slow bone loss and/or maintain bone mass comprising an antiresorptive agent or bone anabolic agent. In another embodiment, the prebiotic composition comprises GOS. In another embodiment, the prebiotic composition comprises GOS and further comprises a probiotic.

In one embodiment, a person with lactose intolerance and who has low bone density, osteoporosis, a sign or symptom of osteoporosis, or a risk factor for osteoporosis, is administered a therapeutic composition comprising, consisting essentially of, or consisting of a prebiotic composition to modulate restriction of dairy products, and can undergo hormone therapy, exercise, or physical therapy to slow bone loss and/or maintain bone mass. In another embodiment, the prebiotic composition comprises GOS. In another embodiment, the prebiotic composition comprises GOS and further comprises a probiotic.

In one embodiment, a person with lactose intolerance and who has low bone density, osteoporosis, a sign or symptom of osteoporosis, or a risk factor for osteoporosis, is administered a therapeutic composition comprising, consisting essentially of, or consisting of a prebiotic composition to modulate restriction of dairy products, and can undergo hormone therapy, exercise, or physical therapy and/or be administered one or more medications to slow bone loss and/or maintain bone mass. In another embodiment, the prebiotic composition comprises GOS. In another embodiment, the prebiotic composition comprises GOS and further comprises a probiotic.

Long QT syndrome (LQT) is so named because of the prolongation of the QT interval seen on electrocardiograms of affected individuals. It is caused by a delayed repolarization of heart muscle fibers following contraction and can manifest as episodes of irregular heartbeat, known as torsade de pointes (TDP). Episodes of TDP may lead to palpitations, fainting, and sudden death. LQT has been linked to an increased risk of sudden death during increased adrenergic states due to, for example, exercise or excitement. Several gene mutations have been identified as risk factors for LQT. Acquired cases of LQT include drugs, hypokalemia, hypomagnesemia, and hypocalcaemia, among others. Multiple risk factors may interplay in precipitating TDP episodes, highlighting the importance of combinatorial therapeutics.

Treatment for LQT involves two options: arrhythmia prevention and arrhythmia termination. Beta blockers decreases the risk of stress induced arrhythmias and are a common treatment for LQT. Implantable cardioverter-defibrillators (ICD) can be used in conjunction with blocker treatment as a method of terminating arrhythmias when they occur.

In one embodiment, a person with lactose intolerance and who has long QT syndrome is administered a therapeutic composition comprising, consisting essentially of, or consisting of a prebiotic composition to modulate restriction of dairy products and can be treated by beta blockers to prevent episodes of arrhythmia and/or implanted with an ICD to terminate or decrease the duration of TDP episodes.

E. Treatment Regimens

In one embodiment, treatment with a prebiotic composition (e.g., a composition comprising or consisting essentially of GOS), optionally in conjunction with a probiotic composition, one or more digestible saccharides, a buffer, or a combination thereof, is used in combination with other treatments to reduce the symptoms of lactose intolerance. Any suitable treatment for the reduction of symptoms of lactose intolerance can be used, e.g., the use of lactase. In another embodiment lactase is administered before, during, or after treatment with a prebiotic composition, or any combination thereof. In one embodiment, when symptoms of lactose intolerance are not completely or substantially completely eliminated by treatment with a prebiotic composition, lactase is administered after prebiotic treatment is terminated. The lactase is used on an as-needed basis.

In one embodiment a subject to be treated for one or more symptoms of lactose intolerance is a human. In one embodiment the human subject is a preterm newborn, a full term newborn, an infant up to one year of age, a young child (e.g., 1 yr to 12 yrs), a teenager, (e.g., 13-19 yrs), an adult (e.g., 20-64 yrs), a pregnant women, an elderly adult (65 yrs and older), a male or a female.

In some embodiments, a subject experiencing one or more symptoms of lactose intolerance is diagnosed with a lactose intolerance diagnostic device or test prior to or concurrently with the beginning of a treatment regimen. In one embodiment, a test for lactose intolerance is a hydrogen breath test. In the hydrogen breath test, the breath is measured to determine the amount of hydrogen produced after consuming a measured amount of lactose. The amount of lactose consumed can be about 1 g, 2 g, 3 g, 4 g, 5 g, 6 g, 7 g, 8 g, 9 g, 10 g, 11 g, 12 g, 13 g, 14 g, 15 g, 16 g, 17 g, 18 g, 19 g, 20 g, 21 g, 22 g, 23 g, 24 g, 25 g, 26 g, 27 g, 28 g, 29 g, 30 g, 31 g, 32 g, 33 g, 34 g, 35 g, 36 g, 37 g, 38 g, 39 g, 40 g, or more. In one embodiment, the amount of lactose consumed is about 15 g. The lactose is administered by drinking a lactose mixture, and the subject exhales into a vacuum-sealed collection tube at three one hour time intervals. A high level of hydrogen in the breath indicates an improper digestion of lactose. An increase in hydrogen breath of greater than 5 ppm, 6 ppm, 7 ppm, 8 ppm, 9 ppm, 10 ppm, 11 ppm, 12 ppm, 13 ppm, 14 ppm, 15 ppm, 16 ppm, 17 ppm, 18 ppm, 19 ppm, 20 ppm, 21 ppm, 22 ppm, 23 ppm, 24 ppm, 25 ppm, 26 ppm, 27 ppm, 28 ppm, 29 ppm, 30 ppm, 31 ppm, 32 ppm, 33 ppm, 34 ppm, 35 ppm, 36 ppm, 37 ppm, 38 ppm, 39 ppm, 40 ppm, or more can indicated a subject has lactose intolerance. In one embodiment, an increase in hydrogen breath of 12 ppm can indicate a subject has lactose intolerance. In another embodiment, an increase in hydrogen breath of 15 ppm can indicate a subject has lactose intolerance. In one embodiment, an increase in hydrogen breath of greater than 20 ppm indicates a subject has lactose intolerance. In another embodiment, a lactose intolerance diagnostic device is a lactose intolerance diagnostic questionnaire wherein a subject rates the severity of exemplary symptoms of lactose intolerance. In one embodiment, the symptoms are rated on a scale of 0 to 5, wherein 0 indicates no symptoms, 1 indicates slight symptoms, 2 indicates mild symptoms, 3 indicates moderate symptoms, 4 indicates moderately severe symptoms, and 5 indicates severe symptoms. In one embodiment, the symptoms include abdominal pain/cramps, bloating, flatulence, diarrhea and/or nausea/upset stomach. In one embodiment, a questionnaire can be filled out after a lactose challenge. In another embodiment, a questionnaire can be filled out after a milk challenge. In another embodiment, a questionnaire can be filled out without a challenge. In one embodiment, a single score of 4 or 5 indicates a subject has lactose intolerance. In another embodiment, two or more scores of 3 or greater indicates a subject has lactose intolerance. In another embodiment, a score of 3 or greater for a single symptom at two different timepoints indicates a subject has lactose intolerance. In another embodiment, a change in the average scores over time is used to evaluate the effectiveness of a treatment regimen. In some embodiments, a lactose intolerance diagnostic questionnaire is given in conjunction with a hydrogen breath test or lactose challenge with, for example, about 1 g, 2 g, 3 g, 4 g, 5 g, 6 g, 7 g, 8 g, 9 g, 10 g, 11 g, 12 g, 13 g, 14 g, 15 g, 16 g, 17 g, 18 g, 19 g, 20 g, 21 g, 22 g, 23 g, 24 g, 25 g, 26 g, 27 g, 28 g, 29 g, 30 g, 31 g, 32 g, 33 g, 34 g, 35 g, 36 g, 37 g, 38 g, 39 g, 40 g, or more of lactose consumed. In some embodiments, a lactose intolerance diagnostic questionnaire is given in conjunction with a milk challenge involving the consumption of about 0.5, 1, 1.5, 2, 2.5, 3, 3.5, 4 or more cups of milk.

In one embodiment, a treatment regimens lasts, for about 1-20 days, about 1-25 days, about 1-30 days, about 1-35 days, about 1-40 days, about 1-45 days, about 1-50 days, about 5-30 days, about 5-35 days, about 5-40 days, about 5-45 days, about 5-50 days, about 5-55 days, about 5-60 days, or about 5-90 days. In another embodiment a treatment regimen lasts exactly or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 days. In one embodiment the amount of each dose in a treatment regimen is constant. For example, a constant dose of prebiotics can be administered each day to a subject for the duration of the treatment regimens described above. In one embodiment the dosing regimen is a constant 0.1-20 g of prebiotic per day. In another embodiment the dosing regimen can be an escalating regimen, for example, 2 g of prebiotic on day 1 and 20 g of prebiotic on day 20. In one embodiment the dose escalates by about 0.1 g, 0.2 g, 0.3 g, 0.4 g, 0.5 g, 0.6 g, 0.7 g, 0.8 g, 0.9 g, 1.0 g, 1.1 g, 1.2 g, 1.3 g, 1.4 g, 1.5 g, 1.6 g, 1.7 g, 1.8 g, 1.9 g, 2.0 g, 2.1 g, 2.2 g, 2.3 g, 2.4 g, 2.5 g, 2.6 g, 2.7 g, 2.8 g, 2.9 g, 3.0 g, 3.1 g, 3.2 g, 3.3 g, 3.4 g, 3.5 g, 3.6 g, 3.7 g, 3.8 g, 3.9 g, 4.0 g, 4.1 g, 4.2 g, 4.3 g, 4.4 g, 4.5 g, 4.6 g, 4.7 g, 4.8 g, 4.9 g, or 5.0 g per day. The dosing regimen can include between 0.1 and 20 g of prebiotic per day. The regimen can also include escalating the number of doses per day, for example, 1 dose per day, 2 doses per day, 3 doses per day, 4 doses per day, 5 doses per day, 6 doses per day, 7 doses per day, 8 doses per day, 9 doses per day, or 10 doses per day. For example, 1 dose per day is administered on day 1, 2 doses per day on day 10, and 3 doses per day on day 20 of a treatment regimen.

In one embodiment, the treatment occurs in phases. One phase utilizes a single administration of a prebiotic composition per day, generally though not necessarily with food, e.g., dinner. The dose of a prebiotic composition increases over time. For example, the dose of a prebiotic composition can increase each day. Another phase, generally following the first phase, utilizes two administrations of a prebiotic composition per day, again, generally with food, e.g., with breakfast and dinner. Again, during this phase the dose of a composition comprising a prebiotic increases over time, e.g., increasing each day. In one embodiment, the treatment includes one phase in which a composition comprising a prebiotic composition is administered once per day in conjunction with a probiotic (e.g., live bacteria). This phase, if used, is generally the first phase of the method.

Optionally a probiotic microbe(s) is administered during some or all of the entire period of treatment. For example, in one embodiment, a probiotic is included in a prebiotic-containing product that is administered to a subject. Typically, during the preceding phases no dairy products are consumed. A final phase of the protocol can involve the gradual reintroduction of dairy into the diet, either with or without the continuing use of the prebiotic composition used in the first phases of treatment. Finally, treatment is concluded and no further ingestion of a prebiotic composition is required.

In another embodiment the dosing regimen comprises five phases. The first phase comprises administration of a prebiotic composition for two days, optionally with a probiotic. In the second phase, a prebiotic composition is taken with food once a day (e.g., breakfast, lunch, or dinner) for a period of about 10 to 30 days, or about 14 to 24 days, or about 16 to 20 days, or about 18 days. In the third phase, a prebiotic composition is taken twice a day with food (e.g., both breakfast and dinner) for another period of about 6 to 18 days, or about 8 to 16 days, or about 10 to 14 days, or about 12 days. For the fourth phase lasting another 2, 3, 4, 5, or 6 days (e.g., about 4 days) thereafter, a prebiotic composition is administered with both dinner and breakfast, along with the addition of a lactose containing product (e.g., a dairy product). Prior to this time, dairy products are not administered during the first phases, e.g., the first about 30-34 days of the regimen. This total period, e.g., of approximately 38 days, can constitute the full period in which a prebiotic composition is administered, but more importantly administered essentially in these time periods. In one embodiment, following the actual administration of a prebiotic composition, the regimen optionally includes a fifth phase: the actual ingestion of dairy products every few days to maintain and build up tolerance to lactose, but without the administration of a prebiotic composition (to test the establishment of lactose tolerance). If lactose tolerance is not established, the regimen can be repeated. In the first period of time, through the first, roughly 18 days, the amount of a prebiotic composition administered at dinner time increases regularly each day. Thereafter, and in the third period, a prebiotic composition is administered regularly each day in combination with a breakfast meal. Moreover, and for the final days, e.g., the final four days, a lactose containing food item, such as milk, also is regularly increased for those 4 days.

If an initial treatment regimen is successful in generating lactose tolerance in a lactose intolerant person, and the lactose intolerance recurs, one or more treatment regimens can be repeated.

In one embodiment, a first dose of a prebiotic composition is administered in increasing amounts for a 6-week period. On the first and second days of this period, probiotic bacteria comprising one or more strains of bacteria (e.g., in a food containing product also having a live culture bacteria) is administered with the prebiotic composition. One such food item containing live cultured bacteria is yogurt. Further, during the third phase during this 6-week period, a second dose of a prebiotic composition (such as a composition comprising or consisting essentially of GOS) is administered, typically at breakfast time.

In one embodiment a prebiotic composition and a probiotic composition are administered to a subject in need thereof. In one embodiment, in the first day of the regimen, a subject ingests 8 ounces (about 226.4 g) or less of a probiotic composition along with 1 tablespoon (about 14.8 mL) of a prebiotic composition, at the dinner meal. In one embodiment, a subject in need thereof will ingest 8 ounces (about 226.4 g) or less of a probiotic composition on the first day, along with 1 tablespoon (about 14.8 mL) of a prebiotic composition with dinner. On the second day, the amount of the yogurt ingested is reduced by half to 4 ounces (about 113.2 g) or less of a probiotic composition, although the administration of the a prebiotic composition remains the same. On the third day, administration of the probiotic composition is stopped, but administration of a prebiotic composition remains at 1 tablespoon (about 14.8 mL). During the 4th through the 18th days, the amount of a prebiotic composition (e.g., a composition comprising or consisting essentially of GOS) ingested with dinner is increased by 1 tablespoon (about 14.8 mL) each day until 16 tablespoons (about 237 mL) are reached on the day 18.

In the third phase of the regimen, both 1 tablespoon (about 14.8 mL) of a prebiotic composition (such as a composition comprising or consisting essentially of GOS) is ingested in the morning, with breakfast, and 16 tablespoons (about 237 mL) of a prebiotic composition (e.g., a composition comprising or consisting essentially of GOS) are ingested with dinner. From day 16 until day 34, the same ratio of a prebiotic composition (e.g., a composition comprising or consisting essentially of GOS) with dinner is maintained, but the morning dose increases daily at a rate of a tablespoon (about 14.8 mL) per day. In this way, by day 34, the subject in need thereof is ingesting 32 tablespoons (about 474 mL) of a prebiotic composition (such as a composition comprising or consisting essentially of GOS).

On day 35, ingestion of the a prebiotic composition (such as a composition comprising or consisting essentially of GOS) is discontinued and in place thereof, a dairy product such as milk (without prebiotic composition) is ingested, with 9 ounces (about 255 g) of milk in the morning and an additional 9 ounces (about 255 g) in the evening. The milk amounts are increased incrementally at a rate of an ounce (about 28.3 g) per day, such that, by day 38, the subject is ingesting 12 ounces (about 340 g) of milk with breakfast and an additional 12 ounces (about 340 g) of milk at dinner. Optionally, on days 39 through 42, cheese is substituted for milk.

In another embodiment the number of days in which a prebiotic or probiotic composition is administered can vary, and the quantity of the dosages can similarly be modified according to the needs of a particular subject and the symptoms of the subject. Even though there can be variations in both the time period and the dosage rates, the concept of increasing the dosages of a prebiotic composition for specific time periods is maintained and encompassed by the methods herein.

In another embodiment a subject in need thereof can ingest more than 5 tablespoons (about 74 mL) of a prebiotic composition by day 7. As a result, the amount of a prebiotic composition ingested by day 7 can be increased to 6 tablespoons (about 89 mL) on day 8. Determination of whether or not the subject is capable of increasing the dosage or the time period depends on whether or not the subject encounters any adverse affects.

The same alterations can be made in the time intervals between the administration of a prebiotic composition and a lactose containing food item. Thus, if desired, the subject in need thereof could potentially alter the amount of a prebiotic composition every 12 hours. In like manner, that time period could vary to 36 or even 48 hours. In one embodiment, a prebiotic composition of the invention is administered in a powder formulation of a prebiotic composition (e.g., a composition comprising or consisting essentially of GOS), the latter of which can be mixed with water and administered much in the same manner as a soft drink. In one embodiment a prebiotic composition is incorporated in one or more capsules, capsules, or gels, as indicated. In another embodiment a prebiotic composition is supplied in a liquid formulation for oral administration.

In one embodiment a subject in need thereof is treated with a regimen using a powdered prebiotic composition using a dosing schedule as set forth in FIG. 5, 6, or 7. For FIGS. 5 and 6, 70% GOS refers to a GOS composition comprising 70% by weight GOS, about 20% by weight lactose, and 10% by weight digestible saccharides. In FIG. 5, a prebiotic composition contains a GOS composition (starting at 0.5 g and increased to 8.00 g over 34 days) with 0% by weight additional lactose. For example, the amount of 70% GOS composition administered can be about 0.5 g, 1 g, 1.5 g, 2 g, 2.5 g, 3 g, 3.5 g, 4 g, 4.5 g, 5 g, 5.5 g, 6 g, 6.5 g, 7 g, 7.5 g, or 8.0 g. In FIG. 6, a prebiotic composition contains a 70% GOS composition (starting at 0.29 g and increased to 4.69 g over 34 days) with additional lactose (starting at 0.33 g and increased to 5.3 g over 34 days). For example, the amount of 70% GOS composition administered can be about 0.29 g, 0.59 g, 0.88 g, 1.17 g, 1.46 g, 1.76 g, 2.05 g, 2.34 g, 2.64 g, 2.93 g, 3.22 g, 3.52 g, 3.81 g, 4.10 g, 4.39 g, or 4.69 g. In FIG. 7, the 90% GOS are a GOS composition comprising 90% by weight GOS and 10% by weight digestible saccharides. In this figure, a prebiotic composition contains a GOS composition (starting at 0.42 g and increased to 6.74 g over 34 days) with 0% by weight additional lactose. For example, the amount of 90% GOS composition administered can be about 0.42 g, 0.84 g, 1.26 g, 1.68 g, 2.11 g, 2.53 g, 2.95 g, 3.37 g, 3.79 g, 4.21 g, 4.63 g, 5.05 g, 5.47 g, 5.89 g, 6.32 g, or 6.74 g. In FIG. 8, the 93% GOS composition is a GOS composition comprising 90% by weight GOS (starting at 0.42 g and increased to 6.74 g over 34 days). For example, the amount of 93% GOS composition administered can be about 0.42 g, 0.84 g, 1.26 g, 1.68 g, 2.11 g, 2.53 g, 2.95 g, 3.37 g, 3.79 g, 4.21 g, 4.63 g, 5.05 g, 5.47 g, 5.89 g, 6.32 g, or 6.74 g. In FIG. 9, the 95% GOS composition is a GOS composition comprising 95% by weight GOS. For example, the amount of 95% GOS composition administered can be about 0.42 g, 0.84 g, 1.26 g, 1.68 g, 2.11 g, 2.53 g, 2.95 g, 3.37 g, 3.79 g, 4.21 g, 4.63 g, 5.05 g, 5.47 g, 5.89 g, 6.32 g, or 6.74 g. In another embodiment, a prebiotic composition contains a GOS composition (starting at a certain amount and increasing to a maximum amount over 34 days) with additional lactose (starting at a certain amount and increasing to a maximum amount over 34 days). In one embodiment a capsule containing GOS composition powder, is administered to a subject in need thereof. At day 34, the subject in need thereof has completed the protocol and can now enjoy dairy products pain-free. In one embodiment, no future protocol, supplements, or medication is needed for these subjects in need thereof to consume dairy products. In another embodiment, the protocol is re-administered as needed.

In one embodiment, a prebiotic composition is administered in a 16 day program. Examples of 16 day programs are shown in Tables 7, 8, and 9. Milk can be provided to the subject after completion of the 16 day program.

TABLE 7

Two examples of 16 day treatment programs.

| | Low | | | High | |
|---|---|---|---|---|---|
| | PM dose (g of GOS) | AM dose (g of GOS) | | PM dose (g of GOS) | AM dose (g of GOS) |
| Day 1 | 1.50 | 1.50 | Day 1 | 1.50 | 1.50 |
| Day 2 | 1.50 | 1.50 | Day 2 | 1.50 | 1.50 |
| Day 3 | 1.50 | 1.50 | Day 3 | 1.50 | 1.50 |
| Day 4 | 1.50 | 1.50 | Day 4 | 1.50 | 1.50 |
| Day 5 | 1.50 | 1.50 | Day 5 | 3.00 | 3.00 |
| Day 6 | 1.50 | 1.50 | Day 6 | 3.00 | 3.00 |
| Day 7 | 1.50 | 1.50 | Day 7 | 3.00 | 3.00 |
| Day 8 | 1.50 | 1.50 | Day 8 | 3.00 | 3.00 |
| Day 9 | 3.00 | 3.00 | Day 9 | 4.50 | 4.50 |
| Day 10 | 3.00 | 3.00 | Day 10 | 4.50 | 4.50 |
| Day 11 | 3.00 | 3.00 | Day 11 | 4.50 | 4.50 |
| Day 12 | 3.00 | 3.00 | Day 12 | 4.50 | 4.50 |
| Day 13 | 3.00 | 3.00 | Day 13 | 6.00 | 6.00 |
| Day 14 | 3.00 | 3.00 | Day 14 | 6.00 | 6.00 |
| Day 15 | 3.00 | 3.00 | Day 15 | 6.00 | 6.00 |
| Day 16 | 3.00 | 3.00 | Day 16 | 6.00 | 6.00 |
| | 8 oz Milk | 8 oz Milk | | 8 oz Milk | 8 oz Milk |
| | 10 oz Milk | 10 oz Milk | | 10 oz Milk | 10 oz Milk |
| | 12 oz Milk | 12 oz Milk | | 12 oz Milk | 12 oz Milk |

TABLE 8

Two examples of 16 day treatment programs.

| | PM dose (g of GOS) | AM dose (g of GOS) | | PM dose (g of GOS) | AM dose (g of GOS) |
|---|---|---|---|---|---|
| Day 1 | 0.40 | 0.40 | Day 1 | 1.20 | 1.20 |
| Day 2 | 0.80 | 0.80 | Day 2 | 1.20 | 1.20 |
| Day 3 | 1.20 | 1.20 | Day 3 | 1.20 | 1.20 |
| Day 4 | 1.60 | 1.60 | Day 4 | 3.00 | 3.00 |
| Day 5 | 2.00 | 2.00 | Day 5 | 3.00 | 3.00 |
| Day 6 | 2.40 | 2.40 | Day 6 | 3.00 | 3.00 |
| Day 7 | 2.80 | 2.80 | Day 7 | 3.00 | 3.00 |
| Day 8 | 3.20 | 3.20 | Day 8 | 4.60 | 4.60 |
| Day 9 | 3.60 | 3.60 | Day 9 | 4.60 | 4.60 |
| Day 10 | 4.00 | 4.00 | Day 10 | 4.60 | 4.60 |
| Day 11 | 4.40 | 4.40 | Day 11 | 4.60 | 4.60 |
| Day 12 | 4.80 | 4.80 | Day 12 | 6.10 | 6.10 |
| Day 13 | 5.20 | 5.20 | Day 13 | 6.10 | 6.10 |
| Day 14 | 5.60 | 5.60 | Day 14 | 6.10 | 6.10 |
| Day 15 | 6.00 | 6.00 | Day 15 | 6.10 | 6.10 |
| Day 16 | 6.40 | 6.40 | Day 16 | 6.10 | 6.10 |
| | 8 oz Milk | 8 oz Milk | | 8 oz Milk | 8 oz Milk |
| | 10 oz Milk | 10 oz Milk | | 10 oz Milk | 10 oz Milk |
| | 12 oz Milk | 12 oz Milk | | 12 oz Milk | 12 oz Milk |

TABLE 9

Example of a 16 day treatment program

| | PM dose (g of GOS) | AM dose (g of GOS) |
|---|---|---|
| Day 1 | 3.00 | |
| Day 2 | 3.00 | |
| Day 3 | 3.00 | |
| Day 4 | 3.00 | 3.00 |
| Day 5 | 3.00 | 3.00 |
| Day 6 | 3.00 | 3.00 |
| Day 7 | 3.00 | 3.00 |
| Day 8 | 4.60 | 4.60 |
| Day 9 | 4.60 | 4.60 |
| Day 10 | 4.60 | 4.60 |
| Day 11 | 4.60 | 4.60 |
| Day 12 | 6.10 | 6.10 |
| Day 13 | 6.10 | 6.10 |
| Day 14 | 6.10 | 6.10 |
| Day 15 | 6.10 | 6.10 |
| Day 16 | 6.10 | 6.10 |
| | 8 oz Milk | 8 oz Milk |
| | 10 oz Milk | 10 oz Milk |
| | 12 oz Milk | 12 oz Milk |

In another embodiment, a prebiotic composition is administered during a 30 or 34 day treatment program. Examples of 30 and 34 day treatment programs are shown in Tables 10, 11, and 12. Milk is provided after the treatment program.

TABLE 10

Two examples of 30 day treatment programs.

| | Low | | | High | |
|---|---|---|---|---|---|
| | PM dose (g of GOS) | AM dose (g of GOS) | | PM dose (g of GOS) | AM dose (g of GOS) |
| Day 1 | 1.50 | 1.50 | Day 1 | 3.00 | |
| Day 2 | 1.50 | 1.50 | Day 2 | 3.00 | |
| Day 3 | 1.50 | 1.50 | Day 3 | 3.00 | |
| Day 4 | 1.50 | 1.50 | Day 4 | 3.00 | 3.00 |

TABLE 10-continued

Two examples of 30 day treatment programs.

| | Low | | | High | |
|---|---|---|---|---|---|
| | PM dose (g of GOS) | AM dose (g of GOS) | | PM dose (g of GOS) | AM dose (g of GOS) |
| Day 5 | 1.50 | 1.50 | Day 5 | 3.00 | 3.00 |
| Day 6 | 1.50 | 1.50 | Day 6 | 3.00 | 3.00 |
| Day 7 | 1.50 | 1.50 | Day 7 | 3.00 | 3.00 |
| Day 8 | 1.50 | 1.50 | Day 8 | 3.00 | 3.00 |
| Day 9 | 1.50 | 1.50 | Day 9 | 3.00 | 3.00 |
| Day 10 | 1.50 | 1.50 | Day 10 | 3.00 | 3.00 |
| Day 11 | 1.50 | 1.50 | Day 11 | 4.60 | 4.60 |
| Day 12 | 1.50 | 1.50 | Day 12 | 4.60 | 4.60 |
| Day 13 | 1.50 | 1.50 | Day 13 | 4.60 | 4.60 |
| Day 14 | 1.50 | 1.50 | Day 14 | 4.60 | 4.60 |
| Day 15 | 1.50 | 1.50 | Day 15 | 4.60 | 4.60 |
| Day 16 | 3.00 | 3.00 | Day 16 | 4.60 | 4.60 |
| Day 17 | 3.00 | 3.00 | Day 17 | 4.60 | 4.60 |
| Day 18 | 3.00 | 3.00 | Day 18 | 4.60 | 4.60 |
| Day 19 | 3.00 | 3.00 | Day 19 | 4.60 | 4.60 |
| Day 20 | 3.00 | 3.00 | Day 20 | 4.60 | 4.60 |
| Day 21 | 3.00 | 3.00 | Day 21 | 6.10 | 6.10 |
| Day 22 | 3.00 | 3.00 | Day 22 | 6.10 | 6.10 |
| Day 23 | 3.00 | 3.00 | Day 23 | 6.10 | 6.10 |
| Day 24 | 3.00 | 3.00 | Day 24 | 6.10 | 6.10 |
| Day 25 | 3.00 | 3.00 | Day 25 | 6.10 | 6.10 |
| Day 26 | 3.00 | 3.00 | Day 26 | 6.10 | 6.10 |
| Day 27 | 3.00 | 3.00 | Day 27 | 6.10 | 6.10 |
| Day 28 | 3.00 | 3.00 | Day 28 | 6.10 | 6.10 |
| Day 29 | 3.00 | 3.00 | Day 29 | 6.10 | 6.10 |
| Day 30 | 3.00 | 3.00 | Day 30 | 6.10 | 6.10 |
| | 8 oz Milk | 8 oz Milk | | 8 oz Milk | 8 oz Milk |
| | 10 oz Milk | 10 oz Milk | | 10 oz Milk | 10 oz Milk |
| | 12 oz Milk | 12 oz Milk | | 12 oz Milk | 12 oz Milk |

TABLE 11

Examples of a 30 and 34 day treatment program.

| | PM dose (g of GOS) | AM dose (g of GOS) | | PM dose (g of GOS) | AM dose (g of GOS) |
|---|---|---|---|---|---|
| Day 1 | 1.20 | | Day 1 | 0.40 | |
| Day 2 | 1.20 | | Day 2 | 0.40 | |
| Day 3 | 1.20 | | Day 3 | 0.40 | |
| Day 4 | 1.20 | | Day 4 | 0.80 | |
| Day 5 | 3.00 | | Day 5 | 1.20 | |
| Day 6 | 3.00 | | Day 6 | 1.60 | |
| Day 7 | 3.00 | | Day 7 | 2.00 | |
| Day 8 | 3.00 | | Day 8 | 2.40 | |
| Day 9 | 4.60 | | Day 9 | 2.80 | |
| Day 10 | 4.60 | | Day 10 | 3.20 | |
| Day 11 | 4.60 | | Day 11 | 3.60 | |
| Day 12 | 4.60 | | Day 12 | 4.00 | |
| Day 13 | 6.10 | | Day 13 | 4.40 | |
| Day 14 | 6.10 | 1.20 | Day 14 | 4.80 | |
| Day 15 | 6.10 | 1.20 | Day 15 | 5.20 | |
| Day 16 | 6.10 | 1.20 | Day 16 | 5.60 | |
| Day 17 | 6.10 | 1.20 | Day 17 | 6.00 | |
| Day 18 | 6.10 | 3.00 | Day 18 | 6.40 | |
| Day 19 | 6.10 | 3.00 | Day 19 | 6.40 | 0.40 |
| Day 20 | 6.10 | 3.00 | Day 20 | 6.40 | 0.80 |
| Day 21 | 6.10 | 3.00 | Day 21 | 6.40 | 1.20 |
| Day 22 | 6.10 | 4.60 | Day 22 | 6.40 | 1.60 |
| Day 23 | 6.10 | 4.60 | Day 23 | 6.40 | 2.00 |
| Day 24 | 6.10 | 4.60 | Day 24 | 6.40 | 2.40 |
| Day 25 | 6.10 | 4.60 | Day 25 | 6.40 | 2.80 |
| Day 26 | 6.10 | 6.10 | Day 26 | 6.40 | 3.20 |
| Day 27 | 6.10 | 6.10 | Day 27 | 6.40 | 3.60 |
| Day 28 | 6.10 | 6.10 | Day 28 | 6.40 | 4.00 |
| Day 29 | 6.10 | 6.10 | Day 29 | 6.40 | 4.40 |
| Day 30 | 6.10 | 6.10 | Day 30 | 6.40 | 4.80 |
| | 8 oz Milk | 8 oz Milk | Day 31 | 6.40 | 5.20 |
| | 10 oz Milk | 10 oz Milk | Day 32 | 6.40 | 5.60 |
| | 12 oz Milk | 12 oz Milk | Day 33 | 6.40 | 6.00 |
| | | | Day 34 | 6.40 | 6.40 |
| | | | Day 35 | 8 oz Milk | 8 oz Milk |
| | | | Day 36 | 10 oz Milk | 10 oz Milk |
| | | | Day 37 | 12 oz Milk | 12 oz Milk |

TABLE 12

Examples of 30 day treatment programs.

| | PM dose (g of GOS) | AM dose (g of GOS) | | PM dose (g of GOS) | AM dose (g of GOS) |
|---|---|---|---|---|---|
| Day 1 | 1.20 | 1.20 | Day 1 | 3.00 | |
| Day 2 | 1.20 | 1.20 | Day 2 | 3.00 | |
| Day 3 | 1.20 | 1.20 | Day 3 | 3.00 | |
| Day 4 | 1.20 | 1.20 | Day 4 | 3.00 | 3.00 |
| Day 5 | 1.20 | 1.20 | Day 5 | 3.00 | 3.00 |
| Day 6 | 1.20 | 1.20 | Day 6 | 3.00 | 3.00 |
| Day 7 | 1.20 | 1.20 | Day 7 | 3.00 | 3.00 |
| Day 8 | 3.00 | 3.00 | Day 8 | 3.00 | 3.00 |
| Day 9 | 3.00 | 3.00 | Day 9 | 3.00 | 3.00 |
| Day 10 | 3.00 | 3.00 | Day 10 | 3.00 | 3.00 |
| Day 11 | 3.00 | 3.00 | Day 11 | 4.60 | 4.60 |
| Day 12 | 3.00 | 3.00 | Day 12 | 4.60 | 4.60 |
| Day 13 | 3.00 | 3.00 | Day 13 | 4.60 | 4.60 |
| Day 14 | 3.00 | 3.00 | Day 14 | 4.60 | 4.60 |
| Day 15 | 4.60 | 4.60 | Day 15 | 4.60 | 4.60 |
| Day 16 | 4.60 | 4.60 | Day 16 | 4.60 | 4.60 |
| Day 17 | 4.60 | 4.60 | Day 17 | 4.60 | 4.60 |
| Day 18 | 4.60 | 4.60 | Day 18 | 4.60 | 4.60 |
| Day 19 | 4.60 | 4.60 | Day 19 | 4.60 | 4.60 |
| Day 20 | 4.60 | 4.60 | Day 20 | 4.60 | 4.60 |
| Day 21 | 4.60 | 4.60 | Day 21 | 6.10 | 6.10 |
| Day 22 | 6.10 | 6.10 | Day 22 | 6.10 | 6.10 |
| Day 23 | 6.10 | 6.10 | Day 23 | 6.10 | 6.10 |
| Day 24 | 6.10 | 6.10 | Day 24 | 6.10 | 6.10 |
| Day 25 | 6.10 | 6.10 | Day 25 | 6.10 | 6.10 |
| Day 26 | 6.10 | 6.10 | Day 26 | 6.10 | 6.10 |
| Day 27 | 6.10 | 6.10 | Day 27 | 6.10 | 6.10 |
| Day 28 | 6.10 | 6.10 | Day 28 | 6.10 | 6.10 |
| Day 29 | 6.10 | 6.10 | Day 29 | 6.10 | 6.10 |
| Day 30 | 6.10 | 6.10 | Day 30 | 6.10 | 6.10 |
| | 8 oz Milk | 8 oz Milk | | 8 oz Milk | 8 oz Milk |
| | 10 oz Milk | 10 oz Milk | | 10 oz Milk | 10 oz Milk |
| | 12 oz Milk | 12 oz Milk | | 12 oz Milk | 12 oz Milk |

In one embodiment dosages of a prebiotic are administered to a subject in gelatin caps "00", which can hold between 0.546-1.092 g (e.g., of powder); gelatin caps "0", which can hold between 0.408-0.816 g (e.g., of powder), and gelatin caps "#1", which can hold between 0.300 and 0.600 g (e.g. of powder). In another embodiment, approximately 3 g of prebiotic composition is administered to a subject in three gelatin cap 00 pills. In another embodiment, approximately 1.5 g of prebiotic composition is administered two gelatin caps "00" or two gelatin caps "0." In another embodiment, a prebiotic composition is measured using a scoop.

Variations in the doses and timing in which the prebiotic compositions are administered can result in an effective treatment for increasing tolerance for lactose containing product. In one embodiment, the presented doses will be tested on subjects in need thereof. Thus, when applying the protocol of the present invention to younger subjects in need thereof, the weight of the subject might be a consideration. In one embodiment, a subject weighing 50 pounds (about 22.5 kg) is administered a lower dosage of a prebiotic composition than an adult. In another embodiment the timing of administration of a prebiotic composition to a pediatric subject can be different (e.g., once per day for 4 weeks) or the duration of administration can be shorter or longer than the duration of administration to an adult. In one embodiment the duration of administration of a prebiotic composition to a pediatric subject is shorter than the duration of administration to an adult. In one embodiment the duration of administration of a prebiotic composition to a pediatric subject is longer than the duration of administration to an adult.

In one embodiment the amount of a prebiotic composition administered to a subject can be proportionally adjusted based on the subject's weight. Although the doses are disclosed as being administered with breakfast and dinner, alternatively the order of the doses can be switched, or can be administered at other times of the day with meals such as lunch or snacks (or conceivably with no meals). The program can also be reduced into a shortened or lengthened program. In one embodiment a program of administration of a prebiotic composition to a subject in need thereof can be an abbreviated 1 week program or it can be lengthened up to a 10 week program. Although the methods and compositions herein have been described for use in humans, they are also capable of being administered to other mammals.

VII. Kits

In another aspect, the invention provides kits for the treatment of the symptoms of lactose intolerance. The kits include a prebiotic composition in suitable packaging for use by a subject in need thereof in the treatment of one or more symptoms of lactose intolerance. Any of the compositions described herein can be packaged in the form of a kit. A kit can contain an amount of a prebiotic composition and, optionally, other ingredients as described herein, sufficient for an entire course of treatment, or for a portion of a course of treatment. Thus, in one embodiment, a kit includes sufficient prebiotic composition for the first, second, third, fourth, fifth, and sixth weeks of treatment, or additional weeks of treatment if used, or any combination thereof. Doses of a prebiotic composition can be individually packaged, or the prebiotic composition can be provided in bulk, or combinations thereof. In one embodiment the individually packaged prebiotic composition is provided as a tablet, caplet, capsule or container of powder. In another embodiment the prebiotic composition is provided in a controlled release formulation. In another embodiment the prebiotic composition is provided as a formulation with an enteric coating. Thus, in one embodiment, a kit provides, in suitable packaging, individual doses of a prebiotic composition that correspond to dosing points in a treatment regimen, wherein the doses are packaged in one or more packages intended for use in the treatment of symptoms of lactose intolerance. For example, a kit can contain doses of a prebiotic composition, as described herein, for a treatment program, where the prebiotic composition is taken in increasing doses, so that individual packets of a prebiotic composition are increasing in amount of a prebiotic composition contained in the packet, from lower doses intended for use at the start of the program to higher doses as the program progresses. As doses are provided for later points in the program, two or more doses per day can be provided, each in its individual packet. Each packet can be labeled to indicate the day and time of day that it is intended to be taken, or the packaging containing the packets can be so labeled, or both. A "packet," as used in this context, is any individual container that contains a prebiotic composition, whether the prebiotic composition is in solid or liquid form, and includes a packet that contains powder, tablets, or pills, or a packet that contains a liquid.

In one embodiment, the prebiotic composition can be provided in bulk in a single container, or in two, three, four, five, or more than five containers (e.g., where each container contains enough of a prebiotic composition for a particular week of a treatment program). If more than one bulk container is provided, the bulk containers can be suitably packaged together to provide sufficient prebiotic composition for all or a portion of a treatment protocol. The container or containers can be labeled with a label indicating information useful to the subject in need thereof performing the treatment protocol, such as dosing schedules.

The prebiotic composition can be packaged with other suitable substances, such as probiotic bacteria, FOS, or buffer, as described herein. The other substance or substances can be packaged separately from the prebiotic composition, or mixed with the prebiotic composition, or combinations thereof. Thus, in one embodiment, kits of the invention include a powder or liquid containing all the ingredients intended to be used in a course of treatment or a portion of a course of treatment, e.g., a prebiotic composition and optionally a probiotic, FOS, or a buffer. In one embodiment, a prebiotic composition is packaged in one package or set of packages, and additional components, such as bacteria, FOS, or buffer, are packaged separately from the prebiotic composition.

Kits can further include written materials, such as instructions, expected results, testimonials, explanations, warnings, clinical data, information for health professionals, and the like. In one embodiment, the kits contain a label or other information indicating that the kit is only for use under the direction of a health professional, such as a dietician, nutritionist, nurse, physician, or other appropriate health professional. In another embodiment, the kits contain or include information, such as a label, designating the material within as a medical food.

In one embodiment, the invention provides a kit that includes a container of powder, where the powder includes a prebiotic composition, and optionally FOS, bacteria, or buffer, and a label on the container that indicates proper dosage and schedule of use for the powder. The container can further include scoops or other measuring or serving devices. In one embodiment, the invention provides a kit that includes a container of liquid, where the liquid includes a prebiotic composition and additionally FOS, bacteria, or buffer, and a label on the container that indicates proper dosage and schedule of use for the liquid. The container can further include measuring or serving devices.

VIII. Business Methods

The invention also provides business methods for marketing compositions and methods for the treatment of the symptoms of lactose intolerance or for overall improvement in gastrointestinal health. In one embodiment, the invention provides a method of doing business that includes marketing a composition for the treatment of symptoms of lactose intolerance wherein the treatment is by administering increasing doses of a prebiotic composition according to any of the methods described herein, optionally in combination with other substances such as FOS, lactose, bacteria, and buffers. In one embodiment, the composition is part of a kit, as described herein. The methods can further include producing such compositions or kits. The marketing can be directly to the consumer, or to suitable health professionals, or combinations thereof. The methods of marketing used in these embodiments of the invention include, but are not limited to, print, television, or radio commercials, infomercials, internet advertising, testimonials, word of mouth, telemarketing, and the like.

Also provided herein is a method of doing business such as providing a prebiotic composition as described herein to another entity that manufactures an already existing brand or product (such as a drink or dairy product) already available to the public. Methods encompass a method of doing business comprising marketing a prebiotic composition for use with an existing brand or product (drink or dairy product), wherein the prebiotic composition, when combined with the existing brand or product, causes the existing brand or product to have the added beneficial effects of lactose intolerance treatment or improving overall GI health.

EXAMPLES

Example 1

Clinical Trial Synopsis

A, multicenter, randomized, placebo-controlled trial will be conducted of a GOS composition, comprising 96% GOS by weight versus a placebo in subjects with moderate to severe symptoms on a hydrogen breath test, milk challenge, and stool bacterial analysis that are associated with lactose intolerance.

There will be two primary study objectives of the clinical trial:

1. The first primary objective will be to assess the ability of a 30 day treatment with the GOS composition to improve lactose digestion and tolerance in 60 subjects in comparison with placebo (n=30), and to determine if their symptoms caused by a lactose challenge during their Hydrogen Breath Test (HBT) are reduced 90 days after the end of treatment, and to demonstrate that any effect observed at the end of the 30 days persists for at least 90 days after treatment is completed.

2. The second primary objective will be to assess the safety of the GOS composition in this population by assessing adverse events throughout the period the population is receiving the GOS composition or the placebo and the population's ability to tolerate the GOS composition. This will be assessed by data collected at weekly telephone calls during the 30 days of treatment, and every other week calls for the next three months after the treatment is completed.

There will be five secondary study objectives:

1. Patient compliance will be measured by subject responses at weekly telephone calls and by assessing the amount of the GOS composition or the placebo the subject returns at the end of treatment when they visit the clinic for their HBT.

2. The GOS composition and placebo groups will be compared in terms of their symptom scores in the presence of dairy intake (Days 35 to 90) versus their original baseline (historical) scores.

3. The duration of any improvement in symptoms reported during the HBT observed at the end of treatment (Day 30) will be evaluated by comparing symptom scores at the end of treatment with those obtained during the HBT three months later for the active treatment and placebo groups.

4. The effect observed at the end of treatment (Day 30) versus baseline will be assessed by comparing the decreased scores of those on treatment versus those on placebo, using scores obtained on a lactose challenge in the two HBT.

5. The trial will compare the amount of dairy products ingested during days 35 to 90 versus baseline in the two groups, as measured from a dietary sheet completed by subjects.

Study Design:

This will be a parallel group trial of a 30-day course on the GOS composition (total n=60 subjects) or a placebo (n=30 subjects) following a dosing schedule to be provided to each subject. Subjects will be enrolled who exceed a pre-specified level of symptoms on a lactose challenge test during the HBT at baseline. This test will be repeated at the end of treatment and approximately three months later. Each of three symptoms of lactose intolerance (see next paragraph) will be assessed hourly as 0 (no symptoms); 1 (mild symptoms); 2 (moderate symptoms); 3 (strong symptoms); and 4 (severe symptoms). Adverse events will be collected at weekly telephone calls for six weeks and calls every other week for the next three months, as well as during each visit to the clinic where the HBT is conducted. Patients will be instructed to eat a fixed amount of dairy portions during days 35 to 90 (3 to 7 dairy servings per week, where the definition of a serving is defined on an instruction sheet to be given to each subject).

Rationale for the Doses to be Used:

The goal of this study will be to develop tolerance in subjects who are lactose intolerant, and a primary principle of developing tolerance is to gradually increase the dose of the drug. The doses of the GOS composition (given once daily in sachets) will be gradually increased over Days 1 to 19 to reach the level of lactose equivalent to that in an 8 ounce (about 226 g) glass of milk (one serving of dairy). During the second half of the dose titration, the sachets will contain the equivalence of 8 ounces (about 226 g) of milk in the PM, while a second set of the same incremental doses used over Days 3-19 will be repeated in the AM. Once subjects receive the equivalence of 8 ounces (about 226 g) of milk twice daily, dosages will be further increased to reach the equivalence of 12 ounces (about 340 g) of milk in both the morning and afternoon. This level of 12 ounces (about 340 g) of milk is chosen to develop tolerance to a total of three servings of dairy per day, the recommended level in the US Dietary Guidelines to meet calcium and other nutrient needs. This approach has previously been used successfully in many thousands of patients. In this clinical trial each day's dosage will be individually labeled in a sachet and printed with instructions for how to take it with water.

Primary Clinical Endpoint:

The severity of three symptoms of lactose intolerance: gas, diarrhea, and "stomach pain" (any bloating, cramps or stomach pain) on ingesting 20 grams of lactose in solution will be assessed during the HBT.

To be enrolled subjects can experience one of the three following scores during baseline testing:

a. at least one strong or severe score (i.e., 3 or 4) on a single symptom on at least two time points during the six hour HBT;

b. at least two moderate scores (i.e., 2 each) on a single symptom on at least two time points during the six hour HBT; or c. at least one moderate score or greater (i.e., a 2 or more) on each of two symptoms on at least two time points during the six hour HBT.

However, the efficacy of the GOS composition will be assessed by calculating the average score for subjects on the GOS composition versus those on placebo. Scores will be based on the following rating system: 0 (no symptoms); 1 (mild symptoms); 2 (moderate symptoms); 3 (strong symptoms) and 4 (severe symptoms). Therefore the maximal score is 3 (symptoms) times 6 hourly reports times 4 points maximally or 72. This score will be assessed during each of the three HBT evaluations, at baseline, within one week of completing the 30 day program and three months later. No distinction will be made between the importance of the three symptoms, and there will not be any weighting of the scores based on the specific symptom. The primary assessment of efficacy will be determined by comparing the decrease in the average score (baseline score minus the score at 90 days after the end of treatment) for those receiving the GOS composition versus those receiving the placebo. (See the statistical section for additional details). The baseline score minus the score at the end of treatment will be a secondary measure of efficacy.

Secondary Clinical Endpoints:

1. Symptom score of lactose intolerance collected on questionnaires presented to subjects at baseline and read over the telephone every other week during Days 38 to 90. (Note that these scores will not be obtained during the HBT).

2. Score of the amount of hydrogen on the HBT in parts per million at the end of the trial and three months later, as compared with the amount at baseline. Hydrogen will be measured hourly during the six hour test and the sum of the six hour production will be compared to the baseline test.

3. Symptom scores after the lactose challenge during the HBT at the end of the 30-day treatment versus the baseline score.

4. Symptom scores after the lactose challenge during the HBT at three months after the treatment is completed versus the symptoms score at the end of the 30-day treatment.

Number of Subjects:

A total of 90 subjects will be enrolled, 60 subjects in the active treatment group and 30 in the placebo group. It is anticipated that three clinical trial sites will be used. The unbalanced number of patients per group will be used to stimulate recruitment and to encourage subjects to enroll in the trial. The power of this trial is discussed in the statistical section. Subjects who do not complete the initial post-treatment HBT will be replaced to obtain 60 and 30 completers in the two groups.

Diagnosis of Lactose Intolerance:

Patients can have symptoms of lactose intolerance with a total score of at least 8 for any one of the three symptoms or a total score of 16 for the three symptoms evaluated, on being challenged with 14 g of lactose solution during the HBT, whether or not the HBT data for hydrogen are positive. The HBT will be conducted in the investigator's clinic or other facility and will consist of 14 g of lactose in solution, with a positive score defined at 10 parts per million of hydrogen above the subject's baseline at anytime during the six hour treatment. Patients with a positive HBT will be defined as lactose maldigesters. Because of the relatively large number of both false positives and false negatives reported in the literature with the HBT (although it is a diagnostic tool available for lactose intolerance) it is not scientifically appropriate to only enroll patients with a positive HBT and also symptoms of lactose intolerance. Therefore, the HBT is primarily used to evaluate symptoms of lactose intolerance and not the amount of hydrogen produced, although the latter will be used as a secondary endpoint.

Major Inclusion Criteria:

1. Subjects of either sex aged 12 years and above.

2. History of intolerance to milk and other dairy products of at least three months duration.

3. During the lactose challenge (during the HBT) subjects can have one of the following ratings of their symptoms:

a. At least one score of strong or severe on any one symptom.

b. At least two scores of moderate on one symptom.

c. At least one score of moderate on each of two symptoms.

4. An HBT will also be administered to assess the amount of hydrogen produced. Note that there is no specific score on the amount of hydrogen measured in the HBT required for entry, but 10 parts per million of hydrogen above baseline is an amount that can be used to classify the patient as a lactose maldigester.

5. Subjects can agree to refrain from all other treatments and products used for lactose intolerance during the trial.

Duration of Treatment:

30-days on investigational treatment, followed by a HBT and a three month period to evaluate the duration of any benefit.

Dropouts:

Subjects who drop out or are discontinued will not be replaced.

Study Drug Dose and Mode of Administration:

The GOS composition will be self-administered by subjects on an out-patient basis using a dosing schedule to be provided. The GOS composition will be packaged in individual sachet packs for dilution in water. Each pack will be labeled with the study day and time (i.e., am or pm).

Comparator Therapy:

Placebo (dextrose) will be given in equal amounts and using the same dosing schedule and packaging as the GOS composition.

Subjects will be asked about symptoms and also about the amount of dairy intake at their weekly or bi-weekly telephone calls.

Criteria for Evaluation

Efficacy Measures:

A five point Likert scale (severe (4), strong (3), moderate (2), mild (1) or none (0)) will be used to score each of the three cardinal signs of lactose intolerance (i.e., gas, diarrhea, and cramps). The scale will be used following the HBT and during the bi-weekly telephone calls for the following three months after treatment is completed (Days 35 to 90). Note that the form for cramps will indicate to the subjects that it includes abdominal pain and bloating, which maintains the three cardinal signs. Experts in this field state that many, if not most, patients cannot separate these three overlapping symptoms (i.e. cramps, bloating, and abdominal pain), and that it makes most sense to refer to three cardinal signs (i.e. gas, diarrhea, and cramps).

Safety Assessments:

The incidence and severity of adverse events, blood pressure, and heart rate will be assessed during the three HBTs, and adverse events will be solicited during the weekly (Days 1-30) and the bi-weekly (Days 35-90) telephone calls to subjects using a standard script that will be read to them.

Statistical Plan:

Hydrogen production during the HBT and symptom comparisons will be evaluated according to the method of Hertzler and Savaiano (1996).

Efficacy Measures:

The primary efficacy assessment will be made by comparing changes in symptoms reported by each group during the HBT after the lactose challenge. Secondary efficacy will be assessed by responses to symptom questionnaires administered by telephone at bi-weekly intervals during the three month follow-up period. Finally, the reported amount of dairy portions ingested by subjects in each group will be compared for Days 35-90.

The primary efficacy measure for this study will be the total symptom score during the HBT lactose challenges (maximum score=72) at baseline, following treatment, and 90 days following treatment. Primary efficacy will be analyzed through a 2 group (Treatment and Control)×2 time points (baseline and 90 days after 30 days of treatment) analysis of variance (ANOVA) for alpha at 0.05. Using the results of Landon, et al. (2006), the power for this study (with 60 Treatment vs. 30 Control subjects) is 95%. Note that the primary assessment of efficacy is 90 days after the end of the 30-day treatment, which will demonstrate that the effect persists for at least three months past the time of treatment.

The secondary efficacy measure is to compare the scores of lactose intolerance symptoms obtained during the HBT challenge conducted three months after treatment with scores obtained at baseline and at the end of treatment. This analysis will be conducted employing a 2 group×3 time points ANOVA.

Another secondary efficacy measure of bi-weekly subject reports will be computed and charted on patient listings, but not subjected to analysis since they are based on self-reporting of symptoms under non-standard conditions.

Finally, breath hydrogen concentrations will be summed for hours 1 to 6 after lactose challenge during the HBT at each of the three HBT evaluations. These scores will also be compared using a 2 group×3 time points ANOVA for significant differences in mean breath hydrogen concentrations.

Safety Measures

Summary statistics will be calculated for subject disposition, demographics, and baseline characteristics, patient compliance, blood pressure and heart rate. All adverse events will be recorded and reported for subjects in both Treatment and Control groups. These will be presented as lists, appropriate figures and in summary tables. All Serious Adverse Events will be reported to regulatory agencies per regulations and guidelines.

Subjects will visit the clinic once at baseline for screening and baseline assessments. Those who sign an informed consent and pass the lactose challenge given during HBT, and also the other screening evaluations will be randomized and given sachets of the GOS composition or placebo to take according to an attached sheet that labeled with each day and time of treatment. A page of instructions will also be provided. Subjects will return to clinic (with their unused medication) for a follow-up HBT within a week of completing the 30-day treatment period. A follow-up visit will take place approximately three months after the second HBT, for a lactose challenge and final HBT.

Time and Events Chart:

Subjects will be evaluated for adverse events, blood pressure and heart rate at each clinic visit. Safety with taking the GOS composition or placebo will be evaluated weekly during the 30-day treatment period and adverse events will be assessed during biweekly telephone calls from Day 35 to 90.

Dosage Schedule:

The GOS composition that will be ingested orally for 30 days using the regimen that follows the schedule to be provided at baseline after subjects are enrolled.

Subjects will not use any dairy products from Days 1 to 30 apart from what is listed in their instructions. From Days 35 to Day 90 subjects will be instructed to take from 3 to 7 dairy servings per week. All of the specific details will be presented in the full protocol.

Example 2

Study of GOS Treatment of Subjects

Subjects will take a 90% purity level GOS compound according to the schedule in Table 13. The subjects will be instructed to daily measure the exact dosage amount in Table 13 with the scoops provided and mix the powder in 6 to 8 ounces (about 170 to 226 g) of room temperature water. The mixtures will be stirred for 2 minutes before drinking. Alternatively, subjects will take gel capsules containing GOS. Subjects will be instructed not to skip any doses; if dosing for a day is forgotten, subjects will be instructed to back up a day in the routine and not to double on doses. The subjects will conduct self reported symptom scoring before, after, and 30 days thereafter program. A likert scale scoring system will be used: 1-5 symptom rating [(1) no symptoms, (2) minor symptoms, (3) moderate symptoms, (4) strong symptoms, (5) severe symptoms)] of subject's reported gas, cramps, bloating and/or diarrhea from dairy consumption.

TABLE 13

Dosing schedule for small study of GOS treatment of subjects.

|  | PM - Dosages | AM- Dosage |
| --- | --- | --- |
| Day 1 | 0.40 |  |
| Day 2 | 0.40 |  |
| Day 3 | 0.40 |  |
| Day 4 | 0.80 |  |
| Day 5 | 1.20 |  |
| Day 6 | 1.60 |  |
| Day 7 | 2.00 |  |
| Day 8 | 2.40 |  |
| Day 9 | 2.80 |  |
| Day 10 | 3.20 |  |
| Day 11 | 3.60 |  |
| Day 12 | 4.00 |  |
| Day 13 | 4.40 |  |
| Day 14 | 4.80 |  |
| Day 15 | 5.20 |  |
| Day 16 | 5.60 |  |
| Day 17 | 6.00 |  |
| Day 18 | 6.40 |  |
| Day 19 | 6.40 | 0.40 |
| Day 20 | 6.40 | 0.80 |
| Day 21 | 6.40 | 1.20 |
| Day 22 | 6.40 | 1.60 |
| Day 23 | 6.40 | 2.00 |
| Day 24 | 6.40 | 2.40 |
| Day 25 | 6.40 | 2.80 |
| Day 26 | 6.40 | 3.20 |
| Day 27 | 6.40 | 3.60 |
| Day 28 | 6.40 | 4.00 |
| Day 29 | 6.40 | 4.40 |
| Day 30 | 6.40 | 4.80 |
| Day 31 | 6.40 | 5.20 |
| Day 32 | 6.40 | 5.60 |

TABLE 13-continued

Dosing schedule for small study of GOS treatment of subjects.

| | PM - Dosages | AM- Dosage |
|---|---|---|
| Day 33 | 6.40 | 6.00 |
| Day 34 | 6.40 | 6.40 |

Dosages are in grams; PM-take with evening meal; AM-take with morning meal

Example 3

Growth of *Lactobacillus* and *Bifidobacterium* Strains in a GOS Solution

Figure 12:
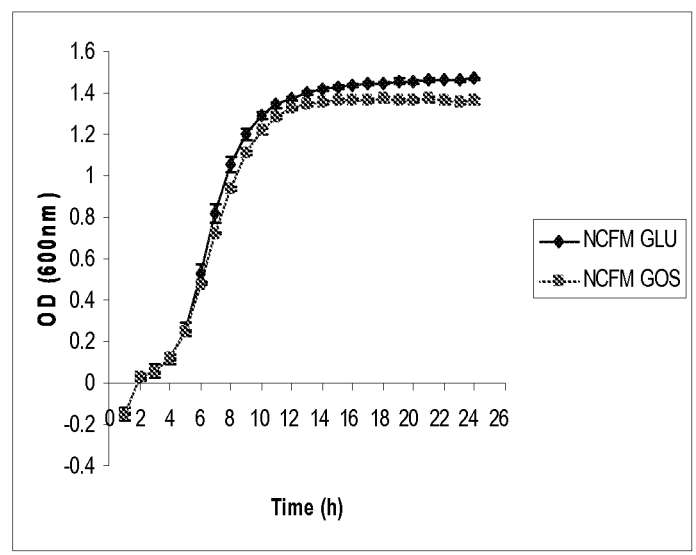
FIG. 12 illustrates *Lactobacillus acidophilus* NCFM growth on 2% GOS1 (95%) or glucose.

The growth of *Lactobacillus* and *Bifidobacterium* strains was evaluated in scratch MRS (Table 14) supplemented with either 2% glucose or 2% GOS and automatically monitored by determining the change in absorbance (A600) as a function of the time using a FLUOStar OPTIMA microtiter plate reader. The strains were incubated at 37° C. aerobically. Results are shown in FIG. 12. Some strains were grown under anaerobic conditions at 37° C. and OD's were read manually over time, when indicated.

TABLE 14

Scratch MRS formula:

| Reagents | Amount (g) per liter |
|---|---|
| Proteose peptone N3 | 10.0 |
| Beef extract | 10.0 |
| Yeast extract | 5.0 |
| Polysorbate 80 | 1.0 |
| Ammonium citrate | 2.0 |
| Sodium acetate | 5.0 |
| Magnesium sulfate | 0.1 |
| Manganese sulfate | 0.05 |
| Dipotassium phosphate | 2.0 |
| Glucose or GOS | 20 |

Example 4

HPLC-RI Method for Assay and Purity Analysis of a GOS Composition Syrup

The purpose of this method is to assay by area percent and purity of a GOS composition syrup by an ion exclusion isocratic method.

Preparing Samples for HPLC

An approximately 10 mg/mL TP-G28 solution is prepared, in a 50 mL volumetric flask, by diluting 500 mg of a GOS composition syrup with 0.015N sulfuric acid ($H_2SO_4$). The solution is filtered using a 0.2 μm polyvinylidene fluoride (PVDF) filter (Whatman). The first 2 mL are discarded; the remaining solution is collected in an HPLC vial. An approximately 0.19 mg/mL lactose solution is prepared, in a 100 mL volumetric flask, by diluting 19 mg of lactose with 0.015N $H_2SO_4$. The solution is filtered using a 0.2 μm PVDF filter. The first 2 mL are discarded; the remaining solution is collected in an high performance liquid chromatography (HPLC) vial. An approximately 0.005 mg/mL glucose solution is prepared, in a 100 mL volumetric flask, by diluting 5 mg of lactose with 0.015N $H_2SO_4$. The solution is filtered using a 0.2 μm PVDF filter. The first 2 mL are discarded; the remaining solution is collected in an HPLC vial. An approximately 0.11 mg/mL solution of galactose is prepared, in a 100 mL volumetric flask, by diluting 11 mg of lactose with 0.015N sulfuric acid ($H_2SO_4$). The solution is filtered using a 0.2 μm PVDF filter. The first 2 mL are discarded; the remaining solution is collected in an HPLC vial.

Running Samples on an HPLC Machine

Figure 20:
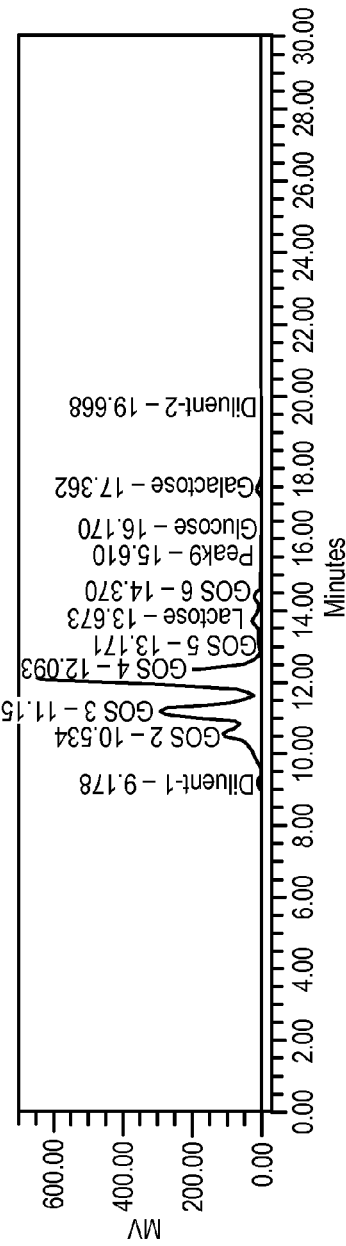
FIG. 20 illustrates an HPLC chromatograph of a sample containing GOS 95.
Figure 20:
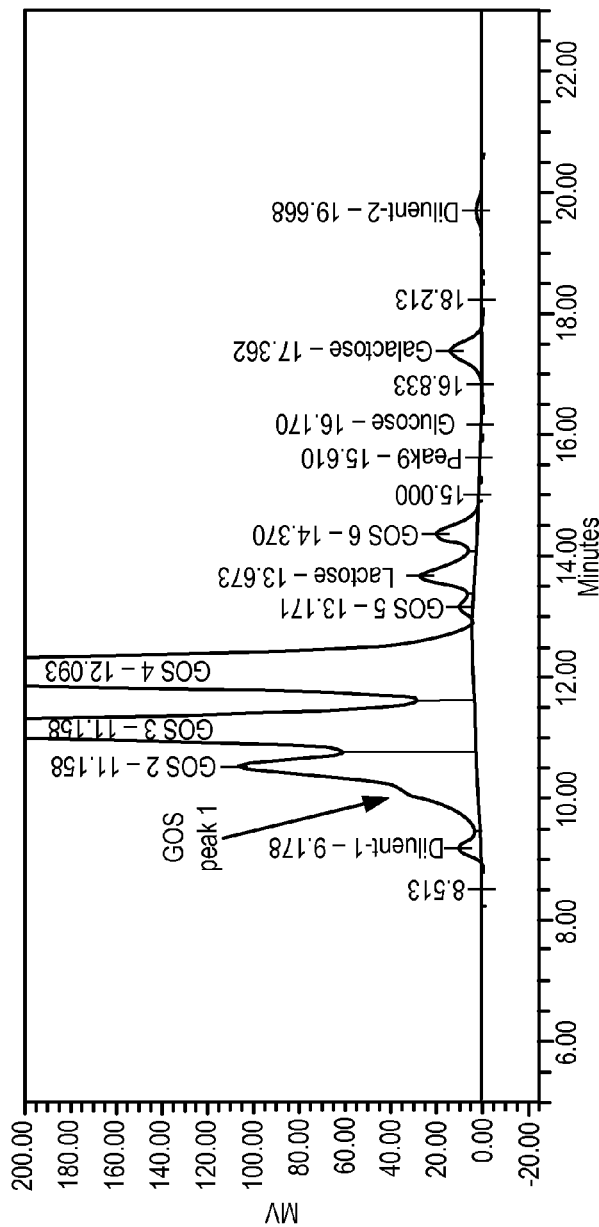
Figure 21:
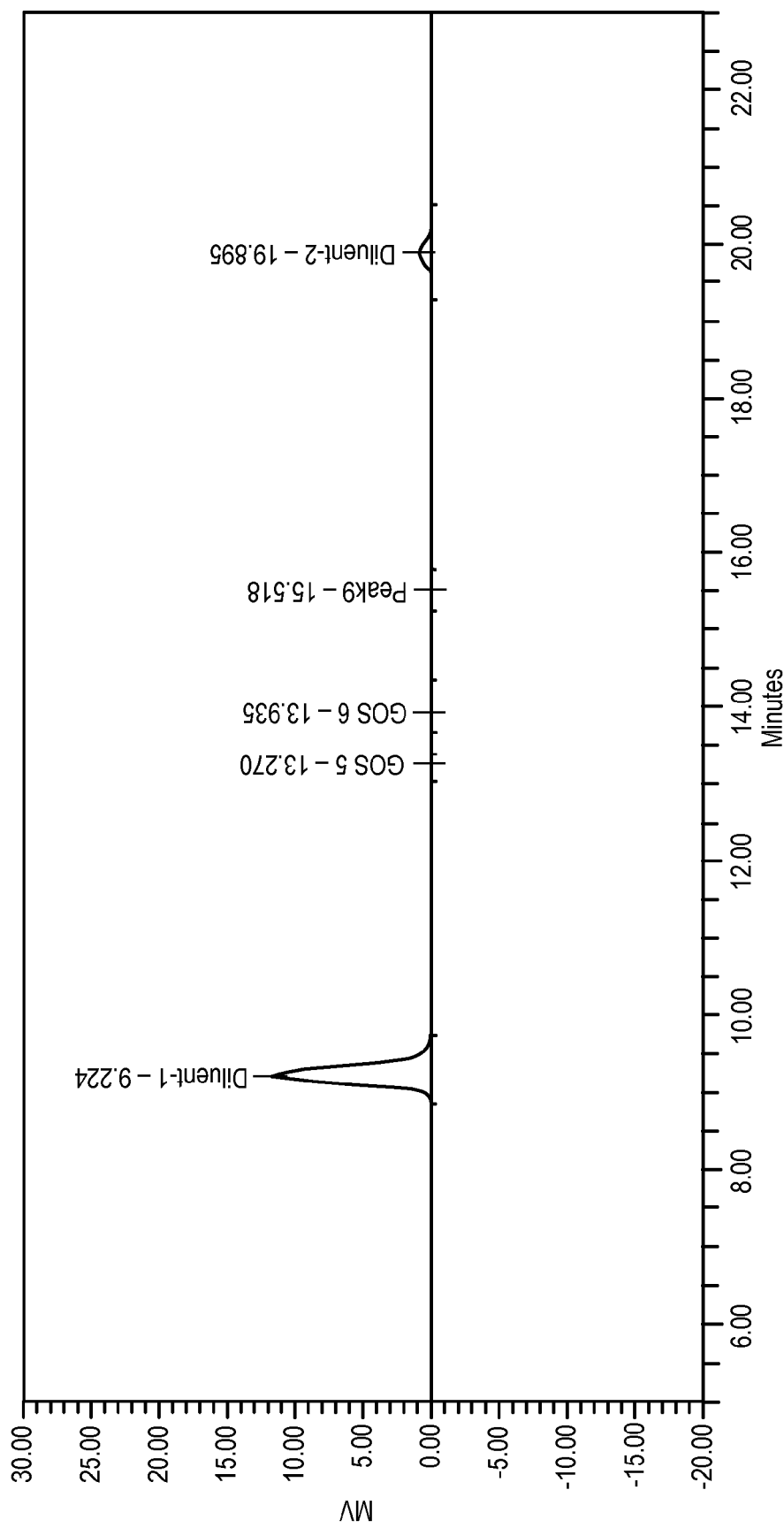
FIG. 21 illustrates an HPLC chromatograph of a blank sample (PVDF filtered 0.015N $H_2SO_4$).
Figure 22:
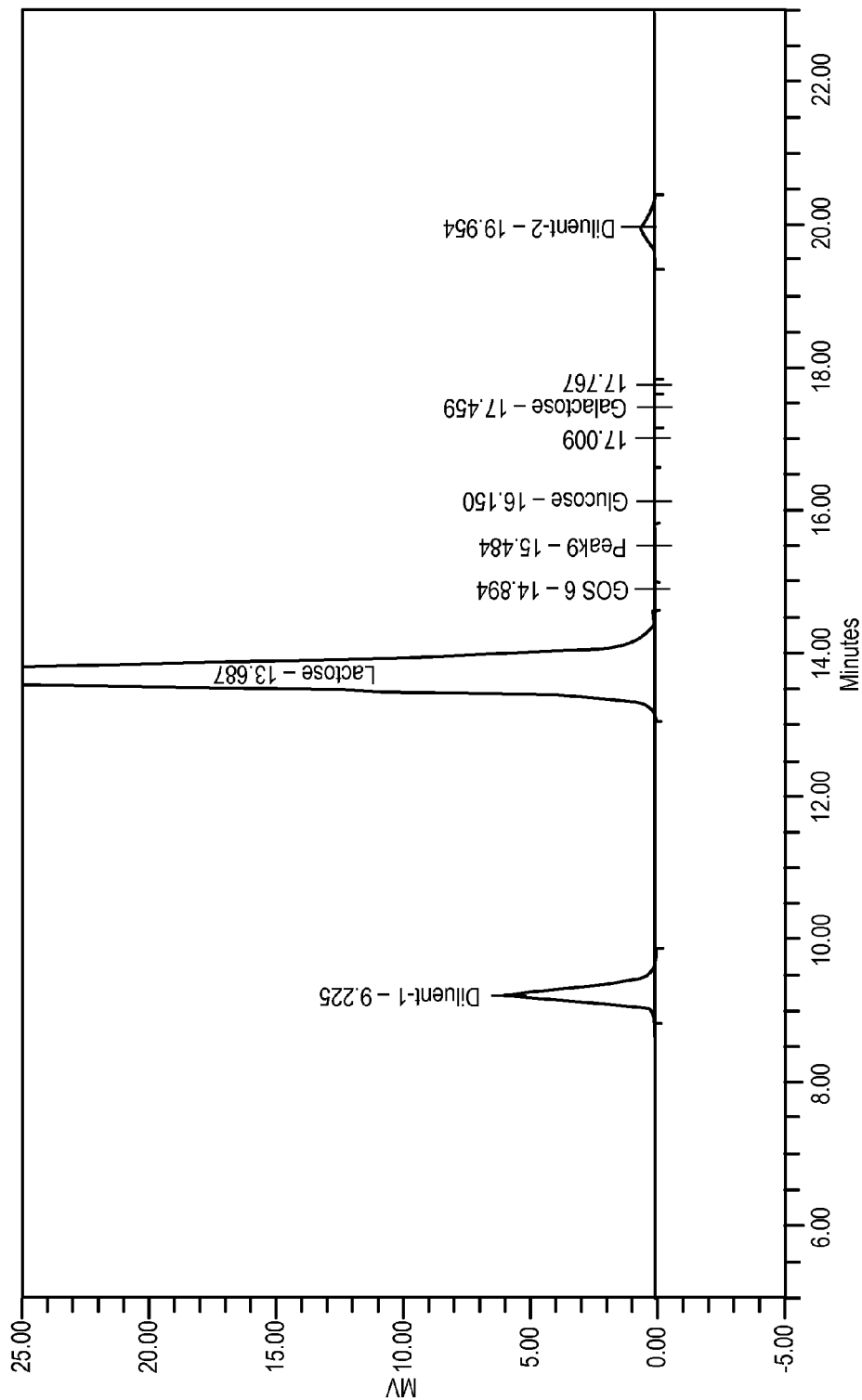
FIG. 22 illustrates an HPLC chromatograph of a sample containing Lactose.
Figure 23:
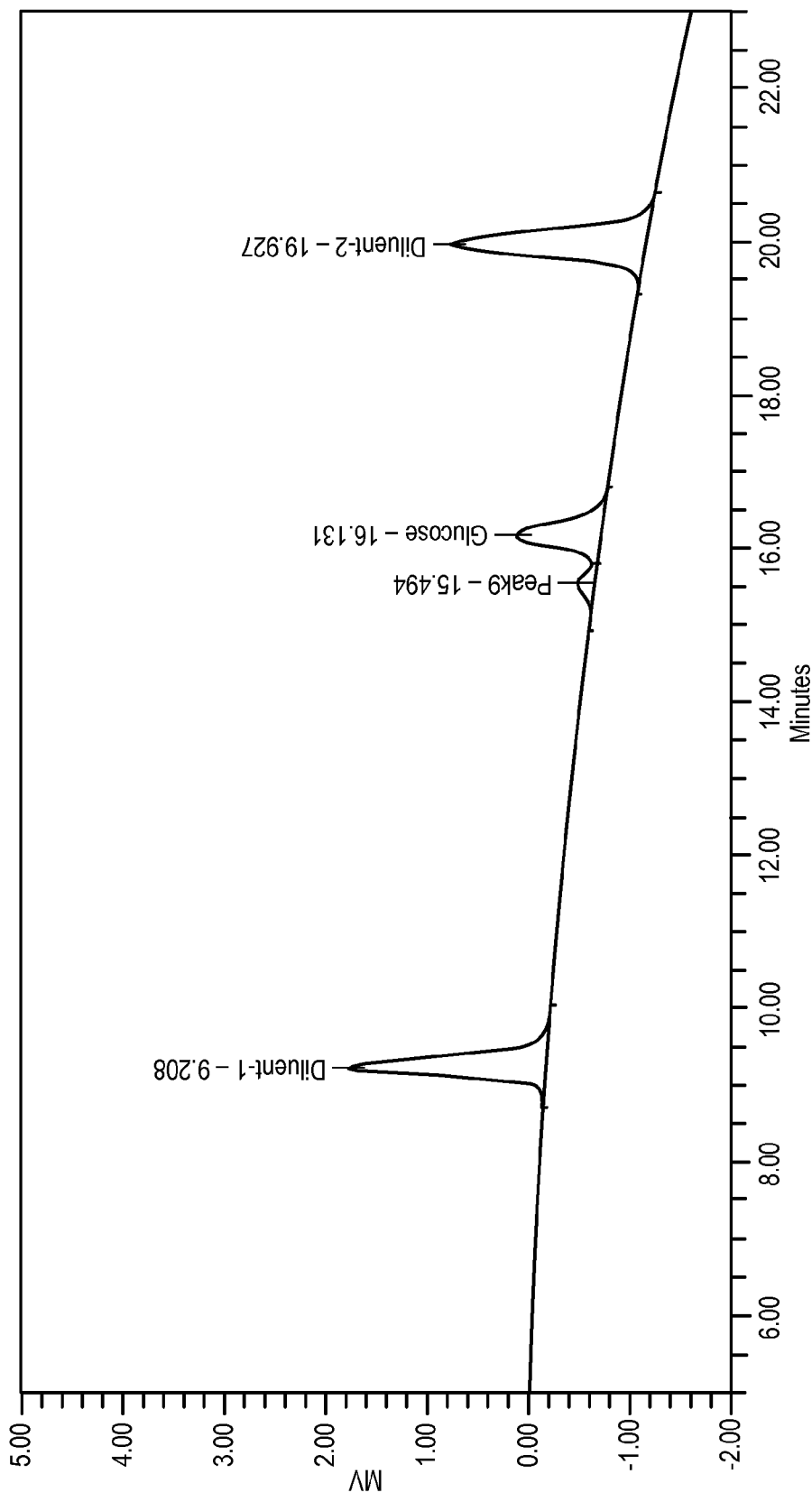
FIG. 23 illustrates an HPLC chromatograph of a sample containing α-D-Glucose.
Figure 24:
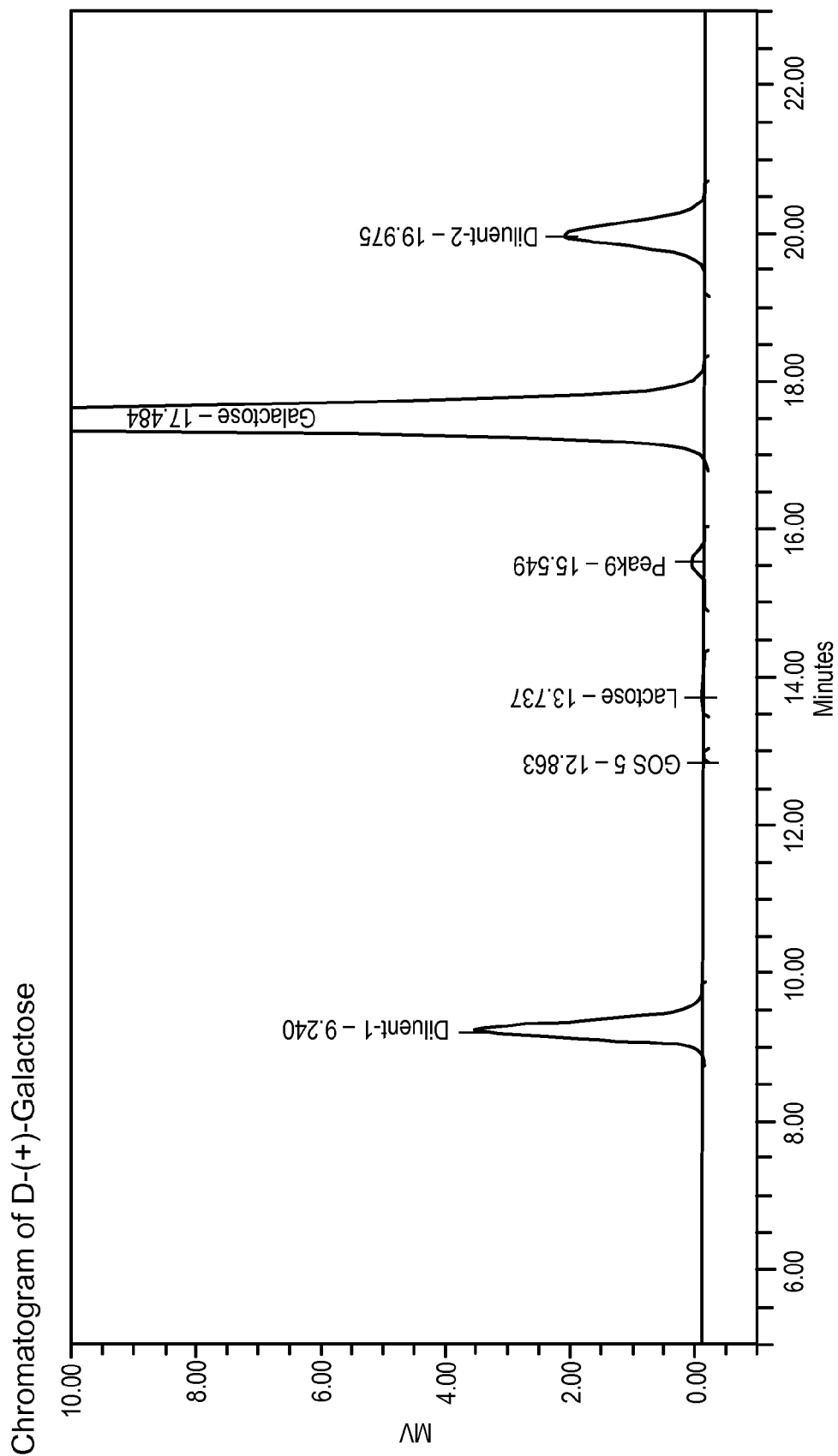
FIG. 24 illustrates an HPLC chromatograph of a sample containing D-(+)-Galactose.

An Agilent 1100 Series HPLC, equipped with a Transgenomic ICSep ICE-ION-300, 300×7.8 mm column, is conditioned with 0.015N $H_2SO_4$ at 40° C. run at 0.4 mL/minute for 60 minutes. Prior to an analytical run, consecutive blank injections, consisting of 60 μl of 0.015N $H_2SO_4$, are performed until a stable baseline is observed. For the analytical run, 60 μL of prepared the GOS composition sample is injected and the column is run at 0.4 mL/min for 30 minutes. The sample is analyzed with a Waters 2414 RI detector set to a sensitivity level of 16. The expected retention times of the GOS composition syrup components are shown in Table 15. The HPLC chromatograph of the GOS composition can be found in FIG. 20; a zoomed in version of the GOS composition is located underneath. Comparison samples were run under identical conditions. FIG. 21 shows the chromatograph of a blank sample (0.015N $H_2SO_4$); FIG. 22 shows the chromatograph of lactose; FIG. 23 shows the chromatograph of glucose; and, FIG. 24 shows the chromatograph of galactose.

TABLE 15

Expected retention times (approximate)

| Species | Retention Time |
|---|---|
| Diluent peak | 9.3 min |
| GOS 1/2 | 10.5 min |
| GOS 3 | 11.2 min |
| GOS 4 | 12.1 min |
| GOS 5 | 13.2 min |
| Lactose | 13.7 min |
| GOS 6 | 14.4 min |
| Glucose | 16.2 min |
| Galactose | 17.4 min |
| Diluent peak | 19.7 min |

Analysis of the GOS Composition HPLC Chromatograph

Chromatographs are analyzed using Waters Empower software. GOS elutes as 6 peaks; however, peaks 1 and 2 overlap. The area of all 6 GOS peaks are measured, divided by the total area of all non-solvent peaks, and multiplied by 100 to determine the percent Area of the sample. To determine the percent impurity, the total area of all non-GOS/non-solvent peaks is divided by the total area of the GOS peaks and multiplied by 100.

Example 5

Purification of a GOS Composition

Figure 13A:
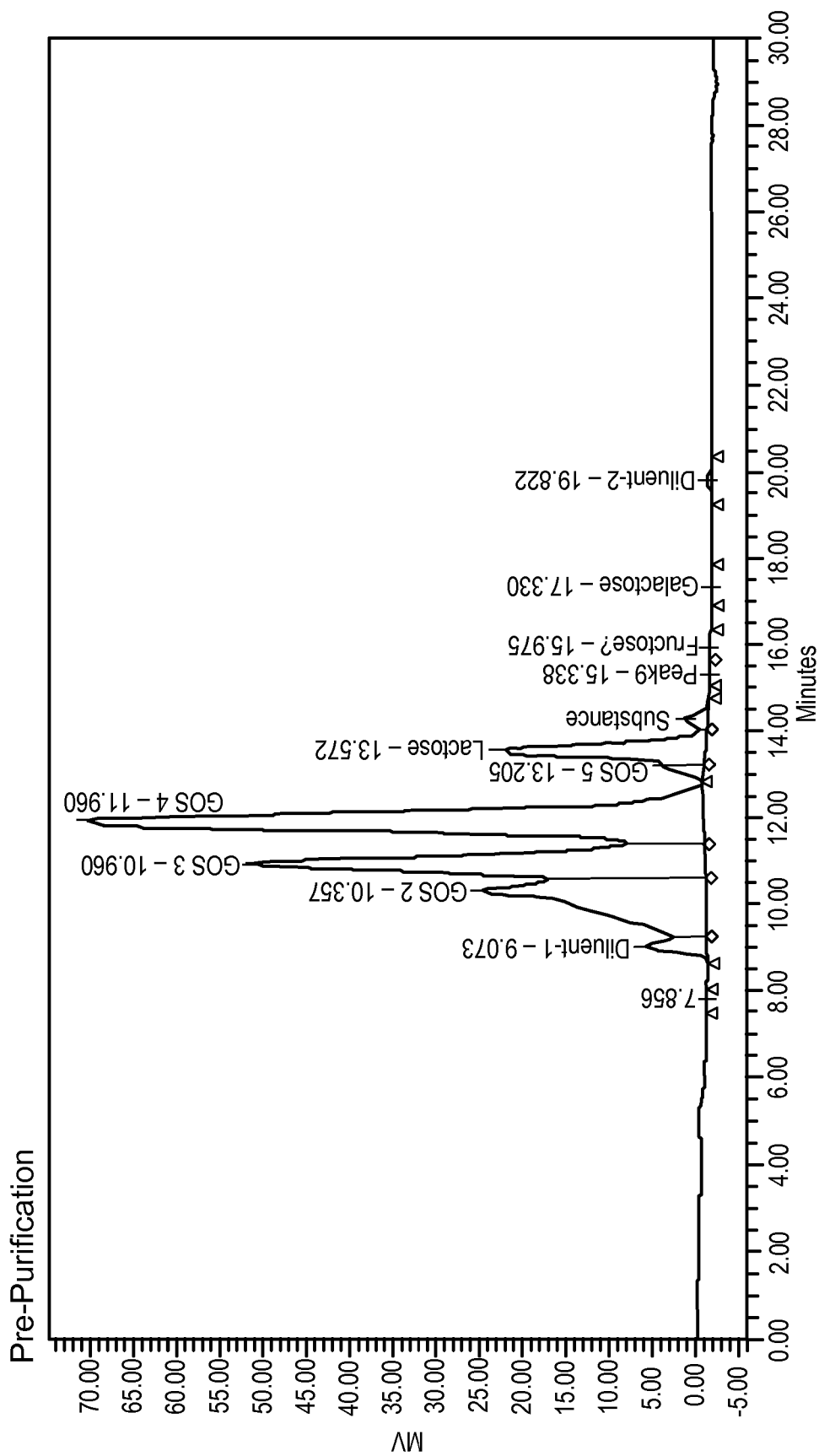
FIGS. 13A and 13B illustrate HPLC chromatograms of GOS compositions of the present invention before (13A) and after (13B) a purification step.
Figure 13B:
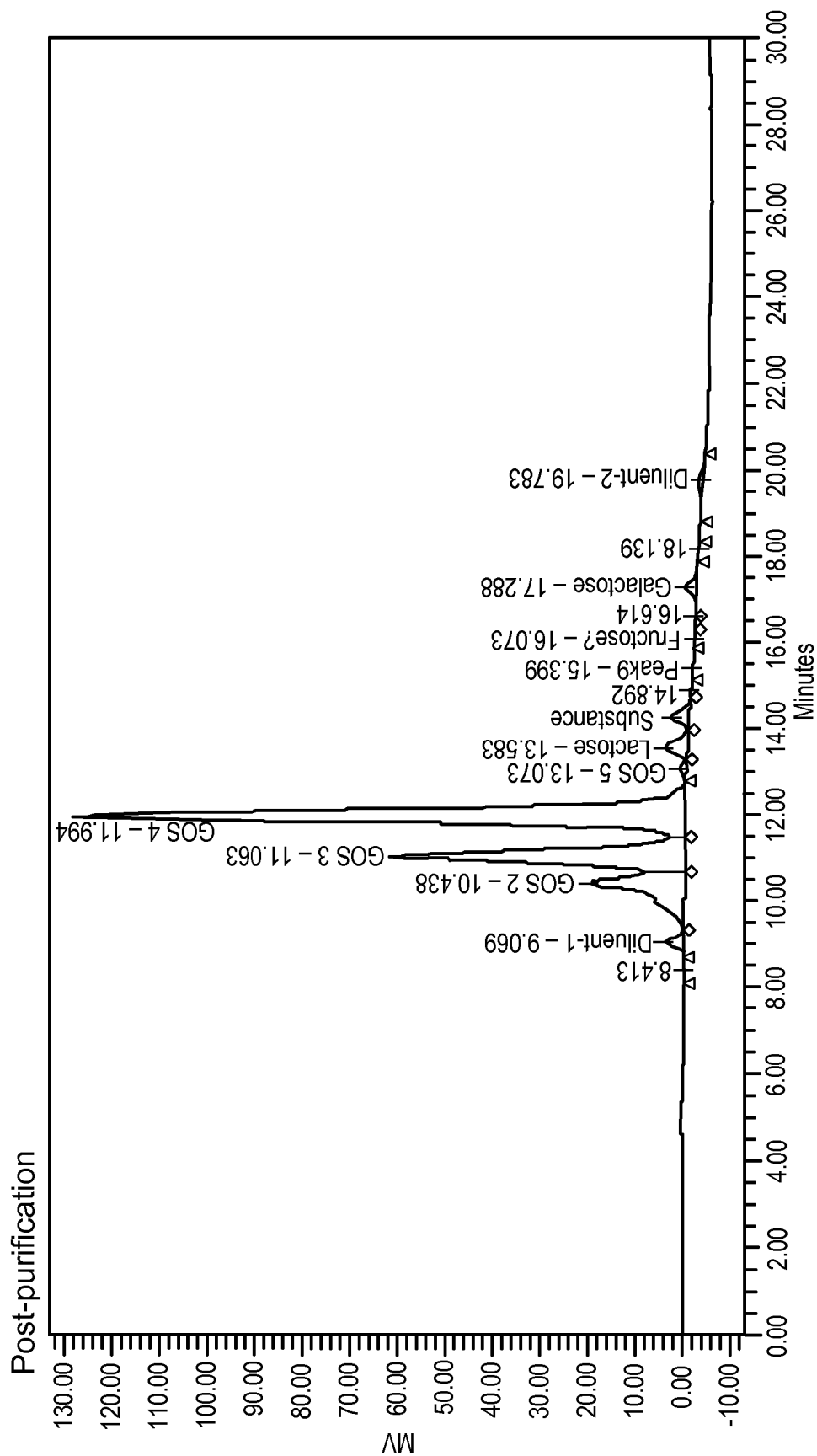

FIGS. 13A and B illustrate HPLC chromatograms of GOS compositions of the present invention before (13A) and after (13B) a purification procedure.

Example 6

Comparative Growth of *Bifidobacterium* Species on Galactooligosaccharides

The objective of the study was to determine the ability of various *Bifidobacterium* species and strains to grow on galactooligosaccharides.

The growth of *Lactobacillus* and *Bifidobacterium* strains was evaluated in scratch MRS (Table 16) supplemented with 2% of a carbohydrate solution. The carbohydrates used in the experiments were: Glucose—Fisher; Lactose—Fisher; GOS1—95% GOS purity from Inalco SPA—Provided by Ritter Pharmaceuticals; GOS2—90% GOS purity from GTC—provided by Ritter Pharmaceuticals.

Carbohydrate stock solutions were filter sterilized and then added to either a scratch MRS formulation (Table 16), or a semisynthetic medium (Table 17).

TABLE 16

Scratch MRS composition

| Reagents | Amount (g) per liter |
|---|---|
| Proteose peptone N3 | 10.0 |
| Beef extract | 10.0 |
| Yeast extract | 5.0 |
| Polysorbate 80 | 1.0 |
| Ammonium citrate | 2.0 |
| Sodium acetate | 5.0 |
| Magnesium sulfate | 0.1 |
| Manganese sulfate | 0.05 |
| Dipotassium phosphate | 2.0 |
| Carbohydrates | 20 |

TABLE 17

Semisynthetic medium for *Escherichia coli* (Barrangou, R., E. Altermann, R. Hutkins, R. Cano, and T. Klaenhammer. 2003. Functional and comparative genomic analyses of an operon involved in fructooligosaccharide utilization by *Lactobacillus acidophilus*. Proc. Nat. Acad. Sci. USA. 100: 8957-8962).

1% bactopeptone (w/v) (Difco),
0.5% yeast extract (w/v) (Difco),
0.2% dipotassium phosphate (w/v) (Fisher),
0.5% sodium acetate (w/v) (Fisher),
0.2% ammonium citrate (w/v) (Sigma),
0.02% magnesium sulfate (w/v) (Fisher),
0.005% manganese sulfate (w/v) (Fisher),
0.1% Tween 80 (v/v) (Sigma).
Carbohydrates were added at 2%.

Culture Methods:

*Lactobacillus* and *Bifidobacterium* cultures were propagated in MRS broth overnight, and then transferred once through the test medium. For growth experiments, cultures were inoculated into the MRS scratch medium containing one of the 4 carbohydrates to be examined. Growth was monitored either: automatically, using a FLUOStar OPTIMA microtiter plate reader to monitor the change in absorbance (A600) as a function of the time. The strains were incubated at 37 C aerobically for these experiments; or  manually, using a standard spectrophotometer to monitor the change in OD600 nm over time, in 5 ml liquid culture tubes. These cultures were incubated anaerobically at 37° C. in a COY anaerobic chamber, flushed with anaerobic gas.

Species Identification:

All bifidobacterial cultures used in these experiments were confirmed by taxonomic identification using 16S rRNA sequencing, via standard methods (Kullen, M. J., R. B. Sanozky Dawes, D. C. Crowell and T. R. Klaenhammer (2000) Use of DNA sequence of variable regions of the 16SrRNA gene for rapid and accurate identification of bacteria in the *Lactobacillus acidophilus* complex. *J. Appl. Microbiol.* 89:511-518.

Results:

FIGS. 14-19 illustrate the growth of *Lactobacillus acidophilus* NCFM and various strains of *Bifidobacterium* and *Escherichia coli* over time. Key conclusions from these data are detailed below.

Figure 14:
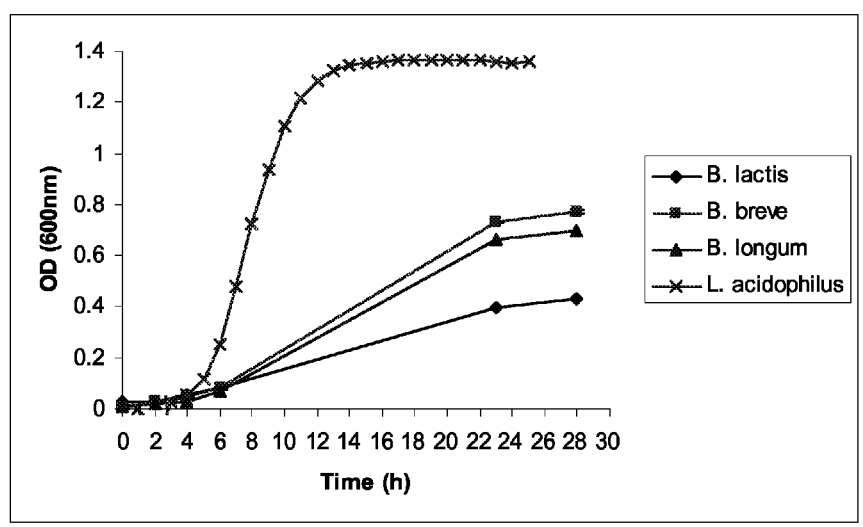
FIG. 14 illustrates comparative growth of *L. acidophilus, Bifidobacterium lactis, Bifidobacterium. breve*, and *Bifidobacterium longum* on GOS1 (95%).

First, *Lactobacillus acidophilus* NCFM grows equally well on GOS1 (95%) as on glucose, indicating that the microbe efficiently metabolizes GOS1 (95%) (FIG. 14).

Figure 15:
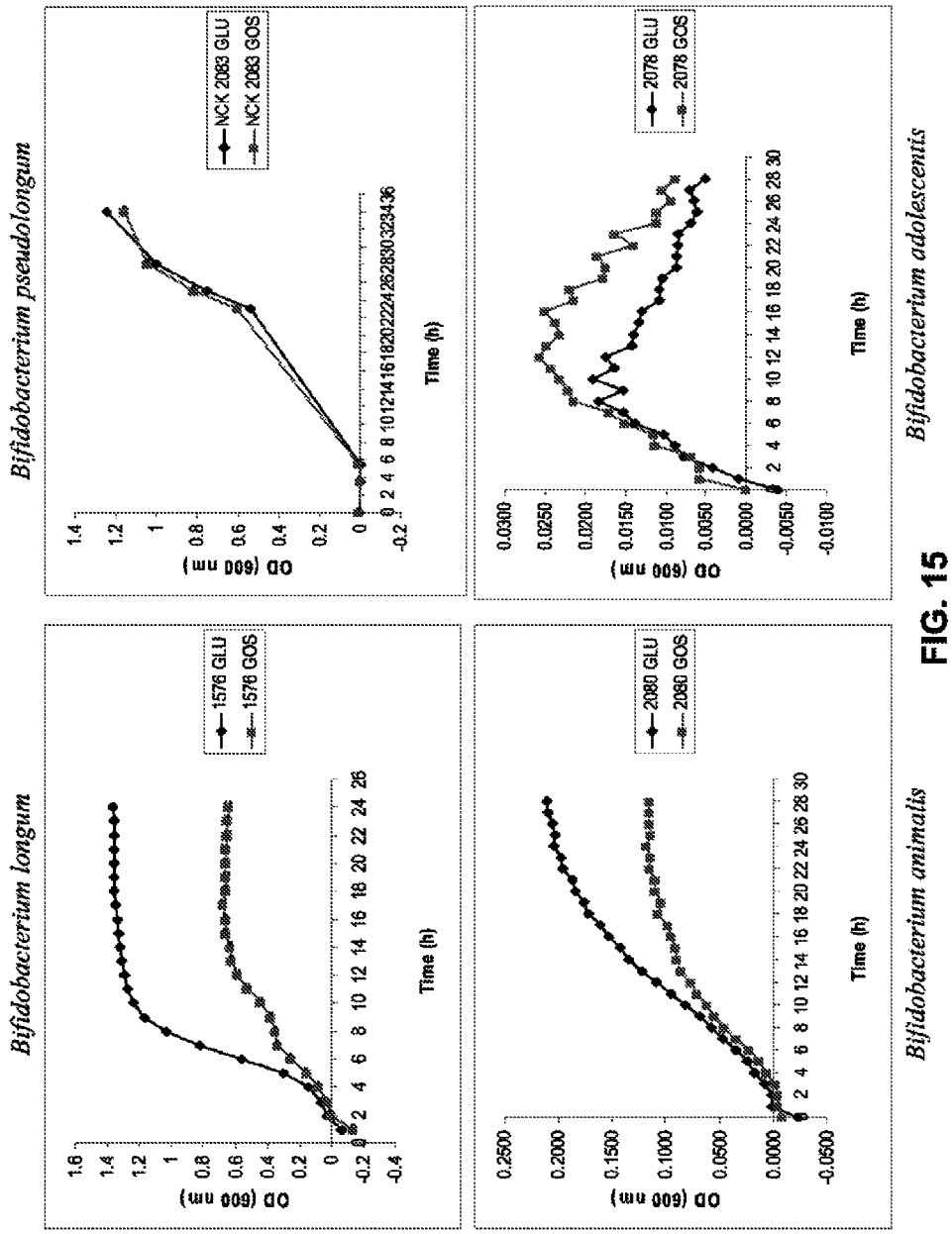
FIG. 15 illustrates comparative growth of *B. longum, Bifidobacterium pseudolongum, Bifidobacterium animalis*, and *Bifidobacterium adolescentis* on glucose and GOS1 (95%).
Figure 16:
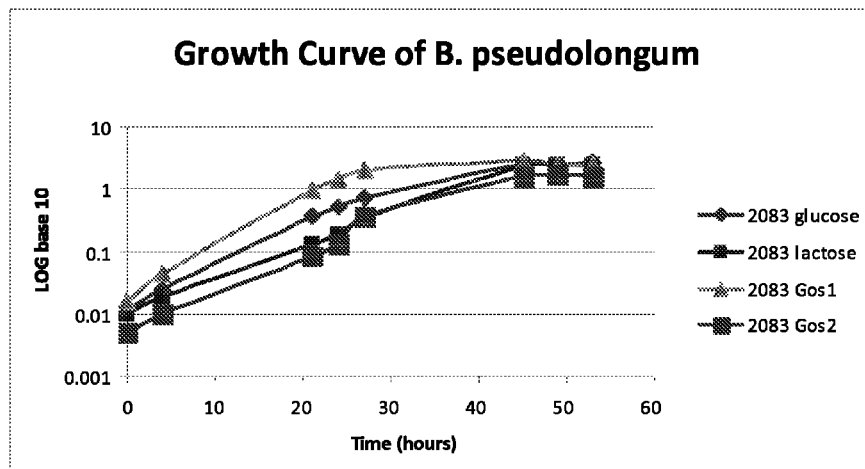
FIG. 16 illustrates comparative growth of *B. pseudolongum* NCK20383 on glucose, lactose, GOS1 (95%), and GOS2 (90%).

Second, six different species of *Bifidobacterium* were examined for their ability to grow on GOS1 (95%) (FIGS. 15 & 16). The results showed that most strains grew on GOS1 (95%), but at rates that were slower than when growing on glucose. The exceptions were *B. pseudolongum* which grew equally well on GOS1 (95%) and glucose (FIG. 15), and *B. adolescentis*, which grew better on GOS1 (95%) than on glucose. The species of *B. adolescentis* and *B. longum* predominate in the feces of adult humans. (Hoover, D G. 2000. *Bifidobacterium*. Pp 210-217. In The Encyclopedia of Food Microbiology. Carl Batt and P. D. Patel (Eds). Academic Press, San Diego.

Figure 17:
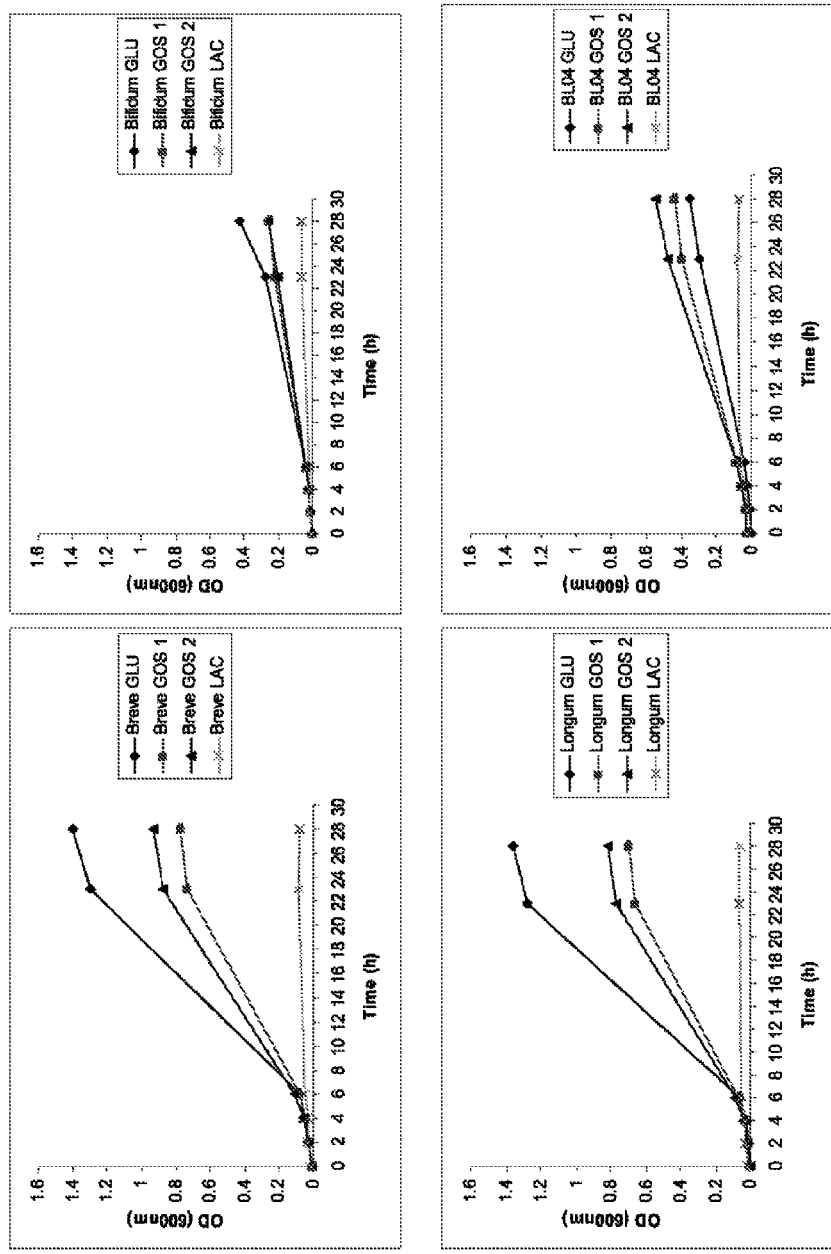
FIG. 17 illustrates comparative growth of four bifidobacterial strains on glucose, GOS1 (95%), GOS2 (90%), and lactose.
Figure 18:
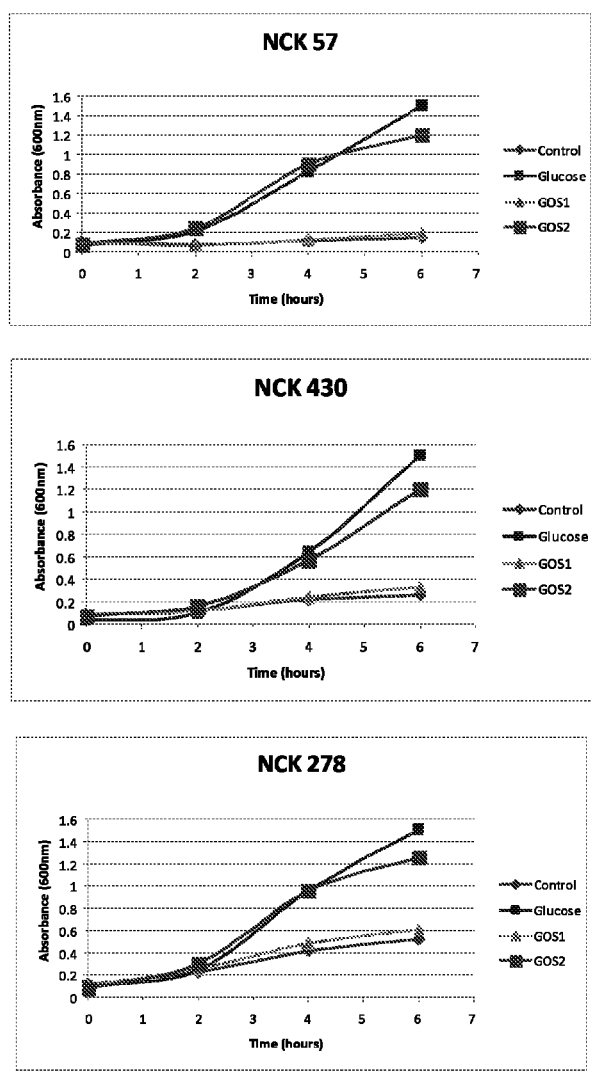
FIG. 18 illustrates growth of 3 *Escherichia coli* strains in media with no added carbohydrate (control), or 2% added glucose, GOS1 (95% GOS), or GOS2 (90% GOS).

Third, five different species of *Bifidobacterium* were also examined for their comparative growth on four different carbohydrate sources; glucose, lactose, GOS1 (95%) and GOS2 (90%) (FIGS. 17 & 18). Notable in these results was that all four of the species grew reasonably well on GOS, but in each case slightly better on GOS2 (90%), than on GOS 1 (95%). This difference was attributed to the larger percentage of simple carbohydrates present in the GOS2 sample. These contaminating carbohydrates would be expected to be galactose, lactose and glucose, all of which could stimulate slightly more growth from the GOS2 substrate. The *B. bifidum* strain used in the experiments grew poorly on all carbohydrates. Surprisingly, none of the *Bifidobacterium* strains used in these experiments grew on lactose, except for *B. pseudolongum*. It is speculated that contaminating glucose carried over from the initial propagation cultures in standard MRS broth may have been sufficient to elicit catabolite repression of the lactose metabolic pathways during these experiments.

Figure 19:
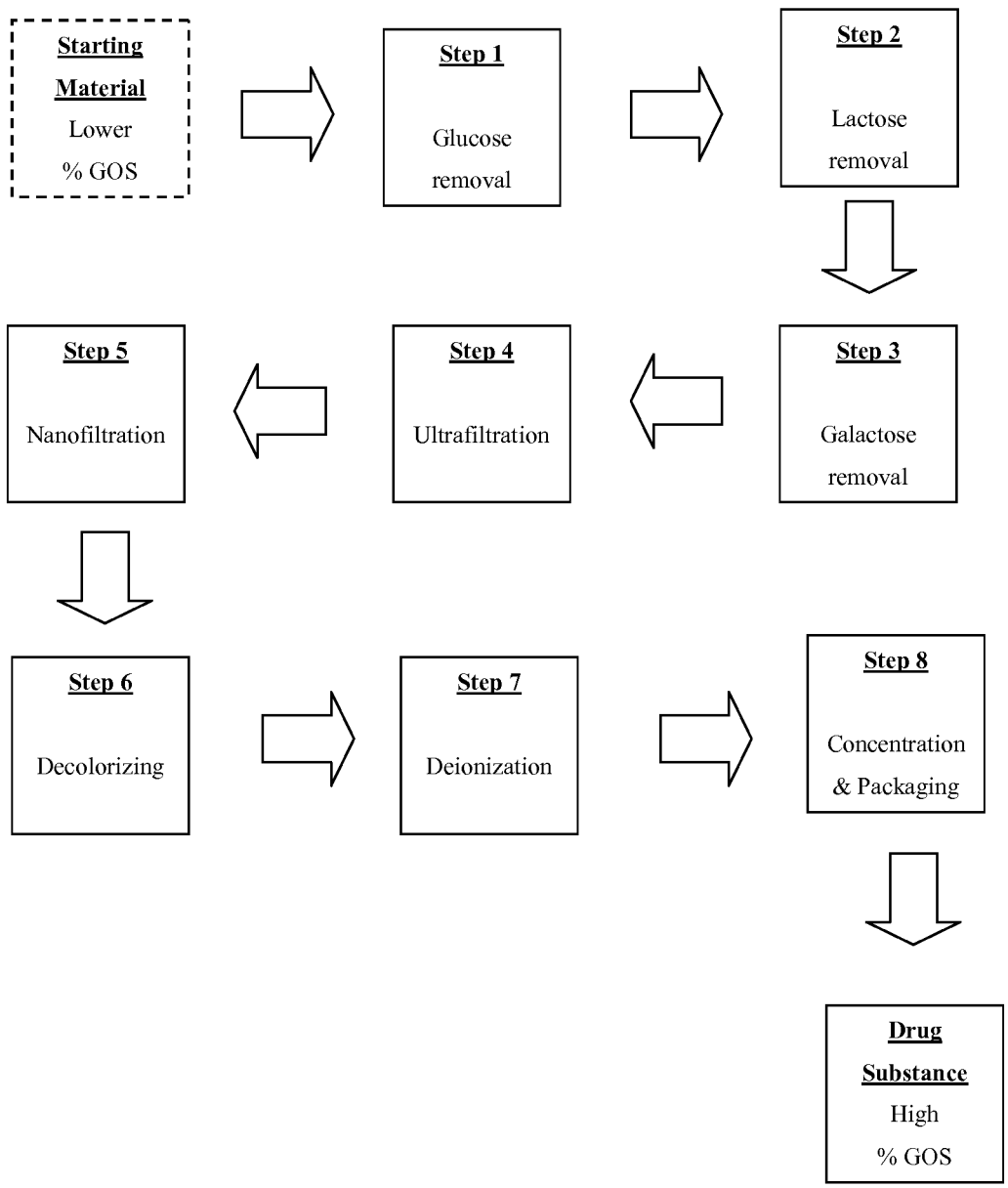
FIG. 19 illustrates a schematic of a high percentage GOS composition manufacturing process.

Fourth, three different strains of *Escherichia coli* were examined for their ability to grow on GOS1 (95%) and GOS2 (90%) (FIG. 19). The results show that the *E. coli* strains could not grow on GOS1 (95%), or in the absence of added carbohydrate (control). In contrast, all three strains grew well on GOS2 (90%) at rates that were comparable to growth on glucose. The results indicate that the 10% contaminating carbohydrates (e.g. glucose, galactose, lactose) in the GOS2 (90%) sample were sufficient to stimulate growth of *E. coli* strains to levels equal to free glucose. These results argue for the importance of the purity of the GOS compound in order to promote growth of the targeted beneficial microbes in the GI tract (e.g. lactobacilli and bifidobacteria), rather than stimulate *E. coli* and potentially other coliform bacteria in the GI tract.

Example 7

Study Treatments

Doses from 1.5 g to 12 g/day (6 g BID) for this study will be selected with the following rationale: 1. Bracket the expected therapeutic dose based on GOS human exposure-response relationship and pharmacokinetics, 2. Select a starting dose with low potential for undesirable GI adverse effects, 3. Allow for reasonable and meaningful dose escalation through the 15-day and 30-day regimens, 4. Select a dosing regimen for GOS that would result in a steady-state exposure of the gut to GOS facilitating optimal gut microflora population; and 5. Select a maximum dose that is not expected to be associated with significant safety or tolerance risks based on preclinical toxicology findings.

Doses of a GOS will be gradually increased over 30 days or at a more rapid rate over 15 days beginning with 1.5-3 g/day and increasing to 12 g/day (6 g BID) which is equivalent to the amount of lactose found in approximately 24 ounces of milk. This level of 24 ounces of milk was chosen to develop tolerance to a total of three servings of dairy per day, the recommended level in the US Dietary Guidelines to meet calcium and other nutrient needs.

Description

All subjects meeting entry criteria will be enrolled into a 15-day, single-blind placebo run-in phase. After successful completion of this run-in phase, subjects will be randomized to either a 15-day or 30-day treatment course of GOS or placebo (PBO).

30-Day Dosing Regimen:

Approximately 12 subjects will be randomized to the 30-day regimen with nine subjects receiving active drug and three subjects receiving placebo.

TABLE 18

30-day Dosing Regimen

| | |
|---|---|
| Days 1-5 | low dose (1.5 g) QD at dinner |
| Days 6-10 | medium dose (3 g) QD at dinner |
| Days 11-15 | high dose (6 g) QD at dinner |
| Days 16-20 | BID dosing with low dose (1.5 g) at breakfast and continuing high dose (6 g) at dinner |
| Days 1-25 | BID dosing with medium dose (3 g) at breakfast and continuing high dose (6 g) at dinner |
| Days 26-30 | BID dosing high dose (6 g) at both breakfast and at dinner |

15-day dosing regimen (BID dosing): Approximately 12 subjects will be randomized to the 15-day regimen with nine subjects receiving active drug for 15 days during the dosing phase and three subjects receiving placebo.

TABLE 19

15-day Dosing Regimen

| | |
|---|---|
| Days 1-15 | placebo dosing with dinner |
| Days 16-20 | low dose (1.5 g) BID with breakfast and dinner |
| Days 21-25 | medium dose (3 g) BID with breakfast and dinner |
| Days 26-30 | high dose (6 g) BID with breakfast and dinner |

Double-blind treatment compliance measures are to be taken at Visits 4, 5, and 6 to ensure that subjects were compliant with double-blind treatment.

Subjects are directed to bring any used and unused portions of product to each visit after the single-blind run-in phase and after randomization. Typically, the number of bottles issued minus the number of bottles returned will be used to calculate the number of bottles taken (unless the subject reports losing bottles and this loss is well-documented).

Example 8

GOS 95 Administration

GOS 95 is administered in two dosing regimens of different durations and will facilitate improved lactose metabolism via the adaptation of intestinal bacterial metabolism in subjects with symptoms of lactose intolerance.

The Hydrogen Breath Test (HBT) is utilized to determine if GOS 95 facilitates lactose metabolism, thereby resulting in less hydrogen production following lactose challenge as compared to baseline levels. The HBT test involves administering 25 mg of lactose and determining the amount of hydrogen in the breath at periodic intervals, usually for four to eight hours (Bhatnagar and Aggarwal 2007). Fecal bacteria levels is also assessed. The mechanism of action of GOS 95 is determined by fecal bacterial DNA samples to assess the bacterial adaptation. Symptom relief by regimen is captured through a validated symptom questionnaire using a Likert scale to monitor daily symptoms throughout the study.

Subjects ingest a daily (corn syrup) liquid mixed with water. During this phase, all lactose-containing food products will be eliminated in order to ensure the colon is maximally "unadapted" to lactose. Subjects completing the single-blind, placebo run-in phase will be randomized to either a 15-day or a 30-day treatment phase in a 1:1 ratio. One set of subjects will receive placebo for 30 days; another set of subjects will receive placebo for 15 days and GOS 95 for 15 days; another group will receive GOS 95 for 30 days. Within each treatment group, subjects will be randomized in a 3:1 ratio of active treatment to placebo. Subjects will begin this phase of the study with their first 25 mg lactose challenge and HBT with symptom scoring. The subjects will then commence double-blind treatment. There will be daily symptom questionnaires for the subjects to complete each evening. Subjects will return for clinic visits at Days 8, 15, and 30. On Day 30, subjects will have a second 25 mg lactose challenge and HBT with symptom scoring.

After a 15-day single-blind placebo run-in phase, the doses of GOS are gradually increased over 30 days or at a more rapid rate over 15 days beginning with 1.5 g-3 g/day and increasing to 12 g/day (6 g BID). Doses will be in liquid form and will be mixed with water and taken as directed by the dosing scheme.

Example 9

Specific Study Visit Procedures

Screening Dairy Intolerance Questions

The subjects will be asked questions relating to their symptoms of lactose-intolerance. In general, the questions will be "Have you ever been diagnosed as lactose intolerant?" and "Do you avoid milk or milk products because of the symptoms?" and "Do you think you are lactose intolerant?" Answering "yes" to any of these questions satisfies one of the entry inclusion criteria.

Dietary Considerations

Subjects will also be counseled on dietary considerations throughout the trial. Specifically, subjects will be asked to refrain from ingesting lactose-containing beverages/foods during the single-blind run-in phase as well as the double-blind treatment phase of the study. After completion of Visit 5, subjects will be asked to incorporate dairy products into their diets from Day 30 to Day 60 as tolerated. Subjects will be asked to maintain a daily diary to capture the type and amount of lactose-containing foods ingested during the 30-day follow-up phase as well as the symptoms they experience.

Daily Symptom Diary

During the placebo run-in, double-blind treatment phase, and 30-day follow-up phase, subjects will be asked to rate their symptoms on a daily basis each evening before bedtime.

Hydrogen Breath Test (HBT)/Lactose Challenge Procedure and Considerations

An 8-hour HBT will be done at three time-points throughout the study: Visit 3 (baseline), Visit 6 (end of treatment phase), and Visit 7 (follow-up phase). A calibrated QuinTron SC machine will be used. On the evening before the hydrogen breath test, subjects will be instructed to ingest their usual amounts of meat and vegetables from dinnertime until midnight and to ingest smaller amounts of sugar and starch (e.g., bread, pasta, cake). Subjects will be instructed to fast (only water allowed) for at least 8 hours prior to their HBT test. Subjects will be asked not to use morning mouthwash or toothpaste and to refrain from strenuous exercise on the morning of these clinic visits.

At the start of the HBT, the patient blows into an apparatus and the breath concentration of hydrogen and methane is measured. The subject will then ingest a 25 mg load of lactose. Additional breath samples are collected and analyzed for hydrogen at various time-points: 30 minutes, 1, 2, 3, 4, 5, 6, 7, and 8 hours post-lactose load. Data will be recorded on the Case Report Forms (CRFs). The subjects will be asked to remain in the clinic during this time and shall have immediate access to restroom facilities throughout the HBT. Subjects will not be able to eat, smoke, or engage in strenuous exercise during the HBT. Sites should provide water to the subjects throughout the test and should provide a meal upon completion of the test.

Lactose Symptom Scoring

During the HBT, four symptoms of lactose intolerance [abdominal pain, bloating, flatulence/gas, diarrhea/loose stools] will be assessed at multiple time-points as 0 (no symptoms), 1 (slight symptoms), 2 (mild symptoms), 3 (moderate symptoms), 4 (moderately severe symptoms), or 5 (severe symptoms). The maximum score is 180 [Calculation: 4 (symptoms)×5 (maximum score)×9 time-points].

This score will be assessed during each of the four HBT evaluations: screening, Visit 3/baseline, Visit 6/Day 30 and Visit 7/Day 60 (30-day follow-up). No distinction is being made between the importance of the symptoms, and there will not be any weighting of the scores based on the specific symptom. In addition to the total score, each of the individual symptoms will be analyzed separately. As the expected symptoms of lactose intolerance are being induced by the HBT, they will not be recorded as adverse events.

Fecal Bacterial Assessment

Fecal samples will be collected at baseline (Visit 3), end of treatment (Visit 6) and follow-up (Visit 7). Subjects will be provided with the appropriate stool collection materials. The collection, handling process and sample analysis will be described further in the study manual.

Example 10

Study Treatments

Doses from 1.5 g to 12 g/day (6 g BID) for this study will be selected with the following rationale: 1. Bracket the expected therapeutic dose based on GOS human exposure-response relationship and pharmacokinetics, 2. Select a starting dose with low potential for undesirable GI adverse effects, 3. Allow for reasonable and meaningful dose escalation through the 15-day and 30-day regimens, 4. Select a dosing regimen for GOS 95 that would result in a steady-state exposure of the gut to GOS facilitating optimal gut microflora population; and 5. Select a maximum dose that is not expected to be associated with significant safety or tolerance risks based on preclinical toxicology findings.

Doses of a GOS 95 will be gradually increased over 30 days or at a more rapid rate over 15 days beginning with 1.5-3 g/day and increasing to 12 g/day (6 g BID) which is equivalent to the amount of lactose found in approximately 24 ounces of milk. This level of 24 ounces of milk was chosen to develop tolerance to a total of three servings of dairy per day, the recommended level in the US Dietary Guidelines to meet calcium and other nutrient needs.

Description

All subjects meeting entry criteria will be enrolled into a 15-day, single-blind placebo run-in phase. After successful completion of this run-in phase, subjects will be randomized to either a 15-day or 30-day treatment course of GOS 95 or placebo (PBO).

30-Day Dosing Regimen:

Approximately 12 subjects will be randomized to the 30-day regimen with nine subjects receiving active drug and three subjects receiving placebo.

TABLE 20

| 30-day Dosing Regimen | |
|---|---|
| Days 1-5 | low dose (1.5 g) QD at dinner |
| Days 6-10 | medium dose (3 g) QD at dinner |
| Days 11-15 | high dose (6 g) QD at dinner |
| Days 16-20 | BID dosing with low dose (1.5 g) at breakfast and continuing high dose (6 g) at dinner |
| Days 21-25 | BID dosing with medium dose (3 g) at breakfast and continuing high dose (6 g) at dinner |
| Days 26-30 | BID dosing high dose (6 g) at both breakfast and at dinner |

15-day dosing regimen (BID dosing): Approximately 12 subjects will be randomized to the 15-day regimen with nine subjects receiving active drug for 15 days during the dosing phase and three subjects receiving placebo.

TABLE 21

| 15-day Dosing Regimen | |
|---|---|
| Days 1-15 | placebo dosing with dinner |
| Days 16-20 | low dose (1.5 g) BID with breakfast and dinner |
| Days 21-25 | medium dose (3 g) BID with breakfast and dinner |
| Days 26-30 | high dose (6 g) BID with breakfast and dinner |

Administration

GOS 95 will be provided to subjects as a liquid in high-density polyethylene (HDPE) bottles. Each HDPE bottle will contain one dose of Investigational Product. Subjects will add water to the bottle to dilute GOS 95 prior to ingestion. Investigational Product will be dosed with a meal. Detailed daily instructions on proper dosing will be provided to each subject participating in the study. Placebo comparator therapy will be corn syrup given in equal amounts and using the same dosing schedule and packaging as GOS 95.

Storage

GOS 95 should be kept at room temperature and out of reach of children. Bottles should be protected from extreme heat and sunlight.

Drug Accountability

Double-blind treatment compliance measures are to be taken at Visits 4, 5, and 6 to ensure that subjects were compliant with double-blind treatment.

Subjects are directed to bring any used and unused portions of product to each visit after the single-blind run-in phase and after randomization. Typically, the number of bottles issued minus the number of bottles returned will be used to calculate the number of bottles taken (unless the subject reports losing bottles and this loss is well-documented).

Example 11

Clinical and Safety Assessments

Clinical Assessments
Primary Efficacy Endpoint
Change from baseline to Day 30 in 8-hour HBT total hydrogen production
Secondary Endpoints of Efficacy, Safety, and Tolerability
Change from baseline to Day 30 in HBT peak hydrogen production.
Change from baseline to Day 30 in HBT symptom assessment total score
Change from baseline to Day 60 in HBT symptom assessment total score
Vital signs
Clinical laboratory results
Exploratory Measures
Change from baseline to Day 30 in fecal bacteria levels.
Change from baseline to Day 30 and to Day 60 in HBT symptom assessment individual symptom score.
Total score and individual symptom score on daily symptom questionnaire over time.
Change from baseline to Day 30 in serial blood glucose AUC.
Correlation of individual symptom assessment scores and HBT.
Physical Examinations and Vital Sign Measurements
Subjects are expected to be in overall good health. A brief physical exam is required at Visit 2 to ensure the subject is in good health.
Vital signs (blood pressure, heart rate) will be obtained at each visit.
12-Lead Electrocardiograms
A twelve-lead ECG will be obtained at Visit 1 to evaluate entry criteria. Sites will use their own calibrated ECG equipment and provide a print-out source documentation for each ECG obtained. The ECG will be reviewed by the Investigator prior to enrolling the subject.
Laboratory Assessments
The Investigator must assess the clinical significance of all abnormal laboratory values. All clinically significant abnormalities must be characterized by the Investigator as treatment-related, not treatment-related, possibly treatment related, or uncertain. All abnormal lab values (outside lab normal ranges) judged to be clinically-significant and possibly treatment-related must be repeated.
Blood samples will be collected at Visits 1, 3, 4, 6 and 7 for the chemistry test panel. The chemistry panel includes: sodium, potassium, chloride, bicarbonate, blood urea nitrogen, creatinine, fasting glucose, AST, ALT, Alkaline phosphatase, bilirubin (total and direct), and CK.
Blood samples will be collected at Visits 1, 3, 4, 6 and 7 for hematology test panel which includes: hemoglobin, hematocrit, white blood cell count (WBC), platelet count, red blood cell count (RBC), and WBC differential.
Urine samples will be collected at Visits 1 and 6. Dipstick analyses will be done at the site and will include specific gravity, pH, protein, glucose, blood, nitrate, and leukocyte esterase. A microscopic analysis (RBCs, WBCs, epithelial cells, bacteria, yeast, casts, crystals) is required at a local laboratory if the dipstick results are positive for blood and/or protein.

A serum pregnancy test (B-HCG) will performed on all females with an intact uterus.

Example 12

Choice of Dose for Efficacy Studies

The dose of GOS 95 is increased over 15 days or at a slower rate over 30 days beginning with 1.5-3 g/day and increasing to 12 g/day (6 g BID) to reach the level of galacto-oligosaccharides per day in approximately 24 ounces of milk. This level of 24 ounces of milk was chosen to develop tolerance to a total of three servings of dairy per day, the recommended level in the US Dietary Guidelines to meet calcium and other nutrient needs. This approach has previously been used successfully with RP-L27 (using lactose as the guiding modifier instead of GOS) in many thousands of patients (Landon et al. 2006).

Doses from 1.5 g to 12 g/day (6 g BID) for the Phase 2a FIH study were selected with the following rationale: 1) bracket the expected therapeutic dose based on GOS human exposure-response relationship and pharmacokinetics; 2) select a starting dose with low potential for undesirable GI adverse effects; 3) allow for reasonable and meaningful dose escalation through the 15- and 30-day regimens; 4) select a dosing regimen for GOS 95 that would result in a steady-state exposure of the gut to GOS facilitating optimal gut microflora re-population; and 5) select a maximum dose that is not expected to be associated with significant safety or tolerance risks based on preclinical toxicology findings.

Since GOS 95 is being explored for the treatment of the symptoms of lactose intolerance in adults through the repopulation of normal and healthy gastrointestinal flora, it is expected that this beneficial effect on the bacterial flora will require acute administration (≤30 days). The dose range (5.5-15 g/day) administered for up to 21 days in adults borders the highest dose proposed for GOS 95 (12 g/day for up to 7 days).

Example 13

People with lactose intolerance have a decrease in the activity of lactase (β-galactosidase), the enzyme responsible for breaking down lactose, in the brush border membrane of the small intestine. This decrease results in a demonstrated maldigestion of the sugar lactose, either with or without symptoms after ingesting dairy products such as milk, ice cream, cheese and pizza. Lactose maldigestion is often defined more specifically as those people with an "increase in blood glucose concentration of <1.12 mmol/L or breath hydrogen of >20 ppm after ingestion of 1 g/kg body weight or 50 g lactose" (de Vrese et al, 2001). The condition is primarily hereditary; however, it may also be induced by infections, chemotherapy, reactions to penicillin, and avoidance of dairy products for a prolonged period of time.

Lactose intolerance is a common gastrointestinal disorder that develops in lactose maldigesters when consuming too much lactose or when lactose is added to a previously low-lactose diet. Its development is dependent on the dose of lactose consumed, gastrointestinal transit, type of dairy food consumed, and the ability of the colon to metabolize lactose. Lactose intolerance is characterized by one or more of the cardinal symptoms following the ingestion of lactose-containing foods including abdominal pain/cramps, bloating, flatulence [gas] and diarrhea. These symptoms arise from undigested lactose in the large intestine, where it is a fermentable substrate for the bacterial flora.

The relatively high incidence of symptoms resulting from intolerance to milk and dairy products in various populations has been well documented (Paige and Bayless 1981; Delmont 1983; Jackson and Savaiano 2001; Buchowski et al. 2002). The FDA's Consumer Health Information on the FDA's own website (2008) states that NIH "estimates that 30 to 50 million Americans are lactose intolerant." The NIH's website contains a substantial amount of information on this condition (NIH website).

Currently, there is no universally accepted therapy for the treatment of lactose intolerance. As such, most lactose intolerant individuals avoid the ingestion of milk and dairy products, while others substitute non-lactose containing products in their diet. A wide variety of nutritional supplements are currently sold such as the once daily probiotic Digestive Advantage™(Ganeden); however, they offer no proven benefit. An oral agent, Lactaid™, is perhaps the most widely accepted product and has been marketed for over 30 years to people with mild to moderate lactose intolerance. However, Lactaid™ must be ingested prior to eating dairy, and the outcome is dependent on the dose of Lactaid™ and the amount of lactose consumed, requiring as many as 5 or more pills per day. Finally, RP-L27 (Lactagen™, Ritter Pharmaceuticals, LLC), a marketed compound consisting of lactose and *lactobacillus acidophilus* and fructo-oligosaccharide (FOS), is given as a powder in increasing doses multiple times a day over 34 days.

Based on the health implications from insufficient calcium intake over a lifetime, including increased risk of osteoporosis and hypertension (McCarron and Heaney 2004) and possibly cancer (Barger-Lux and Heaney 1994; Consensus Conference: Optimal Calcium Intakes, NIH 1994), there is need in the medical community for a tolerable and convenient treatment that allows for all levels of milk and dairy product consumption in people suffering from mild to severe lactose intolerance. A treatment that provides a simplified dosing regimen as well as the potential for extended relief from symptoms following a limited therapy regimen (ie, <30 days) would result in greater compliance and address an unmet medical need.

Example 14

Study Drug: Directions for Use

The doses of GOS 95 (given twice daily in syrup form) are gradually increased over 15 days or at a slower rate over 30 days beginning with 1.5-3 g/day and increasing to 12 g/day (6 g BID).

All subjects meeting entry criteria will be enrolled into a 15-day, single-blind, placebo run-in phase. After successful completion of this run-in phase, subjects will be randomized to either a 15-day or 30-day treatment course of GOS 95 or placebo (PBO) in a 3:1 ratio (active:PBO).

GOS 95 will be provided orally to patients as a syrup in a bottle that will be diluted with water or juice prior to ingestion with a meal. Detailed daily instructions on proper dosing will be provided to each subject participating in the study. Placebo comparator therapy will be dextrose given in equal amounts and using the same dosing schedule and packaging as GOS 95.

30-Day Dosing Regimen:

Approximately 12 subjects will be randomized to the 30-day regimen with 9 subjects receiving active drug and 3 subjects receiving placebo.

Days 1-5: placebo dosing with breakfast; low dose (1.5 grams) QD at dinner

Days 6-10: placebo dosing with breakfast; medium dose (3 grams) QD at dinner

Days 11-15: placebo dosing with breakfast; high dose (6 grams) QD at dinner

Days 16-20: BID dosing with low dose (1.5 grams) at breakfast and continuing high dose (6 grams) at dinner Days 21-25: BID dosing with medium dose (3 grams) at breakfast and continuing high dose (6 grams) at dinner Days 26-30: BID dosing high dose (6 grams) at both breakfast and at dinner 15-Day Dosing Regimen (BID Dosing):

Approximately 12 subjects will be randomized to the 15-day regimen with 9 subjects receiving active drug and 3 subjects receiving placebo.

Days 1-15: placebo dosing BID with breakfast and dinner

Days 16-20: low dose (1.5 grams) BID with breakfast and dinner

Days 21-25: medium dose (3 grams) BID with breakfast and dinner

Days 26-30: high dose (6 grams) BID with breakfast and dinner

Example 15

Phase 2 Proof-of-Concept Study Design

This study is designed to assess the ability of RP-G28, a high purity GOS composition also known as GOS 95, to rapidly and effectively modify intestinal metabolism to improve lactose digestion and tolerance. The study design includes a Screening phase (with an optional 25 gm lactose challenge for symptom assessment), a 15-day single-blind, Placebo Run-in phase, a 35-day double-blind, placebo-controlled Treatment phase, and a 30-day post-treatment Follow-up period. A 25 gm lactose challenge with 6-hour hydrogen breath test (HBT) will be conducted after the single-blind placebo Run-in (baseline), after 35 days of treatment (Day 36), and 30 days after treatment in follow-up (Day 66). Lactose will be restricted during the single-blind Placebo Run-in and during the double-blind 35-day Treatment period. Subjects will be instructed regarding lactose exposure following the 35-day Treatment period. Symptoms will be assessed during each lactose challenge and during follow-up for 30 days after treatment. Approximately 100 male and female subjects with symptoms of lactose intolerance may be enrolled at up to five investigative sites, to complete approximately 66 subjects through Visit 6 (end of double-blind Treatment).

Figure 25:
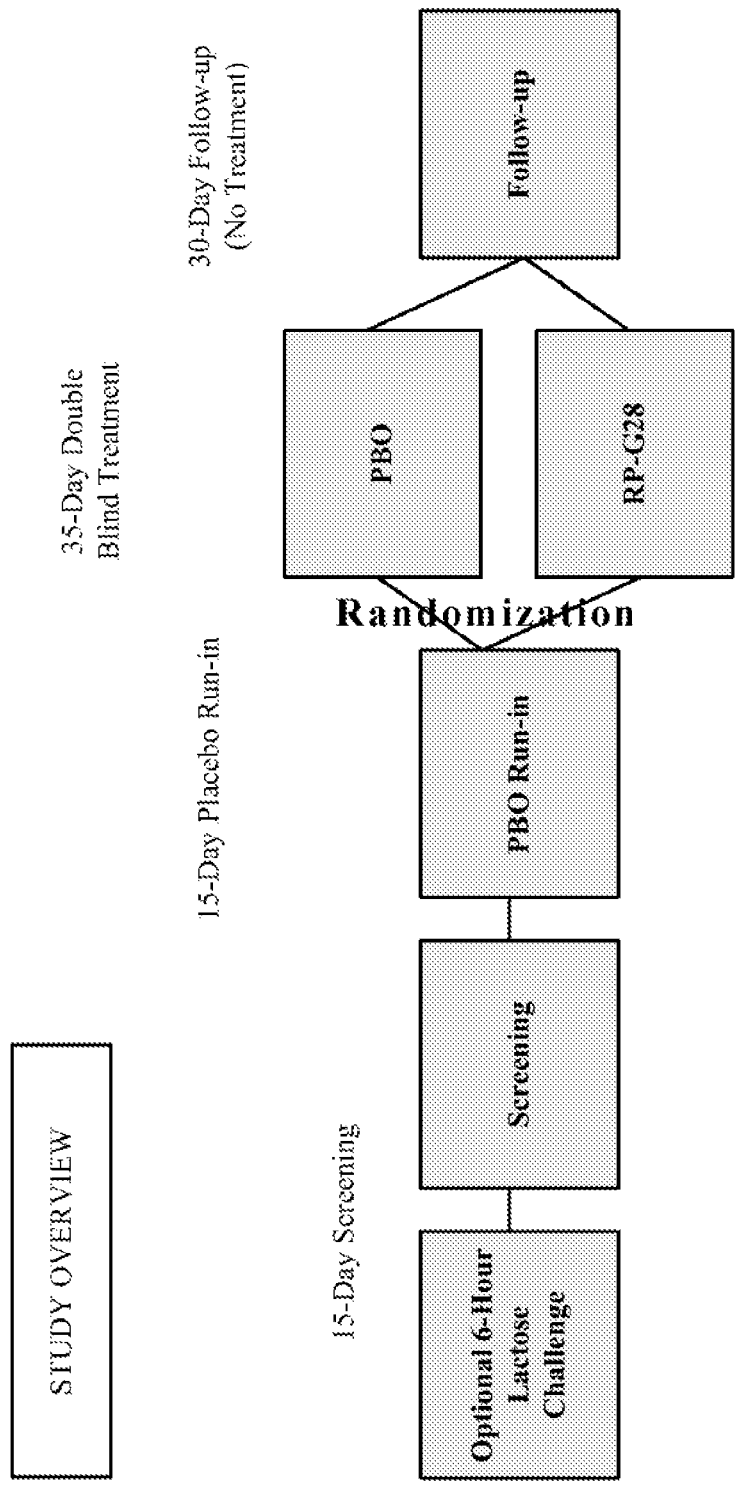
FIG. 25 illustrates an overview of a Phase II proof-of-concept study.

This Phase 2 proof of concept study will include four distinct phases, outlined in FIG. 25: a 15 day Screening Phase (Day −30 to Day −16), a 15 day placebo run-in (Day −15 to Day −1), a 35 day double blind treatment (Day 1 to Day 35, and a 30 day follow-up (Day 36 to Day 66).

Example 15A

Screening Phase

Subjects must meet all of the following inclusion criteria to be eligible for enrollment into the study:

1. Non-smoking males and females. Female subjects must be non-pregnant, and non-lactating. Female subjects and female sexual partners of male subjects, if of child-bearing potential, must use adequate birth control during study participation.
2. 18 to 64 years of age inclusive at Screening 3. Current or recent history of intolerance to milk and other dairy products of at least one month duration (by self-reported symptoms)
4. Baseline [Visit 3] lactose challenge symptom score (4 symptom categories with severity measured from 0 to 5) as defined by one of the following:
   a. At least one score of 4 (moderately severe) or 5 (severe) on a single symptom during the 6-hour HBT test;
   b. A score of 3 (moderate) or greater for a single symptom on at least two (2) time-points during the 6-hour HBT test; or
   c. At least one 3 (moderate) score or greater on each of two symptoms during the 6-hour HBT test.
5. Baseline [Visit 3] lactose challenge HBT of at least 20 parts per million greater than baseline [25-gm lactose load] on at least 2 times during the 6-hour HBT
6. Subjects must agree to refrain from all other treatments and products used for lactose intolerance (e.g., Lactaid® Dietary Supplements) during the trial, including the follow-up period
7. Subjects must agree to refrain from dairy products during certain portions of the trial and be willing to ingest dairy products as required by the protocol
8. Subjects must be willing to return for all clinic visits and complete all study-related procedures, including fasting before and during the HBT test
9. Subjects must be verbally fluent and able to provide written informed consent in English Subjects presenting with any of the following will not be included in the study:
1. Disorders known to be associated with abnormal gastrointestinal motility such as: gastroparesis, amyloidosis, neuromuscular diseases (including Parkinson's disease), collagen vascular diseases, alcoholism, uremia, malnutrition, or untreated hypothyroidism
2. History of surgery that alters the normal function of the gastrointestinal tract including, but not limited to: gastrointestinal bypass surgery, bariatric surgery, gastric banding, vagotomy, fundoplication, pyloroplasty [Note: history of uncomplicated abdominal surgeries such as removal of an appendix more than 12 months prior to Screening will not be excluded]
3. Past or present: Organ transplant, chronic pancreatitis, pancreatic insufficiency, symptomatic biliary disease, Celiac disease, chronic constipation, diverticulosis, inflammatory bowel disease (IBD), ulcerative colitis (UC), Crohn's disease (CD), small intestine bacterial overgrowth syndrome (SIBO)
4. Past or present: Irritable Bowel Syndrome (IBS)
5. Active gastric or duodenal ulcers, or history of severe ulcers
6. Diabetes mellitus (type 1 and type 2)
7. Congestive Heart Failure (CHF)
8. History of Human Immunodeficiency Virus (HIV), Hepatitis B or Hepatitis C
9. BMI>35 kg/m²; candidates with a BMI between 35 and 40 kg/m² may be considered on a case by case basis and enrolled with approval of the Medical Monitor
10. Recent bowel preparation for endoscopic or radiologic investigation within 4 weeks of Screening (e.g., colonoscopy prep)
11. Use of concurrent therapy(ies) considered as possibly interfering with RP-G28 or other products (e.g., laxatives, stool softeners, Pepto-Bismol™, Lactaid® Dietary Supplements) used for symptoms of lactose intolerance within 7 days of Screening
12. Recent use of systemic antibiotics or recent high colonic enema, defined as use within 30 days prior to Screening; bowel patterns must have returned to normal following antibiotic use
13. Any concurrent disease or symptoms which may interfere with the assessment of the cardinal symptoms of lactose intolerance (i.e., abdominal pain [cramps], bloating, flatulence [gas], diarrhea [loose stools]
14. Resting 12-lead ECG showing QTcF >450 msec (males) or QTcF >470 msec (females), any tachyarrhythmia, pathologic Q waves, significant sinus bradycardia (<40 beats per minute (bpm) or any other clinically significant abnormality
15. Uncontrolled BP defined as the mean sitting systolic blood pressure (SBP≥160 mmHg or diastolic blood pressure (DBP) ≥95 mmHg at Visit 2
    a. Hypertensive medication(s) may be modified or added during the Screening phase in consideration of this criterion
    b. Repeat BP measurements during Screening are permissible if the subject is otherwise qualified
16. History of ethanol abuse in the past 12 months defined as three or more alcoholic beverages per day; history of drug abuse within 12 months prior to Screening
17. Cigarette smoking or other use of tobacco or nicotine containing products within 3 months of Screening
18. History or presence of malignancy within the past 5 years with the exception of a basal cell or squamous cell carcinoma successfully removed from a sun-exposed area of the body
19. Use of any investigational drug or participation in any investigational study within 30 days prior to Screening
20. Conjugated bilirubin greater than 1.2×upper limit of normal unless approved by the Medical Monitor; creatinine ≥2.0 mg/dL; AST (SGOT) or ALT (SGPT) >2×the upper limit of normal; alkaline phosphatase >1.5×the upper limit of normal; or hemoglobin <11 g/dL (<110 g/L)
21. Any condition, disease, disorder (including personality disorders), or clinically relevant lab abnormality which, in the opinion of the Investigator and/or the Medical Monitor, would jeopardize the subject's participation in this study, obscure the effects of treatment or lead to non-compliance/non-cooperation in the study
22. In the opinion of the Investigator and/or the Medical Monitor, any serious uncontrolled disorders including: pulmonary, cardiovascular, hematologic, renal, endocrine, neurological, immunosuppressive, urogenital or dermatologic diseases that would jeopardize the safety of the subject or impact the validity of the study results
23. Allergy to galacto-oligosaccharides or a component of the study drug or placebo
24. History of fructose intolerance or fructose maldigestion
25. Prior enrollment in this study At the screening visit (Visit 1) subjects will give informed consent and a detailed medical history will be taken. At this time, subjects will be evaluated according the entry criteria detailed supra. Additionally, subjects will be asked questions relating to their symptoms of lactose intolerance. In general, the questions will be "Have you ever been diagnosed as lactose intolerant?" and "Do you avoid milk or milk products because of the symptoms?" and "Do you think you are lactose intolerant?" If these symptoms have been present for more than one month, answering "yes" to any of these questions satisfies one of the entry inclusion criteria. Vital signs (blood pressure, heart rate), weight, and height will be measured for each subject and a 12-lead electrocardiogram will be taken to ensure subjects are in good overall health. Chemistry and hematology labs will be run, as well as a urinalysis (dipstick) at this visit. Additionally, pregnancy screenings will be performed, if appropriate.

Subjects may be provided the opportunity to take part in an optional pre-screening lactose challenge. After obtaining informed consent (separate document) for this optional study phase, subjects will undergo a fasting lactose challenge with 25-gm of lactose. Informed consent may be obtained under non-fasting conditions prior to scheduling the lactose challenge, which shall be done under fasting conditions.

Subjects participating in the optional challenge will be interviewed regarding symptoms observed over a 6-hour period after administration of the lactose challenge dose. The interviews will be performed by trained Mapi Values interviewers according to instructions and scripts found in FIGS. 26-29. After the subjects report symptoms, they will be asked to rate the severity of these symptoms using a questionnaire like the one in FIG. 30. These symptoms and the severity ratings will be collected and analyzed by trained staff as the basis for the development of a Patient-Reported Outcome (PRO) measure to assess symptoms of lactose intolerance.

Subjects reporting no symptoms or only symptoms of "slight" or "mild" severity during the lactose challenge will not be eligible for any further study participation.

Subjects reporting symptoms of "moderate" severity or greater during the lactose challenge and who wish to further participate may proceed with Screening procedures for the study. Although the "pre-screening" lactose challenge may precede or be combined with and overlap Screening procedures a separate informed consent will be obtained prior to Screening procedures.

Note: Subjects with a positive hydrogen breath test (H2 levels ≥20 ppm above baseline at two or more time-points) at Visit 3 will have their lactose challenge symptoms included in the development of the PRO measure. Subjects with negative HBT results (H2 levels <20 ppm above baseline) will not contribute symptom data for PRO instrument development.

Example 15B

Single Blind Placebo Run-In

All subjects who qualify at the Screening visit will be assigned to a 15-day single-blind, placebo Run-in phase. This phase begins on Day −15 with Visit 2. During this visit, subjects are given a physical exam, a urine drug screen, and recordings are made of vital signs, weight and height. At this time, subjects are counseled on dietary considerations throughout the trial. Specifically, subjects will be asked to refrain from ingesting lactose-containing beverages/foods during the Placebo Run-in following Visit 2 as well as during the Treatment phase of the study through completion of Visit 6. During the placebo run-in, and throughout the 35 day treatment regimen, subjects will be asked to keep a daily symptom diary. An example of the diary can be found in FIG. 31. The placebo run-in period ends with Visit 3, during which a hydrogen breath test (HBT)/lactose challenge is performed, a lactose symptom questionnaire is filled out and fecal samples are taken to determine bacterial levels.

Hydrogen Breath Test (HBT)/Lactose Challenge Procedure and Considerations

A 6-hour HBT will be done at three time-points during the study: Visit 3 (Baseline), Visit 6 (End of Study), and Visit 7 (Follow-up). Each HBT will be conducted using a calibrated device provided by the sponsor.

On the evening before the HBT, subjects will be instructed regarding dinner restrictions, particularly sugar, carbohydrate, and fiber. Subjects will be instructed to fast (only water allowed) for at least 8 hours prior to their HBT test. Subjects will be asked not to use mouthwash or toothpaste and to refrain from strenuous exercise on the evening before and the morning of these clinic visits.

At the start of the HBT, the patient blows into an apparatus and the breath concentration of hydrogen and methane is measured. The subject will then ingest a 25-gm load of lactose. Additional breath samples are collected and analyzed for hydrogen and methane at the following time-points: 30 minutes, 1, 2, 3, 4, 5, and 6 hours post-lactose load. Hydrogen and methane data will be recorded in the source document and on the case report forms (CRFs). The subjects will be asked to remain in the clinic during this time and shall have immediate access to restroom facilities throughout the HBT. Subjects will not be able to eat, smoke, sleep, or engage in strenuous exercise during the HBT. Sites should provide water to the subjects throughout the test and should provide a meal upon completion of the test.

Total hydrogen production is calculated as the sum of the hydrogen level in ppm above baseline at each hour for 6 hours following lactose challenge.

Lactose Symptom Scoring

During the HBT, four symptoms of lactose intolerance (abdominal pain [cramps], bloating, flatulence [gas], diarrhea [loose stools]) will be inquired before the lactose is administered and assessed hourly for 6 hours following the lactose challenge. Symptoms are rated as 0 (no symptoms), 1 (slight symptoms), 2 (mild symptoms), 3 (moderate symptoms), 4 (moderately severe symptoms), or 5 (severe symptoms). The total of the hourly scores after the lactose challenge will be used to assess treatment effect. The total score can range from 0 to 160.

This score will be assessed during each of the three HBT evaluations: Visit 3/Baseline, Visit 6/Day 36 and Visit 7/Day 66 (30-day Follow-up). As the expected symptoms of lactose intolerance are being induced by the lactose challenge, they will not be recorded as adverse events unless the event meets the criteria for an SAE.

During the HBT, the occurrence and severity of nausea [upset stomach] will be captured and rated using the same symptom score scale of 0 (no symptoms), 1 (slight symptoms), 2 (mild symptoms), 3 (moderate symptoms), 4 (moderately severe symptoms), or 5 (severe symptoms).

Fecal Bacterial Assessment

Fecal samples will be collected at Baseline (Visit 3), End of Study (Visit 6) and Follow-up (Visit 7). Subjects will be provided with the appropriate stool collection materials. Stool samples may be collected for analysis any time before or during the lactose challenge. The collection, handling process and sample analysis will be described further in the study manual.

Example 15C

Double Blind Study Treatments

Subjects who qualify after the baseline lactose challenge, HBT and symptom assessment will be randomized to 35 days of double-blind Treatment in a 2:1 ratio to RP-G28 or placebo. The doses of RP-G28 are gradually increased over 35 days beginning with 1.5 gm/day and increasing to 15 gm/day (7.5 gm twice daily), which is equivalent to the amount of lactose found in approximately 24 ounces of milk. This quantity of milk was chosen to develop tolerance to a total of three servings of dairy per day, the recommended level in the US, per the Sixth edition of Dietary Guidelines for Americans in January 2005 to meet calcium and other nutrient needs. Doses are in liquid form and will be mixed with water and taken as directed by the dosing scheme in Table 22. Doses from 1.5 gm/day to 15 gm/day (7.5 gm BID) for this Phase 2 study were selected with the following rationale:

1. Bracket the expected therapeutic dose based on GOS human exposure-response relationship and pharmacokinetics,
2. Select a starting dose with low potential for undesirable GI adverse effects from published GOS clinical data,
3. Allow for reasonable and meaningful dose escalation through the 35-day regimen,
4. Select a dosing regimen for RP-G28 that would result in a steady-state exposure of the gut to GOS facilitating optimal gut microflora population; and
5. Select a maximum dose that is not expected to be associated with significant safety or tolerance risks based on preclinical toxicology findings and the composite of published clinical data with GOS.

TABLE 22

35-Day Dosing Regimen

| Treatment Days | Treatment Dose (RP-G28 or Placebo) |
|---|---|
| Days 1-5 | 1.5 g at dinner |
| Days 6-10 | 3 g at dinner |
| Days 11-15 | 6 g at dinner |
| Days 16-20 | 1.5 g at breakfast |
|  | 6 g at dinner |
| Days 21-25 | 3 g at breakfast |
|  | 6 g at dinner |
| Days 26-30 | 6 g at breakfast |
|  | 6 g at dinner |
| Days 31-35 | 7.5 g at breakfast |
|  | 7.5 g at dinner |

The placebo will be corn syrup with a similar consistency and sweetness to the RP-G28. Treatment doses will be provided to the subjects in high-density polyethylene (HDPE) bottles with detailed daily instructions regarding proper dosing. The daily dose will be diluted with water and taken with the indicated meal.

At Day 8 and Day 17, Visits 4 and 5 are conducted. Vital signs, height, and weight are recorded. The daily symptom diaries are returned, investigations products are returned/distributed, and any adverse events are assessed. The amount of product returned is one measure of subject compliance.

At the end of the double blind treatment period, Visit 6 is conducted. During this visit, a second physical exam in performed on the subjects. Labs, including chemistry and hematology panels, are run and dipstick urinalysis is performed. Vital signs and subject height and weight are recorded. As at Visit 3, a hydrogen breath test (HBT)/lactose challenge is performed, a lactose symptom questionnaire is filled out and fecal samples are taken to determine bacterial levels.

Example 15D

30-Day Follow Up

After completion of Visit 6, subjects will be asked to incorporate dairy products into their diets from Day 37 to Day 66, as tolerated. Subjects will also be asked to complete a daily symptom diary, such as the one found in FIG. 32. The final visit (Visit 7) occurs at the end of the 30-day follow up period. At this time, subjects are asked the screening dairy intolerance questions and the daily symptom diaries are returned. Additionally, as a Visits 3 and 6, a hydrogen breath test (HBT)/lactose challenge is performed, a lactose symptom questionnaire is filled out and fecal samples are taken to determine bacterial levels.

Example 15E

Clinical Assessments

Primary Efficacy Endpoints

Baseline values for total 6-hour hydrogen breath test (HBT) total hydrogen production and HBT symptom assessment total score during lactose challenge are determined prior to the 35 day course of treatment (Day 0/Visit 3). Primary efficacy endpoints of the study are a change in these values at the end of a 35 day course of treatment (Day 36/Visit 6).

Secondary Efficacy Endpoints

Secondary efficacy endpoints include a change from baseline to Day 36 in 6-hour HBT peak hydrogen production; a change from baseline to Day 66 in 6-hour HBT peak hydrogen production; a change from baseline to Day 66 in 6-hour HBT total hydrogen production; a change from baseline to Day 66 in HBT symptom assessment total score during lactose challenge; a change from baseline to Day 36 in fecal bacteria measurements; a change from baseline to Day 66 in fecal bacteria measurements; and changes in dairy consumption amounts, total score, and individual symptom scores on daily symptom questionnaires over time.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A pharmaceutically acceptable oral dosage form of galactooligosaccharides (GOS), comprising one or more dosing units, each of said dosing units comprising 0.1 to 10 g of a GOS composition, wherein said GOS composition is a liquid encapsulated in a gelatin capsule, and wherein the GOS composition comprises at least about 95% GOS by weight and less than about 5% digestible saccharides by weight, wherein the GOS comprises at least 45% by weight trisaccharides.

2. The oral dosage form of claim 1, wherein the GOS comprises about 1-20% by weight pentasaccharides.

3. The oral dosage form of claim 1, wherein said gelatin capsule is size 000, 00, 0, 1, 2, 3, 4, or 5.

4. The oral dosage form of claim 1, wherein said GOS composition comprises at least about 80% GOS by weight.

5. The oral dosage form of claim 1, wherein said GOS composition does not comprise a probiotic.

6. The oral dosage form of claim 1, wherein said gelatin capsule further comprises an enteric coating.

7. The oral dosage form of claim 1, wherein the digestible saccharides comprise lactose, galactose, or glucose.

8. The oral dosage form of claim 1, wherein the GOS composition comprises about 0.001% to about 1% glucose.

9. The oral dosage form of claim 1, wherein the GOS composition comprises about 0.01% to about 0.1% glucose.

10. The oral dosage form of claim 1, wherein the GOS composition comprises about 0.1% galactose to about 2% galactose.

11. The oral dosage form of claim 1, wherein the GOS composition comprises less than 2% lactose.

12. The oral dosage form of claim 1, wherein the GOS composition comprises less than about 10 ppm heavy metals.

13. The oral dosage form of claim 1, wherein the GOS composition comprises less than about 0.10% by weight sulphated ash.

14. The oral dosage form of claim 1, comprising about 1 mg to about 20 g of the GOS composition.

15. The oral dosage form of claim 1, further comprising a flavoring and/or colorant.

16. The oral dosage form of claim 1, wherein the dosage form does not comprise a probiotic.

\* \* \* \* \*